(12) United States Patent
He et al.

(10) Patent No.: US 9,409,871 B2
(45) Date of Patent: *Aug. 9, 2016

(54) PYRIDAZINYL DERIVATIVES AS SMO INHIBITORS

(71) Applicant: NOVARTIS AG, Basel OT (CH)

(72) Inventors: Feng He, Shanghai (CN); Stefan Peukert, Arlington, MA (US); Karen Marie Miller-Moslin, Princeton, NJ (US); Naeem Yusuff, Cambridge, MA (US); Zhuoliang Chen, Belmont, MA (US); Bharat Lagu, Acton, MA (US)

(73) Assignee: NOVARTIS AG, Basel (CH)

( * ) Notice: Subject to any disclaimer, the term of this patent is extended or adjusted under 35 U.S.C. 154(b) by 206 days.

This patent is subject to a terminal disclaimer.

(21) Appl. No.: 13/905,686

(22) Filed: May 30, 2013

(65) Prior Publication Data
US 2013/0261299 A1  Oct. 3, 2013

Related U.S. Application Data

(60) Continuation of application No. 13/553,870, filed on Jul. 20, 2012, now Pat. No. 8,481,542, which is a division of application No. 12/503,565, filed on Jul. 15, 2009, now abandoned.

(60) Provisional application No. 61/081,900, filed on Jul. 18, 2008.

(51) Int. Cl.

| C07D 401/14 | (2006.01) |
|---|---|
| C07D 403/14 | (2006.01) |
| C07D 403/04 | (2006.01) |
| C07D 413/14 | (2006.01) |
| A61K 31/501 | (2006.01) |
| A61K 31/4523 | (2006.01) |
| A61K 31/4427 | (2006.01) |
| C07D 237/20 | (2006.01) |
| C07D 401/12 | (2006.01) |
| C07D 403/12 | (2006.01) |
| C07D 471/04 | (2006.01) |
| C07D 237/26 | (2006.01) |
| A61P 35/00 | (2006.01) |

(52) U.S. Cl.
CPC .......... *C07D 237/20* (2013.01); *A61K 31/4427* (2013.01); *A61K 31/4523* (2013.01); *A61K 31/501* (2013.01); *C07D 237/26* (2013.01); *C07D 401/12* (2013.01); *C07D 401/14* (2013.01); *C07D 403/12* (2013.01); *C07D 403/14* (2013.01); *C07D 413/14* (2013.01); *C07D 471/04* (2013.01)

(58) Field of Classification Search
CPC .. C07D 401/14; C07D 403/14; C07D 413/14; A61K 31/501; A61K 31/4523; A61K 31/4427
USPC ..................... 544/238; 514/252.02
See application file for complete search history.

(56) References Cited

U.S. PATENT DOCUMENTS

| 3,668,207 A | 6/1972 | Carney et al. |
| 4,569,934 A | 2/1986 | Moran et al. |
| 4,734,418 A | 3/1988 | Yokoyama et al. |
| 4,760,064 A | 7/1988 | Tominaga et al. |
| 5,935,958 A | 8/1999 | Kozlowski et al. |

(Continued)

FOREIGN PATENT DOCUMENTS

| DE | 2021195 | 11/1970 |
| DE | 2643753 | 4/1978 |

(Continued)

OTHER PUBLICATIONS

Hutchin, et al., Genes Dev. 2005 19: 214-223.

(Continued)

*Primary Examiner* — Venkataraman Balasubramanian
(74) *Attorney, Agent, or Firm* — Qian Zhang

(57) ABSTRACT

The present invention relates to compounds of formula I:

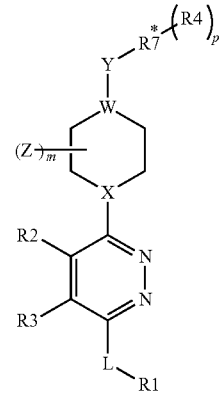

in which L, W, X, Y, Z, m, p, R1, R2, R3, R4 and R7 are defined in the Summary of the Invention; capable of inhibiting the Hedgehog and Smo signaling pathway. The invention further provides a process for the preparation of compounds of the invention, pharmaceutical preparations comprising such compounds and methods of using such compounds and compositions in the diagnosis and treatment of pathologies relating to the Hedgehog and Smo signaling pathway, for example, tumor formation, cancer, neoplasia and non-malignant hyperproliferative disorders.

2 Claims, No Drawings

(56) References Cited

U.S. PATENT DOCUMENTS

| | | | |
|---|---|---|---|
| 6,066,636 A | 5/2000 | Kozlowski et al. | |
| 6,689,797 B2 | 2/2004 | Baroni et al. | |
| 7,960,556 B2 | 6/2011 | Griffioen et al. | |
| 8,193,362 B2 | 6/2012 | Cassayre et al. | |
| 8,236,947 B2 | 8/2012 | Ahmed et al. | |
| 8,481,542 B2 * | 7/2013 | He et al. ................. | 514/252.02 |
| 8,536,168 B2 | 9/2013 | Dai et al. | |
| 8,778,927 B2 | 7/2014 | Dorsch et al. | |
| 2005/0054651 A1 | 3/2005 | Natarajan et al. | |
| 2006/0281712 A1 | 12/2006 | Yen et al. | |
| 2007/0010248 A1 | 1/2007 | Dravida et al. | |
| 2008/0318933 A1 | 12/2008 | Ahmed et al. | |
| 2009/0054410 A1 | 2/2009 | Griffioen et al. | |
| 2010/0029655 A1 | 2/2010 | Leivers et al. | |
| 2010/0112107 A1 | 5/2010 | Xie et al. ...................... | 424/769 |
| 2010/0166655 A1 | 7/2010 | Imogai et al. | |
| 2010/0168093 A1 | 7/2010 | Pericas-Brondo et al. | |
| 2011/0112107 A1 | 5/2011 | Bartolme-Nebreda et al. | |
| 2011/0190304 A1 | 8/2011 | Bastian et al. | |
| 2011/0301162 A1 | 12/2011 | Deak et al. | |
| 2012/0010208 A1 | 1/2012 | Pacaud et al. ................. | 514/248 |
| 2012/0157466 A1 | 6/2012 | Zeng | |

FOREIGN PATENT DOCUMENTS

| | | |
|---|---|---|
| EP | 0 055 583 B1 | 7/1982 |
| EP | 0156433 A2 | 10/1985 |
| EP | 0722936 A1 | 7/1996 |
| EP | 1277754 A1 | 1/2003 |
| GB | 1570374 | 7/1980 |
| JP | 64-061468 | 3/1989 |
| JP | 01061468 | 3/1989 |
| JP | 02193992 | 7/1990 |
| JP | H03106875 A | 5/1991 |
| JP | 2000-507580 A | 6/2000 |
| JP | 2000281660 | 10/2000 |
| JP | 2003 073578 | 3/2003 |
| JP | 2003 073578 A | 12/2003 |
| JP | 2007-500715 A | 1/2007 |
| JP | 2007-501828 A | 2/2007 |
| JP | 2007-503392 A | 2/2007 |
| WO | 97/36889 A1 | 10/1997 |
| WO | 98/05292 A2 | 2/1998 |
| WO | WO 99/54305 A1 | 10/1999 |
| WO | 00/00488 A1 | 1/2000 |
| WO | 00/44376 A1 | 8/2000 |
| WO | 00/66558 A1 | 9/2000 |
| WO | 00/59509 A1 | 10/2000 |
| WO | WO 00/59509 A1 | 10/2000 |
| WO | 00/75130 A1 | 12/2000 |
| WO | WO 00/74706 A1 | 12/2000 |
| WO | 02/20491 A1 | 3/2002 |
| WO | 02/36589 A1 | 5/2002 |
| WO | WO 02/053160 A1 | 7/2002 |
| WO | WO 02/080952 A2 | 10/2002 |
| WO | WO 02/080954 A2 | 10/2002 |
| WO | WO 03/032984 A1 | 4/2003 |
| WO | 03/088970 A2 | 10/2003 |
| WO | WO 2004/076413 A2 | 9/2004 |
| WO | 2005/011653 A2 | 2/2005 |
| WO | 2005/019208 A1 | 3/2005 |
| WO | 2005/020897 A2 | 3/2005 |
| WO | 2005/033288 A2 | 4/2005 |
| WO | 2005/117909 A2 | 12/2005 |
| WO | 2006/028958 A2 | 3/2006 |
| WO | WO 2006/028958 A2 | 3/2006 |
| WO | 2006/094187 A2 | 9/2006 |
| WO | WO 2006/122773 A1 | 11/2006 |
| WO | 2007/048779 A1 | 5/2007 |
| WO | WO 2007/059157 A1 | 5/2007 |
| WO | 2007/064797 A2 | 6/2007 |
| WO | 2007/127375 A1 | 8/2007 |
| WO | 2007/109238 A1 | 9/2007 |
| WO | WO 2007/127375 A2 | 11/2007 |
| WO | WO 2007/127448 A2 | 11/2007 |
| WO | WO 2007/127475 A2 | 11/2007 |
| WO | 2008/008453 A1 | 1/2008 |
| WO | 2008071405 A1 | 6/2008 |
| WO | 2008/098892 A1 | 8/2008 |
| WO | 2008/107479 A1 | 9/2008 |
| WO | 2008/107480 A1 | 9/2008 |
| WO | 2008/110488 A1 | 9/2008 |
| WO | 2008/110611 A1 | 9/2008 |
| WO | 2008107481 A1 | 9/2008 |
| WO | 2008115381 A1 | 9/2008 |
| WO | WO 2008/110611 A1 | 9/2008 |
| WO | WO 2009/035568 A1 | 3/2009 |
| WO | 2010/007316 A2 | 1/2010 |
| WO | 2010/007317 A1 | 1/2010 |
| WO | 2010/007318 A2 | 1/2010 |
| WO | 2010/007382 A1 | 1/2010 |
| WO | 2010/009220 A2 | 1/2010 |

OTHER PUBLICATIONS

Sheng, et al., Molecular Cancer 2004, 3:29, 13 pages.
Wikipedia, Acyl, last modified Mar. 23, 2010.
IUPAC, (1997) http://www.iupac.org/goldbook/A00123.pdf, downloaded Oct. 29, 2010.
Hawley's Condensed Chem. Dict., 14th Ed., 2002.
Hackh's Chem. Dict., 3rd Ed., 1944, Title page.
Berman, David M. et al., "Medulloblastoma Growth Inhibition by Hedgehog Pathway Blockade", Science, vol. 297, pp. 1559-1561, (2002).
Berman, David M. et al., "Widespread requirement for Hedgehog ligand stimulation in growth of digestive tract tumours", Nature, vol. 425, pp. 846-851, (2003).
Frank-Kamenetsky, Maria et al., "Small-molecule modulators of Hedgehog signaling: identification and characterization of Smoothened agonists and antagonists", Journal of Biology, vol. 1, Issue 2, Article 10, pp. 10.1-10.19, (2002).
Karhadkar, Sunil S. et al., "Hedgehog signalling in prostate regeneration, neoplasia and metastasis", Nature, vol. 431, pp. 707-712 (2004).
Kubo, Makoto et al., "Hedgehog Signaling Pathway is a New Therapeutic Target for Patients with Breast Cancer", Cancer Research, vol. 64, pp. 6071-6074 (2004).
Sanchez, Pilar et al., "Inhibition of prostate cancer proliferation by interference with SONIC HEDGEHOG-GLI1 signaling", vol. 101, No. 35, pp. 12561-12566 (2004).
Thayer, Sarah P. et al., "Hedgehog is an early and late mediator of pancreatic cancer tumorigenesis", Nature, vol. 425, pp. 851-856 (2003).
Tostar, Ulrica et al., "Deregulation of the hedgehog signalling pathway: a possible role for the PTCH and SUFU genes in human rhabdomyoma and rhabdomyosarcoma development", J Pathol, 208, pp. 17-25 (2005).
Watkins, D. Neil et al., "Hedgehog signalling within airway epithelial progenitors and in small-cell lung cancer", Nature, vol. 422, pp. 313-317 (2003).
Williams, Juliet A. et al., "Identification of a small molecule inhibitor of the hedgehog signaling pathway: Effects on basal cell carcinoma-like lesions", PNAS, vol. 100, No. 8, pp. 4616-4621 (2003).
Xie, Jingwu et al., "Activating Smoothened mutations in sporadic basal-cell carcinoma", Nature, vol. 391, pp. 90-92 (1998).
Chemical Book, CUR61414 Basic Information, 2008 http://www.chemicalbook.com/ProductChemicalPropertiesCB31565488_EN.htm, downloaded Sep. 20, 2012.
Kimura, et al., Cancer Cell, 13, 249-260, 2008.
Lee, et al., Oncogene, 2007, 26, 6442-6447.
Martin, et al., Cancer Biology & Therapy 4:7, 728-733, Jul. 2005.
Ng, et al., Nature Reviews: Cancer, 11, Jul. 2011, 493-501.
Rudin, et al., New England J. of Medicine, 361: 12, Sep. 17, 2009, 1173-1178.
Wikipedia, Cyclopamine, last modified Jun. 5, 2012, http://en.wikipedia.org/wiki/Cyclopamine, downloaded Sep. 20, 2012.
Schairer, et al., 53rd ASH Annual Meeting & Exposition, Dec. 10-13, 2011.

(56) References Cited

OTHER PUBLICATIONS

"The Effects of Smoothened(Smo) siRNA on Expression of Smo Gene and Proliferation, Apoptosis of Lovo Cells," http://www.tumor-res.com/tumor-marker/29544.htm, downloaded Apr. 4, 2012.
Tauchi, Arthritis Research & Therapy 2012, vol. 14 Suppl 1, 17.
Ruiz-Heiland, et al., Ann Rheum Dis. Mar. 2012;71(3):400-7. Epub Jan. 10, 2012.
Gelain et al., "3-Heptylamino-5-Phenylpyridazine Derivatives as Analogues of Acyl-CoA: Cholesterol Acyltransferase Inhibitors Containing the N-Heptyl-N9-Arylureidic Moiety", Archiv der Pharmazie—Chemistry in Life Sciences, 2006 vol. 339 pp. 645-651.
Hu et al., "Development of a novel therapeutic suppressor of brain proinflammatory cytokine up-regulation that attenuates synaptic dysfunction and behavioral deficits", Bioorganic & Medicinal Chemistry Letters, 2007 vol. 17 pp. 414-418.
Miller-Moslin et al., "1-Amino-4-benzylphthalazines as Orally Bioavailable Smoothened Antagonists with Antitumor Activity", Journal of Medicinal Chemistry, 2009 vol. 52 pp. 3954-3968.
Eiden et al., "2-Aminochinoline und Pyrrolo[2,3-b]chinoline", Arch. Pharm., 1986 vol. 319 No. 4 pp. 338-347.
Holava et al., "1-substituted 4-aryl-(or 4-arakyl-) phthalazines", Journal of Medicinal Chemistry, 1969 vol. 12, pp. 555-556.
Ojea et al., "Synthesis of pyrazino[1,2-a:4,5-a']di[1,9]naphthyridine and pyrazin0[1,2-a][1,8] Naphthyridines", Heterocycles, 1993 vol. 36 No. 6 pp. 1337-1349.
Byth et al., "Imidazo[1,2-b]pyridazines: a potent and selective class of CDK inhibitors" Bioorganic & Medicinal Chemistry Letters, Oxford, GB, vol. 14, 2004, pp. 2249-2252, XP002415769 ISSN : 0960-894X abstract; compound 4B.

\* cited by examiner

PYRIDAZINYL DERIVATIVES AS SMO INHIBITORS

BACKGROUND OF THE INVENTION

Hedgehog (Hh) signaling was first identified in *Drosophila* as an important regulatory mechanism for embryonic pattern formation, or the process by which embryonic cells form ordered spatial arrangements of differentiated tissues (Nusslein-Volhard et al. (1980) Nature 287, 795-801). In mammalian cells, three Hedgehog genes, Sonic Hedgehog (Shh), Indian Hedgehog (Ihh) and Desert Hedgehog (Dhh), have been identified. Hedgehog genes encode secreted proteins, which undergo post-translational modifications, including autocatalytic cleavage and lipid modification (palmitoylation) at the N-terminus and cholesterol modification of the C-terminus.

The lipid-modified N-terminal Hedgehog protein triggers the signaling activity of the protein pathway, and cell to cell communication is engendered by the dispatch of soluble Hedgehog protein from a signaling cell and receipt by a responding cell. In responding cells, the 12-pass transmembrane receptor Patched (Ptch) acts as negative regulator of Hh signaling and the 7-pass transmembrane protein Smoothened (Smo) acts as a positive regulator of Hh signaling. At resting state, free Ptch (i.e., unbound by Hh) substoichiometrically suppresses pathway activity induced by Smo (Taipale et al. (2002) Nature 418: 892); upon binding ligand Hh protein, however, repression of Smo is relieved, and the resulting signaling cascade leads to the activation and nuclear translocation of Gli transcription factors (Gli1, Gli2 and Gli3).

Downstream target genes of Hh signaling transcription include Wnts, TGFβ, and Ptc and Gli1, which are elements of the positive and negative regulatory feedback loop. Several cell-cycle and proliferation regulatory genes, such as c-myc, cyclin D and E are also among the target genes of Hh signaling.

Hh signaling is known to regulate a diverse range of biological processes, such as cellular proliferation, differentiation, and organ formation in a tissue specific and dose dependent manner. In the development of neural tubes, Shh is expressed in the floorplate and directs the differentiation of specific subtypes of neurons, including motor and dopaminergic neurons. Hh is also known to regulate the proliferation of neuronal progenitor cells, such as cerebella granule cells and neural stem cells. In the developing intestinal tract, a low-level of Hh signaling is required for pancreatic development, while a high-level of Hh signaling blocks pancreatic organogenesis. Hh is also known to play important roles in stem cell proliferation and organogenesis in skin, prostate, testis and bone marrow.

Normally, Hh signaling is strictly controlled during cellular proliferation, differentiation and embryonic pattern formation. However, aberrant activity of the Hedgehog signaling pathway, due to mutations that constitutively activate the pathway, for instance, may have pathological consequences. By way of example, loss-of-function mutations of Patched are found in Gorlin's syndrome (a hereditary syndrome with high risk of skin and brain cancers, also known as Basal Cell Nevus Syndrome (BCNS)); and gain-of-function mutations of Smo and Gli are linked to basal cell carcinoma and glioblastoma. Basal cell carcinoma (BCC) is the most common form of skin cancer, affecting more than 90,000 Americans each year. Constitutive activation of Hh has been found to promote tumorigenesis in BCC, medulloblastoma (the most common childhood brain tumor), rhabdomyosarcoma, pancreatic cancer, small cell lung cancer, prostate cancer and breast cancer. Besides the roles in tumorigenesis, Hh signaling is also implicated in the metastasis of prostate cancer. Hh signaling may be involved in many additional types of tumors and such links are expected to continue to be discovered; this is an area of active research in many cancer centers around the world.

Proliferation of these cancer cells requires Hh pathway activation, and blocking Hh signaling pathways often inhibits cancer cell proliferation. Indeed, Hh antagonist cyclopamine and Gli1 siRNA can effectively block the proliferation of these cancer cells, and can reduce tumor size in Xenograft models, suggesting that novel Hh antagonists could provide new chemotherapeutic agents for the treatment of these cancers. Hh antagonist cyclopamine has been shown to suppress the metastasis of prostate cancer in animal models.

In addition to being involved in cancer, Hh signaling plays important roles in normal tissue homeostasis and regeneration. Hh pathway is activated after the injury of retina, bile duct, lung, bone and prostate in mouse models. Hh pathway is also constantly active in hair follicles, bone marrow, and certain regions of the central nervous system (CNS), and benign prostate hyperplasia and blood vessel formation in wet macular degeneration require Hedgehog pathway activity. Cellular regeneration processes can be blocked by anti-Shh antibody and cyclopamine. Therefore, small molecule antagonists of Hh signaling pathway might be useful in the treatment of neuronal proliferative diseases, benign prostate hyperplasia, wet macular degeneration, psoriasis, bone marrow proliferative diseases and leukemias, osteopetrosis and hair removal.

Evidence that constitutive activation of Smo results in cancers (e.g., BCC), and that Smo may be oncogenic upon its release from inhibition by Ptch, suggests utility of Smo antagonists as therapeutic agents in the treatment of such disorders. (Stone et al. (1996) Nature 384: 129). Accordingly, molecules that modulate the activity of the Hedgehog signaling pathway, e.g., which modulate Smo activity, are therapeutically useful.

SUMMARY OF THE INVENTION

The present invention relates generally to novel compounds relating to the diagnosis and treatment of pathologies relating to the Hedgehog pathway, including but not limited to tumor formation, cancer, neoplasia, and non-malignant hyperproliferative disorders. The present invention includes novel compounds, novel compositions, methods of their use and methods of their manufacture, where such compounds are generally pharmacologically useful as agents in therapies whose mechanism of action involve methods of inhibiting tumorigenesis, tumor growth and tumor survival using agents that inhibit the Hedgehog and Smo signaling pathway. The compounds and methods of the present invention (e.g., a compound of Formula I) relate to inhibiting activation of the Hedgehog signaling pathway, e.g., by inhibiting aberrant growth states resulting from phenotypes such as Ptc loss-of-function, Hedgehog gain-of-function, Smoothened gain-of-function or Gli gain-of-function, and comprise contacting the cell with a compound of the invention (e.g., a compound of Formula I) in a sufficient amount to agonize a normal Ptc activity, antagonize a normal Hedgehog activity, or antagonize Smoothened activity (e.g., to reverse or control the aberrant growth state).

The present invention relates to compounds of the formula (I):

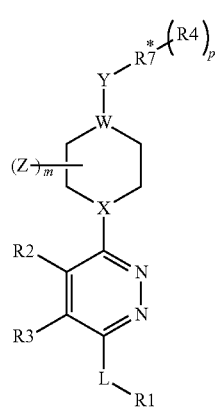

or a pharmaceutically acceptable salt thereof, wherein

R1 is a $C_{6-14}$ aryl group, or a 5-14 membered heteroaryl group which may be unsubstituted or substituted by one or more of $C_{1-8}$ alkyl, a $C_{6-14}$ aryl group, $C_{1-8}$ haloalkyl, $C_{1-8}$ alkoxy, halo, $NH_2$, CN, $OCF_3$, OH, C(O)NR6R8, C(O)R6, NR6R8, NHC(O)R6, $SO_2$R6, or $SO_2$NR6R8;

R2 and R3 are independently $C_{1-8}$ alkyl, $C_{1-8}$ alkylOH, or R2 and R3 form a fused $C_{3-14}$ cycloalkyl group;

L is a bond, $C_{1-8}$ alkylene, —C(O)O—, —C(O)NR9-, —$C_{1-8}$ alkylOH—, —$C_{1-8}$ haloalkyl-, —C(O)—, —NH— or —O—;

X and W are independently N or CR5, and at least one of X or W is N;

R7 is a $C_{6-14}$ aryl group, a 5-14 membered heteroaryl group, or a 3-14 membered cycloheteroalkyl group;

R4 is $C_{1-8}$ alkyl, $C_{2-8}$ alkenyl, $C_{3-14}$ cycloalkyl, a $C_{6-14}$ aryl group, a 5-14 membered heteroaryl group, a 3-14 membered cycloheteroalkyl group, $C_{1-8}$ alkoxy, halo, NR6R8, C(O)OR6, C(O)NR6R8, $C_{1-8}$haloalkyl, formyl, carbalkoxy, $C_{1-8}$alkylOH, C(O)R6, $SO_2$R6, C(O)NHC$_{1-8}$alkylR6, NR6R8, $SO_2$NR6R8, $OCF_3$, NHC(O)R6, $CH_2$OC(O)NR6R8, $CH_2$NR6R8, NHC(O)OR6, NHC(O)NR6R8, $CH_2$NHSO$_2$R6, $CH_2$NHC(O)OR6, OC(O)R6, or NHC(O)R6, which may be substituted or unsubstituted;

Z is $C_{1-8}$ alkyl, CN, OH, or halogen;

m and p are independently 0-3;

Y is a bond, $C_{1-8}$ alkylene, —C(O)—, —C(O)O—, —CH(OH)—, or —C(O)NR10;

R5 is H, halogen, CN, lower alkyl, OH, $OCH_3$ or $OCF_3$;

R9 and R10 are independently $C_{1-8}$ alkyl or H;

R6 and R8 are independently H, $C_{1-8}$ alkyl, $C_{2-8}$ alkenyl, $C_{3-14}$ cycloalkyl, a $C_{6-14}$ aryl group, a 5-14 membered heteroaryl group, a 3-14 membered cycloheteroalkyl group, $C_{1-8}$haloalkyl, $C_{1-8}$ alkylOH, $C_{1-8}$alkoxy, or two R6, or an R6 and a R8 on one atom can form a heteroatom containing ring; and Wherein R4, R6, and R8 can be unsubstituted or substituted by one or more of $C_{1-8}$ alkyl, $C_{3-14}$ cycloalkyl, a $C_{6-14}$ aryl group, a 5-14 membered heteroaryl group, a 3-14 membered cycloheteroalkyl group, $C_{1-8}$ alkylOH, OH, oxo, $C_{1-8}$ haloalkyl, carbox$C_{1-8}$ alkyl, or $SO_2C_{1-8}$alkyl, halo, —$OCH_3$, —$OCF_3$, —OH, —$NH_2$.

In an embodiment, the present invention includes compounds of formula (I) wherein R7 is

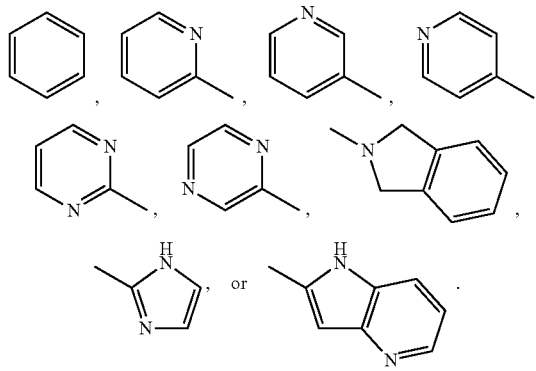

In another embodiment, the present invention includes compounds of formula (I) according to claim 1 wherein R1 is

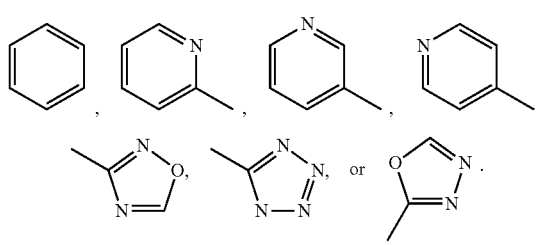

In another embodiment, the present invention includes compounds of formula (I) wherein R7 is

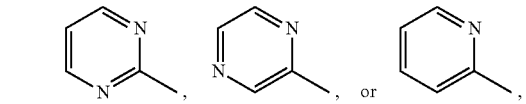

and
R1 is

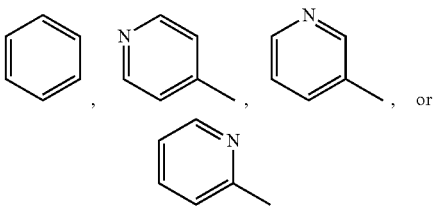

In yet another embodiment, the present invention includes compounds of formula (I) wherein R4 is C(O)OC$_{1-8}$ alkyl, $CF_3$, C(O)OR6, C(O)NR6R8, $C_{1-8}$ haloalkyl, $C_{1-8}$ alkylOH, C(O)R6, $SO_2$R6, C(O)NHC$_{1-8}$alkylR6, C(CH$_3$)(CH$_3$)(OH), C(O)CH$_3$, C(CH$_2$)CH$_3$, or C(CH$_3$)(CH$_2$OH)OH; and R6 and R8 are independently H, $C_{1-8}$ alkyl, $C_{1-8}$ alkenyl, $C_{3-14}$ cycloalkyl, a $C_{6-14}$ aryl group, a 5-14 membered heteroaryl group, or a 3-14 membered cycloheteroalkyl group.

In another embodiment, the present invention includes compounds of formula (I) wherein R7 is

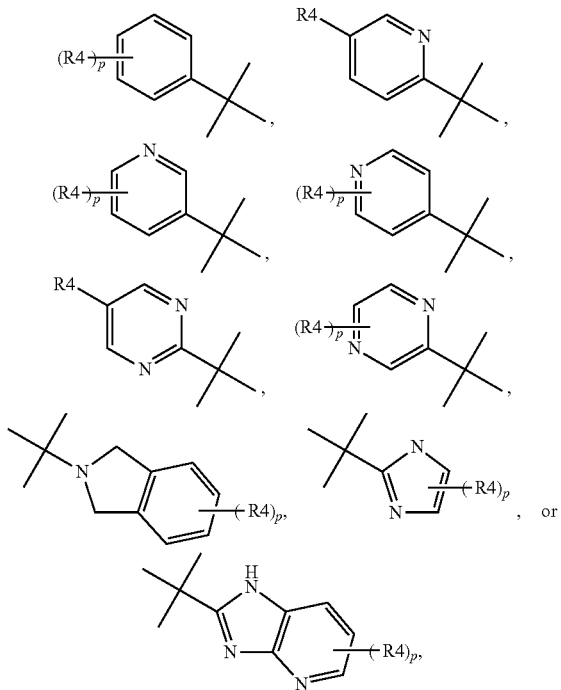

and R4 is $C_{1-8}$ alkyl, such as methyl, ethyl, proply, or butyl; $C_{2-8}$ alkenyl, such as ethenyl or propenyl; $C_{3-14}$ cycloalkyl, such as cyclopropyl, cyclobutyl, cyclopentyl, or cyclohexyl; a $C_{6-14}$ aryl group, such as phenyl; a 5-14 membered heteroaryl group, such as pyridinyl or imidazolyl, a 3-14 membered cycloheteroalkyl group, such as piperidinyl, morpholinyl, pyrrolidinyl, or piperazinyl; $C_{1-8}$ alkoxy, such as methoxy, ethoxy, or propoxy; halo, such as Cl, F, Br, or I; NR6R8, such as $NHC_{1-8}$alkyl; C(O)OR6, such as $C(O)OC_{1-8}$alkyl, or C(O)OH; C(O)NR6R8, such as $C(O)NHC_{6-14}$aryl, $C(O)NC_{6-14}arylC_{1-8}$alkyl, or C(O)-5-14 membered heteroaryl group, or C(O)-3-14 membered cycloheteroalkyl group, $C_{1-8}$haloalkyl, such as $CF_3$; formyl, carbalkoxy, $C_{1-8}$alkylOH, such as $CH_2OH$, ethyl substituted with OH at any position, propyl substituted with OH at any position, or butyl substituted with OH at any position; C(O)R6, such as $C(O)C_{1-8}$alkyl; $SO_2R6$, such as $SO_2C_{1-8}$alkyl or $SO_2CF_3$; $C(O)NHC_{1-8}$alkylR6, such as $C(O)NHC_{1-8}$alkylOH, or $C(O)NHC_{1-8}$alkylCF_3$; $SO_2NR6R8$, such as $SO_2NHC_{1-8}$alkyl; $OCF_3$, NHC(O)R6, such as $NHC(O)C_{1-8}$alkyl; $CH_2OC(O)NR6R8$, $CH_2NR6R8$, NHC(O)OR6, NHC(O)NR6R8, $CH_2NHSO_2R6$, $CH_2NHC(O)OR6$, OC(O)R6, or NHC(O)R6, and wherein R4 may be unsubstituted or substituted; and p is 0, 1, or 2.

In another embodiment, R6 and R8 are independently H, $C_{1-8}$ alkyl, such as methyl, ethyl, propyl, or butyl; $C_{2-8}$ alkenyl, such as alkenyl, propenyl; $C_{3-14}$ cycloalkyl, such as cyclopropyl, cyclobutyl, cyclopentyl, or cyclohexyl; a $C_{6-14}$ aryl group, such as phenyl; a 5-14 membered heteroaryl group, such as pyridinyl or pyrimidinyl; a 3-14 membered cycloheteroalkyl group, such as morpholinyl, piperidinyl, pyrrolidinyl, or piperazinyl; $C_{1-8}$haloalkyl, such as $CF_3$; $C_{1-8}$ alkylOH, $C_{1-8}$alkoxy, such as methoxy or ethoxy; or two R6, or R6 and R8 on one atom can form a heteroatom containing ring, such as a 5-14 membered heteroaryl group or a 3-14 membered cycloheteroalkyl group.

In another embodiment of the present invention, R4 may be unsubstituted or substituted with one or more of $C_{1-8}$ alkyl, such as methyl, ethyl, propyl, butyl, or pentyl; $C_{3-14}$ cycloalkyl, such as cyclopropyl, cyclobutyl, cyclopentyl, or cyclohexyl; a $C_{6-14}$ aryl group, such as phenyl; a 5-14 membered heteroaryl group, such as pyridinyl or pyrimidinyl; a 3-14 membered cycloheteroalkyl group, such as morpholinyl, piperidinyl, pyrrolidinyl, or piperazinyl; $C_{1-8}$ alkylOH, such as $CH_3OH$; OH, oxo, $C_{1-8}$ haloalkyl, such as $CF_3$; carboxy$C_{1-8}$alkyl, or $SO_2C_{1-8}$alkyl, halo, such as Cl, F, Br, or I; —$OCH_3$, —$OCF_3$, or —$NH_2$.

In another embodiment, and R4 is methyl, phenyl, pyridinyl, methoxy, Cl, F, $C(O)OC_{1-8}$alkyl, C(O)OH, $C(O)NHC_{6-14}$aryl, $C(O)NC_{6-14}arylC_{1-8}$alkyl, C(O)-5-14 membered heteroaryl group, C(O)-3-14 membered cycloheteroalkyl group, $CF_3$; $CH_2OH$, $CH_2CH_2OH$, $C(CH_3)(CH_3)$ OH, $C(O)CH_3$, $C(O)CH_2CH_3$, $SO_2C_{1-8}$alkyl, $SO_2CF_3$, $C(O)NHC_{1-8}$alkylOH, $C(O)NHC_{1-8}$alkylCF_3$, $SO_2NHC_{1-8}$alkyl, $OCF_3$, $NHC(O)CH_3$, or $CH_2OC(O)NHCH_3$; each of which may be unsubstituted or substituted; and p is 0, 1, or 2.

In another embodiment, R4 is $C(O)CH_3$, C(O)NH-phenyl, C(O)OH, $CF_3$, $C(CH_3)(CH_3)OH$, $C(O)OCH_3$, $CF_3$, $C(O)OCH_2CH_3$, or $C(O)NCH_2CH_3$, optionally substituted with piperazinyl, morpholinyl, or pyridinyl.

In a preferred embodiment, R7 is

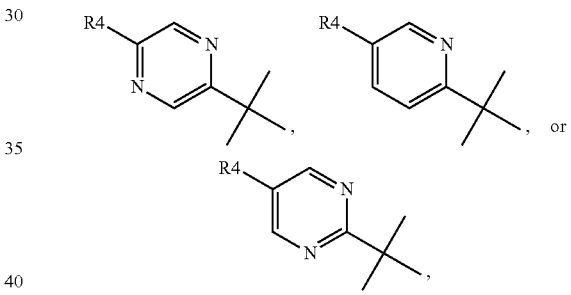

and
R4 is $C(O)CH_3$, C(O)NH-phenyl, C(O)OH, $CF_3$, $C(CH_3)(CH_3)OH$, $C(O)OCH_3$, $CF_3$, or $C(O)OCH_2CH_3$.

In another embodiment, the present invention includes compounds of formula (I) wherein R1 is

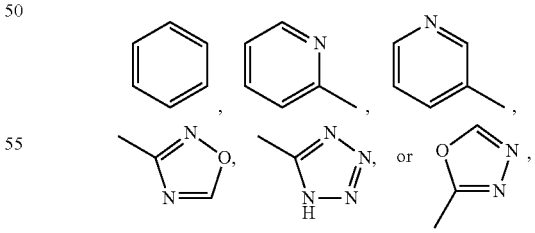

each of which may be unsubstituted or substituted by one or more of $C_{1-8}$ alkyl, such as methyl, ethyl, propyl (e.g., isopropyl), butyl, pentyl, or hexyl; a $C_{6-14}$ aryl group, such as phenyl; $C_{1-8}$ haloalkyl, such as CF3; $C_{1-8}$ alkoxy, such as methoxy or ethoxy; halo, such as Cl, F, Br, or I; $NH_2$, CN, $OCF_3$, OH, C(O)NR6R8, C(O)R6, NR6R8, NHC(O)R6, $SO_2R6$, or $SO_2NR6R8$.

In a further embodiment, R1 is

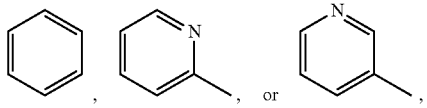

which may be unsubstituted or substituted with each of which may be unsubstituted or substituted by one or more of methyl, ethyl, CF3, methoxy, Cl, F, NH$_2$, CN, OCF$_3$, or OH. In another embodiment, R1 may be unsubstituted or substituted with CH$_3$, Cl, F, methoxy, or CH.

In another embodiment, the present invention includes compounds of formula (I) wherein R7 is

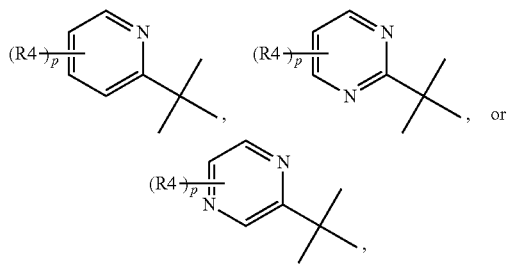

and
R1 is

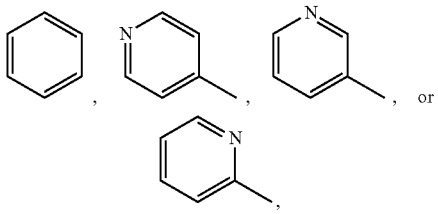

which may be unsubstituted or substituted with one or more of methyl, ethyl, isopropyl, Cl, F, CN, methoxy, or CF$_3$.

In yet another embodiment, the present invention includes compounds of formula (I) wherein R4 is C(O)OC$_{1-8}$ alkyl, CF$_3$, C(O)OR6, C(O)NR6R8, C$_{1-8}$ haloalkyl, C$_{1-8}$ alkylOH, C(O)R6, SO$_2$R6, C(O)NHC$_{1-8}$alkylR6, C(CH$_3$)(CH$_3$)(OH), C(O)CH$_3$, CH$_2$—CH$_2$—CH$_3$, or C(CH$_3$)(CH$_2$OH)OH.

In an embodiment R6 and R8 are independently H, methyl, ethyl, cyclopentyl, cyclohexyl, phenyl, pyridinyl, morpholinyl, piperidinyl, pyrrolidinyl, or piperazinyl, CF$_3$, methoxy, two R6, or R6 and R8 on one atom can form a heteroatom containing ring, such as a 5-14 membered heteroaryl group, such as pyridinyl or pyrimidinyl; or a 3-14 membered cycloheteroalkyl group, such as piperidinyl or piperazinyl.

In another embodiment, the present invention includes compounds of formula (I) wherein R4 is

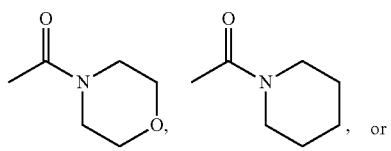

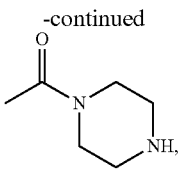

which may be unsubstituted or substituted.

In another embodiment, the present invention includes compounds of formula (I) wherein R2 and R3 are C$_{1-8}$ alkyl, such as methyl, ethyl, or together with the carbon atoms to which they are attached form a C$_{4-7}$cycloalkyl group. In another embodiment, R2 and R3 are each methyl, or form a cyclopentyl or cyclohexyl group.

In a still further embodiment, the present invention includes compounds of formula (I) wherein R2 and R3 are CH$_3$.

In another embodiment, the present invention includes compounds of formula (I) wherein L is —O—, —NH—, —C(O)—, —CH(OH)—, —CH$_2$—, —CF$_2$—, —CHF—, —C(OH)—, or a bond. In another embodiment, the present invention includes compounds of formula (I) wherein L is —CH$_2$—. In another embodiment, the present invention includes compounds of formula (I) wherein both X and W are N, and Z is CH$_3$, and m is 1.

In another embodiment, p is 0, 1, or 2. In another embodiment, p is 0 or 1. In yet another embodiment, p is 1.

In another embodiment, Y is a bond, C$_{1-8}$ alkylene, such as methylene, ethylene, propylene —C(O)—, —C(O)O—, —CH(OH)—, or —C(O)NR10, where R10 is C$_{1-8}$alkyl, such as methyl, ethyl, propyl, or butyl, or H. In another embodiment, Y is a bond, methylene, —C(O)O—, or C(O)NH. In another embodiment, Y is a bond.

In another embodiment, the present invention includes a compound of formula (Ia):

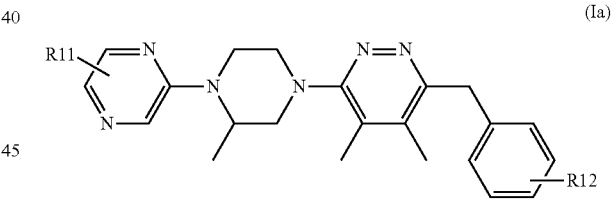

(Ia)

or a pharmaceutically acceptable salt thereof, wherein
R11 is C$_{1-8}$ alkyl, C$_{2-8}$ alkenyl, C$_{3-14}$ cycloalkyl, a C$_{6-14}$ aryl group, a 5-14 membered heteroaryl group, a 3-14 membered cycloheteroalkyl group, C$_{1-8}$ alkoxy, halo, NR13R14, C(O)OR13, C(O)NR13R14, C$_{1-8}$haloalkyl, formyl, carbalkoxy, C$_{1-8}$alkylOH, C(O)R13, SO$_2$R13, C(O)NHC$_{1-8}$ alkylR13, NR13R14, SO$_2$NR13R14, OCF$_3$, NHC(O)R13, CH$_2$OC(O)NR13R14, CH$_2$NR13R14, NHC(O)OR13, NHC(O)NR13R14, CH$_2$NHSO$_2$R13, CH$_2$NHC(O)OR13, OC(O)R13, or NHC(O)R13, which may be substituted or unsubstituted;
R12 is H, C$_{1-8}$ alkyl, a C$_{6-14}$ aryl group, C$_{1-8}$ haloalkyl, C$_{1-8}$ alkoxy, halo, NH$_2$, CN, OCF$_3$, OH, C(O)NR13R14, C(O)R13, NR13R14, NHC(O)R13, SO$_2$R13, SO$_2$NR13R14;
R13 and R14 are independently H, C$_{1-8}$ alkyl, C$_{2-8}$ alkenyl, C$_{3-14}$ cycloalkyl, a C$_{6-14}$ aryl group, a 5-14 membered heteroaryl group, a 3-14 membered cycloheteroalkyl group, C$_{1-8}$haloalkyl, C$_{1-8}$ alkylOH, C$_{1-8}$alkoxy, or R13 and R14 on one atom can form a heteroatom containing ring; and Wherein R11, R13, and R14 can be unsubstituted or substituted by one or more of $C_{1-8}$ alkyl, $C_{3-14}$ cycloalkyl, a $C_{6-14}$ aryl group, a 5-14 membered heteroaryl group, a 3-14 membered cycloheteroalkyl group, $C_{1-8}$ alkylOH, OH, oxo, $C_{1-8}$ haloalkyl, carbox$C_{1-8}$ alkyl, or $SO_2C_{1-8}$alkyl, halo, —$OCH_3$, —$OCF_3$, —OH, —$NH_2$.

In another embodiment, the present invention includes a compound selected from:

2-[(R)-4-(4,5-Dimethyl-6-phenoxy-pyridazin-3-yl)-2-methyl-3,4,5,6-tetra-hydro-2H-[1,2']bipyrazinyl-5'-yl]-propan-2-ol;

2-{(R)-4-[6-(Hyrdoxyl-phenyl-methyl0-4,5-dimethyl-pyridazin-3-yl)-2-methyl-3,4,5,6-tetrahydro-2H-[1,2']bipyrazinyl-5'-yl]-propan-2-ol;

2-[(R)-4-(4,5-Dimethyl-6-pyridin-4-ylmethyl-pyridazin-3-yl)-2-methyl-3,4,5,6-tetrahydro-2H-[1,2']bipyrazinyl-5'-yl]-propan-2-ol;

2-[(R)-4-(4,5-Dimethyl-6-pyridin-2-ylmethyl-pyridazin-3-yl)-2-methyl-3,4,5,6-tetrahydro-2H-[1,2']bipyrazinyl-5'-yl]-propan-2-ol;

2-[(R)-4-(6-Benzyl-4,5-dimethyl-pyridazin-3-yl)-2-methyl-3,4,5,6-tetrahydro-2H-[1,2']bipyrazinyl-5'-yl]-propan-2-ol;

2-[4-(6-Benzyl-4,5-dimethyl-pyridazin-3-yl)-3,4,5,6-tetrahydro-2H-[1,2']bipyrazinyl-5'yl]-propan-2-ol;

2-[(S)-4-(6-Benzyl-4,5-dimethyl-pyridazin-3-yl)-2-methyl-3,4,5,6-tetrahydro-2H-[1,2']bipyrazinyl-5'-yl]-propan-2-ol;

2-[(R)-4-(6-Benzyl-4,5-dimethyl-pyridazin-3-yl)-2-ethyl-3,4,5,6-tetrahydro-2H-[1,2']bipyrazinyl-5'-yl]-propan-2-ol;

2-[4-(4-Benzyl-6,7-dihydro-5H-cyclopenta[d]pyridazin-1-yl)-3,4,5,6-tetrahydro-2H-[1,2']bipyrazinyl-5'-yl]-propan-2-ol;

2-[(R)-4-(4-Benzyl-6,7-dihydro-5H-cyclopenta[d]pyridazin-1-yl)-2-methyl-3,4,5,6-tetrahydro-2H-[1,2']bipyrazinyl-5'-yl]-propan-2-ol;

1-[(R)-4-(6-Benzyl-4,5-dimethyl-pyridazin-3-yl)-2-methyl-3,4,5,6-tetrahydro-2H-[1,2']bipyrazinyl-5'-yl]-ethanone; and 2-[(R)-4-(6-Benzyl-4,5-dimethyl-pyridazin-3-yl)-2-methyl-3,4,5,6-tetrahydro-2H-[1,2']bipyrazinyl-5'-yl]-propane-1,2-diol.

One aspect of the present invention makes available methods employing compounds for inhibiting Smo-dependent pathway activation. Another aspect of the present invention makes available methods employing compounds for inhibiting Hedgehog (ligand)-independent pathway activation. In certain embodiments, the present methods can be used to counteract the phenotypic effects of unwanted activation of a Hedgehog pathway, such as resulting from Hedgehog gain-of-function, Ptc loss-of-function or smoothened gain-of-function mutations. For instance, the subject method can involve contacting a cell (in vitro or in vivo) with a Smo antagonist, such as a compound of the invention (e.g., a compound of Formula I) or other small molecule in an amount sufficient to antagonize a smoothened-dependent and/or Hedgehog independent activation pathway.

The compounds and methods of the present invention may be used to regulate proliferation and/or differentiation of cells in vitro and/or in vivo, e.g., in the formation of tissue from stem cells, or to prevent the growth of hyperproliferative cells. In another particular embodiment, contacting the cell with—or introducing into the cell—a compound of the invention (e.g., a compound of Formula I) results in inhibition of cellular proliferation, inhibition of tumor cell growth and/or survival, and/or inhibition of tumorigenesis. Thus, another particular embodiment provides methods for inhibiting and/ or antagonizing the Hh pathway by employing compounds of the invention (e.g., a compound of Formula I) in a tumor cell.

The methods of the present invention may employ compounds of the invention (e.g., a compound of Formula I) as formulated as pharmaceutical preparations comprising a pharmaceutically acceptable excipient or carrier, and said preparations may be administered to a patient to treat conditions involving unwanted cell proliferation such as cancers and/or tumors (such as medullablastoma, basal cell carcinoma, etc.), and non-malignant hyperproliferative disorders.

One embodiment of the present invention provides a compound and method for inhibiting the synthesis, expression, production, stabilization, phosphorylation, relocation within the cell, and/or activity of a Smo protein in a cell in vitro or in vivo comprising, contacting said cell with, or introducing into said cell, a compound of the invention (e.g., a compound of Formula I).

Another aspect of the invention provides a compound and method of diagnosing, preventing and/or treating cellular debilitations, derangements, and/or dysfunctions; hyperplastic, hyperproliferative and/or cancerous disease states; and/or metastasis of tumor cells, in a mammal characterized by the presence and/or expression of a Smo gene or gene product (e.g., a Smo protein), comprising compounds of formula (I) and their administration to a mammal in a therapeutically effective amount.

DETAILED DESCRIPTION OF THE INVENTION

In another embodiment, the present invention includes a pharmaceutical composition comprising a therapeutically effective amount of a compound according to formula I or Ia. In another embodiment, the present invention includes a method of treating a mammal suffering from a pathology relating to the Hedgehog pathway which comprises administering to said mammal in need of treatment a therapeutically effective amount of a compound according to formula I or Ia.

In the present description, the term "treatment" includes both prophylactic or preventive treatment as well as curative or disease suppressive treatment, including treatment of patients at risk for a disorder of the invention (e.g., a Hedgehog-related disorder (e.g., cancer)) as well as ill patients. This term further includes the treatment for the delay of progression of the disease.

By "suppress and/or reverse," e.g., a Hedgehog-related disorder (e.g., cancer), Applicants mean to abrogate said Hedgehog-related disorder (e.g., diabetes), or to render said condition less severe than before or without the treatment.

"Cure" as used herein means to lead to the remission of the Hedgehog-related disorder (e.g., cancer) in a patient, or of ongoing episodes thereof, through treatment.

The terms "prophylaxis" or "prevention" means impeding the onset or recurrence of metabolic disorders, e.g., diabetes.

"Treatment" or "treating" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted.

"Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

"Subject" or "patient" refers to a mammal, preferably a human, in need of treatment for a condition, disorder or disease.

"A compound(s) of the invention" as used herein includes but is not limited to compounds of Formula I (e.g., a compound of Formulae (I), including all variants thereof). A compound of the invention includes the specifically listed compounds listed herein, including those listed in the Examples of the present application.

"Delay of progression" as used herein means that the administration of a compound of the invention (e.g., a compound of Formula I) to patients in a pre-stage or in an early phase of a Hedgehog-related disorder (e.g., cancer) prevents the disease from evolving further, or slows down the evolution of the disease in comparison to the evolution of the disease without administration of the active compound.

"Hedgehog gain-of-function" refers to an aberrant modification or mutation of a Ptc gene, Hedgehog gene, or smoothened gene, or a change (e.g., decrease) in the level of expression of such a gene, which results in a phenotype which resembles contacting a cell with a Hedgehog protein, e.g., aberrant activation of a Hedgehog pathway. The gain-of-function may include a loss of the ability of the Ptc gene product to regulate the level of expression of Gli genes, e.g., Gli1, Gli2, and Gli3, or loss of the ability to regulate the processing, stability, localization or activity of the Gli proteins, e.g., Gli1, Gli2, and Gli3. The term "Hedgehog gain-of-function" is also used herein to refer to any similar cellular phenotype (e.g., exhibiting excess proliferation) which occurs due to an alteration anywhere in the Hedgehog signal transduction pathway, including, but not limited to, a modification or mutation of Hedgehog itself. For example, a tumor cell with an abnormally high proliferation rate due to activation of the Hedgehog signaling pathway would have a "Hedgehog gain-of-function" phenotype, even if Hedgehog is not mutated in that cell.

"Patched loss-of-function" refers to an aberrant modification or mutation of a Ptc gene, or a decreased level of expression of the gene, which results in a phenotype which resembles contacting a cell with a Hedgehog protein, e.g., aberrant activation of a Hedgehog pathway. The loss-of-function may include a loss of the ability of the Ptc gene product to regulate the level of expression, processing, stability, localization, regulation or activity of Gli genes and proteins, e.g., Gli1, Gli2 and Gli3.

"Gli gain-of-function" refers to an aberrant modification or mutation of a Gli gene, or an increased level of expression of the gene, which results in a phenotype which resembles contacting a cell with a Hedgehog protein, e.g., aberrant activation of a Hedgehog pathway.

"Smoothened gain-of-function" refers to an aberrant modification or mutation of a Smo gene, or an increased level of expression of the gene, which results in a phenotype which resembles contacting a cell with a Hedgehog protein, e.g., aberrant activation of a Hedgehog pathway.

As used herein a "small organic molecule" is an organic compound (or organic compound complexed with an inorganic compound (e.g., metal)) that has a molecular weight of less than 3 kilodaltons, and preferably less than 1.5 kilodaltons.

As used herein a "reporter" gene is used interchangeably with the term "marker gene" and is a nucleic acid that is readily detectable and/or encodes a gene product that is readily detectable such as luciferase.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease Si), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host.

"Agent" refers to all materials that may be used to prepare pharmaceutical and diagnostic compositions, or that may be compounds, nucleic acids, polypeptides, fragments, isoforms, variants, or other materials that may be used independently for such purposes, all in accordance with the present invention.

"Analog" as used herein, refers to a small organic compound, a nucleotide, a protein, or a polypeptide that possesses similar or identical activity or function(s) as the compound, nucleotide, protein or polypeptide or compound having the desired activity and therapeutic effect of the present invention. (e.g., inhibition of tumor growth), but need not necessarily comprise a sequence or structure that is similar or identical to the sequence or structure of the preferred embodiment "Derivative" refers to either a compound, a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein or polypeptide possesses a similar or identical function as the parent polypeptide.

"Inhibitors," or "antagonists" refer to inhibitory molecules identified using in vitro and in vivo assays for Hh pathway function, e.g., Smo antagonists. In particular, inhibitors and antagonists refer to compounds or agents that decrease signaling that occurs via the Hh pathway Inhibitors may be compounds that decrease, block, or prevent, signaling via this pathway.

"Hedgehog-related disorder(s)" as used herein includes disorders associated with disruption or aberrance of the Hedgehog pathway, as well as disorders associated with normal but undesired growth states relating to activation of the Hedgehog pathway. "Hedgehog-related disorder(s)" include but are not limited to tumor formation, cancer, neoplasia, malignant hyperproliferative disorders, and non-malignant hyperproliferative disorders. "Hedgehog-related disorder(s)" also include benign prostate hyperplasia, psoriasis, wet macular degeneration, osteopetrosis and unwanted hair growth.

As used herein, the term "cancer" includes solid mammalian tumors as well as hematological malignancies. "Solid mammalian tumors" include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin, central nervous system including brain; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. In addition, a cancer at any stage of progression can be treated, such as primary, metastatic, and recurrent cancers. Information regarding numerous types of cancer can be found, e.g., from the American Cancer Society, or from, e.g., Wilson et al. (1991) Harrison's Principles of Internal Medicine, 12th Edition, McGraw-Hill, Inc. Both human and veterinary uses are contemplated.

Cancers which are particularly amenable to treatment by the compounds and methods of the invention include but are not limited to gliomas, medulloblastomas, primitive neuroectodermal tumors (PNETS), basal cell carcinoma (BCC), small cell lung cancers, large cell lung cancers, tumors of the gastrointestinal tract, rhabdomyosarcomas, soft tissue sarcomas, pancreatic tumors, bladder tumors and prostate tumors.

As used herein, the term "malignant hyperproliferative disorder(s)" includes but is not limited to cancers, neuronal proliferative disorders, bone marrow proliferative diseases and leukemias.

As used herein, the term "non-malignant hyperproliferative disorder(s)" includes but is not limited to non-malignant and non-neoplastic proliferative disorders, such as smooth muscle hyperplasia in blood vessels, cutaneous scarring, and pulmonary fibrosis.

As used herein, "halo" or "halogen" refers to fluoro, chloro, bromo, and iodo.

As used herein, "alkyl" refers to a straight-chain or branched saturated hydrocarbon group. In some embodiments, an alkyl group can have from 1 to 10 carbon atoms (e.g., from 1 to 8 carbon atoms). Examples of alkyl groups include methyl (Me), ethyl (Et), propyl (e.g., n-propyl and isopropyl), butyl (e.g., n-butyl, isobutyl, s-butyl, t-butyl), pentyl groups (e.g., n-pentyl, isopentyl, neopentyl), and the like. A lower alkyl group typically has up to 4 carbon atoms. Examples of lower alkyl groups include methyl, ethyl, propyl (e.g., n-propyl and isopropyl), and butyl groups (e.g., n-butyl, isobutyl, s-butyl, t-butyl).

As used herein, "alkenyl" refers to a straight-chain or branched alkyl group having one or more carbon-carbon double bonds. In some embodiments, an alkenyl group can have from 2 to 10 carbon atoms (e.g., from 2 to 8 carbon atoms). Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene).

As used herein, "alkynyl" refers to a straight-chain or branched alkyl group having one or more carbon-carbon triple bonds. In some embodiments, an alkynyl group can have from 2 to 10 carbon atoms (e.g., from 2 to 8 carbon atoms). Examples of alkynyl groups include ethynyl, propynyl, butynyl, pentynyl, and the like. The one or more carbon-carbon triple bonds can be internal (such as in 2-butyne) or terminal (such as in 1-butyne).

As used herein, "alkoxy" refers to an —O-alkyl group. Examples of alkoxy groups include methoxy, ethoxy, propoxy (e.g., n-propoxy and isopropoxy), t-butoxy groups, and the like. As used herein, "alkylthio" refers to an —S-alkyl group. Examples of alkylthio groups include methylthio, ethylthio, propylthio (e.g., n-propylthio and isopropylthio), t-butylthio groups, and the like.

The term "carbalkoxy" refers to an alkoxycarbonyl group, where the attachment to the main chain is through the carbonyl group (C(O)). Examples include but are not limited to methoxy carbonyl, ethoxy carbonyl, and the like.

As used herein, "oxo" referres to a double-bonded oxygen (i.e., =O). It is also to be understood that the terminology C(O) refers to a —C=O group, whether it be ketone, aldehyde or acid or acid derivative. Similarly, S(O) refers to a —S=O group.

As used herein, "haloalkyl" refers to an alkyl group having one or more halogen substituents. In some embodiments, a haloalkyl group can have 1 to 10 carbon atoms (e.g., from 1 to 8 carbon atoms). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl." For example, a $C_{1-10}$ haloalkyl group can have the formula $—C_iH_{2i+1-j}X_j$, wherein X is F, Cl, Br, or I, i is an integer in the range of 1 to 10, and j is an integer in the range of 0 to 21, provided that j is less than or equal to 2i+1.

As used herein, when an alkyl group is followed by a functional group, such as alkylOH, it is recognized that it refers to an alkyl group having one or more of the functional group substituents, which may be located at any location on the alkyl chain. Example of $C_{1-8}$ alkylOH groups include without limitation, $CH_2OH$, $CH_2CH_2OH$, $C(CH_3)(CH_3)OH$, $C(CH_3)(CH_2OH)OH$, and the like.

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiroring systems), wherein the carbon atoms are located inside or outside of the ring system. A cycloalkyl group, as a whole, can have from 3 to 14 ring atoms (e.g., from 3 to 8 carbon atoms for a monocyclic cycloalkyl group and from 7 to 14 carbon atoms for a polycyclic cycloalkyl group). Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like.

As used herein, "heteroatom" refers to an atom of any element other than carbon or hydrogen and includes, for example, nitrogen, oxygen, sulfur, phosphorus, and selenium.

As used herein, "cycloheteroalkyl" refers to a non-aromatic cycloalkyl group that contains at least one (e.g., one, two, three, four, or five) ring heteroatom selected from O, N, and S, and optionally contains one or more (e.g., one, two, or three) double or triple bonds. A cycloheteroalkyl group, as a whole, can have from 3 to 14 ring atoms and contains from 1 to 5 ring heteroatoms (e.g., from 3-6 ring atoms for a monocyclic cycloheteroalkyl group and from 7 to 14 ring atoms for a polycyclic cycloheteroalkyl group). The cycloheteroalkyl group can be covalently attached to the defined chemical structure at any heteroatom(s) or carbon atom(s) that results in a stable structure. One or more N or S atoms in a cycloheteroalkyl ring may be oxidized (e.g., morpholine N-oxide, thiomorpholine S-oxide, thiomorpholine S,S-dioxide). Cycloheteroalkyl groups can also contain one or more oxo groups, such as phthalimidyl, piperidonyl, oxazolidinonyl, 2,4(1H,3H)-dioxo-pyrimidinyl, pyridin-2(1H)-onyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothienyl, piperidinyl, piperazinyl, and the like.

As used herein, "aryl" refers to an aromatic monocyclic hydrocarbon ring system or a polycyclic ring system where at least one of the rings in the ring system is an aromatic hydrocarbon ring and any other aromatic rings in the ring system include only hydrocarbons. In some embodiments, a monocyclic aryl group can have from 6 to 14 carbon atoms and a polycyclic aryl group can have from 8 to 14 carbon atoms. The aryl group can be covalently attached to the defined chemical structure at any carbon atom(s) that result in a stable structure. In some embodiments, an aryl group can have only aromatic carbocyclic rings, e.g., phenyl, 1-naphthyl, 2-naphthyl, anthracenyl, phenanthrenyl groups, and the like. In other embodiments, an aryl group can be a polycyclic ring system in which at least one aromatic carbocyclic ring is fused (i.e., having a bond in common with) to one or more cycloalkyl or cycloheteroalkyl rings. Examples of such aryl groups include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like.

As used herein, "heteroaryl" refers to an aromatic monocyclic ring system containing at least one ring heteroatom selected from O, N, and S or a polycyclic ring system where at least one of the rings in the ring system is aromatic and contains at least one ring heteroatom. A heteroaryl group, as a whole, can have from 5 to 14 ring atoms and contain 1-5 ring heteroatoms. In some embodiments, heteroaryl groups can include monocyclic heteroaryl rings fused to one or more aromatic carbocyclic rings, non-aromatic carbocyclic rings, or non-aromatic cycloheteroalkyl rings. The heteroaryl group can be covalently attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like.

As defined herein the term "lower alkyl", when used alone or in combination refers to alkyl containing 1-6 carbon atoms. The alkyl group may be branched or straight-chained, and is as defined hereinabove.

The term "lower alkenyl" refers to a alkenyl group which contains 2-6 carbon atoms. An alkenyl group is a hydrocarbyl group containing at least one carbon-carbon double bond. As defined herein, it may be unsubstituted or substituted with the substituents described herein. The carbon-carbon double bonds may be between any two carbon atoms of the alkenyl group. It is preferred that it contains 1 or 2 carbon-carbon double bonds and more preferably one carbon-carbon double bond. The alkenyl group may be straight chained or branched. Examples include but are not limited to ethenyl, 1-propenyl, 2-propenyl, 1-butenyl, 2-butenyl, 2-methyl-1-propenyl, 1,3-butadienyl, and the like.

The term "lower alkynyl", as used herein, refers to an alkynyl group containing 2-6 carbon atoms. An alkynyl group is a hydrocarbyl group containing at least one carbon-carbon triple bond. The carbon-carbon triple bond may be between any two carbon atom of the alkynyl group. In an embodiment, the alkynyl group contains 1 or 2 carbon-carbon triple bonds and more preferably one carbon-carbon triple bond. The alkynyl group may be straight chained or branched. Examples include but are not limited to ethynyl, 1-propynyl, 2-propynyl, 1-butynyl, 2-butynyl and the like.

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable salts of any acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium salts.

Similarly acid addition salts, such as of mineral acids, organic carboxylic, and organic sulfonic acids e.g., hydrochloric acid, methanesulfonic acid, maleic acid, are possible provided a basic group, such as amino or pyridyl, constitutes part of the structure.

The present invention relates to the discovery that signal transduction pathways regulated by Hh and/or Smo can be modulated by the compounds of the invention.

In one embodiment, the compounds and methods of the present invention comprise compounds of formula (I) for inhibiting Smo-dependent pathway activation. Another aspect of the present invention includes compounds and methods for inhibiting Hedgehog (ligand)-independent pathway activation. In certain embodiments, the present compounds and methods can be used to counteract the phenotypic effects of unwanted activation of a Hedgehog pathway, such as resulting from Hedgehog gain-of-function, Ptc loss-of-function or smoothened gain-of-function mutations. For instance, the subject compounds and method can involve contacting a cell (in vitro or in vivo) with a Smo antagonist, such as a compound of Formula (I) in an amount sufficient to antagonize a smoothened-dependent and/or Hedgehog independent activation pathway.

In one embodiment, the compounds of the invention (e.g., compounds of Formula I) inhibit Hh signaling by locking the three dimensional structure of the Smo protein in an inactive conformation or preventing Smo from adopting an active conformation. In another embodiment, the compounds of the invention (e.g., compounds of Formula I) inhibit Hh signaling by preventing endogenous activating ligands for Smo from binding to or activating Smo (i.e., acting via negative cooperativity with endogenous agonists). In another embodiment, the compounds of the invention (e.g., compounds of Formula I) inhibit Hh signaling by increasing binding of endogenous inactivating ligands for Smo from binding to or inactivating Smo (i.e., acting via positive cooperativity with endogeous antagonist).

In another embodiment, the compounds of the invention (e.g., compounds of Formula I) inhibit Hh signaling by preventing Smo from localizing to the plasma membrane. In another embodiment, the compounds of the invention (e.g., compounds of Formula I) inhibit Hh signaling by preventing signaling from Ptch to Smo, in the presence or absence of Hh ligand. In another embodiment, the compounds of the invention (e.g., compounds of Formula I) inhibit Hh signaling by preventing the stabilization of Smo. In another embodiment, the compounds of the invention (e.g., compounds of Formula I) inhibit Hh signaling by preventing the phosphorylation of Smo on activating sites. In another embodiment, the compounds of the invention (e.g., compounds of Formula I) inhibit Hh signaling by increasing the phosphorylation of Smo on inhibitory sites.

In still another embodiment, the compounds of the invention (e.g., compounds of Formula I) inhibit Hh signaling by preventing Smo from activating downstream targets, such as transcription factor Gli. In another embodiment, the compounds of the invention (e.g., compounds of Formula I) inhibit Hh signaling by effecting the inactivation, sequestration, and/or degradation of Smo.

In another embodiment, the methods of the present invention may be used to regulate proliferation and/or differentiation of cells in vitro and/or in vivo, e.g., in the formation of tissue from stem cells, or to prevent the growth of hyperproliferative cells. In another particular embodiment, contacting the cell with—or introducing into the cell—a compound of the invention (e.g., a compound of Formula I) results in inhibition of cellular proliferation, inhibition of cancer/tumor cell growth and/or survival, and/or inhibition of tumorigenesis. Thus, another particular embodiment provides methods for inhibition and/or antagonism of the Hh pathway by employing compounds of the invention (e.g., a compound of Formula I) in a tumor cell.

In yet another embodiment, the methods of the present invention employ compounds of the invention (e.g., a compound of Formula I) as formulated as a pharmaceutical preparation comprising a pharmaceutically acceptable excipient or carrier, and said preparations may be administered to a patient to treat conditions involving unwanted cell proliferation such as cancers and/or tumors (such as medulloblastoma, basal cell carcinoma, etc.), and non-malignant hyperproliferative disorders.

One embodiment of the present invention provides a method for inhibiting the synthesis, expression, production, and/or activity of a Smo protein in a cell in vitro or in vivo comprising, contacting said cell with, or introducing into said cell, a compound of the invention (e.g., a compound of Formula I).

Another embodiment of the invention provides a method of diagnosing, preventing and/or treating cellular debilitations, derangements, and/or dysfunctions; hyperplastic, hyperproliferative and/or cancerous disease states; and/or metastasis of tumor cells, in a mammal characterized by the presence and/or expression of a Smo gene or gene product (e.g., a Smo protein), comprising administering to a mammal a therapeutically effective amount of an agent that inhibits or antagonizes the synthesis and/or expression and/or activity of a compound of the invention (e.g., a compound of Formula I).

It is, therefore, specifically contemplated that compounds of Formula I which interfere with aspects of Hh, Ptc, or smoothened signal transduction activity will likewise be capable of inhibiting proliferation (or other biological consequences) in normal cells and/or cells having a patched loss-of-function phenotype, a Hedgehog gain-of-function phenotype, a smoothened gain-of-function phenotype or a Gli gain-of-function phenotype. Thus, it is contemplated that in certain embodiments, these compounds may be useful for inhibiting Hedgehog activity in normal cells, e.g., which do not have a genetic mutation that activates the Hedgehog pathway. In preferred embodiments, the compounds are capable of inhibiting at least some of the biological activities of Hedgehog proteins, preferably specifically in target cells.

Thus, the methods of the present invention include the use of compounds of Formula I which agonize Ptc inhibition of Hedgehog signaling, such as by inhibiting activation of smoothened or downstream components of the signal pathway, in the regulation of repair and/or functional performance of a wide range of cells, tissues and organs, including normal cells, tissues, and organs, as well as those having the phenotype of Ptc loss-of-function, Hedgehog gain-of-function, smoothened gain-of-function or Gli gain-of-function. For instance, the subject method has therapeutic and cosmetic applications ranging from regulation of neural tissues, bone and cartilage formation and repair, regulation of spermatogenesis, regulation of benign prostate hyperplasia, regulation of blood vessel formation in wet macular degeneration, psoriasis, regulation of smooth muscle, regulation of lung, liver and other organs arising from the primitive gut, regulation of hematopoietic function, regulation of skin and hair growth, etc. Moreover, the subject methods can be performed on cells which are provided in culture (in vitro), or on cells in a whole animal (in vivo).

In certain embodiments, a compound of Formula I can inhibit activation of a Hedgehog pathway by binding to smoothened or its downstream proteins.

In another embodiment, the present invention provides the use of pharmaceutical preparations comprising, as an active ingredient, a Hedgehog signaling modulator such as a compound of Formula I, a smoothened antagonist such as described herein, formulated in an amount sufficient to inhibit, in vivo, proliferation or other biological consequences of Ptc loss-of-function, Hedgehog gain-of-function, smoothened gain-of-function or Gli gain-of-function.

The treatment of subjects by administering compounds of the invention (e.g., compounds of Formula I) can be effective for both human and animal subjects. Animal subjects to which the invention is applicable extend to both domestic animals and livestock, raised either as pets or for commercial purposes. Examples are dogs, cats, cattle, horses, sheep, hogs, goats, and llamas.

The present invention also makes available methods and compounds for inhibiting activation of the Hedgehog signaling pathway, e.g., to inhibit normal but undesired growth states, for example benign prostate hyperplasia or blood vessel formation in wet macular degeneration, resulting from physiological activation of the Hedgehog signaling pathway, comprising contacting the cell with a compound of Formula I, in a sufficient amount to antagonize smoothened activity, or antagonize Gli activity, e.g., to reverse or control the normal growth state.

The present invention makes available methods and compounds for inhibiting activation of the hedgehog signaling pathway, e.g., to inhibit aberrant growth states resulting from phenotypes such as Ptc loss-of-function, hedgehog gain-of-function, smoothened gain-of-function or Gli gain-of-function, comprising contacting the cell with a compound of Formula I, in a sufficient amount to agonize a normal Ptc activity, antagonize a normal hedgehog activity, antagonize smoothened activity, or antagonize Gli activity e.g., to reverse or control the aberrant growth state.

Members of the Hedgehog family of signaling molecules mediate many important short- and long-range patterning processes during vertebrate development. Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation. The effects of developmental cell interactions are varied: responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation.

The vertebrate family of hedgehog genes includes three members that exist in mammals, known as Desert (Dhh), Sonic (Shh) and Indian (Ihh) hedgehogs, all of which encode secreted proteins. These various Hedgehog proteins consist of a signal peptide, a highly conserved N-terminal region, and a more divergent C-terminal domain. Biochemical studies have shown that autoproteolytic cleavage of the Hh precursor protein proceeds through an internal thioester intermediate which subsequently is cleaved in a nucleophilic substitution. It is likely that the nucleophile is a small lipophilic molecule which becomes covalently bound to the C-terminal end of the N-peptide, tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities.

Smoothened (Smo) encodes a 1024 amino acid transmembrane protein that acts as a transducer of the Hedgehog (Hh) signal. Smo protein has 7 hydrophobic membrane-spanning domains, an extracellular amino-terminal region, and an intracellular carboxy-terminal region. Smo bears some similarity to G protein-coupled receptors and is most homologous to the Frizzled (Fz) family of serpentine proteins. (Alcedo et al. (1996) Cell 86: 221)

An inactive Hedgehog signaling pathway is where the transmembrane protein receptor Patched (Ptc) inhibits the activity of Smoothened (Smo), a seven transmembrane protein. The transcription factor Gli, a downstream component of Hh signaling, is prevented from entering the nucleus through interactions with cytoplasmic proteins, including Fused and Suppressor of fused (Sufu). As a consequence, transcriptional activation of Hedgehog target genes is repressed. Activation of the pathway is initiated through binding of any of the three mammalian ligands (Dhh, Shh or Ihh) to Ptc. Ligand binding results in a reversal of the repression of Smo, thereby activating a cascade that leads to the translocation of the active form of the transcription factor Gli to the nucleus. Nuclear Gli activates target gene expression, including Ptc and Gli itself.

Ligand binding by Hh alters the interaction of Smo and Ptc, reversing the repression of Smo, whereupon Smo moves from internal structures within the cell to the plasma membrane. The localization of Smo to the plasma membrane triggers activation of Hh pathway target genes in an Hh-independent manner. (Zhu et al. (2003) Genes Dev. 17(10):1240) The cascade activated by Smo leads to the translocation of the active form of the transcription factor Gli to the nucleus. The activation of Smo, through translocated nuclear Gli, activates Hh pathway target gene expression, including of Wnts, TGFβ, and Ptc and Gli themselves.

Increased levels of Hedgehog signaling are sufficient to initiate cancer formation and are required for tumor survival.

These cancers include, but are not limited to, prostate cancer ("Hedgehog signalling in prostate regeneration, neoplasia and metastasis", Karhadkar S S, Bova G S, Abdallah N, Dhara S, Gardner D, Maitra A, Isaacs J T, Berman D M, Beachy P A., Nature. 2004 Oct. 7; 431(7009):707-12; "Inhibition of prostate cancer proliferation by interference with SONIC HEDGEHOG-GLI1 signaling", Sanchez P, Hernandez A M, Stecca B, Kahler A J, DeGueme A M, Barrett A, Beyna M, Datta M W, Datta S, Ruiz i Altaba A., Proc Natl Acad Sci USA. 2004 Aug. 24; 101(34):12561-6), ("Cytotoxic effects induced by a combination of cyclopamine and gefitinib, the selective hedgehog and epidermal growth factor receptor signaling inhibitors, in prostate cancer cells," Mimeault M, Moore E, Moniaux N, et al (2006), International Journal of Cancer; 118 (4):1022-31) breast cancer ("Hedgehog signaling pathway is a new therapeutic target for patients with breast cancer", Kubo M, Nakamura M, Tasaki A, Yamanaka N, Nakashima H, Nomura M, Kuroki S, Katano M., Cancer Res. 2004 Sep. 1; 64(17):6071-4), ("Hedgehog signaling and Bmi-1 regulate self-renewal of normal and malignant human mammary stem cells," Liu S, Dontu G, Mantle I D, et al (2006) Cancer Res; 66 (12):6063-71), ("Constitutive activation of smoothened (SMO) in mammary glands of transgenic mice leads to increased proliferation, altered differentiation and ductal dysplasia," Moraes R C, Zhang X M, Harrington N, et al (2007), Development; 134 (6):1231-42), medulloblastoma ("Medulloblastoma growth inhibition by hedgehog pathway blockade", Berman D M, Karhadkar S S, Hallahan A R, Pritchard J I, Eberhart C G, Watkins D N, Chen J K, Cooper M K, Taipale J, Olson J M, Beachy P A., Science. 2002 Aug. 30; 297(5586):1559-61), non-melanoma skin cancer, i.e. squamous cell carcinoma (SCC) and basal cell carcinoma (BCC) ("Identification of a small molecule inhibitor of the hedgehog signaling pathway: effects on basal cell carcinoma-like lesions", Williams J A, Guicherit O M, Zaharian B I, Xu Y, Chai L, Wichterle H, Kon C, Gatchalian C, Porter J A, Rubin L L, Wang F Y., Proc Natl Acad Sci USA. 2003 Apr. 15; 100(8):4616-21; "Activating Smoothened mutations in sporadic basal-cell carcinoma", Xie J, Murone M, Luoh S M, Ryan A, Gu Q, Zhang C, Bonifas J M, Lam C W, Hynes M, Goddard A, Rosenthal A, Epstein E H Jr, de Sauvage F J., Nature. 1998 Jan. 1; 391(6662):90-2), pancreatic, esophagus, stomach, and billary cancers ("Hedgehog is an early and late mediator of pancreatic cancer tumorigenesis", Thayer S P, di Magliano M P, Heiser P W, Nielsen C M, Roberts D J, Lauwers G Y, Qi Y P, Gysin S, Fernandez-del Castillo C, Yajnik V, Antoniu B, McMahon M, Warshaw A L, Hebrok M., Nature. 2003 Oct. 23; 425(6960):851-6; "Widespread requirement for Hedgehog ligand stimulation in growth of digestive tract tumours", Berman D M, Karhadkar S S, Maitra A, Montes De Oca R, Gerstenblith M R, Briggs K, Parker A R, Shimada Y, Eshleman J R, Watkins D N, Beachy P A., Nature. 2003 Oct. 23; 425(6960):846-51), ("Nuclear factor-kappa B contributes to hedgehog signaling pathway activation through sonic hedgehog induction in pancreatic cancer," Nakashima H, Nakamura M, Yamaguchi H, et al (2006), Cancer Research; 66 (14):7041-9), ("Blockade of hedgehog signaling inhibits pancreatic cancer invasion and metastases: A new paradigm for combination therapy in solid cancers," Feldmann G, Dhara S, Fendrich V, et al (2007) Cancer Research; 67 (5): 2187-96), ("Oncogenic KRAS suppresses Gli1 degradation and activates Hedgehog signaling pathway in pancreatic cancer cells," Ji Z, Mei F C, Xie J, et al (2007), J Biol Chem; 282 (19):14048-55), and small-cell lung cancer ("Hedgehog signalling within airway epithelial progenitors and in small-cell lung cancer", Watkins D N, Berman D M, Burkholder S G, Wang B, Beachy P A, Baylin S B., Nature. 2003 Mar. 20; 422(6929):313-7), ("Hedgehog signaling in small-cell lung cancer: Frequent in vivo but a rare event in vitro," Vestergaard J, Pedersen M W, Pedersen N, et al (2006), Lung Cancer; 52 (3):281-90).

Additional cancers in which increased levels of Hedgehog signaling are sufficient to initiate cancer formation and are required for tumor survival include, but are not limited to colon cancer ("Sonic Hedgehog-dependent proliferation in a series of patients with colorectal cancer," Douard R, Moutereau S, Pernet P, et al (2006) Surgery; 139 (5):665-70), ("Hedgehog signalling in colorectal tumour cells: Induction of apoptosis with cyclopamine treatment," Qualtrough D, Buda A, Gaffield W, et al (2004), International Journal of Cancer; 110 (6):831-7), glioma, ("Cyclopamine-mediated Hedgehog pathway inhibition depletes stem-like cancer cells in glioblastoma," Bar E E, Chaudhry A, Lin A, et al, Neuro-Oncology; 2007, 9 (4):594), ("HEDGEHOG-GLI1 signaling regulates human glioma growth, cancer stem cell self-renewal, and tumorigenicity," Clement V, Sanchez P, de Tribolet N, et al, (2007) Current Biology 17 (2):165-72), ("Ligand-dependent activation of the hedgehog pathway in glioma progenitor cells," Ehteshan M, Sarangi A, Valadez J G, et al (2007) Oncogene; Mar. 12, 2007, Epub ahead of print), melanoma ("Melanomas require HEDGEHOG-GLI signaling reaulated by interactions between Gill and the RAS-MEK/AKT pathways," Stecca B, Mas C, Clement V, et al (2007), Proceedings of the National Academy of Sciences of the United States of America; 104 (14):5895-900), non small cell lung cancer (NSCLC) ("Frequent requirement of hedgehog signaling in non-small cell lung carcinoma," Yuan Z, Goetz J A, Singh S, et al (2007), Oncogene; 26 (7):1046-55), ovarian, ("Hedgehog signal pathway is activated in ovarian carcinomas, correlating with cell proliferation: It's inhibition leads to growth suppression and apoptosis," Chen X J, Horiuchi A, Kikuchi N, et al, Cancer Science; (2007) 98 (1):68-76), liver ("Activation of the hedgehog pathway in human hepatocellular carcinomas," Huang S H, He J, Zhang X L, et al (2006), Carcinogenesis; 27 (7):1334-40), ("Dysregulation of the Hedgehog pathway in human hepatocarcinogenesis," Sicklick J K, Li Y X, Jayaraman A, et al (2006), Carcinogenesis; 27 (4):748-57), renal ("Clear cell sarcoma of the kidney: Up-regulation of neural markers with activation of the sonic hedgehog and Akt pathways," Cutcliffe C, Kersey D, Huang C C, et al (2005), Clinical Cancer Research; 11 (22):7986-94), Rhabdomyosarcoma, ("Rhabdomyosarcomas and radiation hypersensitivity in a mouse model of Gorlin syndrome," Hahn H, Wojnowski L, Zimmer A M, et al (1998), Nature Medicine; 4 (5):619-22), ("Deregulation of the hedgehog signalling pathway: a possible role for the PTCH and SUFU genes in human rhabdomyoma and rhabdomyosarcoma development," Tostar U, Malm C J, Meis-Kindblom J M, et al (2006), Journal of Pathology; 208 (1):17-25), and Chondrosarcoma ("Constitutive hedgehog signaling in chondrosarcoma up-regulates tumor cell proliferation," Tiet T D, Hopyan S, Nadesan P, et al (2006), American Journal of Pathology; 168 (1):321-30).

Hedgehog pathway inhibitors (e.g. cyclopamine) have been shown to be useful in the treatment of psoriasis ("Cyclopamine: inhibiting hedgehog in the treatment of psoriasis" Cutis, 2006, 78(3):185-8; Br. J. Dermatology, 2006 April; 154(4):619-23, "Psoriatic skin expresses the transcription factor Gli1: possible contribution of decreased neurofibromin expression", Endo H, Momota Y, Oikawa A, Shinkai H.).

Malignant lymphoma (ML) involves the cells of the lymphatic system, and is the fifth most common cancer in the U.S. ML includes Hodgkin's disease, and non-Hodgkin's diseases which are a heterogeneous group of lymphoid proliferative diseases. Hodgkin's disease accounts for approximately 14% of all malignant lymphomas. The non-Hodgkin's lymphomas are a diverse group of malignancies that are predominately of B-cell origin. In the Working Formulation classification scheme, these lymphomas been divided into low-, intermediate-, and high-grade categories by virtue of their natural histories (see "The Non-Hodgkin's Lymphoma Pathologic Classification Project," Cancer 49:2112-2135, 1982). The low-grade lymphomas are indolent, with a median survival of 5 to 10 years (Horning and Rosenberg, N. Engl. J. Med. 311: 1471-1475, 1984). Although chemotherapy can induce remissions in the majority of indolent lymphomas, cures are rare and most patients eventually relapse, requiring further therapy. The intermediate- and high-grade lymphomas are more aggressive tumors, but they have a greater chance for cure with chemotherapy. However, a significant proportion of these patients will relapse and require further treatment.

Multiple myeloma (MM) is malignant tumor composed of plasma cells of the type normally found in the bone marrow. These malignant plasma cells accumulate in bone marrow and typically produce monoclonal IgG or IgA molecules. The malignant plasma cells home to and expand in the bone marrow causing anemia and immunosuppression due to loss of normal hematopoiesis. Individuals suffering from multiple myeloma often experience anemia, osteolytic lesions, renal failure, hypercalcemia, and recurrent bacterial infections. MM represents the second most common hematopoietic malignancy.

The present invention is predicated in part on the discoveries by the present inventors that lymphoma and multiple myeloma diseases are dependent on the hedgehog (Hh) signaling pathway using lymphoma and plasmacytoma cells isolated from transgenic Eµ-Myc mice and Cdkn2a knockout mice, and discovering that hedgehog ligands mediate the interaction between stroma and lymphoma cells. The same was found for lymphoma and multiple myeloma samples isolated from patient samples from the bone (multiple myeloma) or from lymph nodes, bone marrow or spleens from non-Hodgkin's lymphoma (NHL) patients and also for chronic lymphocytic leukemia (CLL) samples. In addition, it was found that inhibition of the Hh signaling pathway induces apoptosis of stroma dependent lymphoma cells, and that overexpression of hedgehog pathway members inhibit cyclopamine induced apoptosis of lymphoma cells in vitro. Further, the inventors found that treating mice with hedgehog pathway inhibitors abrogates lymphoma expansion in vivo. Finally, the inventors discovered that there is no expression of Gli3 in spleen B-cells and in the majority of cyclopamine responsive lymphomas, but a predominant expression in all cyclopamine resistant lymphomas.

These data indicate that Hh signaling provides an important anti-apoptotic signal for the initial steps of transformation by c-Myc and plays an important role for lymphoma maintenance. Thus, disruption of the Hh signaling pathway provides novel means for treating lymphomas (e.g., NHL), multiple myelomas, CLL and other hematopoietic malignancies. In addition, expression of Gli3 in lymphomas provides a negative predictive factor for responsiveness to Hh inhibition and an important means for patient stratification.

In accordance with these discoveries, the invention provides methods for inhibiting growth of tumor cells, e.g., lymphoma and myeloma cells. The invention provides methods and compositions to treat lymphoma or myeloma in a subject by inhibiting growth of tumor cells. The methods are also useful to prevent tumorigenesis in a subject. Some of the methods are directed to treating lymphomas which do not have significant expression of Gli3 relative to spleen B cells. The methods involve administering to the subject in need of treatment a pharmaceutical composition that contains an antagonizing agent of Hh signaling (e.g., a compound of Formula I). Compound of the invention down-regulate cellular level or inhibit a biological activity of an Hh signaling pathway member.

This invention provides methods of prophylactic or therapeutic treatment of cancers of the blood and lymphatic systems, including lymphomas, leukemia, and myelomas. The methods employ an antagonist of hedgehog signaling pathway to inhibit growth and proliferation of lymphoma cells, leukemia cells, or myeloma cells. Lymphoma is malignant tumor of lymphoblasts derived from B lymphocytes. Myeloma is a malignant tumor composed of plasma cells of the type normally found in the bone marrow. Leukemia is an acute or chronic disease that involves the blood forming organs. NHLs are characterized by an abnormal increase in the number of leucocytes in the tissues of the body with or without a corresponding increase of those in the circulating blood and are classified according to the type of leucocyte most prominently involved.

By way of example, subjects suffering from or at risk of development of lymphoma (e.g., e.g., B-cell lymphoma, plasmoblastoma, plasmacytoma or CLL) can be treated with methods of the invention. Preferably, the subject is a human being. The methods entail administering to the subject a pharmaceutical composition containing an effective amount of a compound of Formula I to inhibit the hedgehog signaling pathway. The subject can be one who is diagnosed with lymphoma, with or without metastasis, at any stage of the disease (e.g., stage I to IV, Ann Arbor Staging System). Lymphomas suitable for treatment with methods of the invention include but are not limited to Hodgkin's disease and non-Hodgkin's disease. Hodgkin's disease is a human malignant disorder of lymph tissue (lymphoma) that appears to originate in a particular lymph node and later spreads to the spleen, liver and bone marrow. It occurs mostly in individuals between the ages of 15 and 35. It is characterized by progressive, painless enlargement of the lymph nodes, spleen and general lymph tissue. Classic Hodgkin's disease is divided into four subtypes: (1) nodular sclerosis Hodgkin's disease (NSHD); (2) mixed cellularity Hodgkin's disease (MCHD); (3) lymphocyte depletion Hodgkin's disease (LDHD); and (4) lymphocyte-rich classic Hodgkin's disease (cLRHD).

In some preferred embodiments, the present methods are used to treat non-Hodgkin's Lymphoma (NHL). Non-Hodgkin's disease is also called lymphosarcoma and refers to a group of lymphomas which differ in important ways from Hodgkin's disease and are classified according to the microscopic appearance of the cancer cells. Non-Hodgkin's lymphoma includes but is not limited to (1) slow-growing lymphomas and lymphoid leukemia (e.g., chronic lymphocytic leukemia, small lymphocytic leukemia, lymphoplasmacytoid lymphoma, follicle center lymphoma, follicular small cleaved cell, follicular mixed cell, marginal zone B-cell lymphoma, hairy cell leukemia, plasmacytoma, myeloma, large granular lymphocyte leukemia, mycosis fungoides, szary syndrome); (2) moderately aggressive lymphomas and lymphoid leukemia (e.g., prolymphocytic leukemia, mantle cell lymphoma, follicle center lymphoma, follicular small cleaved cell, follicle center lymphoma, chronic lymphocytic leukemia/prolymphocytic leukemia, angiocentric lymphoma, angioimmunoblastic lymphoma); (3) aggressive lymphomas (e.g., large B-cell lymphoma, peripheral T-cell lymphomas, intestinal T-cell lymphoma, anaplastic large cell lymphoma); and (4) highly aggressive lymphomas and lymphoid leukemia (e.g., B-cell precursor B-lymphoblastic leukemia/lymphoma, Burkitt's lymphoma, high-grade B-cell lymphoma, Burkitt's-like T-cell precursor T-lymphoblastic leukemia/lymphoma). The methods of the present invention can be used for adult or childhood forms of lymphoma, as well as lymphomas at any stage, e.g., stage I, II, III, or IV. The methods described herein can also be employed to treat other forms of leukemia, e.g., acute lymphocytic leukemia (ALL).

Some of the therapeutic methods of the invention are particularly directed to treating lymphomas or myelomas which do not express Gli3. As disclosed in the Examples below, it was observed that, while Gli1 and Gli2 were expressed in all lymphomas, detectable Gli3 expression was present mainly in lymphomas which were resistant to Hh pathway inhibition by cyclopamine. There is no expression of Gli3 in normal spleen B-cells and in the majority of cyclopamine responsive lymphomas. Thus, prior to treatment with Hh antagonists, subjects with lymphomas can be first examined for expression of Gli3 in a lymphoma cell sample obtained from the subject. Gli3 expression level in the sample can be compared to Gli3 expression level in normal spleen B cells obtained from the subject. Gli3 expression levels in the lymphoma or myeloma samples and the control cells can be determined using methods well known in the art, e.g., as described in the Examples below. A likely responsiveness to treatment with Hh antagonists described herein is indicated by the lack of detectable Gli3 expression in the lymphoma or myeloma samples or an expression level that is not significantly higher (e.g., not more than 25%, 50%, or 100% higher) than Gli3 expression level in the normal B cell. Other than being an additional step of the therapeutic methods of the invention, the pre-screening for lack of Gli3 expression can be used independently as a method for patient stratification.

In addition to lymphomas, the methods and compositions described above are also suitable for the treatment of myelomas. Multiple myeloma is a fatal neoplasm characterized by an accumulation of a clone of plasma cells, frequently accompanied by the secretion of Ig chains. Bone marrow invasion by the tumor is associated with anemia, hypogammaglobinemia, and granulocytopenia with concomitant bacterial infections. An abnormal cytokine environment, principally raised IL-6 and IL-1β levels, often results in increased osteoclasis leading to bone pain, fractures, and hypercalcemia. Despite aggressive chemotherapy and transplantation, multiple myeloma is a universally fatal plasma proliferative disorder.

Compounds of the invention are useful in the treatment of hedgehog related disorders such as basal cell nevus syndrome (also called Gorlin's syndrome and/or nevoid basal cell carcinoma), a rare autosomal dominant cancer genetic syndrome.

Compounds of the invention are useful in the treatment of basal cell carcinoma (BCC or rodent ulcer), tumors of the adrenal glands arising from the cortex or the medulla part of the adrenal gland medulla, and ovarian tumors.

Compounds of the invention are useful in the treatment of bone overgrowth disorders including, but are not limited to, acromegaly, macrocephaly, Sotos syndrome, progressive diaphyseal dysplasia (PDD or Camurati-Engelmann disease), craniodiaphyseal dysplasia, and endosteal hyperostosis disorders including Van Buchem disease (types I and II) and sclerosteosis.

Compounds of the invention are useful in the treatment of unwanted hair growth, for example, hairy moles and cosmetic prevention of hair regrowth after epilation.

Compounds of the invention are useful in the treatment of Liver fibrosis.

Thus, the methods of the present invention include the use of compounds of the invention which agonize Ptc inhibition of Hedgehog signaling, such as by inhibiting activation of smoothened or downstream components of the signal pathway, in the regulation of repair and/or functional performance of a wide range of cells, tissues and organs, including normal cells, tissues, and organs, as well as those having the phenotype of Ptc loss-of-function, Hedgehog gain-of-function, smoothened gain-of-function or Gli gain-of-function. For instance, the subject method has therapeutic and cosmetic applications ranging from regulation of neural tissues, bone and cartilage formation and repair, regulation of spermatogenesis, regulation of benign prostate hyperplasia, regulation of blood vessel formation in wet macular degeneration, psoriasis, regulation of smooth muscle, regulation of lung, liver and other organs arising from the primitive gut, regulation of hematopoietic function, regulation of skin and hair growth, etc. Moreover, the subject methods can be performed on cells which are provided in culture (in vitro), or on cells in a whole animal (in vivo).

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

The invention relates to the use of pharmaceutical compositions comprising compounds of Formula (I) in the therapeutic (and, in a broader aspect of the invention, prophylactic) treatment of a Hedgehog-related disorder(s).

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions.

The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with immunomodulatory, anti-inflammatory substances, other anti-tumor therapeutic agents, chemotherapeutic agents, ablation or other therapeutic hormones, antineoplastic agents and/or monoclonal antibodies useful against lymphomas or myelomas. Some of the well known anti-cancer drugs are described in the art, e.g., *Cancer Therapeutics: Experimental and Clinical Agents*, Teicher (Ed.), Humana Press (1*st* ed., 1997); and *Goodman and Gilman's The Pharmacological Basis of Therapeutics*, Hardman et al. (Eds.), McGraw-Hill Professional (10*th* ed., 2001). Examples of suitable anti-cancer drugs include 5-fluorouracil, vinblastine sulfate, estramustine phosphate, suramin and strontium-89. Examples of suitable chemotherapeutic agents include Asparaginase, Bleomycin Sulfate, Cisplatin, Cytarabine, Fludarabine Phosphate, Mitomycin and Streptozocin.

Where the compounds of the invention are administered in conjunction with other therapies, dosages of the co-administered compounds will of course vary depending on the type of co-drug employed, on the specific drug employed, on the condition being treated and so forth.

An Hh inhibitor of the present invention may be usefully combined with another pharmacologically active compound, or with two or more other pharmacologically active compounds, particularly in the treatment of cancer. For example, a compound of the formula (I), or a pharmaceutically acceptable salt thereof, as defined above, may be administered simultaneously, sequentially or separately in combination with one or more agents selected from chemotherapy agents, e.g. mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine.

Such combinations may offer significant advantages, including synergistic activity, in therapy. A compound of the formula (I) may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylamino-gelda-namycin, NSC330507), 17-DMAG (17-dimethylaminoethylamino-17-demethoxy-geldana-mycin, NSC707545), IPI-504, CNF1010, CNF2024, CNF1010 from Conforma Therapeutics; temozolomide (TEMODAL); kinesin spindle protein inhibitors, such as SB715992 or SB743921 from GlaxoSmithKline, or pentamidine/chlorpromazine from CombinatoRx; PI3K inhibitors; RAF inhibitors; EDG binders, antileukemia compounds, ribonucleotide reductase inhibitors, S-adenosylmethionine decarboxylase inhibitors, antiproliferative anti-bodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

Representative examples of synthesis of the compounds of the invention, e.g., compounds of Formula (I), can be found in the Examples section of the present application.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

EXAMPLES

The present invention is further exemplified, but not limited, by the following representative examples, which are intended to illustrate the invention and are not to be construed as being limitations thereon. The structure of final products described herein can be confirmed by standard analytical methods, e.g., spectrometric and spectroscopic methods (e.g. MS, NMR). Abbreviations used are those conventional in the art. Compounds are purified by standard methods, e.g. crystallization, flash chromatography or reversed phase HPLC.

The following abbreviations will be used throughout the examples:

LIST OF ABBREVIATIONS

BINAP (±)-(1,1'-binaphthalene-2-2'diyl)bis(diphenylphosphine)

DAST Diethylaminosulfur trifluoride

Deoxofluor Bis(2-methoxyethyl)aminosulfur trifluoride

DCM Dichloromethane

Di-$^t$bu-X-Phos 2-(Di-tert. Butylphosphino) 2',4',6'-triisopropyl-1,1'-biphenyl DIEA Diethylamine DIPEA Diisoproylethylamine DMF Dimethylformamide HPLC High pressure liquid chromatography HR MS High resolution mass spectrometry HATU 1-[Bis(dimethylamino)-methylene]-1H-1,2,3-triazolo[4,5-b]pyridinium-3-oxide hexafluorophosphate HBTU O-Benzotriazol-1-yl-N,N,N',N'-tetramethyluronium hexafluorophosphate HOBt 1-Hydroxy-1H-benzotriazol HMDS Hexamethyldisilazane MS Mass spectrometry NB S N-Brom succinimide NMM N-methylmorpholine NMO N-Methylmorpholine-N-oxide NMP N-methylpyrrolidine NMR Nuclear magnetic resonance n.a. Not available n.d. Not determined RT, rt Room temperature SEM 2-(Trimethylsilyl)ethoxymethyl TFA Trifluoroacetic acid THF Tetrahydrofuran X-Phos 2-(Dicyclohexylphosphino)-2',4',6'-triisopropyl-1,1'-biphenyl

Compound Synthesis

Pyridazine-Arylethers and -Anilines

As illustrated in Scheme 1, compounds of Formula Ia can be prepared from intermediates IIIa (preparation described in Scheme 6), which can either react with a phenol or aniline by direct thermal nucleophilic displacement or palladium-catalyzed nucleophilic displacement. Compounds Ia can be converted into further examples by functional group manipulations of R".

SCHEME 1

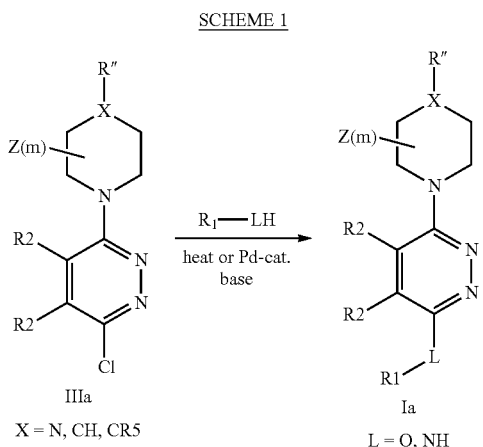

X = N, CH, CR5  
L = O, NH

Synthesis of Examples 1-5

Example 1

(R)-4-(4,5-Dimethyl-6-phenoxy-pyridazin-3-yl)-2-methyl-3,4,5,6-tetrahydro-2H-[1,2']bipyrazinyl-5'-carboxylic methyl ester

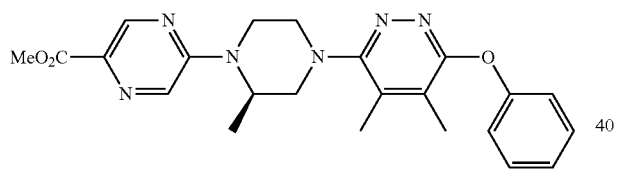

To a solution of (R)-4-(6-Chloro-4,5-dimethyl-pyridazin-3-yl)-2-methyl-3,4,5,6-tetrahydro-2H-[1,2']bipyrazinyl-5'-carboxylic acid methyl ester (compound 54, 40 mg, 0.106 mmol) in 2 mL toluene is added phenol (45 mg, 0.48 mmol), potassium phosphate (40.6 mg, 0.19 mmol) and di-$^t$bu X-Phos (5.3 mg, 0.014 mmol) in a 2 drum screw-top vial. The vial is evacuated and flushed with nitrogen, followed with the additon of palladium (II) acetate (2 mg, 0.01 mmol). The reaction mixture is flushed with nitrogen again and heated to 100° C. for 16 h. The mixture is filtered through Celite and the filtrate is concentrated to afford a brown oil. The crude product is purified by HPLC, eluting with 15-95% acetonitrile in water (both mobile phases modified with 3% n-PrOH) to provide the desired product as a white solid (9 mg, 22%).

$^1$H NMR (400 MHz, DMSO-$d_6$) δ=8.69 (s, 1H), 8.39 (s, 1H), 7.40 (t, J=7.5 Hz, 2H) 7.19 (t, J=7.5 Hz, 1H), 7.10 (d, J=7.5 Hz, 2H), 4.84-4.82 (m, 1H), 4.42-4.38 (m, 1H), 3.81 (s, 3H), 3.45-3.25 (m, 3H), 3.02-2.99 (m, 1H), 2.93-2.86 (m, 1H), 2.35 (s, 3H), 2.26 (s, 3H), 1.36 (d, J=6.6 Hz, 3H).

HR MS (m/z, MH+) meas. 435.2157, calc. 435.2145.

Example 2

2-[(R)-4-(4,5-Dimethyl-6-phenoxy-pyridazin-3-yl)-2-methyl-3,4,5,6-tetra-hydro-2H-[1,2']bipyrazinyl-5'-yl]-propan-2-ol

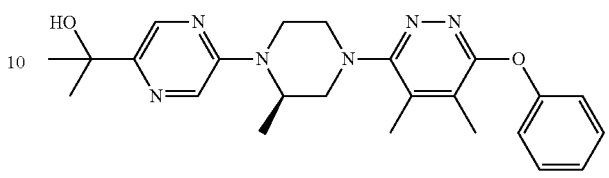

To a solution of (R)-4-(4,5-dimethyl-6-phenoxy-pyridazin-3-yl)-2-methyl-3,4,5,6-tetrahydro-2H-[1,2']bi-pyrazinyl-5'-carboxylic methyl ester (98 mg, 0.226 mmol) in 2 mL anhydrous THF is added 3 M methylmagensium bromide (600 µL, 1.8 mmol) in a 2 drum septum-top vial at −78° C. under nitrogen atmosphere. The reaction mixture is stirred at −78° C. for 1.5 h, before being warmed to 0° C. and stirred for additional 2 h. The reaction mixture is quenched with sat. aq. NH$_4$Cl at −78° C. and diluted with DCM. The organic solution is washed with brine, dried over Na$_2$SO$_4$ and concentrated to afford the crude material. The resulting solid is purified by prep. HPLC, eluting with 10%-100% acetonitrile in water (both mobile phases modified by 3% n-PrOH). Fractions containing the desired product are combined and freeze-dried to afford a white solid (58 mg, 59%).

$^1$H NMR (400 MHz, DMSO-$d_6$) δ=8.33 (s, 1H), 8.19 (s, 1H), 7.41 (t, J=7.6 Hz, 2H) 7.20 (t, J=7.6 Hz, 1H), 7.11 (d, J=7.6 Hz, 2H), 5.09 (s, 1H), 4.64 (m, 1H), 4.16-4.13 (m, 1H), 3.44-3.41 (m, 2H), 3.02-2.99 (m, 1H), 2.89-2.85 (m, 1H), 2.34 (s, 3H), 2.25 (s, 3H), 1.41 (s, 6H), 1.28 (d, J=6.6 Hz, 3H).

HR MS (m/z, MH+) meas. 435.2508, calc. 435.2508.

Example 3

(R)-4-(4,5-Dimethyl-6-phenylamino-pyridazin-3-yl)-2-methyl-3,4,5,6-tetra-hydro-2H-[1,2']bipyrazinyl-5'-carboxylic acid methyl ester

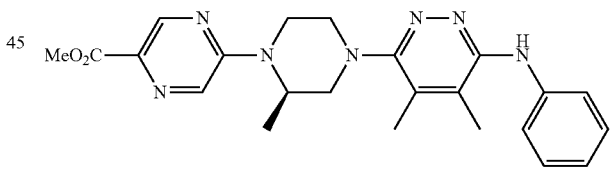

and

Example 4

(R)-4-(4,5-Dimethyl-6-phenylamino-pyridazin-3-yl)-2-methyl-3,4,5,6-tetra-hydro-2H-[1,2']bipyrazinyl-5'-carboxylic acid penylamide

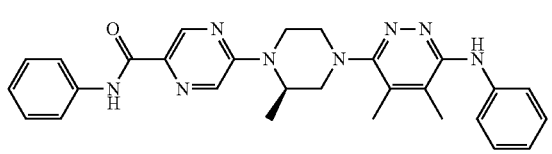 [SMILES: Cc1c(Nc2ccccc2)nnc(N2CCN(c3cnc(C(=O)Nc4ccccc4)cn3)[C@H](C)C2)c1C]

To (R)-4-(6-chloro-4,5-dimethyl-pyridazin-3-yl)-2-methyl-3,4,5,6-tetrahydro-2H-[1,2]bipyrazinyl-5'-carboxylic acid methyl ester (compound 54, 250 mg, 0.663 mmol) is added aniline (2.4 mL, 26.5 mmol) in a microwave tube. The reaction mixture is heated at 190° C. for 30 min in a microwave reactor. The reaction mixture is loaded on silica gel and purified by flash chromatography, eluting with 50%-100% EtOAc: heptane for six column volumes, followed with 3%-10% MeOH in DCM. Both example 3 and 4 are collected and concentrated to afford white solids.

Example 3

130 mg, 45%.
$^1$H NMR (400 MHz, CDCl$_3$) δ=8.83 (s, 1H), 8.16 (s, 1H), 7.41-7.32 (m, 4H), 7.14-7.10 (m, 1H), 4.79-4.77 (m, 1H), 4.39-4.35 (m, 1H), 3.96 (s, 3H) 3.52-3.45 (m, 2H), 3.35-3.42 (m, 1H), 3.24-3.21 (m, 1H), 3.12-3.07 (m, 1H), 2.38 (s, 3H), 2.15 (s, 3H), 1.44 (d, J=6.7 Hz, 3H).
MS (m/z, MH+) meas. 434.4, calc. 434.2.

Example 4

30 mg, 9%.
MS (m/z, MH+) meas. 495.6, calc. 495.2.

Example 5

2-[(R)-4-(4,5-Dimethyl-6-phenylamino-pyridazin-3-yl)-2-methyl-3,4,5,6-tetrahydro-2H-[1,2']bipyrazinyl-5'-yl]-propan-2-ol

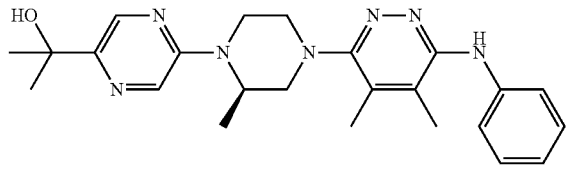

To a solution of (R)-4-(4,5-dimethyl-6-phenylamino-pyridazin-3-yl)-2-methyl-3,4,5,6-tetrahydro-2H-[1,2']bipyrazinyl-5'-carboxylic acid methyl ester (example 3, 360 mg, 0.14 mmol) in 2 mL anhydrous THF is added 3 M methylmagnesium bromide (554 μL, 1.7 mmol) in a 2 drum septum-top vial at −78° C. under nitrogen atmosphere. The reaction mixture is stirred at −78° C. for 1.5 h, before warmed to 0° C. and stirred for an additional 1 h. The reaction mixture is quenched with sat. aq. NH$_4$Cl at −78° C. and diluted with DCM. The organic solution is washed with brine, dried over Na$_2$SO$_4$ and concentrated to afford the crude material. The resulting solid is purified by prep. HPLC, eluting with 10%-100% acetonitrile in water (both mobile phases modified by 3% n-PrOH). Fractions containing the desired product are combined and freeze-dried to afford a white solid (25 mg, 42%).

$^1$H NMR (400 MHz, CDCl$_3$) δ=8.25 (s, 1H), 8.04 (s, 1H), 7.49 (d, J=7.5 Hz, 2H), 7.31 (t, J=7.5 Hz, 2H), 7.02 (t, J=7.5 Hz, 1H), 6.59 (b, 1H), 4.63-4.61 (m, 1H), 4.16-4.12 (m, 1H), 3.44-3.09 (m, 5H), 2.36 (s, 3H), 2.18 (s, 3H), 1.56 (s, 6H), 1.39 (d, J=7.1 Hz, 3H).

HR MS (m/z, MH+) meas. 434.2667, calc. 434.2668.

Aryl-Pyridazines

As illustrated in Scheme 2, compounds of Formula Ib can be prepared for example by chloride displacement from a 1,4-dichloropyridazine II with a piperazine to yield intermediates III, which react with a boronic acid or ester in a Suzuki coupling to yield compounds IV. Nucleophilic aromatic substitution with e.g. arylchlorides under basic conditions yields examples Ib (Route A). Alternatively, intermediates II can react with substituted amines to compounds IIIa which are substrates for Suzuki coupling reactions with boronic acids or esters to yield examples Ib (Route B, X=N, CH). Compounds Ib can be converted into further examples by functional group manipulations of R" e.g. by ester hydrolysis and amid formation or Grignard addition to ester functionalities.

SCHEME 2

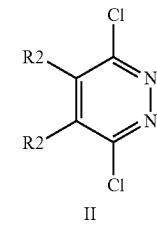

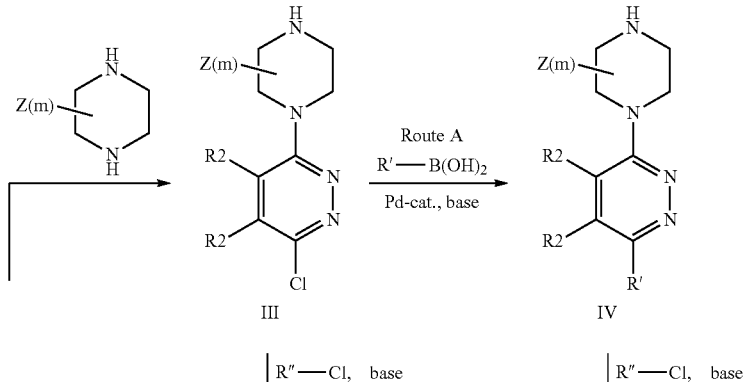

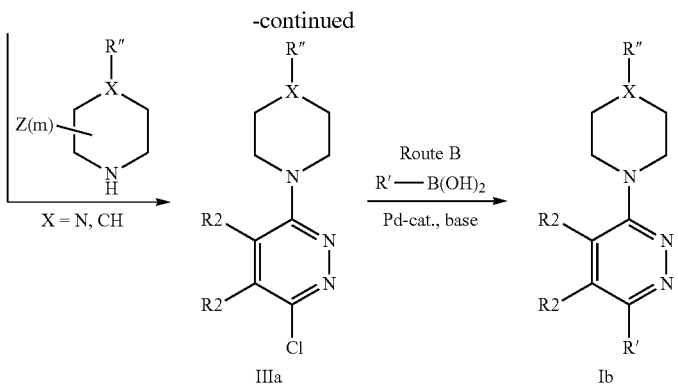

Synthesis of Intermediates

3-(4-Fluoro-phenyl)-4,5-dimethyl-6-((R)-3-methyl-piperazin-1-yl)-pyridazine (compound 1)

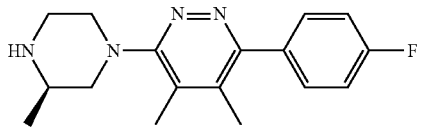

To a round bottom flask is added 3-chloro-4,5-dimethyl-6-((R)-3-methyl-piperazin-1-yl)-pyridazine (500 mg, 2.07 mmol), 4-fluorophenylboronic acid (580 mg, 4.15 mmol) sodium carbonate (440 mg, 4.15 mmol), toluene (16 mL) and water (8 mL). The reaction mixture is purged with nitrogen for 20 min. Tetrakis(triphenylphosphine) palladium (50 mg, 0.103 mmol) is added and the mixture is heated to 110° C. for 18 h. The reaction mixture is concentrated and partitioned between ethylacetate and water. It is extracted with ethylacetate twice and the combined organic phases are dried with sodium sulfate and concentrated. It is purified by column chromatography (0-25% methanol/methylene chloride) to give 480 mg of 3-(4-fluoro-phenyl)-4,5-dimethyl-6-((R)-3-methyl-piperazin-1-yl)-pyridazine (83%).

$^1$H NMR (400 MHz, CDCl$_3$) δ=7.34-7.49 (m, 2H) 7.07 (t, J=8.8 Hz, 2H) 3.35 (m, 2H) 2.84-3.13 (m, 4H) 2.63 (dd, J=12.0 Hz, 10.0 Hz, 1H) 2.20 (s, 3H) 2.14 (s, 3H) 1.67 (br s, 1H) 1.05 (d, J=6.5 Hz, 3H).

HR MS (m/z, MH+) meas. 301.1824, calc. 301.1829.

3-(4-Trifluoromethyl-phenyl)-4,5-dimethyl-6-((R)-3-methyl-piperazin-1-yl)-pyridazine (compound 2)

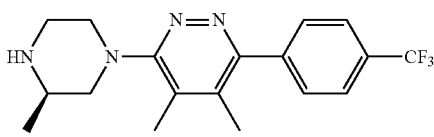

Compound 2 is prepared analogous to compound 1.

$^1$H NMR (400 MHz, CDCl$_3$) δ=7.69-7.80 (m, 2H) 7.60-7.70 (m, 2H) 3.38-3.52 (m, 3H) 2.98-3.22 (m, 4H) 2.69-2.83 (m, 1H) 2.30 (s, 3H) 2.23 (s, 3H) 1.15 (d, J=6.4 Hz, 3H).

HR MS (m/z, MH+) meas. 351.1806, calc. 351.1797.

3-Chloro-4,5-dimethyl-6-[4-(5-trifluoromethyl-pyridin-2-yl)-piperazin-1-yl]-pyridazine (compound 3)

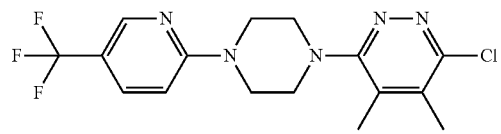 [SMILES: Cc1c(Cl)nnc(N2CCN(c3ccc(C(F)(F)F)cn3)CC2)c1C]

1-(5-Trifluoromethyl-pyridin-2-yl)-piperazine (10 g, 43.3 mmol) is combined with 3,6-dichloro-4,5-dimethyl-pyridazine (14.4 g, 84.3 mmol), triethylamine (8.25 mL), and NMP (40 mL). The reaction mixture is heated to a temperature of 180° C. for 25 min, and then concentrated in vacuo. The residue is purified by flash chromatography on silica gel (0-8% MeOH/CH$_2$Cl$_2$) to afford the title compound (13.2 g, 82%).

$^1$H NMR (400 MHz, DMSO-d$_6$) δ=8.48-8.41 (m, 1H) 7.84 (dd, J=9.1 Hz, 2.4 Hz, 1H) 7.03 (d, J=9.1 Hz, 1H) 3.88-3.76 (m, 4H) 3.28-3.20 (m, 4H) 2.31 (s, 6H).

2-[4-(6-chloro-4,5-dimethyl-pyridazin-3-yl)-piperazin-1-yl]-4-trifluoromethyl-pyrimidine-5-carboxylic acid methyl ester (compound 4)

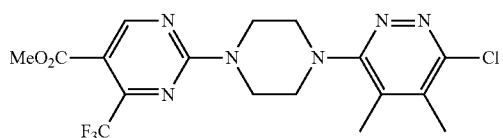

To a roundbottom flask is added 3-chloro-4,5-dimethyl-6-piperazin-1-yl-pyridazine (1 g, 4.41 mmol), 2-chloro-4-trifluoromethyl-pyrimidine-5-carboxylic acid methyl ester (2.12 g, 8.82 mmol) and diisopropylethylamine (2.3 mL, 13.23 mmol) in a dioxane (9 mL) solution and stirred for 18 h at room temperature. Filter the reaction mixture and rinse with water and ethylacetate to give 1.35 g of 2-[4-(6-chloro-4,5-dimethyl-pyridazin-3-yl)-piperazin-1-yl]-4-trifluoromethyl-pyrimidine-5-carboxylic acid methyl ester (71%).

$^1$H NMR (400 MHz, CDCl$_3$) δ=8.96 (s, 1H), 4.09-4.22 (m, 4H), 3.93 (s, 3H), 3.35 (m, 4H), 2.39 (s, 3H), 2.35 (s, 3H).

HR MS (m/z, MH+) meas. 431.1206, calc. 431.1210.

Synthesis of Examples 6-9 Via Route A

Example 6

(R)-4-[6-(4-fluoro-phenyl)-4,5-dimethyl-pyridazin-3-yl]-2-methyl-3,4,5,6-tetrahydro-2H-[1,2']bipyrazinyl-5'-carboxylic acid methyl ester

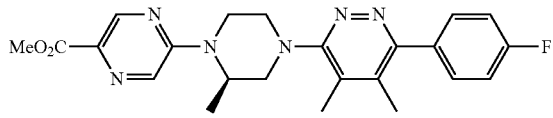 [SMILES: COC(=O)c1cnc(N2CCN(c3nnc(-c4ccc(F)cc4)c(C)c3C)C[C@H]2C)cn1]

Combine 3-(4-fluoro-phenyl)-4,5-dimethyl-6-((R)-3-methyl-piperazin-1-yl)-pyridazine (522 mg, 1.73 mmol), 5-chloro-pyrazine-2-carboxylic acid methyl ester (360 mg, 2.07 mmol), diisopropylethylamine (900 µl, 5.19 mmol) and dioxane (3 mL) in a round bottom flask. Heat to 110° C. for 18 h. Concentrate reaction mixture and purify by column chromatography (0-100% ethylacetate/heptane gradient). Triturate product with acetonitrile to give 480 mg of (R)-4-[6-(4-fluoro-phenyl)-4,5-dimethyl-pyridazin-3-yl]-2-methyl-3,4,5,6-tetrahydro-2H-[1,2']bipyrazinyl-5'-carboxylic acid methyl ester (63%).

$^1$H NMR (400 MHz, CDCl$_3$) δ=8.87 (s, 1H) 8.21 (s, 1H) 7.46-7.60 (m, 2H) 7.19 (t, J=8.5 Hz, 2H) 4.84 (br s, 1H) 4.43 (d, J=13.0 Hz, 1H) 3.99 (s, 3H) 3.68 (d, J=12.5 Hz, 1H) 3.49-3.63 (m, 2H) 3.39 (dd, J=12.8 Hz, 3.8 Hz, 1H) 3.15-3.31 (m, 1H) 2.41 (s, 3H) 2.29 (s, 3H) 1.50 (d, J=6.5 Hz, 3H).

HR MS (m/z, MH+) meas. 437.2097, calc. 437.2101.

Example 7

(R)-4-[6-(4-trifluoromethyl-phenyl)-4,5-dimethyl-pyridazin-3-yl]-2-methyl-3,4,5,6-tetrahydro-2H-[1,2']bipyrazinyl-5'-carboxylic acid methyl ester

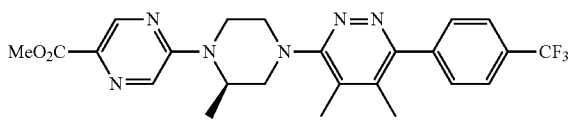 [SMILES: COC(=O)c1cnc(N2CCN(c3nnc(-c4ccc(C(F)(F)F)cc4)c(C)c3C)C[C@H]2C)cn1]

Example 7 is prepared in a analogous fashion to example 6 from compound 2.

$^1$H NMR (400 MHz, CDCl$_3$) δ=8.87 (s, 1H), 8.21 (d, J=1.3 Hz, 1H), 7.72-7.82 (m, 2H), 7.68 (d, J=8.1 Hz, 2H), 4.85 (br s, 1H), 4.44 (d, J=13.3 Hz, 1H), 4.00 (s, 3H), 3.70 (d, J=14.1 Hz, 1H), 3.50-3.64 (m, 2H), 3.41 (dd, J=12.6 Hz, 3.6 Hz, 1H), 3.18-3.31 (m, 1H), 2.42 (s, 3H), 2.29 (s, 3H), 1.50 (d, J=6.7 Hz, 3H).

HR MS (m/z, MH+) meas. 487.2050, calc. 487.2069.

Example 8

(R)-4-[6-(4-trifluoromethyl-phenyl)-4,5-dimethyl-pyridazin-3-yl]-2-methyl-3,4,5,6-tetrahydro-2H-[1,2']bipyrazinyl-5'-carboxylic acid

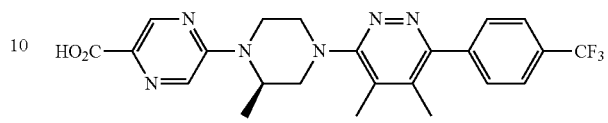

To a solution of example 7 (0.26 g, 0.53 mmol) and methanol (10 mL) is added 50% aqueous LiOH aqueous (10 mL). The mixture is stirred at room temperature overnight. Solvent is removed. The residue is dissolved in water and acidified with 3N HCl to pH about 7 and extracted with ethyl acetate. The ethyl acetate layer is concentrated to afford the title compound (0.25 g, 98%) as a yellow solid.

$^1$H NMR (400 MHz, CD$_2$Cl$_2$) δ=8.90 (s, 1H), 8.12 (s, 1H), 7.81 (d, J=8.0 Hz, 2H), 7.69 (d, J=8.0 Hz, 2H), 4.88 (m, 1H), 4.48 (d, J=13.0 Hz, 1H), 3.66 (m, 3H), 3.40 (m, 1H), 3.23 (m, 1H), 2.43 (s, 3H), 2.27 (s, 3H), 1.53 (d, J=6.5 Hz, 3H).

HR MS (m/z, MH+) meas. 473.1900.

Example 9

(R)-4-[6-(4-fluoro-phenyl)-4,5-dimethyl-pyridazin-3-yl]-2-methyl-3,4,5,6-tetrahydro-2H-[1,2']bipyrazinyl-5'-carboxylic acid

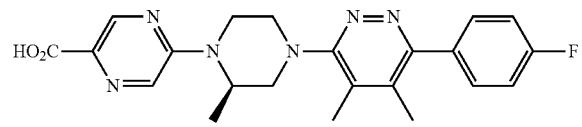

To a solution of example 6 (0.74 g, 1.31 mmol) and methanol (10 mL) is added sodium hydroxide (100 mg). The mixture is stirred at room temperature overnight. Solvent is removed and the residue is dissolved in water and acidified with 3 N HCl to pH about 7, and extracted with ethyl acetate. The ethyl acetate layer is concentrated to afford the title compound (0.68 g, 96%) as a yellow solid.

$^1$H NMR (400 MHz, CD$_2$Cl$_2$) δ=8.90 (s, 1H), 8.11 (s, 1H), 7.52 (m, 2H), 7.22 (m, 2H), 4.67 (m, 1H), 4.48 (d, J=12.0 Hz, 1H), 3.65 (m, 3H), 3.40 (m, 1H), 3.26 (m, 1H), 2.46 (s, 3H), 2.32 (s, 3H), 1.53 (d, J=6.5 Hz, 3H).

HR MS (m/z, MH+) meas. 423.1941.

Synthesis of Examples 10-40 Via Route B

General Protocol for the Suzuki Coupling of Boronic Acids to Pyridazinyl Chlorides IIIa Method A In a round bottom flask, combine 3-chloro-pyridazine (0.268 mmol), boronic acid (0.537 mmol) and sodium carbonate (57 mg, 0.537 mmol) in 1 mL of water and 1.8 mL of THF. Purge reaction mixture with nitrogen for 20 min, then add tetrakis(triphenylphosphine) palladium (10 mg) and heat to 110° C. for 18 h. Purify by column chromatography on silica gel with a 0%-70% ethylacetate/heptane gradient. Triturate products with methanol and acetonitrile to remove other impurity the desired products.

Method B

In a round bottom flask combine 3-chloro-pyridazine (0.268 mmol), boronic acid (0.536 mmol) and cesium carbonate (175 mg, 0.536 mmol) in 2 mL of 1,4-dioxane. Purge reaction mixture with nitrogen for 1 min and add tetrakis (triphenylphosphine) palladium (30 mg, 0.026 mmol). Heat to 115° C. for 18 h. Filter reaction mixture through Celite and concentrate. Partition between ethyl acetate and water, collect organic layer. Extract again with ethyl acetate and combine organics. Dry with sodium sulfate, filter and concentrate. Triturate material with acetonitrile, followed by a recrystallization from hot acetonitrile to give the desired products.

Method C

In a microwave vial, combine 3-chloro-pyridazine (0.080 mmol), boronic acid (0.096 mmol), potassium phosphate (34 mg, 0.161 mmol) and X-Phos (1.3 mg) in a n-butanol solution (1.5 mL). Purge with nitrogen for 1 minute and add palladium acetate (1 mg) then heat in a microwave reactor for 45 min at 150° C. Filter and concentrate reaction mixture, followed by purification on preparative HPLC (water/acetonitrile with 1% ammonium hydroxide) to yield the desired products.

Method D

In a microwave vial, 3-chloro-pyridazine (0.268 mmol), boronic acid (0.322 mmol), potassium phosphate (110 mg, 0.537 mmol) and X-Phos (5 mg) in a n-butanol solution (2.5 mL). Purge with nitrogen for 1 min and add palladium acetate (3.5 mg,) then heat in a microwave reactor for 45 min at 150° C. Filter and concentrate reaction mixture. Partition between ethylacetate and water, collecting the organic layer. Extract again and combine organics, dry with sodium sulfate and concentrate. Purify by column chromatography in a 0-100% ethylacetate/heptane gradient to yield the desired products.

Examples 10-31

The following table (Table 1) lists examples of compounds prepared by Route B using the general methods A-D described above:

TABLE 1

| Example | Structure | | HR MS[m/z, MH+] meas. |
|---|---|---|---|
| 10 | 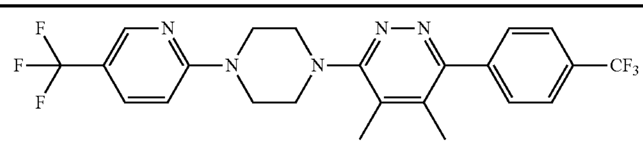 | A | 482.1757 (calc. 482.1779) |
| 11 | 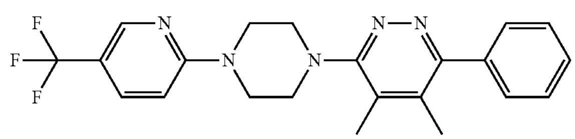 [SMILES: Cc1c(-c2ccccc2)nnc(N2CCN(c3ccc(C(F)(F)F)cn3)CC2)c1C] | A | 414.1904 (calc. 414.1906) |
| 12 | 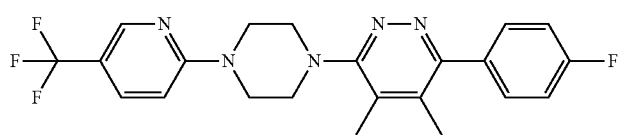 [SMILES: Cc1c(-c2ccc(F)cc2)nnc(N2CCN(c3ccc(C(F)(F)F)cn3)CC2)c1C] | A | 432.1807 (calc. 432.1811) |
| 13 | 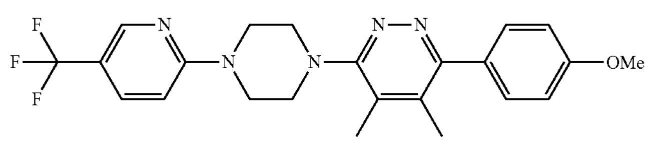 [SMILES: COc1ccc(-c2nnc(N3CCN(c4ccc(C(F)(F)F)cn4)CC3)c(C)c2C)cc1] | B | 444.2008 (calc. 444.2011) |
| 14 | 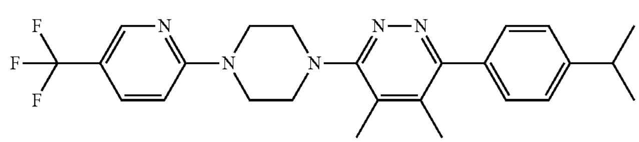 [SMILES: Cc1c(-c2ccc(C(C)C)cc2)nnc(N2CCN(c3ccc(C(F)(F)F)cn3)CC2)c1C] | B | 456.2366 (calc. 456.2375) |
| 15 | 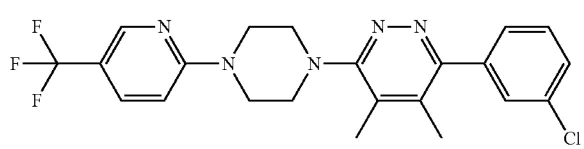 [SMILES: Cc1c(-c2cccc(Cl)c2)nnc(N2CCN(c3ccc(C(F)(F)F)cn3)CC2)c1C] | B | 448.1513 (calc. 448.1516) |
| 16 | 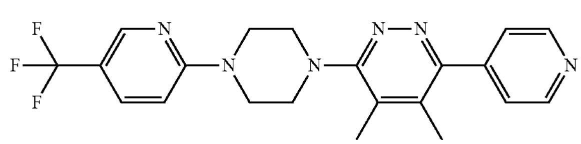 [SMILES: Cc1c(-c2ccncc2)nnc(N2CCN(c3ccc(C(F)(F)F)cn3)CC2)c1C] | C | 415.1859 (calc. 415.1858) |

TABLE 1-continued

| Example | Structure | | HR MS[m/z, MH+] meas. |
|---|---|---|---|
| 17 | [structure] | D | 457.1746 (calc. 457.1764) |
| 18 | [structure] | B | 507.1503 (calc. 507.1523) |
| 19 | [structure] | B | 503.1996 (calc. 503.2018) |
| 20 | [structure] | B | 525.1407 (calc. 525.1429) |
| 21 | [structure] | D | 530.2487 (calc. 530.2487) |
| 22 | [structure] | D | 530.2482 (calc. 530.2491) |
| 23 | [structure] | D | 548.2383 (calc. 548.2397) |
| 24 | [structure] | D | 546.2433 (calc. 546.2440) |
| 25 | [structure] | D | 558.2236 (calc. 558.2241) |
| 26 | [structure] | D | 557.2830 (calc. 557.2852) |

TABLE 1-continued

| Example | Structure | | HR MS[m/z, MH+] meas. |
|---|---|---|---|
| 27 | *(structure)* | B | 471.1700 (calc. 471.1712) |
| 28 | *(structure)* | B | 449.2304 (calc. 449.2304) |
| 29 | *(structure)* | B | 471.1721 (calc. 471.1712) |
| 30 | *(structure)* | B | 495.2520 (calc. 495.2508) |
| 31 | *(structure)* | D | 420.2498 (calc. 420.2512) |

Synthesis of Examples 32-34 Via Grignard Addition to Esters

General Protocol for the Grignard Addition

To a round bottom flask, cooled to −78° C., containing a solution of ester (1 mmol) in anhydrous THF (4 mL) is added a 3M solution of methylmagnesiumbromide (8 mmol) in diethyl ether, dropwise. Allow to warm up to 0° C. and after 20 minutes of stirring quench with a saturated solution of aqueous ammonium chloride. Extract with ethylacetate twice and collect organics. Dry with sodium sulfate and concentrate. Purify by column chromatography in a 0-100% ethylacetate/heptane gradient. Triturate product with acetonitrile and filter to give 2-propan-ol.

Examples 32-34

The following table (Table 2) lists examples of compounds prepared by the general procedure described above:

TABLE 2

| Example | Structure | HR MS [m/z, MH+] meas. |
|---|---|---|
| 32 | *(structure)* | 437.2453 (calc. 437.2465) |

TABLE 2-continued

| Example | Structure | HR MS [m/z, MH+] meas. |
|---|---|---|
| 33 | 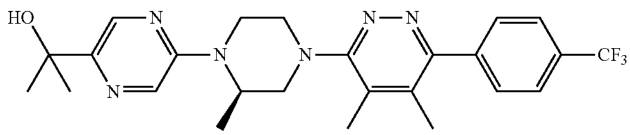 [SMILES: Cc1c(-c2ccc(C(F)(F)F)cc2)nnc(N2CCN(c3cnc(C(C)(C)O)cn3)[C@H](C)C2)c1C] | 487.2430 (calc. 487.2433) |
| 34 | 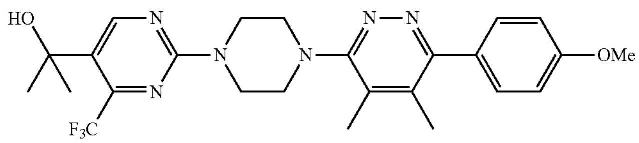 [SMILES: COc1ccc(-c2nnc(N3CCN(c4ncc(C(C)(C)O)c(C(F)(F)F)n4)CC3)c(C)c2C)cc1] | 503.2406 (calc. 503.2382) |

Synthesis of Examples 35-40 Via Amide Formation

General Protocol for the Amide Formation

The mixture of example 8 (40.0 mg, 0.08 mmol), HATU (64.0 mg, 0.17 mmol), diisopropylethyl amine (44.0 mg, 0.34 mmol), dimethylacetamide (1.5 mL) and amine (0.13 mmol) is stirred at room temperature for 10 h. The crude product is purified by HPLC (C18 column, acetonitrile/water (3% propanol), 30%~100%) to afford the examples 35 to 40 (74%~82%).

Examples 35-40

The following table (Table 3) lists examples of compounds prepared by the general procedure described above:

TABLE 3

| Example | Structure | HR MS [m/z, MH+] meas. |
|---|---|---|
| 35 | 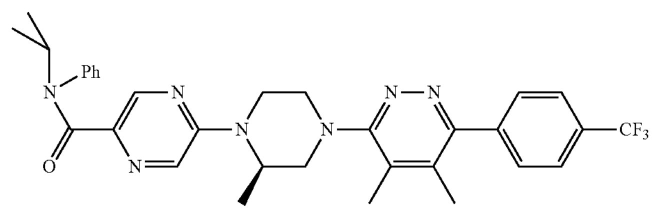 [SMILES: Cc1c(-c2ccc(C(F)(F)F)cc2)nnc(N2CCN(c3cnc(C(=O)N(c4ccccc4)C(C)C)cn3)[C@H](C)C2)c1C] | 604.2988 |
| 36 | 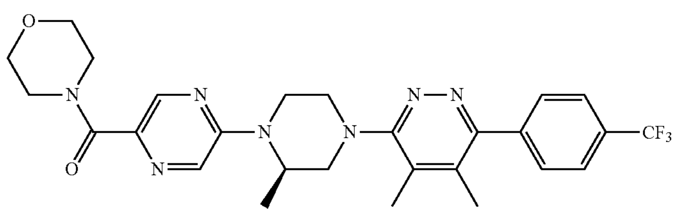 [SMILES: Cc1c(-c2ccc(C(F)(F)F)cc2)nnc(N2CCN(c3cnc(C(=O)N4CCOCC4)cn3)[C@H](C)C2)c1C] | 542.2468 |
| 37 | 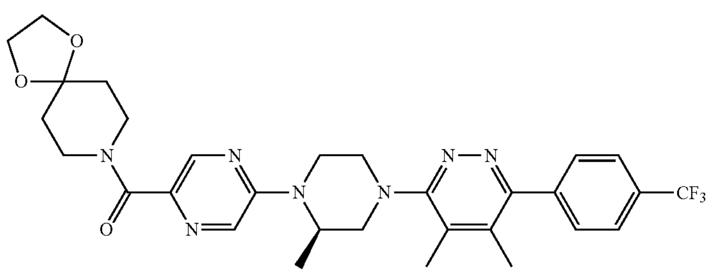 [SMILES: Cc1c(-c2ccc(C(F)(F)F)cc2)nnc(N2CCN(c3cnc(C(=O)N4CCC5(CC4)OCCO5)cn3)[C@H](C)C2)c1C] | 598.2762 |
| 38 | 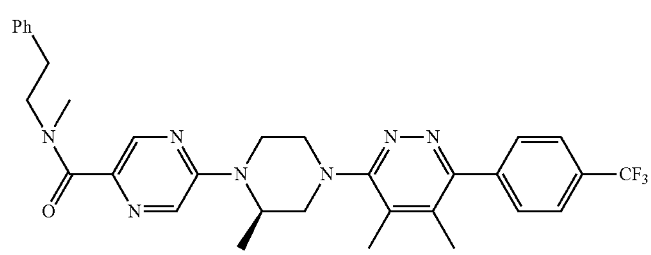 [SMILES: Cc1c(-c2ccc(C(F)(F)F)cc2)nnc(N2CCN(c3cnc(C(=O)N(C)CCc4ccccc4)cn3)[C@H](C)C2)c1C] | 590.2831 |

US 9,409,871 B2

TABLE 3-continued

| Example | Structure | HR MS [m/z, MH+] meas. |
|---|---|---|
| 39 | 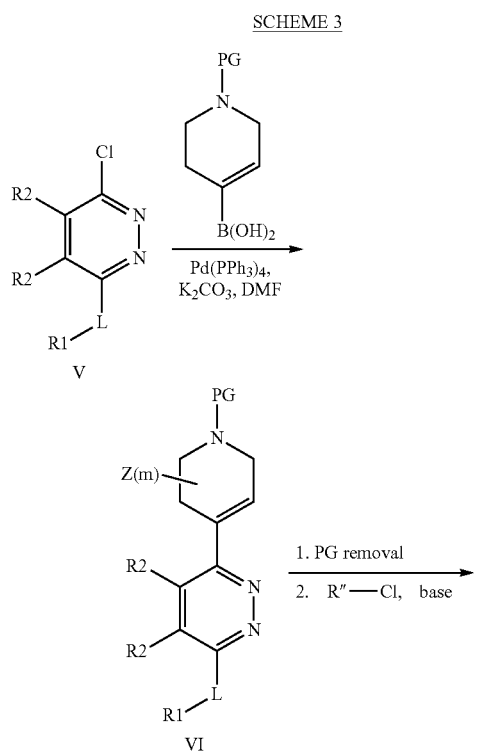 | 583.2758 |
| 40 | 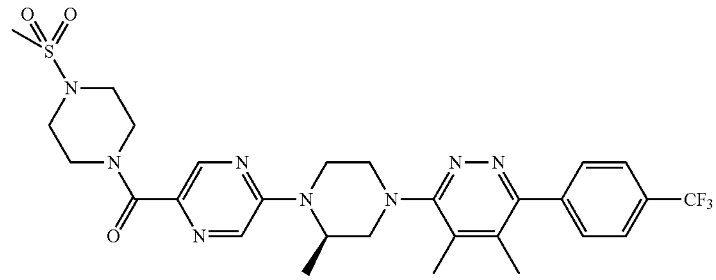 [SMILES: Cc1c(-c2ccc(C(F)(F)F)cc2)nnc(N2CCN(c3cnc(C(=O)N4CCN(S(C)(=O)=O)CC4)cn3)[C@H](C)C2)c1C] | 619.2410 |

Piperidin-4-yl-pyridazines

As illustrated in Scheme 3, compounds of Formula Ic can be prepared by Suzuki coupling of protected 1,2,3,6-tetrahydro-pyridine-4-boronic acids with pyridazine chlorides V to yield intermediates VI which after protecting group removal and nucleophilic displacement provide intermediates VII. Hydrogenation furnishes examples Ic.

SCHEME 3

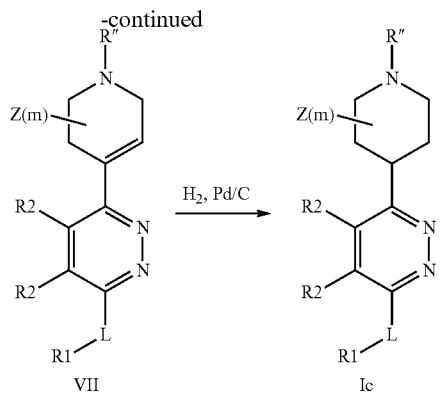

Synthesis of Intermediates 4-(6-Benzyl-4,5-dimethyl-pyridazin-3-yl)-3,6-dihydro-2H-pyridine-1-carboxylic acid tert-butyl ester (compound 5)

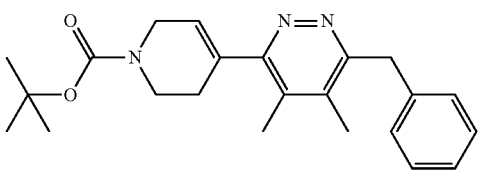 [SMILES: Cc1c(Cc2ccccc2)nnc(C2=CCN(C(=O)OC(C)(C)C)CC2)c1C]

To a solution of 3-benzyl-6-chloro-4,5-dimethylpyridazine (800 mg, 3.44 mmol) in 20 mL DMF is added tert-butyl 4-(4,4,5,5-tetramethyl-1,3,2-dioxaborolan-2-yl)-5,6-dihydropyridine-1(2H)-carboxylate (1.3 g, 4.1 mmol), followed with potassium carbonate (1.43 g, 10.3 mmol) and Pd(PPh$_3$)$_4$ (397 mg, 0.344 mmol) in a round bottom flask. The vial is evacuated and flushed with nitrogen. The reaction mixture is heated to 100° C. for 16 h. The mixture is filtered through Celite and the filtrate is concentrated to afford the crude material. The mixture is purified by flash chromatography on silica gel, eluting with 3%-15% MeOH: DCM. Fractions containing the desired product are combined and concentrated to afford a brown solid (1.0 g, 77%).

$^1$H NMR (400 MHz, CD$_2$Cl$_2$) δ=7.30-7.21 (m, 5H), 5.84-5.82 (s, 1H), 4.43 (s, 2H), 4.13-4.11 (m, 2H), 3.69 (t, J=5.5 Hz, 1H), 2.56-2.54 (m, 2H), 2.26 (s, 3H), 2.20 (s, 3H), 1.49 (s, 9H).

MS (m/z, MH+) meas. 380.7, calc. 380.23.

Methyl 5-(4-(6-benzyl-4,5-dimethylpyridazin-3-yl)-5,6-dihydropyridin-1(2H)-yl)pyrazine-2-carboxylate (compound 6)

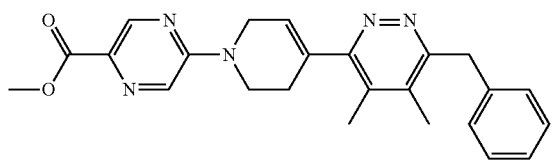 [SMILES: COC(=O)c1cnc(N2CC=C(c3nnc(Cc4ccccc4)c(C)c3C)CC2)cn1]

To 4-(6-benzyl-4,5-dimethyl-pyridazin-3-yl)-3,6-dihydro-2H-pyridine-1-carboxylic acid tert-butyl ester (170 mg, 0.358 mmol) is added 50% TFA in DCM. The reaction mixture is stirred for 10 min and concentrated to afford 3-benzyl-4,5-dimethyl-6-(1,2,3,6-tetrahydropyridin-4-yl)pyridazine as a yellow sticky solid (125 mg, 100%). To a solution of 3-benzyl-4,5-dimethyl-6-(1,2,3,6-tetrahydropyridin-4-yl)pyridazine (180 mg, 0.644 mmol) in dioxane is added methyl-5-chloropyrazine-2-carboxylate (222 mg, 1.29 mmol) and TEA (0.45 mL, 3.22 mmol) in a microwave tube. The reaction mixture is heated at 160° C. for 40 min in a microwave reactor. The mixture is concentrated to afford a brown oil and purified by prep HPLC, eluting with 10%-100% acetonitrile:water (both mobile phases modified by 3% n-PrOH). Fractions containing the desired product are combined and freeze-dried to afford a white solid (80 mg, 30%).

MS (m/z, MH+) meas. 416.5, calc. 416.2.

3-Benzyl-4,5-dimethyl-6-(1-(5-(trifluoromethyl)pyridin-2-yl)-1,2,3,6-tetrahydropyridin-4-yl)pyridazine (compound 7)

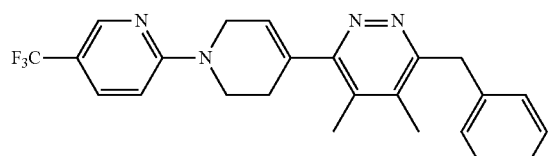

To a solution of 3-benzyl-4,5-dimethyl-6-(1,2,3,6-tetrahydropyridin-4-yl)pyridazine (70 mg, 0.175 mmol) in 2 mL dioxane is added 2-chloro-5-(trifluoromethyl)pyridine (64 mg, 0.35 mmol) and TEA (0.122 mL, 0.88 mmol) in a microwave tube. The reaction mixture is heated at 160° C. for 40 min in a microwave reactor. The mixture is concentrated to afford a brown oil and purified by prep HPLC, eluting with 10%-100% acetonitrile:water (both mobile phases modified by 3% n-PrOH). Fractions containing the desired product are combined and freeze-dried to afford a white solid (33 mg, 42%).

$^1$H NMR (400 MHz, DMSO-d$_6$) δ=8.44 (s, 1H), 7.83 (dd, J=2.5 Hz, 9.1 Hz, 2H), 7.30-7.26 (m, 2H), 7.20-7.16 (m, 3H), 6.99-6.97 (d, J=9.1 Hz, 1H), 5.96-5.94 (m, 1H), 4.32 (s, 2H), 4.27-4.26 (m, 2H), 3.97 (t, J=5.6 Hz, 2H), 2.60-2.58 (m, 2H), 2.22 (s, 3H), 2.16 (s, 3H).

HR MS (m/z, MH+) meas. 425.1958, calc. 425.1953.

Synthesis of Examples 41-44

Example 41

Methyl 5-(4-(6-benzyl-4,5-dimethylpyridazin-3-yl)piperidin-1-yl)pyrazine-2-carboxylate

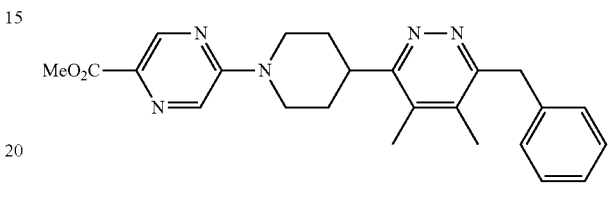

To a solution of methyl 5-(4-(6-benzyl-4,5-dimethylpyridazin-3-yl)-5,6-dihydropyridin-1(2H)-yl)pyrazine-2-carboxylate (60 mg, 0.144 mmol) in 20 mL EtOH is added 10% Pd—C (77 mg, 72 mmol). The reaction mixture is stirred under hydrogen atmosphere for 16 h. The mixture is filtered through Celite and the filtrate is concentrated to afford a yellow solid (60 mg, 100%).

$^1$H NMR (400 MHz, DMSO-d$_6$) δ=8.66 (s, 1H), 8.43 (s, 1H), 7.28-7.26 (m, 2H), 7.19-7.15 (m, 3H), 4.67-4.64 (m, 2H), 4.27 (s, 2H), 3.81 (s, 3H), 3.43-3.39 (m, 1H), 3.26-3.17 (m, 2H), 2.27 (s, 3H), 2.14 (s, 3H), 1.92-1.86 (m, 4H).

HR MS (m/z, MH+) meas. 418.2247, calc. 418.2243.

Example 42

2-{5-[4-(6-Benzyl-4,5-dimethyl-pyridazin-3-yl)-piperidin-1-yl]-pyrazin-2-yl}-propan-2-ol

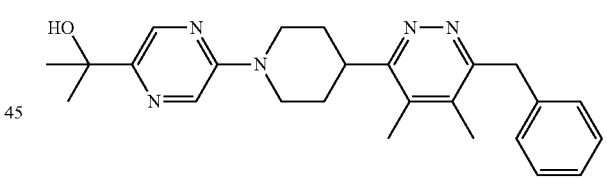

and

Example 43

3-Benzyl-6-{1-[5-(1-methoxy-1-methyl-ethyl)-pyrazin-2-yl]-piperidin-4-yl}-4,5-dimethyl-pyridazine

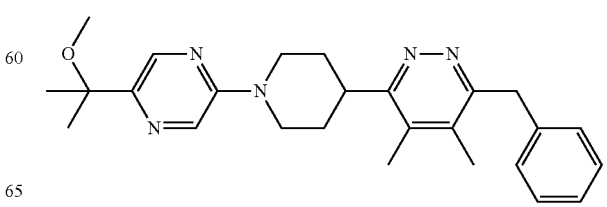

To a solution of methyl 5-(4-(6-benzyl-4,5-dimethylpyridazin-3-yl)piperidin-1-yl)pyrazine-2-carboxylate (30 mg, 0.07 mmol) in 2 mL anhydrous THF is added 3 M CH$_3$MgBr (287 μL, 0.862 mmol) at −78° C. under nitrogen atmosphere. The reaction mixture is stirred at −78° C. for 1 h and stirred at 0° C. for an additional 1 h. The mixture is quenched with sat. aq. ammonium chloride at −78° C. and the mixture is partitioned between DCM and brine. The organic layer is dried over Na$_2$SO$_4$ and concentrated to afford a brown oil. The mixture is purified by prep HPLC, eluting with 10%-100% acetonitrile:water (both mobile phases modified by 3% n-PrOH). Both examples 42 and 43 are collected as white solid.

Example 42

(8 mg, 27%): $^1$H NMR (400 MHz, DMSO-d$_6$) δ=8.33 (s, 1H), 8.26 (s, 1H), 7.28-7.24 (m, 2H), 7.19-7.15 (m, 3H), 5.08 (s, 3H), 5.08 (s, 1H), 4.45-4.41 (m, 2H), 4.27 (s, 2H), 3.34-3.24 (m, 2H), 2.27 (s, 3H), 2.15 (s, 3H), 1.92-1.83 (m, 4H), 1.42 (s, 6H).
HR MS (m/z, MH+) meas. 418.2625, calc. 418.2607.

Example 43

(6 mg, 20%): $^1$H NMR (400 MHz, DMSO-d$_6$) δ=8.30 (s, 1H), 8.20 (s, 1H), 7.28-7.25 (m, 2H), 7.19-7.15 (m, 3H), 4.49-4.45 (m, 2H), 4.27 (s, 2H), 3.34-3.26 (m, 1H), 3.09-3.03 (m, 2H), 3.05 (s, 3H), 2.27 (s, 3H), 2.14 (s, 3H), 1.91-1.84 (m, 4H), 1.45 (s, 6H).
HR MS (m/z, 2M+H') meas. 863.5453, calc. 863.5448.

Example 44

3-Benzyl-6-{1-[5-(trifluoromethyl)pyridin-2-yl]-piperidin-4-yl}-4,5-dimethylpyridazine

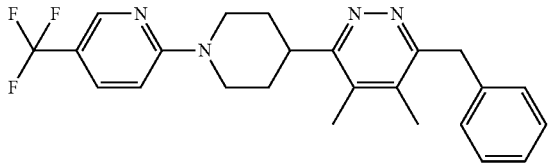 [SMILES: Cc1c(Cc2ccccc2)nnc(C2CCN(c3ccc(C(F)(F)F)cn3)CC2)c1C]

To a solution of 3-benzyl-4,5-dimethyl-6-(1-(5-(trifluoromethyl)pyridin-2-yl)-1,2,3,6-tetrahydropyridin-4-yl)pyridazine (20 mg, 0.047 mmol) in 8 mL EtOH is added 10% Pd—C (25 mg, 19 mmol). The reaction mixture is stirred under hydrogen atmosphere for 16 h. The mixture is filtered throug Celite and the filtrate is concentrated to afford a off-white solid. The mixture is purified by prep HPLC, eluting with 10%-100% acetonitrile:water (both mobile phases modified by 3% n-PrOH). Fractions containing the desired product are combined and freeze-dried to afford a white solid (8 mg, 40%).

MS (m/z, MH+) meas. 427.4, calc. 427.48.

Arylacyl-, arylhydroxymethyl- and arylmethyl-pyridazines

As illustrated in Scheme 4, dichloro-pyridazines II can be reacted with aryl-substituted acetonitrile after deprotonation and subsequent oxidation (e.g with air) to arylacyl compounds VIII. Nucleophilic displacement of the chlorine with amines provides examples Id which can be further reduced with e.g. NaBH$_4$ to examples Ie (Route A) Reaction of intermediates VIII with piperazines provides compounds IX which after Wolf-Kishner reduction yield intermediates X which after a nucleophilic displacement reaction furnish examples If (Route B). Further functional group transformations at R" can provide additional examples. Examples Id and Ie can also be transformed into examples with a —CF2- and —CHF— linker between Ar anf the pyridazine moiety by oxygen-fluor exchange.

SCHEME 4

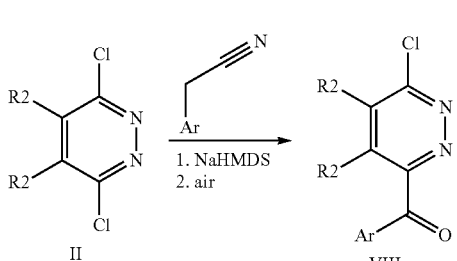

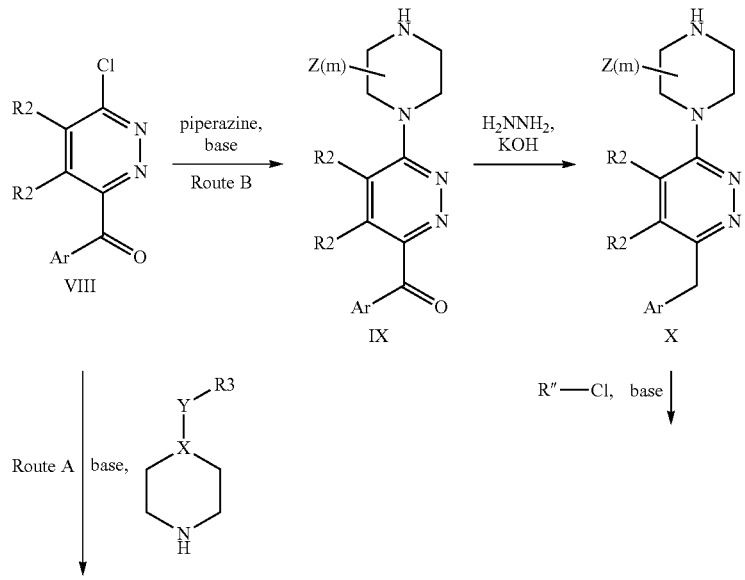

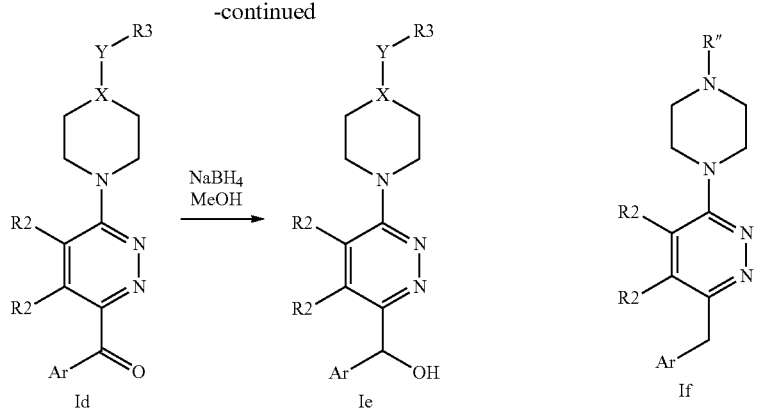

Ar is e.g. phenyl, pyridyl

Synthesis of Intermediates (R)-2-Methyl-4-boc-3,4,5,6-tetrahydro-2H-[1,2']bipyrazinyl-5'-carboxylic acid methyl ester (compound 8)

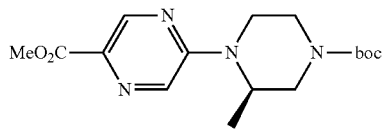

To (R)-1-boc-methylpiperazine (1 g, 5.0 mmol) in DMF (20 mL) is added 5-chloro-pyrazine-2-carboxylic acid methyl ester (862 mg, 5.0 mmol) and $Na_2CO_3$ (2.1 g, 20.0 mmol). The reaction mixture is stirred in a microwave reactor at 140° C. for 3 h. Then the mixture is cooled to rt and the organic solvent is removed in vacuo to afford a brown colored solid as product (1.7 g, quant.).
MS (m/z, MH+) meas. 337.

(R)-2-Methyl-3,4,5,6-tetrahydro-2H-[1,2']bipyrazinyl-5'-carboxylic acid methyl ester (compound 9)

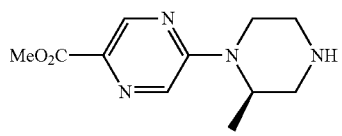 [SMILES: COC(=O)c1cnc(N2CCNC[C@H]2C)cn1]

To a solution of (R)-2-methyl-4-boc-3,4,5,6-tetrahydro-2H-[1,2']bipyrazinyl-5'-carboxylic acid methyl ester (2 g, 5.94 mmol) in MeOH (17 mL) is added HCl (4M in dioxane, 4.5 mL, 18 mmol). The reaction mixture is stirred at 70° C. for 1 h. The reaction solution is concentrated, dissolved in DCM and organic layer is washed with $Na_2CO_3$ to adjust the pH value to 8.0. The solvents are removed under reduced pressure to afford a brown oil (1.2 g, 77%).
1H NMR (400 MHz, DMSO-$d_6$) δ=8.81 (s, 1H), 8.11 (s, 1H), 4.58 (m, 1H), 4.22 (d, J=13.1 Hz, 1H), 3.96 (s, 3H), 3.21 (m, 2H), 3.17 (m, 1H), 3.07 (m, 1H), 2.18 (m, 1H), 1.35 (d, J=6.5 Hz, 3H).
MS (m/z, MH+) meas. 237.

2-((R)-2-Methyl-3,4,5,6-tetrahydro-2H-[1,2']bipyrazinyl-5'-yl)-propan-2-ol (compound 10)

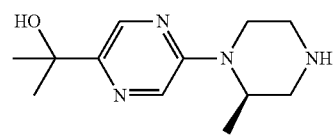 [SMILES: C[C@@H]1CNCCN1c1cnc(C(C)(C)O)cn1]

To a solution of (R)-2-methyl-3,4,5,6-tetrahydro-2H-[1,2']bipyrazinyl-5'-carboxylic acid methyl ester (60 mg, 0.24 mmol) in THF (3 mL) at -78° C. is added MeMgBr (3 M solution in $Et_2O$ 640 μl, 1.9 mmol). The reaction mixture is stirred at 0° C. for 2 h. The reaction mixture is quenched with sat. aqueous $NH_4Cl$ (3 mL). Additional water is added and the mixture is extracted with EtOAc; the organic layer is washed with $NaHCO_3$. Purification by HPLC of the crude product with acetonitrile in water (from 5% to 80% with 3% 1-propanol) at 220 nm wavelength detection provides the desired product as yellow colored oil (20 mg, 35%).
1H NMR (400 MHz, DMSO-$d_6$) δ=8.30 (s, 1H), 8.10 (s, 1H), 5.06 (s, 1H), 4.40 (m, 1H), 3.91 (m, 1H), 3.98 (m, 2H), 2.85 (m, 2H), 2.65 (m, 1H), 1.40 (s, 6H), 1.13 (d, J=6.6 Hz, 3H).
MS (m/z, MH+) meas. 237.

(6-Chloro-4,5-dimethyl-pyridazin-3-yl)-phenyl-methanone (compound 11)

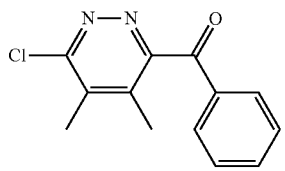 [SMILES: Cc1c(Cl)nnc(C(=O)c2ccccc2)c1C]

3,6-Dichloro-4,5-dimethyl-pyridazine (1.00 g, 5.65 mmol) and phenyl acetonitrile (652 mL, 5.65 mmol) are dissolved in toluene (17.5 mL), cooled to 0° C. and charged with NaHMDS (5.65 mL, 2M in THF, 11.3 mmol). The reaction mixture is stirred for 16 h, slowly warming up from 0° C. to rt. The mixture is stirred vigorously at the open air for another 24 h. The mixture is quenched by the addition of aqueous $NaHCO_3$ solution, the layers are separated and the aqueous phase is extracted with DCM. The combined organic phases are concentrated to give the title compound as a brown solid (1.4 g, quant.).

$^1$H NMR (400 MHz, CDCl$_3$) δ=7.82 (m, 2H), 7.55 (m, 1H), 7.40 (m, 2H), 2.39 (s, 3H), 2.28 (s, 3H).

MS (m/z, MH+) meas. 247.4.

(6-Chloro-4,5-dimethyl-pyridazin-3-yl)-pyridin-4-yl-methanone (compound 12)

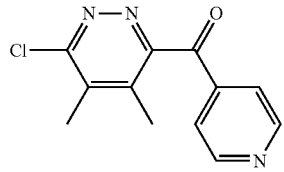 [SMILES: Cc1c(Cl)nnc(C(=O)c2ccncc2)c1C]

According to the protocol described below, 3,6-dichloro-4,5-dimethyl-pyridazine (1.00 g, 5.65 mmol) and 4-pyridylacetonitrile hydrochloride (1.05 g, 6.79 mmol) afforded the title compound as a white solid (822 mg, 59%).

(6-Chloro-4,5-dimethyl-pyridazin-3-yl)-pyridin-3-yl-methanone (compound 13)

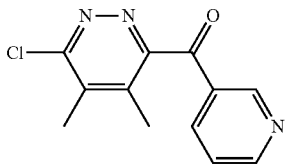 [SMILES: Cc1c(Cl)nnc(C(=O)c2cccnc2)c1C]

3,6-Dichloro-4,5-dimethyl-pyridazine (1.00 g, 5.65 mmol) is added to an oven-dried, 250-mL round-bottom flask under N$_2$ followed by THF (50 mL) and pyridin-3-yl-acetonitrile (800 mg, 7.68 mmol). The reaction is degassed with a flow of N$_2$ for 30 min. NaHMDS (14.13 mL, 1.0 M, 14.13 mmol) is added and the reaction is stirred for 16 h. The reaction mixture is then transferred to a beaker and stirred vigorously under open to the atmosphere for several hours. The reaction is quenched with saturated sodium bicarbonate solution, and the organics are extracted with dichloromethane. The combined organic layers are washed with brine, dried over Na$_2$SO$_4$, filtered and concentrated under reduced pressure. The crude material is purified via flash chromatography on silica gel (0-20% methanol in CH$_2$Cl$_2$) to afford the title compound (1.3 g, 93%).

$^1$H NMR (400 MHz, DMSO-d$_6$) δ=8.97 (s, 1H), 8.80 (d, J=4.5 Hz, 1H), 8.25 (d, J=8.0 Hz, 1H), 7.60-7.64 (m, 1H), 2.44 (s, 3H), 2.33 (s, 3H).

(6-Chloro-4,5-dimethyl-pyridazin-3-yl)-pyridin-2-yl-methanone (compound 14)

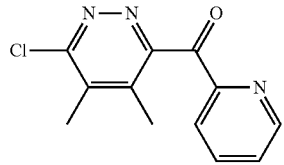 [SMILES: Cc1c(Cl)nnc(C(=O)c2ccccn2)c1C]

3,6-Dichloro-4,5-dimethyl-pyridazine (1.00 g, 5.65 mmol) is added to a dry 250-ml round-bottom flask under N$_2$ followed by THF (50 mL) and pyridin-2-yl-acetonitrile (800 mg, 7.68 mmol). The reaction is degassed for 30 min. NaHMDS (1.0 M, 14.13 mL, 14.13 mmol) is added and the reaction is stirred overnight. The reaction mixture is transferred to a beaker and air stirred vigorously for several hours. The reaction mixture is quenched with saturated sodium bicarbonate solution. The organics are extracted with dichloromethane. The combined organic layers are washed with brine and dried over Na$_2$SO$_4$, filtered and concentrated under reduced pressure. The crude material is purified via flash chromatography on silica gel (0-20% methanol in CH$_2$Cl$_2$) to afford the title compound (616 mg, 44%).

$^1$H NMR (400 MHz, DMSO-d$_6$) δ=8.68 (m, 1H), 8.26 (m, 1H), 8.16 (m, 1H), 7.76 (m, 1H), 2.45 (s, 3H), 2.21 (s, 3H).

[4,5-Dimethyl-6-((R)-3-methyl-piperazin-1-yl)-pyridazin-3-yl]-pyridin-4-yl-methanone (compound 15)

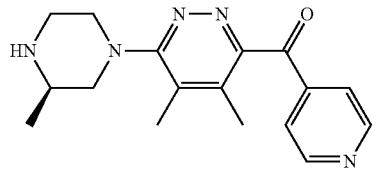 [SMILES: Cc1c(C(=O)c2ccncc2)nnc(N2CCN[C@H](C)C2)c1C]

According to the protocol described below, (6-chloro-4,5-dimethyl-pyridazin-3-yl)-pyridin-4-yl-methanone (750 mg, 3.03 mmol) and (R)-2-methyl-piperazine (364 mg, 3.63 mmol) afforded the title compound as a beige solid (778 mg, 83%).

[4,5-Dimethyl-6-((R)-3-methyl-piperazin-1-yl)-pyridazin-3-yl]-pyridin-3-yl-methanone (compound 16)

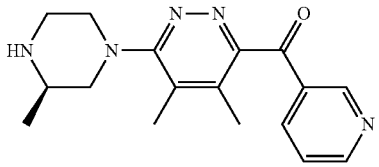 [SMILES: Cc1c(C(=O)c2cccnc2)nnc(N2CCN[C@H](C)C2)c1C]

(6-Chloro-4,5-dimethyl-pyridazin-3-yl)-pyridin-3-yl-methanone (1.2 g, 4.84 mmol) and (R)-2-methyl-piperazine (485 mg, 4.84 mmol) are added to a microwave vial followed by NMP (17 mL) and triethylamine (2.01 mL, 14.49 mmol). The vial is sealed and irradiated in the microwave at 170° C. for 30 min. The crude material is directly purified via flash chromatography on silica gel (0-20% methanol in CH$_2$Cl$_2$). The resulting oil is co-evaporated with CH$_2$Cl$_2$ and heptane to afford the title compound as a powder (1350 mg, 90%).

$^1$H NMR (400 MHz, DMSO-d$_6$) δ=9.56 (br s, 1H), 8.96 (s, 1H), 8.84-8.86 (m, 1H), 8.21-8.24 (m, 1H), 7.60-7.63 (m,

1H), 3.72 (s, 1H), 3.69 (s, 1H), 3.45-3.50 (m, 1H), 3.26-3.31 (m, 4H), 2.30 (s, 6H), 1.32 (d, J=6.5 Hz, 3H).

[4,5-Dimethyl-6-((R)-3-methyl-piperazin-1-yl)-pyridazin-3-yl]-pyridin-2-yl-methanone (compound 17)

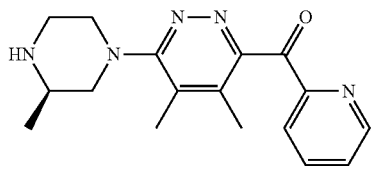 [SMILES: Cc1c(C(=O)c2ccccn2)nnc(N2CCN[C@H](C)C2)c1C]

(6-Chloro-4,5-dimethyl-pyridazin-3-yl)-pyridin-2-yl-methanone (550 mg, 2.22 mmol), (R)-2-methyl-piperazine (320 mg, 3.20 mmol) are added into a microwave vial followed by NMP (6 mL) and triethylamine (0.92 mL, 6.66 mmol). The vial is sealed and irradiated in the microwave at 180° C. for 1 h. The crude material is directly purified via flash chromatography on silica gel (20-70% methanol in CH$_2$Cl$_2$) to afford the title compound (671 mg, 97%).
$^1$H NMR (400 MHz, DMSO-d$_6$) δ=9.57 (br s, 1H), 8.66 (d, J=5.0 Hz, 1H), 8.10-8.17 (m, 2H), 7.69-7.73 (m, 1H), 3.65 (m, 1H), 3.62 (m, 1H), 3.45-3.50 (m, 1H), 3.12-3.33 (m, 4H), 2.29 (s, 3H), 2.15 (s, 3H), 1.32 (d, J=6.5 Hz, 3H).

4,5-Dimethyl-3-((R)-3-methyl-piperazin-1-yl)-6-pyridin-4-ylmethyl-pyridazine (compound 18)

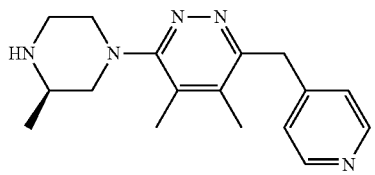 [SMILES: Cc1c(Cc2ccncc2)nnc(N2CCN[C@H](C)C2)c1C]

According to the protocol described below, 4,5-dimethyl-6-((R)-3-methyl-piperazin-1-yl)-pyridazin-3-yl]-pyridin-4-yl-methanone (550 mg, 1.77 mmol), hydrazine monohydrate (0.43 mL, 8.84 mmol), and KOH pellets (495 mg, 8.82 mmol) afforded the title compound (372 mg, 71%).

4,5-Dimethyl-3-((R)-3-methyl-piperazin-1-yl)-6-pyridin-3-ylmethyl-pyridazine (compound 19)

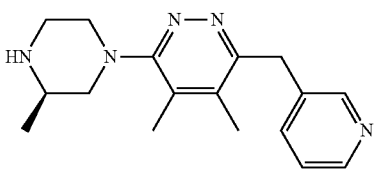 [SMILES: Cc1c(Cc2cccnc2)nnc(N2CCN[C@H](C)C2)c1C]

4,5-Dimethyl-6-((R)-3-methyl-piperazin-1-yl)-pyridazin-3-yl]-pyridin-3-yl-methanone (1300 mg, 4.17 mmol), hydrazine monohydrate (1045 mg, 20.88 mmol), KOH pellets (1171.4 mg, 20.88 mmol), and diethylene glycol (26 mL) are added to a round-bottom flask and the reaction is heated at 190° C. for 4 h. The reaction mixture is allowed to warm to room temperature and poured into water. The organics are extracted with dichloromethane. The combined organic layers are washed with brine, dried over Na$_2$SO$_4$, filtered and concentrated under reduced pressure. The crude material is purified via flash chromatography on silica gel (50/40/10 CH$_2$Cl$_2$/MeOH/NH$_4$OH)) to afford the title compound (1.17 g, 94%).
$^1$H NMR (400 MHz, DMSO-d$_6$) δ=8.47 (s, 1H), 8.41-8.42 (m, 1H), 7.54-7.56 (m, 1H), 7.29-7.32 (m, 1H), 4.25 (s, 2H), 4.12 (br s, 1H), 3.17-3.22 (m, 3H), 2.72-2.94 (m, 4H), 2.17 (s, 3H), 2.13 (s, 3H), 0.99 (d, J=6.0 Hz, 3H).

Synthesis of Examples 45-55

Example 45

(R)-4-(6-Benzoyl-4,5-dimethyl-pyridazin-3-yl)-2-methyl-3,4,5,6-tetrahydro-2H-[1,2']bipyrazinyl-5'-carboxylic acid methyl ester

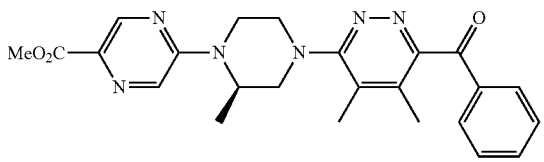 [SMILES: COC(=O)c1cnc(N2CCN(c3nnc(C(=O)c4ccccc4)c(C)c3C)C[C@H]2C)cn1]

To (R)-2-methyl-3,4,56-tetrahydro-2H-[1,2']bipyrazinyl-5'-carboxylic acid methyl ester (100 mg, 0.403 mmol) in DMF (5 mL) is added (6-chloro-4,5-dimethyl-pyridazin-3-yl)-phenyl-methanone (100 mg, 0.402 mmol) and sodium carbonate (170.7 mg, 1.61 mmol) and the reaction mixture is heated in a microwave reactor for 4 h at 180° C. Then the reaction mixture is diluted with DCM (25 mL) and washed with NaHCO$_3$ and water. Organic solvent is extracted and removed under reduced pressure. The crude product is purified by HPLC with acetonitrile in water (from 20% to 100% with 3% 1-propanol) at 220 nm wavelength detection to collect the desired product as an off white powder (58 mg, 32%).
$^1$H NMR (400 MHz, DMSO-d$_6$) δ=8.65 (s, 1H), 8.35 (s, 1H), 7.48-7.65 (m, 5H), 4.39 (d, J=13.1 Hz, 1H), 3.54 (d, J=12.6 Hz, 1H), 3.29 (m, 2H), 3.17 (m, 3H), 2.31 (s, 3H), 2.18 (s, 3H), 1.30 (s, 3H).
HR MS (m/z, MH+) meas. 446.5098, calc. 446.5104.

Example 46

(6-{(R)-4-[4-(1-Hydroxy-1-methyl-ethyl)-phenyl]-3-methyl-piperazin-1-yl}-4,5-dimethyl-pyridazin-3-yl)-phenyl-methanone

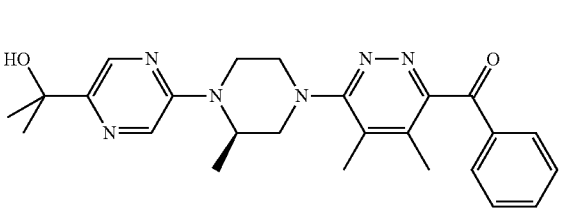 [SMILES: Cc1c(C(=O)c2ccccc2)nnc(N2CCN(c3cnc(C(C)(C)O)cn3)[C@H](C)C2)c1C]

To (6-chloro-4,5-dimethyl-pyridazin-3-yl)-phenyl-methanone (50 mg, 0.20 mmol) in DMF (3 mL) was added 2-[4-(R)-2-methyl-piperazine-1-yl]-phenyl]-propan-2-ol (47.4 mg, 0.20 mmol) and sodium carbonate (86.2 mg, 0.81 mmol), the reaction mixture was heated in a microwave reactor for 4 h at 180° C. Then the reaction mixture is diluted with DCM (15 mL) and washed with NaHCO$_3$ and water. Organic solvent is extracted and removed under reduced pressure. Purification by HPLC of the crude product with ACN in water (from 20% to 100% with 3% 1-propanol) at 220 nm UV detection provides the desired product as off white powder (25 mg, 28%).

$^1$H NMR (400 MHz, DMSO-d$_6$) δ=8.42 (s, 1H), 8.23 (s, 1H), 7.61-7.89 (m, 5H), 4.77 (m, 1H), 4.25 (d, J=12.6 Hz, 1H), 3.75 (d, J=12.6 Hz, 1H), 3.65 (d, J=12.6 Hz, 1H), 3.29 (m, 2H), 3.11 (m, 2H), 2.50 (s, 3H), 2.32 (s, 3H), 1.47 (s, 6H), 1.35 (d, J=6.6 Hz, 3H).

HR MS (m/z, MH+) meas. 444.2256, calc. 444.2651.

Example 47

(R)-4[6-(hydroxyl-phenyl-methyl)-4,5-dimethyl-pyridazin-3-yl]-2-methyl-3,4,5,6-tetrahydro-2H-[1,2']bipyrazinyl-5'-carboxylic acid methyl ester

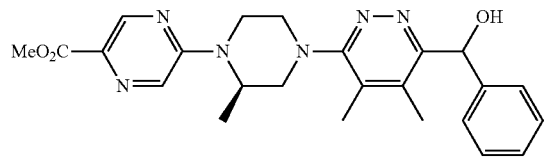 [SMILES: COC(=O)c1cnc(N2CCN(c3nnc(C(O)c4ccccc4)c(C)c3C)C[C@H]2C)cn1]

To (R)-4-(6-benzoyl-4,5-dimethyl-pyridazin-3-yl)-2-methyl-3,4,5,6-tetrahydro-2H-[1,2']bipyrazinyl-5'-carboxylic acid methyl ester (8 mg, 0.017 mmol) in MeOH (2 mL) is added sodium borohydride (170 μg, 0.004 mmol) in 15 minutes and the reaction mixture is stirred at room temperature for 1 h. The reaction mixture is diluted with DCM and washed with NaHCO$_3$ and water. The organic solvent is separated and the solvent is removed under reduced pressure. Purification by HPLC of the crude product with acetonitril in water (from 10% to 100% with 3% 1-propanol) at 220 nm wavelength detection provides the desired product as off white powder. (6 mg, 79%).

$^1$H NMR (400 MHz, DMSO-d$_6$) δ=8.77 (s, 1H), 8.47 (s, 1H), 7.29-7.38 (m, 5H), 6.15 (s, 1H), 4.92 (m, 1H), 4.50 (m, 1H), 3.89 (s, 3H), 3.49-3.61 (m, 3H), 3.17-3.02 (m, 2H), 2.30 (s, 3H), 2.14 (s, 3H), 1.43 (d, J=6.6 Hz, 3H).

MS (m/z, MH+) meas. 449.

Example 48

2-{(R)-4-[6-(Hyrdoxyl-phenyl-methyl0-4,5-dimethyl-pyridazin-3-yl)-2-methyl-3,4,5,6-tetrahydro-2H-[1,2']bipyrazinyl-5'-yl]-propan-2-ol

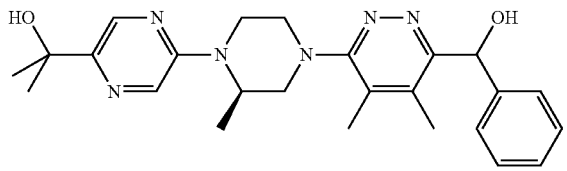 [SMILES: Cc1c(C(O)c2ccccc2)nnc(N2CCN(c3cnc(C(C)(C)O)cn3)[C@H](C)C2)c1C]

To (R)-4[6-(hydroxyl-phenyl-methyl)-4,5-dimethyl-pyridazin-3-yl]-2-methyl-3,4,5,6-tetrahydro-2H-[1,2']bipyrazinyl-5'-carboxylic acid methyl ester (15 mg, 0.032 mmol) in THF (2 mL) is added methyl magnesium bromide (32 μl, 0.095 mmol) at −78° C. and the reaction mixture is stirred 0° C. for 2 h. The reaction mixture is diluted with DCM and washed with NH$_4$Cl and water. The organic solvent is separated extracted and concentrated under reduced pressure. Purification by HPLC of the crude product with acetonitrile in water (from 10% to 100% with 3% 1-propanol) at 220 nm wavelength detection provides the desired product as off white powder (11 mg, 77%).

$^1$H NMR (400 MHz, DMSO-d$_6$) δ=8.27 (s, 1H), 8.07 (s, 1H), 7.29-7.34 (m, 5H), 5.88 (s, 1H), 4.67 (m, 1H), 4.19 (m, 1H), 3.61 (m, 1H), 3.52-3.31 (m, 3H), 3.19 (tt, J=3.5 Hz, 12.7 Hz, 1H), 2.29 (s, 3H), 2.05 (s, 3H), 1.57 (s, 6H), 1.40 (d, J=6.6 Hz, 3H).

HR MS (m/z, MH+) meas. 449.2649, calc. 444.2665.

Example 49

(R)-4-(4,5-Dimethyl-6-pyridin-4-ylmethyl-pyridazin-3-yl)-2-methyl-3,4,5,6-tetrahydro-2H-[1,2']bipyrazinyl-5'-carboxylic acid methyl ester

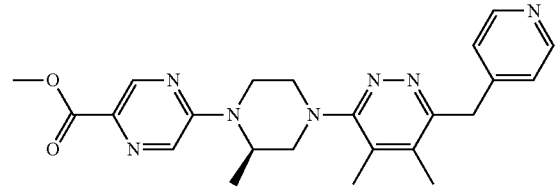 [SMILES: COC(=O)c1cnc(N2CCN(c3nnc(Cc4ccncc4)c(C)c3C)C[C@H]2C)cn1]

According to the protocol described below for example 46, 4,5-dimethyl-3-((R)-3-methylpiperazin-1-yl)-6-pyridin-4-ylmethyl-pyridazine (155 mg, 0.51 mmol) and 5-chloro-pyrazine-2-carboxylic acid methyl ester (99 mg, 0.56 mmol) afforded the title compound as an orange oil (123 mg, 56%).

Example 50

2-[(R)-4-(4,5-Dimethyl-6-pyridin-4-ylmethyl-pyridazin-3-yl)-2-methyl-3,4,5,6-tetrahydro-2H-[1,2']bipyrazinyl-5'-yl]-propan-2-ol

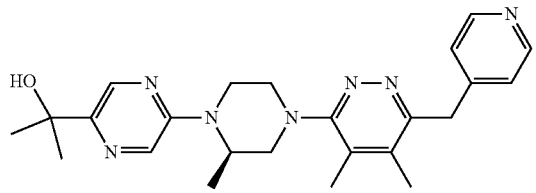 [SMILES: Cc1c(Cc2ccncc2)nnc(N2CCN(c3cnc(C(C)(C)O)cn3)[C@H](C)C2)c1C]

According to the protocol described below, (R)-4-(4,5-dimethyl-6-pyridin-4-ylmethyl-pyridazin-3-yl)-2-methyl-3,4,5,6-tetrahydro-2H-[1,2']bipyrazinyl-5'-carboxylic acid methyl ester (110 mg, 0.25 mmol) and MeMgI (0.660 mL, 1.98 mmol) afforded the title compound as a yellow powder (40 mg, 37%).

$^1$H NMR (400 MHz, DMSO-d$_6$) δ=8.47 (d, J=5.5 Hz, 2H), 8.36 (s, 1H), 8.21 (s, 1H), 7.21 (d, J=5.5 Hz, 2H), 5.15 (s, 1H), 4.68 (br s, 1H), 4.29 (s, 2H), 4.17 (d, J=12.5 Hz, 1H), 3.21-3.59 (m, 3H), 3.07 (dd, J=12.5 Hz, 3.5 Hz, 1H), 2.89-3.00 (m, 1H), 2.28 (s, 3H), 2.13 (s, 3H), 1.42 (s, 6H), 1.28 (d, J=6.5 Hz, 3H).

HR MS (m/z, MH+) meas. 434.2650, calc. 434.2668.

Example 51

(R)-4-(4,5-Dimethyl-6-pyridin-3-ylmethyl-pyridazin-3-yl)-2-methyl-3,4,5,6-tetrahydro-2H-[1,2']bipyrazinyl-5'-carboxylic acid methyl ester

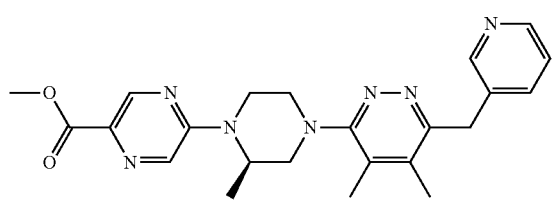 [SMILES: COC(=O)c1cnc(N2CCN(c3nnc(Cc4cccnc4)c(C)c3C)C[C@H]2C)cn1]

4,5-Dimethyl-3-((R)-3-methyl-piperazin-1-yl)-6-pyridin-3-ylmethyl-pyridazine (350 mg, 1.18 mmol) and 5-chloropyrazine-2-carboxylic acid methyl ester (243.7 mg, 1.41 mmol) are added to a microwave vial followed by NMP (7 mL) and triethylamine (0.49 mL, 3.54 mmol). The vial is sealed and irradiated in the microwave at 145° C. for 30 min. The crude material is directly purified via flash chromatography on silica gel (0-20% methanol in $CH_2Cl_2$) to afford the title compound (30 mg, 6%).

$^1$H NMR (400 MHz, DMSO-$d_6$) δ=8.71 (s, 1H), 8.52 (d, J=6 Hz, 1H), 8.48 (s, 1H), 8.42 (s, 1H), 7.57 (d, J=8 Hz, 1H), 7.30-7.33 (m, 1H), 4.85 (m, 1H), 4.45 (d, J=12 Hz, 1H), 4.29 (s, 2H), 3.79 (s, 3H), 3.41-3.55 (m, 3H), 3.08 (m, 1H), 2.93-2.99 (m, 1H), 2.28 (s, 3H), 2.17 (s, 3H), 1.36 (d, J=7 Hz, 3H).

Example 52

2-[(R)-4-(4,5-Dimethyl-6-pyridin-3-ylmethyl-pyridazin-3-yl)-2-methyl-3,4,5,6-tetrahydro-2H-[1,2']bipyrazinyl-5'-yl]-propan-2-ol

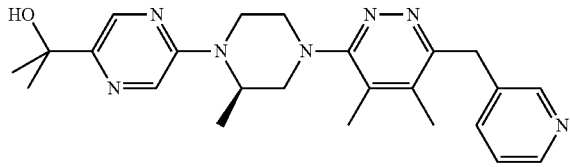 [SMILES: Cc1c(Cc2cccnc2)nnc(N2CCN(c3cnc(C(C)(C)O)cn3)[C@H](C)C2)c1C]

(R)-4-(4,5-Dimethyl-6-pyridin-3-ylmethyl-pyridazin-3-yl)-2-methyl-3,4,5,6-tetrahydro-2H-[1,2']bipyrazinyl-5'-carboxylic acid methyl ester (25 mg, 0.058 mmol) is added to an oven-dried, round-bottom flask under $N_2$ followed by THF (0.6 mL). The reaction is then placed in a dry-ice bath for 15 min. MeMgI (0.15 mL, 3.0 M, 0.461 mmol) is added dropwise and the reaction is stirred at −78° C. for 30 min. The reaction is warmed to 0° C. and stirred 30 min or until complete conversion is observed. The reaction mixture is quenched with saturated ammonium chloride solution. The organics are extracted with ethyl acetate. The combined organic layers are dried over $Na_2SO_4$, filtered and concentrated under reduced pressure. The crude material is purified via flash chromatography on silica gel (2% $CH_2Cl_2$, 98% (50/30/20 ethyl acetate/heptane/MeOH)) to afford the title compound (3.5 mg, 14%).

$^1$H NMR (400 MHz, DMSO-$d_6$) δ=8.49 (s, 1H), 8.42 (d, J=6.7 Hz, 1H), 8.36 (s, 1H), 8.21 (s, 1H), 7.57 (d, J=7.9 Hz, 1H), 7.32 (m, 1H), 5.13 (s, 1H), 4.67 (s, br, 1H), 4.29 (s, 2H), 4.17 (d, J=12.5 Hz, 1H), 3.51 (d, J=12.5 Hz, 1H), 3.34-3.42 (m, 2H), 3.07 (dd, J=12.1 Hz, 1H), 2.93-2.97 (dt, J=3.4 Hz, 12.5 Hz, 1H), 2.28 (s, 3H), 2.17 (s, 3H), 1.43 (s, 6H), 1.28 (d, J=6.5 Hz, 3H).

HR MS (m/z, MH+) meas. 434.2663, calc. 434.2668.

Example 53

(R)-4-(4,5-Dimethyl-6-pyridin-2-ylmethyl-pyridazin-3-yl)-2-methyl-3,4,5,6-tetrahydro-2H-[1,2']bipyrazinyl-5'-carboxylic acid methyl ester

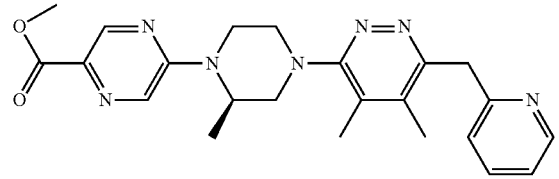 [SMILES: COC(=O)c1cnc(N2CCN(c3nnc(Cc4ccccn4)c(C)c3C)C[C@H]2C)cn1]

Step 1: Preparation of 2,4-dimethyl-3-pyridin-2-ylmethyl-pentan-3-ol (compound 20)

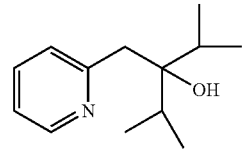

2-Methyl-pyridine (1.86 g, 20 mmol) is dissolved in THF (20 mL) and cooled to −30° C. tert-Butyl lithium (11.8 mL, 1.7M in pentane, 20 mmol) is added dropwise to the solution, and the reaction is stirred for 30 min at −30° C. 2,4-Dimethyl-pentan-3-one (3.4 mL, 24 mmol) is added and the reaction is warmed to room temperature and stirred for 2 h. Add $H_2O$ (30 mL) and extract with EtOAc. Wash combined organics with brine and concentrate in vacuo. The residue is purified by flash chromatography on silica gel (EtOAc/Heptane) to afford 2,4-dimethyl-3-pyridin-2-ylmethyl-pentan-3-ol (4.14 g, quant.).

Step 2: (R)-4-(4,5-Dimethyl-6-pyridin-2-ylmethyl-pyridazin-3-yl)-2-methyl-3,4,5,6-tetrahydro-2H-[1,2']bipyrazinyl-5'-carboxylic acid methyl ester (example 53)

(R)-4-(6-Chloro-4,5-dimethyl-pyridazin-3-yl)-2-methyl-3,4,5,6-tetrahydro-2H [1,2']bipyrazinyl-5'-carboxylic acid methyl ester (250 mg, 0.663 mmol) is combined with 2,4-dimethyl-3-pyridin-2-ylmethyl-pentan-3-ol (114.6 mg, 0.553 mmol), cesium carbonate (216.2 mg, 0.664 mmol), palladium triflate (6.2 mg, 0.028 mmol), tricyclohexyl phosphine (15.5 mg, 0.055), and toluene (2 mL). The reaction mixture is heated to 110° C. for 65 h to reach 10% conversion. Add $H_2O$ and extract with EtOAc. Concentrate combined organics in vacuo. The residue is purified by flash chromatography on silica gel (MeOH/$CH_2Cl_2$) to afford the title compound (13 mg, 5.4%).

$^1$H NMR (400 MHz, DMSO-$d_6$) δ=8.71 (d, J=1.3 Hz, 1H), 8.46-8.43 (m, 1H), 8.41 (d, J=1.3 Hz, 1H), 7.71 (td, J=7.7 Hz, 1.8 Hz, 1H), 7.27-7.18 (m, 2H), 4.86 (br s, 1H), 4.41 (s, 2H), 4.48-4.38 (m, 1H), 3.83 (s, 3H), 3.59-3.38 (m, 3H), 3.08 (dd, J=12.6 Hz, 3.7 Hz, 1H), 2.95 (td, J=12.2 Hz, 3.2 Hz, 1H), 2.28 (s, 3H), 2.16 (s, 3H), 1.36 (d, J=6.6 Hz, 3H).

HR MS (m/z, MH+) meas. 434.2236, calc. 434.2304.

Example 54

2-[(R)-4-(4,5-Dimethyl-6-pyridin-2-ylmethyl-pyridazin-3-yl)-2-methyl-3,4,5,6-tetrahydro-2H-[1,2']bipyrazinyl-5'-yl]-propan-2-ol

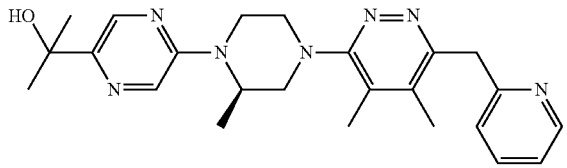 [SMILES: Cc1c(Cc2ccccn2)nnc(N2CCN(c3cnc(C(C)(C)O)cn3)[C@H](C)C2)c1C]

Example 54 is prepared from example 53 by addition of MeMgI as described for example 52.

HR MS (m/z, MH+) meas. 434.2666, calc. 434.2668.

Example 55

2-{(R)-4-[6-(Difluoro-phenyl-methyl)-4,5-dimethyl-pyridazin-3-yl]-2-methyl-3,4,5,6-tetrahydro-2H-[1,2']bipyrazinyl-5'-yl}-propan-2-ol

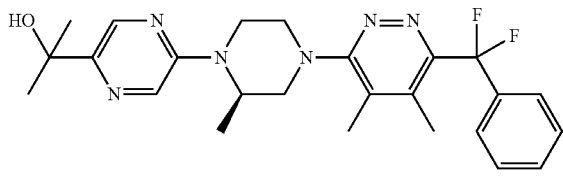 [SMILES: Cc1c(N2CCN(c3cnc(C(C)(C)O)cn3)[C@H](C)C2)nnc(C(F)(F)c2ccccc2)c1C]

Step 1: 3-Chloro-4,5-dimethyl-6-(2-phenyl-[1,3']dithiolan-2-yl)-pyridazine (compound 21)

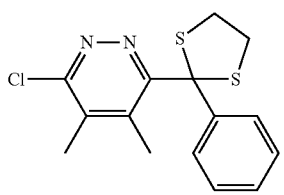 [SMILES: Cc1c(Cl)nnc(C2(c3ccccc3)SCCS2)c1C]

To a DCM solution of (6-chloro-4,5-dimethyl-pyridazin-3-yl)-phenyl-methanone (300 mg, 1.22 mmol) is added 1,2-ethandithiol (0.408 ml, 4.86 mmol) and BF$_3$.OEt$_2$ (0.154 ml, 1.216 mmol) at 0° C. under nitrogen atmosphere. The reaction mixture is stired at room temperature for 16 h. The reaction was charged with BF$_3$.OEt$_2$ (0.154 ml, 1.216 mmol) and 1,2-ethanedithiol (0.408 ml, 4.86 mmol), and heated at 40° C. for 6 h. The reaction is quenched with sat. NaHCO$_3$ at 0° C. and organic phase is washed with brine. The organic layer is dried over Na$_2$SO$_4$, filtered and concentrated to afford a yellow solid. The residue is loaded on silica gel and purified by flash chromatography, eluting with 20-80% EtOAc: heptane.

Fractions containing the desired product are combined and concentrated to afford a white solid (280 mg, 73%).

$^1$H NMR (400 MHz, CDCl$_3$) δ=7.54-7.53 (m, 2H), 7.28-7.22 (m, 3H), 3.46-3.34 (m, 4H), 2.30 (s, 3H), 1.94 (s, 3H).

MS (m/z, MH+) meas. 323.0, calc. 322.88.

Step 2: 3-Chloro-6-(difluoro-phenyl-methyl)-4,5-dimethyl-pyridazine (compound 22)

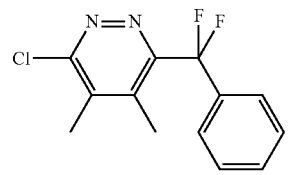 [SMILES: Cc1c(Cl)nnc(C(F)(F)c2ccccc2)c1C]

To a DCM (1 mL) solution of NBS (49.6 mg, 0.279 mmol) is added DAST (0.147 ml, 1.115 mmol). The reaction mixture is cooled to 0° C. before 3-chloro-4,5-dimethyl-6-(2-phenyl-[1,3]dithiolan-2-yl)-pyridazine (90 mg, 0.279 mmol) is added. The mixture is stirred at room temperature for 3 hAdditional 2 eq. of DAST (73.7 µL, 0.558 mmol) are added and the mixture stirred for another 2 h. The reaction mixture is quenched with sat. NaHCO$_3$ at 0° C. The aqueous layer is washed with DCM and the combined organic layers are dried over Na$_2$SO$_4$ and concentrated to afford the crude mixture. The residue is loaded on silica gel and purified by flash chromatography, eluting with 15-45% EtOAc: heptane. Fractions containing the desired product are combined and concentrated to afford a yellow oil (15 mg, 20%).

$^1$H NMR (400 MHz, CDCl$_3$) δ=7.54-7.52 (m, 2H), 7.47-7.43 (m, 3H), 2.42-2.41 (m, 6H).

$^{19}$F NMR (400 MHz, CDCl$_3$) δ=−89.9.

MS (m/z, MH+) meas. 269.2, calc. 269.06

Step 3: 2-{(R)-4-[6-(Difluoro-phenyl-methyl)-4,5-dimethyl-pyridazin-3-yl]-2-methyl-3,4,5,6-tetrahydro-2H-[1,2']bipyrazinyl-5'-yl}-propan-2-ol (example 55)

Example 55 is prepared from compounds 10 and 22 as described for example 46.

Piperidin-1-yl-Pyridazines

As illustrated in Scheme 5, piperidin-1-yl-pyridazines can be prepared by a multitude of routes. According to Route A functionalized piperidines can react with intermediates V to yield examples Ig. Examples Ih and Ii can be prepared via Route B. Reaction of V with a 4-piperidinyl-carboxylic ester provides after ester hydrolysis intermediates XIa which can react either to imidazol-substituted examples Ih or can be condensed with ortho-dianilines to examples Ii. Route C provides examples Ij by reacting intermediates V with 4-cyanopiperidine and subsequent Pd-catalyzed reaction of XIb with R"—Br. Further imidazol-substituted examples Ik can be prepared from intermediates XIc (by condensation reaction in the presence of ammonia and a keto-aldehyde precursor) which are available by reaction of 4-hydroxymethyl-piperidines with V and subsequent oxidation of the alcohol functionality (Route D). Route E provides ketones XId which can act as electrophiles for metallo-organic reagents such as R"—Li to provide tertiary alcohol examples Il. Transformation of the hydroxyl group with fluorination reagants e.g. Deoxofluor yields further examples In. Ketones XId can be used in reductive amination reactions with amines and e.g. NaBH(OAc)$_3$ as reducing agent to yield examples Io.

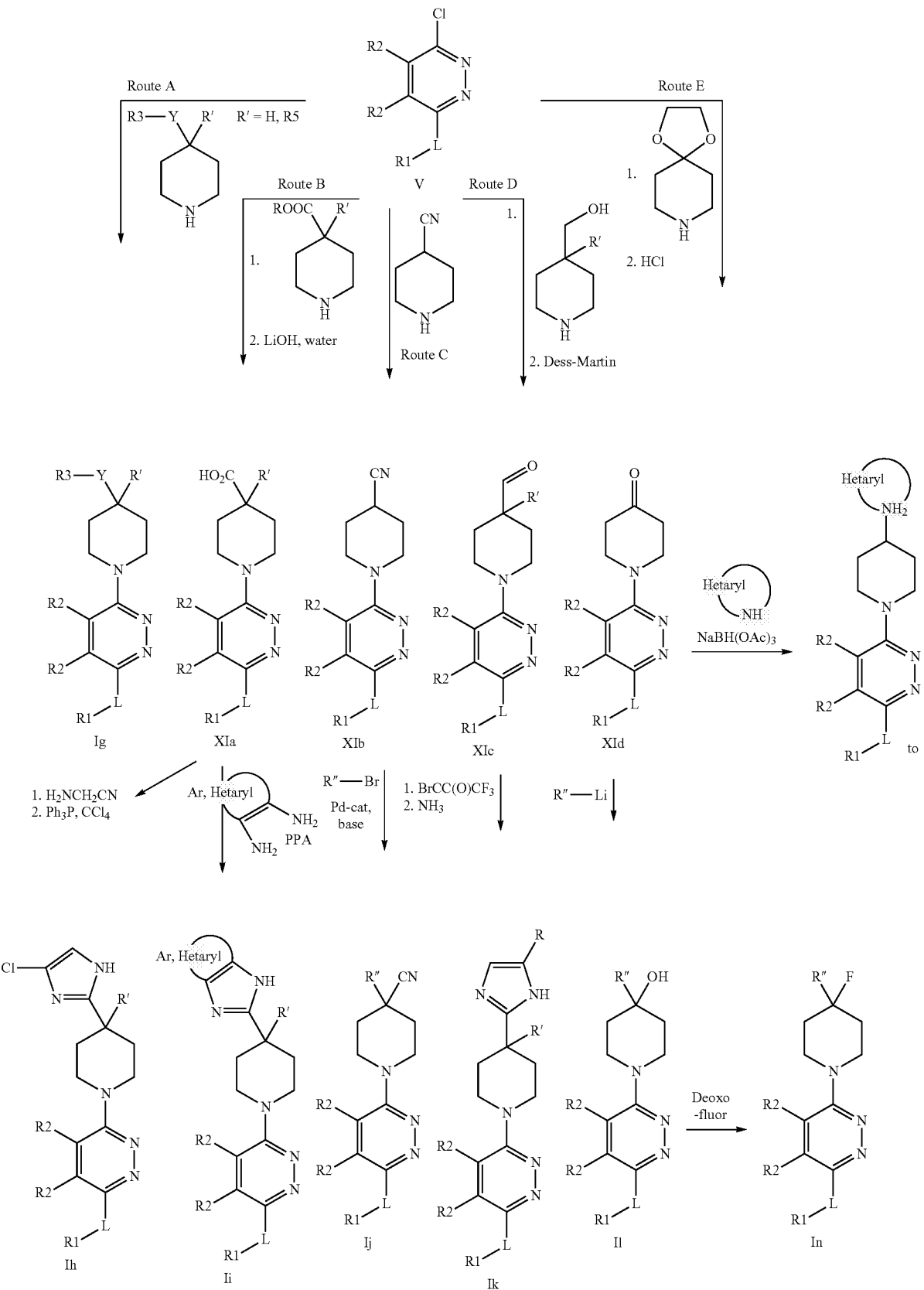

Synthesis of Example 56 by Route A

Example 56

2-[1-(6-Benzyl-4,5-dimethyl-pyridazin-3-yl)-piperidin-4-yl]-2,3dihydro-1H-isoindole

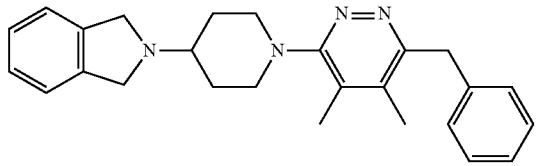 [SMILES: Cc1c(Cc2ccccc2)nnc(N2CCC(N3Cc4ccccc4C3)CC2)c1C]

Step 1: 8-(6-Benzyl-4,5-dimethyl-pyridazin-3-yl)-1,4-dioxa-8-aza-spiro[4,5]decane (compounds 23)

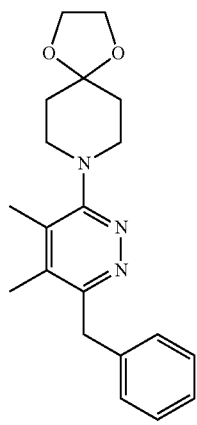 [SMILES: Cc1c(Cc2ccccc2)nnc(N2CCC3(CC2)OCCO3)c1C]

Compound 23 is prepared from 3-benzyl-6-chloro-4,5-dimethylpyridazine and 1,4-dioxa-8-aza-spiro[4.5]decane following the procedure similar to what described for compound 3.

$^1$H-NMR (400 MHz, CDCl$_3$) δ=1.89 (4H, m), 2.08 (3H, s), 2.17 (3H, s), 3.33 (4H, m), 4.00 (4H, s), 4.29 (2H, s), 7.22 (5H, m).

MS (m/z, MH+) meas. 340.4.

Step 2: 1-(6-Benzyl-4,5-dimethyl-pyridazin-3-yl)-piperidin-4-one (compound 24)

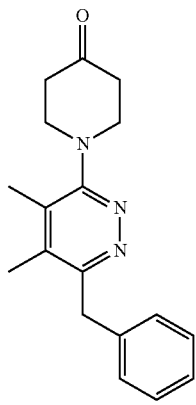 [SMILES: Cc1c(Cc2ccccc2)nnc(N2CCC(=O)CC2)c1C]

To compound 23 (917 mg, 2.46 mmol) in acetone (50 mL) is added hydrochloric acid (1.2 N, 20 mL). The mixture is stirred for 46 h, then treated with saturated sodium bicarbonate to slightly basic, and extracted with ethyl acetate (3×). The organic extracts are washed with brine, dried to give an oil that provides pure 24 as thick oil (565 mg, 78%) after purification by silica gel chromatography (40% ethyl acetate in heptane).

$^1$H-NMR (400 MHz, CDCl$_3$) δ=2.1 (3H, s), 2.2 (3H, s), 2.7 (4H, m), 3.6 (4H, m), 4.3 (2H, s), 7.3 (5H, m).

HR MS (m/z, MH+) meas. 296.1763.

Step 3: 2-[1-(6-Benzyl-4,5-dimethyl-pyridazin-3-yl)-piperidin-4-yl]-2,3dihydro-1H-isoindole (example 56)

To ketone 24 (43 mg, 0.15 mmol) in anhydrous THF/CH$_2$Cl$_2$ (1.5 ml/1.5 mL) is added isoindoline (25 μL, 0.22 mmol) and glacial acidic acid (3 μL) and triacetoxyl sodium borohydride (98 mg, 0.44 mmol). The mixture is stirred for 2 h and, quenched with saturated sodium bicarbonate, and extracted with CH$_2$Cl$_2$. The organic phase is dried, rotavaped, and was subjected to HPLC purification (aetonitrile-water-0.1% TFA) to give the title compound as a TFA salt (67 mg, 89%).

$^1$H-NMR (400 MHz, CDCl$_3$) δ=2.2 (4H, m), 2.3 (3H, s), 2.4 (3H, s), 3.2 (2H, m), 3.6 (1H, m), 3.8 (2H, m), 4.5 (4H, bs), 5.1 (2H, bs), 7.3 (9H, m).

HR MS (m/z, MH+) meas. 399.2547.

Synthesis of Examples 57-59 by Route B

Example 57

3-Benzyl-6-[4-(5-chloro-1H-imidazol-2-yl)-piperidin-1-yl]-4,5-dimethyl-pyridazine

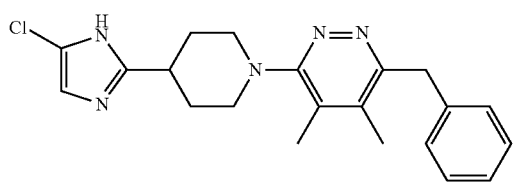 [SMILES: Cc1c(Cc2ccccc2)nnc(N2CCC(c3ncc(Cl)[nH]3)CC2)c1C]

Step 1: 1-(6-Benzyl-4,5-dimethyl-pyridazin-3-yl)-piperidine-4-carboxylic acid ethyl ester (compound 25)

To a solution of 3-benzyl-6-chloro-4,5-dimethyl-pyridazine (1.0 g, 4.31 mmol) in NMP (10 mL) is added piperidine-4-carboxylic acid ethyl ester (2.0 g, 12.9 mmol) and DIPEA (3.7 mL, 21.6 mmol). The mixture is heated in microwave at 210° C. for 1.5 h. The mixture is concentrated at 80° C. by rotovaporation. The crude product is purified by HPLC (CH$_3$CN/H$_2$O: 22%~45% with 0.1% TFA) to give 1-(6-benzyl-4,5-dimethyl-pyridazin-3-yl)-piperidine-4-carboxylic acid ethyl ester (0.94 g, 61%).

$^1$H-NMR (400 MHz, CDCl$_3$) δ=1.28 (3H, t), 1.90 (2H, q), 2.07 (2H, d), 2.23 (3H, s), 2.33 (3H, s), 2.54 (1H, m), 3.03 (2H, t), 3.57 (2H, d), 4.17 (2H, q), 4.50 (2H, s), 7.19 (2H, d), 7.24 (1H, d), 7.29 (2H, t).

HR MS (m/z, MH+) meas. 354.2179.

Step 2: 1-(6-Benzyl-4,5-dimethyl-pyridazin-3-yl)-piperidine-4-carboxylic acid (compound 26)

To a solution of 1-(6-benzyl-4,5-dimethyl-pyridazin-3-yl)-piperidine-4-carboxylic acid ethyl ester (0.88 g, 2.5 mmol) in EtOH (8 mL) is added a solution of sodium hydroxide (0.8 g, 20.1 mmol) in $H_2O$ (8 mL). After being stirred at 25° C. for 2 h, the mixture is concentrated, and extracted with $CH_2Cl_2$ (2×10 mL) to remove impurities. The aqueous layer is acidified by 1N HCl to pH~5, and extracted with $CH_2Cl_2$ (6×20 mL). The combined organic solution is dried over $Na_2SO_4$, filtered and concentrated to give 1-(6-benzyl-4,5-dimethyl-pyridazin-3-yl)-piperidine-4-carboxylic acid (0.68 g, 83%).
$^1$H-NMR (400 MHz, $CDCl_3$) δ=1.92 (2H, q), 2.08 (2H, d), 2.25 (3H, s), 2.35 (3H, s), 2.64 (1H, m), 3.11 (2H, t), 3.60 (2H, d), 4.49 (2H, s), 7.20 (2H, d), 7.26 (1H, t), 7.31 (2H, t).
HR MS (m/z, MH+) meas. 326.1870.

Step 3: 1-(6-Benzyl-4,5-dimethyl-pyridazin-3-yl)-piperidine-4-carboxylic acid cyanomethyl-amide (compound 27)

To a solution of 1-(6-benzyl-4,5-dimethyl-pyridazin-3-yl)-piperidine-4-carboxylic acid (350 mg, 1.08 mmol) in DMF (10 mL) is added DIPEA (0.94 mL, 5.4 mmol) and HATU (490 mg, 1.29 mmol). After being stirred at 25° C., aminoacetonitrile hydrochloride (119 mg, 1.29 mmol) is added. The mixture is stirred for 2 h, and diluted with EtOAc (20 mL) and washed with $H_2O$ (3×10 mL). The organic layer is dried over $Na_2SO_4$, filtered and concentrated. The crude product is purified by chromatography ($CH_2Cl_2$/MeOH: 97%/3%) to give 1-(6-benzyl-4,5-dimethyl-pyridazin-3-yl)-piperidine-4-carboxylic acid cyanomethyl-amide (280 mg, 72%).
$^1$H-NMR (400 MHz, $CDCl_3$) δ=1.97 (4H, m), 2.25 (3H, s), 2.36 (3H, s), 2.58 (1H, m), 3.07 (2H, t), 3.67 (2H, d), 4.12 (2H, d), 4.44 (2H, s), 7.14 (2H, d), 7.31 (3H, m).
MS (m/z, MH+) meas. 364.3.

Step 4: 3-Benzyl-6-[4-(5-chloro-1H-imidazol-2-yl)-piperidin-1-yl]-4,5-dimethyl-pyridazine (example 57)

To a solution of 1-(6-benzyl-4,5-dimethyl-pyridazin-3-yl)-piperidine-4-carboxylic acid cyanomethyl-amide (20 mg, 0.055 mmol) and triphenyl phosphine in acetonitrile (1 mL) at 25° C. is added carbon tetrachloride (42 mg, 0.28 mmol). After being stirred at 50° C. for 3 h, the mixture is concentrated, and diluted with $CH_2Cl_2$ (10 mL) and washed with sodium hydroxide (2 mL, 1N), and $H_2O$ (2 mL), dried over $Na_2SO_4$, filtered and concentrated. The crude product is purified by HPLC ($CH_3CN/H_2O$: 22%~45% with 0.1% TFA) to give 3-benzyl-6-[4-(5-chloro-1H-imidazol-2-yl)-piperidin-1-yl]-4,5-dimethyl-pyridazine (11.8 mg, 56%).
$^1$H-NMR (400 MHz, MeOH-$d_4$) δ=2.09 (2H, m), 2.20 (2H, d), 2.35 (3H, s), 2.50 (3H, s), 3.20 (3H, m), 3.87 (2H, d), 4.46 (2H, s), 7.25 (2H, d), 7.34 (1H, t), 7.35 (1H, s), 7.39 (2H, t).
HR MS (m/z, MH+) calc. 382.1794.

Example 58

2-[1-(6-Benzyl-4,5-dimethyl-pyridazin-3-yl)-piperidin-4-yl]-1H-imidazo[4,5-b]pyridine

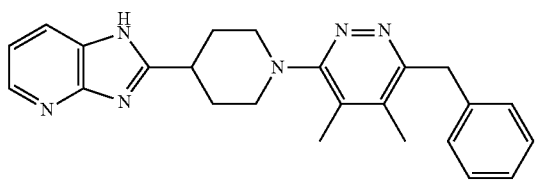 [SMILES: Cc1c(Cc2ccccc2)nnc(N2CCC(c3nc4ncccc4[nH]3)CC2)c1C]

To a solution of 1-(6-benzyl-4,5-dimethyl-pyridazin-3-yl)-piperidine-4-carboxylic acid (compound 26, 50 mg, 0.15 mmol) and 2,3-diaminopyridine (33 mg, 0.30 mmol) in $CH_2Cl_2$ (0.5 mL) is added polyphosphoric acid (1 mL). The mixture is concentrated to remove $CH_2Cl_2$. After being stirred at 150° C. for 1.5 h, the mixture is cooled to 25° C., diluted with water (10 mL), and basified by 10% aqueous solution of sodium hydroxide to pH~8. The aqueous solution is extracted with $CH_2Cl_2$ (5×15 mL). The combined organic layers are concentrated and purified by HPLC ($CH_3CN/H_2O$: 22% 45% with 0.1% TFA) to give 2-[1-(6-benzyl-4,5-dimethyl-pyridazin-3-yl)-piperidin-4-yl]-1H-imidazo[4,5-b]pyridine (33.8 mg, 55%).
$^1$H-NMR (400 MHz, MeOH-$d_4$) δ=2.28 (2H, qd), 2.36 (3H, s), 2.38 (2H, dd), 2.53 (3H, s), 3.29 (2H, t), 3.56 (1H, m), 3.93 (2H, d), 4.48 (2H, s), 7.25 (2H, d), 7.32 (1H, t), 7.39 (2H, t), 7.70 (1H, dd), 8.46 (1H, d), 8.62 (1H, d).
HR MS (m/z, MH+) meas. 399.2294.

Example 59

2-[1-(6-Benzyl-4,5-dimethyl-pyridazin-3-yl)-4-methyl-piperidin-4-yl]-1H-imidazo[4,5-c]pyridine

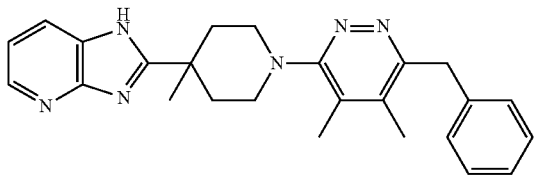 [SMILES: Cc1c(Cc2ccccc2)nnc(N2CCC(C)(c3nc4ncccc4[nH]3)CC2)c1C]

Step 1: 1-(6-Benzyl-4,5-dimethyl-pyridazin-3-yl)-4-methyl-piperidine-4-carboxylic acid ethyl ester (compound 28)

To a solution of 3-benzyl-6-chloro-4,5-dimethyl-pyridazine (1.0 g, 4.3 mmol) in NMP (10 mL) is added 4-methyl-piperidine-4-carboxylic acid ethyl ester (2.0 g, 8.6 mmol) and DIPEA (3.7 mL, 21.6 mmol). The mixture is heated in microwave at 210° C. for 1.5 h. The mixture is concentrated at 80° C. by rotovaporation. The crude product is purified by HPLC ($CH_3CN/H_2O$: 22% 45% with 0.1% TFA) to give 1-(6-benzyl-4,5-dimethyl-pyridazin-3-yl)-4-methyl-piperidine-4-carboxylic acid ethyl ester (0.64 g, 41%).
$^1$H-NMR (400 MHz, $CDCl_3$) δ=1.27 (3H, s), 1.29 (3H, t), 1.62 (2H, t), 2.24 (3H, s), 2.27 (2H, d), 2.34 (3H, s), 3.13 (2H, t), 3.47 (2H, d), 4.20 (2H, q), 4.42 (2H, s), 7.11 (2H, d), 7.28 (3H, m).
HR MS (m/z, MH+) meas. 368.2335.

Step 2: 1-(6-Benzyl-4,5-dimethyl-pyridazin-3-yl)-4-methyl-piperidine-4-carboxylic acid (compound 2)

To a solution of 1-(6-benzyl-4,5-dimethyl-pyridazin-3-yl)-4-methyl-piperidine-4-carboxylic acid ethyl ester (0.60 g, 1.6 mmol) in EtOH (5 mL) is added sodium hydroxide (0.5 g, 13.2 mmol) in $H_2O$ (5 mL). After being stirred at 25° C. for two hr, the mixture is concentrated, and extracted with $CH_2Cl_2$ (2×10 mL) to remove impurities. The aqueous layer is acidified by 1N HCl to pH~5, and extracted with $CH_2Cl_2$ (6×20 mL). The combined organic solution is dried over $Na_2SO_4$, filtered and concentrated to give 1-(6-benzyl-4,5-dimethyl-pyridazin-3-yl)-4-methyl-piperidine-4-carboxylic acid (0.49 g, 89%).

¹H-NMR (400 MHz, CDCl₃) δ=1.33 (3H, s), 1.60 (2H, t), 2.13 (3H, s), 2.23 (3H, s), 2.31 (2H, d), 3.17 (2H, t), 3.38 (2H, d), 4.42 (2H, s), 7.21 (2H, d), 7.27 (3H, t).

HR MS (m/z, MH+) meas. 340.2028.

Step 3: 2-[1-(6-benzyl-4,5-dimethyl-pyridazin-3-yl)-4-methyl-piperidin-4-yl]-1H-imidazo[4,5-c]pyridine (example 59)

To a solution of 1-(6-benzyl-4,5-dimethyl-pyridazin-3-yl)-4-methyl-piperidine-4-carboxylic acid (50 mg, 0.15 mmol) and 2,3-diaminopyridine (32 mg, 0.29 mmol) in CH₂Cl₂ (0.5 mL) is added polyphosphoric acid (1 mL). The mixture is concentrated to remove CH₂Cl₂. After being stirred at 150° C. for 3.5 h, the mixture is cooled to 25° C., diluted with water (3 mL), and basified by 10% aqueous solution of sodium hydroxide to pH~8. The aqueous is extracted with CH₂Cl₂ (3×10 mL). The combined organic layers are concentrated and purified by HPLC (CH₃CN/H₂O: 15%~40% with 0.1% TFA) to give 2-[1-(6-benzyl-4,5-dimethyl-pyridazin-3-yl)-4-methyl-piperidin-4-yl]-1H-imidazo[4,5-c]pyridine (21 mg, 27%).

¹H-NMR (400 MHz, MeOH-d₄) δ=1.60 (3H, s), 2.15 (2H, t), 2.34 (3H, s), 2.49 (3H, s), 2.65 (2H, d), 3.35 (2H, d), 3.65 (2H, d), 4.43 (2H, s), 7.22 (2H, d), 7.31 (1H, t), 7.37 (2H, t), 8.12 (1H, d), 8.56 (1H, d), 9.23 (1H, s).

HR MS (m/z, MH+) meas. 413.2446.

Synthesis of Example 60 by Route C

Example 60

1'-(6-Benzyl-4,5-dimethyl-pyridazin-3-yl)-5-(1-hydroxy-1-methyl-ethyl)-2',3',5',6'-tetrahydro-1'H-[2,4']bipyridinyl-4'-carbonitrile

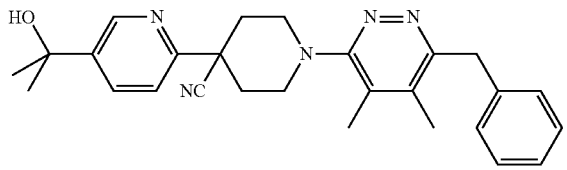 [SMILES: Cc1c(Cc2ccccc2)nnc(N2CCC(C#N)(c3ccc(C(C)(C)O)cn3)CC2)c1C]

Step 1: 1-(6-Benzyl-4,5-dimethyl-pyridazin-3-yl)-piperidine-4-carbonitrile (compound 30)

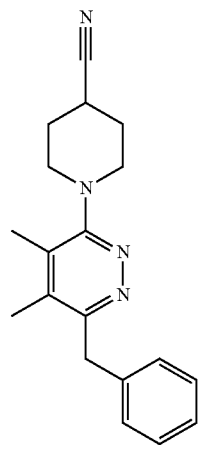 [SMILES: Cc1c(Cc2ccccc2)nnc(N2CCC(C#N)CC2)c1C]

Compound 30 is prepared from compound 10 and piperidine-4-carbonitrile following the procedure similar to what described for compound 3.

¹H-NMR (400 MHz, CDCl₃) δ=2.0-2.2 (4H, m), 2.1 (3H, s), 2.2 (3H, s), 2.8 (1H, m), 3.1 (2H, m), 3.4 (2H, m), 4.3 (2H, s), 7.2 (5H, m).

HR MS (m/z, MH+) meas. 307.1930.

Step 2: 2-(6-Bromo-pyridin-3-yl)-propan-2-ol (compound 31)

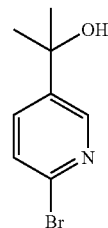

To 2-bromo-5-iodo-pyridine (2.974 g, 10.2 mmol) in a mixture of THF (15 mL) and ether (20 mL) at −78° C. is added dropwise n-butyl lithium (2.5 M in hexane, 4 L, 10.2 mmol). The mixture is stirred at −78° C. for 30 min, then acetone (anhydrous, 0.749 uL, 10.2 mmol) is added drop wise. The mixture is slowly warmed up to −50° C. over 1.5 h and is quenched with saturated ammonium chloride, extracted with ethyl acetate. The organic phase is separated, dried and rotavaped. The residue is purified by silica gel chromatography (10-20% ethyl acetate in heptane) to give the title compound as white solid (1.40 g, 64%).

¹H-NMR (400 MHz, CDCl₃) δ=1.60 (6H, s), 1.96 (1H, s), 7.45 (1H, d, J=8 Hz), 7.70 (1H, dd, J=4, 8 Hz), 8.47 (1H, s).

HR MS (m/z, MH+) meas. 216.0034.

Step 3: 1'-(6-Benzyl-4,5-dimethyl-pyridazin-3-yl)-5-(1-hydroxy-1-methyl-ethyl)-2',3',5',6'-tetrahydro-1'H-[2,4']bipyridinyl-4'-carbonitrile (example 60)

To a mixture of compound 30 (122 mg, 0.398 mmol) and compound 31 (103 mg, 0.478 mmol) in anhydrous toluene (3 mL) is added Pd₂(dba)₃ (18 mg, 0.020 mmol). The mixture is bubbled with nitrogen for 7 min, to which is added tri-t-butylphosphine (1.0 M in toluene, 40 μL, 0.040 mmol) and lithium hexamethyldisilazide (1.0 M in toluene, 0.995 uL. 0.995 mmol). The mixture is stirred at rt for 15 min, then at 60° C. for 3 h, and cooled to rt. Additional Pd₂(dba)₃ (18 mg), tri-t-butylphosphine (40 μL) and lithium hexamethyldisilazide (0.995 μL) are added to the reaction mixture. After being stirred for 17 h, the mixture is quenched with saturated ammonium chloride and extracted with ethyl acetate. The organic phase was washed with brine and dried, rotavaped and purified through preparative HPLC (acetonitrile-water-0.1% THF) to give the title compound as a TFA salt (24 mg, 11%).

¹H-NMR (400 MHz, CDCl₃) δ=1.63 (6H, s), 2.23 (2H, m), 2.27 (3H, s), 2.41 (3H, s), 2.58 (2H, m), 3.57 (2H, m), 3.81 (2H, m), 4.52 (2H, s), 7.30 (5H, m), 7.68 (1H, d, J=12 Hz), 7.96 (1H, m), 8.79 (1H, s).

HR MS (m/z, MH+) meas. 442.2600.

Synthesis of Example 61 by Route D

Synthesis of Intermediates (5'-Benzyl-3'A'-dimethyl-3,4,5,6-tetrahydro-2H-[1,2]bipyridinyl-4-yl)-methanol (compound 32)

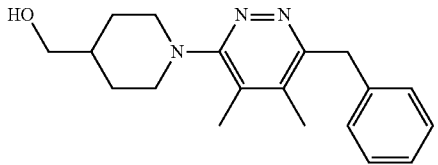 [SMILES: Cc1c(Cc2ccccc2)nnc(N2CCC(CO)CC2)c1C]

To the solution of piperidin-4-yl-methanol (125 mg, 1.03 mmol) in NMP (3 mL) is added 3-benzyl-6-chloro-4,5-dimethyl-pyridazine (60 mg, 0.258 mmol) and TEA. The reaction mixture is stirred at 210° C. in a microwave reactor for 2 h. Then the reaction mixture is diluted with DCM (15 mL) and washed with NaHCO$_3$ and water. The organic solvent is separated and removed under reduced pressure. Purification by HPLC of the crude product with acetonitrile in water (from 20% to 100% with 3% 1-propanol) at 220 nm wavelength detection provides the desired product as off white powder (200 mg, 62%).

$^1$H NMR (400 MHz, DMSO-d$_6$) δ=7.23-7.36 (m, 5H), 4.55 (t, J=5.3 Hz, 1H), 4.29 (s, 2H), 3.45 (m, 2H), 2.85 (m, 2H), 2.57 (s, 1H), 2.21 (s, 3H), 2.14 (s, 3H), 1.84 (m, 2H), 1.62 (m, 1H), 1.40 (m, 2H).

HR MS (m/z, MH+) meas. 312.2069, calc. 312.2076.

1-(6-Benzyl-4,5-dimethyl-pyridazin-3-yl)-piperidine-4-carbaldehyde (compound 33)

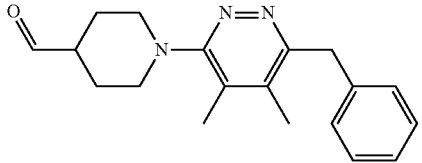 [SMILES: Cc1c(Cc2ccccc2)nnc(N2CCC(C=O)CC2)c1C]

To 5'-benzyl-3',4'-dimethyl-3,4,5,6-tetrahydro-2H-[1,2]bipyridinyl-4-yl)-methanol (155 mg, 0.473 mmol) in DCM (5 mL) is added Dess-Martin reagent (257 mg, 0.59 mmol), the reaction mixture is stirred at room temperature for 2 h. Then the reaction mixture is diluted with DCM and washed with NaHCO$_3$ and water. The organic phase is separated and the solvent removed under reduced pressure. Purification by HPLC of the crude product with acetonitrile in water (from 20% to 95% with 3% 1-propanol) at 220 nm wavelength detection provides the desired product as off white powder (120 mg, 78%).

MS (m/z, MH+) meas. 310.

Example 61

3-Benzyl-4,5-dimethyl-6-[4-(4-trifluoromethyl-1H-imidazol-2-yl)-piperidin-1-yl]-pyridazine

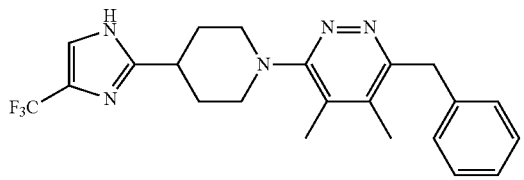 [SMILES: Cc1c(Cc2ccccc2)nnc(N2CCC(c3nc(C(F)(F)F)c[nH]3)CC2)c1C]

To the solution of sodium acetate trihydrate (50 mg, 0.615 mmol) in water (5 mL) is added 1,1-dibromo-3,3,3-trifluoro-acetone (83.5 mg, 0.307 mmol). The solution is heated 45 min at 100° C. bath temperature and then cooled. The solution is added to a solution of 1-(6-benzyl-4,5-dimethyl-pyridazin-3-yl)-piperidine-4-carbaldehyde (100 mg, 0.31 mmol) in MeOH (5 mL) and concentrated aqueous ammonia in MeOH (1.7 mL, 7M, 12 mmol). The reaction mixture is allowed to stand for 3.5 h at room temperature and the reaction mixture is then concentrated under reduced pressure to yield a semi-solid which is recrystallized from heptane to yield crude product. Purification by HPLC of the crude product with acetonitrile in water (from 10% to 100% with 3% 1-propanol) at 220 nm wavelength detection provides the desired product as off white powder (28 mg, 22%).

$^1$H NMR (400 MHz, DMSO-d$_6$) δ=7.72 (s, 1H), 7.23-7.36 (m, 5H), 4.29 (s, 2H), 3.52 (m, 1H), 3.37 (m, 2H), 2.97 (m, 2H), 2.24 (s, 3H), 2.20-1.97 (m, 4H), 2.14 (s, 3H).

HR MS (m/z, MH+) meas. 416.2050, calc. 416.2062.

Synthesis of Examples 62-64 by Route E

Example 62

2-[1-(6-Benzyl-4,5-dimethyl-pyridazin-3-yl)-piperidin-4-yl]-1,2,3,4-tetrahydro-isoquinoline

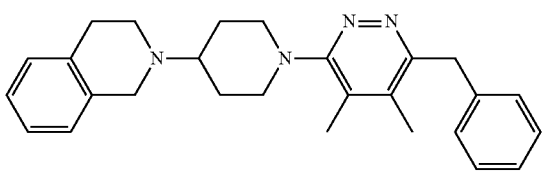 [SMILES: Cc1c(Cc2ccccc2)nnc(N2CCC(N3CCc4ccccc4C3)CC2)c1C]

This compound as a TFA salt is prepared from compound 24 and 1,2,3,4-tetrahydro-isoquinoline following a procedure used in example 56.

$^1$H-NMR (400 MHz, MeOH-d$_4$) δ=2.1 (2H, m), 2.3 (3H, s), 2.3 (2H, m), 2.4 (3H, s), 3.1-3.9 (9H, m), 4.4 (2H, s), 4.6 (2H, s), 7.3 (9H, m).

HR MS (m/z, MH+) meas. 413.2689.

Example 63

1'-(6-Benzyl-4,5-dimethyl-pyridazin-3-yl)-5-(1-hydroxy-1-methyl-ethyl)-2',3',5',6'-tetrahydro-1'H-[2,4']bipyridinyl-4'-ol

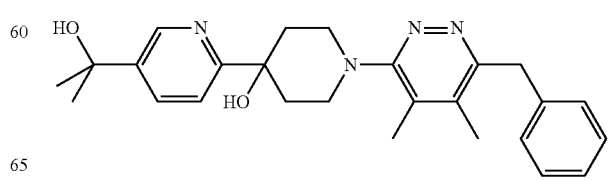

Step 1: 2-Bromo-5-[1-methyl-1-(2-trimethylsilanyl-ethoxymethoxy)-ethyl]-pyridine (compound 34)

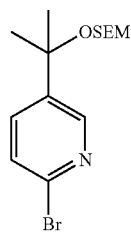

To compound 31 (532 mg, 2.46 mmol) in anhydrous DMF (5 mL) at 0° C. is added sodium hydride (60% in mineral oil, 138 mg, 3.45 mmol). The mixture is stirred at rt for 1 h and then cooled to 0° C., to which is added SEMCl (0.564 uL, 3.2 mmol). The mixture is stirred at rt for 16 h, 50° C. for 1 h, cooled to rt and quenched with water, extracted with ethyl acetate. The organic phase is washed with brine, dried and rotavaped. The oily residue is purified by silica gel chromatography (10-15% ethyl acetate in heptane) to afford the title compound as clear oil (474 mg, 56%).

$^1$H-NMR (400 MHz, CDCl$_3$) δ=0.0 (9H, s), 0.84 (2H, m), 1.59 (6H, s), 3.60 (2H, m), 4.60 (2H, s), 7.43 (1H, d, J=8 Hz), 7.61 (1H, m), 8.42 (1H, s).

HR MS (m/z, MH+) meas. 346.0822.

Step 2: 1'-(6-Benzyl-4,5-dimethyl-pyridazin-3-yl)-5-[1-methyl-1-(2-trimethylsilanyl-ethoxymethoxy)-ethyl]-2',3',5',6'-tetrahydro-1'H-[2,4]bipyridinyl-4'-ol (compound 35)

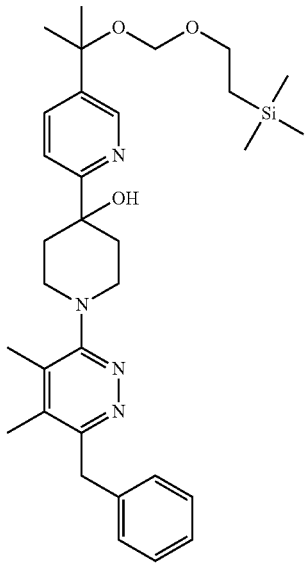

To compound 34 (272 mg, 0.786 mmol) in THF (6 mL) at −78° C. is added t-butyl lithium (1.7 M in pentane, 1.0 mL, 1.7 mmol). The mixture is stirred at −78° C. for 30 min, to which compound 24 (209 mg, 0.707 mmol) in THF (2 mL) is added at −78° C. The mixture is stirred and warmed up slowly to −40° C. in 1 h, then quenched at −40° C. with saturated ammonium chloride. THF is removed and the residue was extracted with ethyl acetate (3×). The organic phase is washed with brine, dried over anhydrous Na$_2$SO$_4$ and concentrated. The residue is purified by silica gel chromatography (40-60% ethyl acetate in heptane) to provide recovered compound 24 (103 mg, 49%) and the title compound 35 (106 mg, 27%) as a white solid.

$^1$H-NMR (400 MHz, CDCl$_3$) δ=0.0 (9H, s), 0.87 (2H, t, J=8 Hz), 1.64 (6H, s), 1.74 (2H, m), 2.10 (3H, s), 2.22 (3H, s), 2.28 (2H, m), 3.57 (6H, m), 4.31 (2H, s), 4.66 (2H, s), 4.95 (1H, s), 7.27 (5H, m), 7.43 (1H, m), 7.80 (1H, m), 8.62 (1H, m).

HR MS (m/z, MH+) meas. 563.3392.

Step 3: 1'-(6-Benzyl-4,5-dimethyl-pyridazin-3-yl)-5-(1-hydroxy-1-methyl-ethyl)-2',3',5',6'-tetrahydro-1'H-[2,4']bipyridinyl-4'-ol (example 63)

To compound 35 (44 mg, 0.078 mol) in CH$_2$Cl$_2$ (1.5 mL) at 0° C. is added TFA (0.15 μL). The mixture is stirred at 0° C. for 2 h and is quenched with 25% ammonium acetate, extracted with ethyl acetate. The organic phase is washed with brine, dried and concentrated to give a yellow residue which is purified by silica gel chromatography (0-5% methanol in CH$_2$Cl$_2$) to give the desired product (17 mg, 50%).

$^1$H-NMR (400 MHz, CDCl$_3$) δ=1.62 (6H, s), 1.72 (2H, m), 2.09 (3H, s), 2.21 (3H, s), 2.25 (2H, m), 3.50 (4H, m), 4.30 (2H, s), 7.20 (5H, m), 7.42 (1H, m), 7.86 (1H, m), 8.66 (1H, b.s).

HR MS (m/z, MH+) meas. 433.2590.

Example 64

2-[1'-(6-Benzyl-4,5-dimethyl-pyridazin-3-yl)-4'-fluoro-1',2',3',4',5',6'-hexahydro-[2,4']bipyridinyl-5-yl]-propan-2-ol

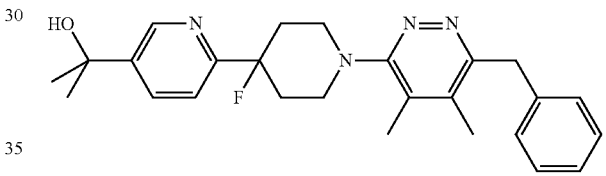

Step 1: 1'-(6-Benzyl-4,5-dimethyl-pyridazin-3-yl)-4'-fluoro-5-[1-methyl-1-(2-trimethylsilanyl-ethoxymethoxy)-ethyl]-1',2',3',4',5',6'-hexahydro-[2,4]bipyridinyl (compound 36)

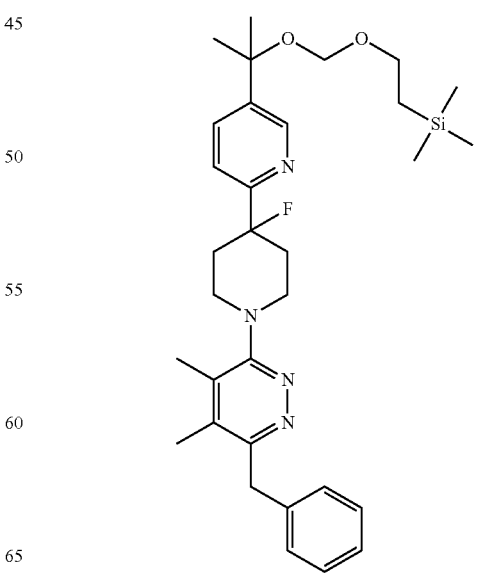

To compound 35 (39 mg, 0.069 mmol) at 0° C. is added cold deoxofluor (50% in THF, 665 μL, 1.38 mmol). The mixture is stirred at rt for 4 h, washed with saturated NaHCO₃, extracted with CH₂Cl₂ (3×). The organic phase is washed with brine, dried and concentrated to afford brown oil. Silica gel chromatography purification affords the titled compound (21 mg, 48%).

$^1$H-NMR (400 MHz, CDCl₃) δ=0.0 (9H, s), 0.9 (2H, t, J=8 Hz), 1.6 (6H, s), 2.0 (2H, m), 2.1 (3H, s), 2.2 (3H, s), 2.6 (2H, m), 3.4 (4H, m), 3.6 (2H, t, J=8 Hz), 4.3 (2H, s), 4.7 (2H, s), 7.2 (5H, m), 7.6 (1H, m), 7.8 (1H, m), 8.6 (1H, b.s).

HR MS (m/z, MH+) meas. 565.3369.

Step 2: 2-[1'-(6-Benzyl-4,5-dimethyl-pyridazin-3-yl)-4'-fluoro-1',2',3',4',5',6'-hexahydro-[2,4']bipyridinyl-5-yl]-propan-2-ol (example 64)

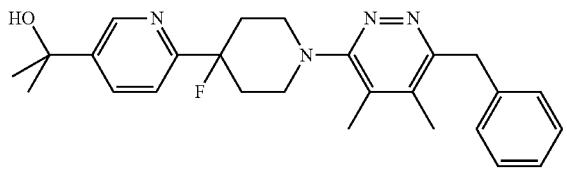 [SMILES: Cc1c(Cc2ccccc2)nnc(N2CCC(F)(c3ccc(C(C)(C)O)cn3)CC2)c1C]

This example is prepared from compound 36 and TFA following a procedure described for example 63.

$^1$H-NMR (600 MHz, CDCl₃) δ=1.63 (6H, s), 2.05 (2H, m), 2.19 (3H, s), 2.32 (3H, s), 2.55 (2H, m), 3.94 (4H, m), 4.53 (2H, b.s), 7.25 (5H, m), 7.59 (1H, d, J=6 Hz), 7.90 (1H, m), 8.71 (1H, b.s).

HR MS (m/z, MH+) meas. 435.2554.

Piperazinyl-Pyridazines

Scheme 6 shows a general synthetic scheme for the preparation of compounds of Formula Ip. Substituted 1,4-dichloropyridazines II can be reacted with organo-zinc reagents under palladium catalysis to form intermediates XII. Displacement of the remaining chlorine with an piperazine in the presence of base yields compounds XIII. Depending on the position of substituent(s) Z the use of a N-protecting group might be required to block the reactivity of one of the piperazine nitrogens. Intermediates XIII can react depending on the desired linker Y with R3-Cl in a nucleophilic displacement reaction under basic conditions, with R—CHO in a reductive amination with e.g. NaBH(OAc)₃, in acylation reactions with R3-OC(O)Cl or R3-NCO, R3-COCl under basic conditions or with R3-CO₂H in a amide coupling with e.g. HATU as coupling reagent to yield examples Ip. Additionally, displacement of the remaining chlorine in intermediate XII with a functionalized piperazine in the presence of base can yield directly examples Ip. (Route A). Alternatively, examples Ip can be prepared utilizing Route B and C in which the piperazine moiety is first installed by nucleophilic displacement reactions and the Negishi coupling is performed subsequently.

SCHEME 6

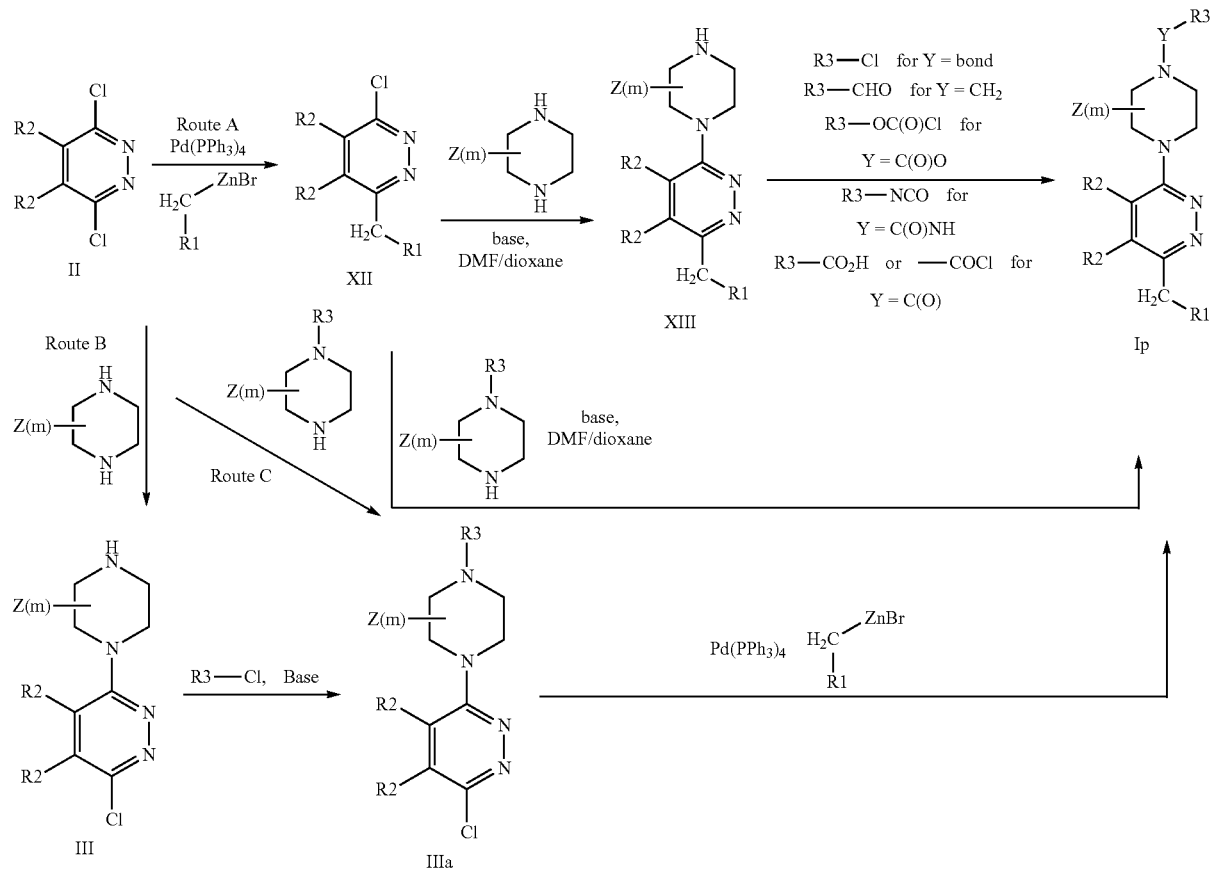

Synthesis of Intermediates II and XII 4,5-Dimethyl-1,2-dihydro-pyridazine-3,6-dione (compound 36)

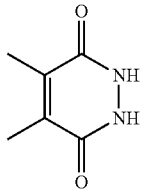

Hydrazine hydrochloride (58 g, 552 mmol) is dissolved in hot water (300 mL) and dimethyl maleic anhydride (58 g, 460 mmol) is added in portions and the suspension stirred at reflux for 16 h. The supension is cooled down to room temperature and the precipitate is filtered, washed with water and dried at 40° C. under vacuum to yield 4,5-dimethyl-1,2-dihydro-pyridazine-3,6-dione (36) (64 g, 99%).

$^1$H-NMR (400 MHz, DMSO-d$_6$) δ=11 (br s, 2H), 2.01 (s, 6H).
MS (m/z, MH+) meas. 141.1.

4,5-Dimethyl-1,4-dichloro-pyridazine (compound 37)

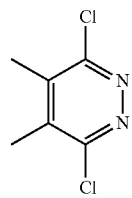

4,5-dimethyl-1,2-dihydro-pyridazine-3,6-dione (50 g, 357 mmol) is added to a 1 L flask and POCl$_3$ (250 mL) is slowly added. The suspension is stirred and heated to reflux and all starting material dissolves. After 2 h approximately 150 mL POCl$_3$ are removed under vacuum. The viscous, brown solution is poured in small portions slowly onto ice in a 1.5 L beaker under stirring. The orange suspension is neutralized with 28% aqueous ammonia under external cooling. The product is filtered with a Buchner funnel, washed with water and dried at 40° C. under vacuum to yield a off white powder (59 g, 93%).

$^1$H-NMR (400 MHz, CDCl$_3$) δ=2.44 (s, 6H).
MS (m/z, MH+) meas. 177.1.

2,3,6,7-Tetrahydro-5H-cyclopenta[d]pyridazine-1,4-dione (compound 38)

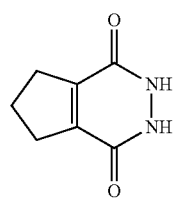 [SMILES: O=c1[nH][nH]c(=O)c2c1CCC2]

A solution of hydrazine hydrochloride (2.4 g, 22.8 mmol) and 1-cyclopentene-1,2-dicarboxylic anhydride (3.0 g, 21.7 mmol) in water (10 mL) is heated to reflux for 3 h. The reaction mixture is cooled down to room temperature and the precipitate is collected by filtration. The yellow solid is mixed with 15 mL 1N NaOH and stirred for 2 h, filtered and dried under vacuum to give 2,3,6,7-tetrahydro-5H-cyclopenta[d]pyridazine-1,4-dione (38) (2.2 g, 67%).
MS (m/z, MH+) meas. 153.1

1,4-Dichloro-6,7-dihydro-5H-cyclopenta[d]pyridazine (compound 39)

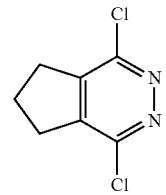 [SMILES: Clc1nnc(Cl)c2c1CCC2]

The compound is prepared analogous to compound 37 starting from compound 36. $^1$H-NMR (400 MHz, DMSO-d$_6$) δ=2.74-2.61 (m, 4H), 2.00 (m, 1H), 1.85 (m, 1H).
HR MS (m/z, MH+) meas. 188.9986.

2,3,5,6,7,8-Hexahydro-phthalazin-1,4-dione (compound 40)

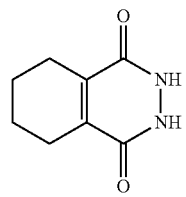 [SMILES: O=c1[nH][nH]c(=O)c2c1CCCC2]

To a solution of hydrazine (392 μL, 13.1 mmol) in water (6 mL) and HOAc (2 mL) is added 4,5,6,7-tetrahydro-isobenzofuran-1,3-dione (2 g, 13.1 mmol). The reaction mixture is refluxed for 3 h, then cooled down to room temperature and the precipitate is collected by filtration, washed with water and dried under vacuum to give 2,3,5,6,7,8-hexahydro-phthalazin-1,4-dione (40) (2.09 g, 96%).
MS (m/z, MH+) meas. 167.05.

1,4-Dichloro-5,6,7,8-tetrahydro-phthalazine (compound 41)

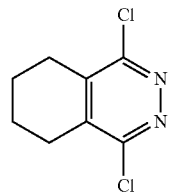 [SMILES: Clc1nnc(Cl)c2c1CCCC2]

The suspension of compound 40 (2.09 g, 12.6 mmol) in POCl$_3$ (10 mL) is refluxed for 1 h, cooled down, and poured into ice. The precipitate is collected by filtration and dried in a vacuum oven to give 1,4-dichloro-5,6,7,8-tetrahydro-phthalazine (41) (2.23 g, 87%).
HR MS (m/z, MH+) meas. 203.0139.

3-Benzyl-6-chloro-4,5-dimethyl-pyridazine (compound 42)

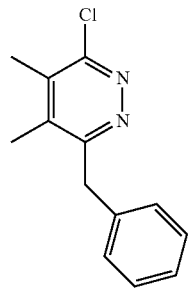 [SMILES: Cc1c(Cl)nnc(Cc2ccccc2)c1C]

A mixture of 4,5-dimethyl-1,4-dichloro-pyridazine (10 g, 56.5 mmol), tetrakis(triphenylphosphine)palladium(0) (3.3 g, 2.80 mmol) and THF (200 mL) is degassed and then benzylzinc bromide (147 mL, 0.5 M in THF, 73.40 mmol) is added. The reaction solution is heated to 65° C. overnight. Solvent is removed. Water is added and the water layer is extracted with EtOAc. The organic layer is concentrated to afford a crude product that is purified by chromatography on silica gel (EtOAc/Heptane: 0%~50%) to give the title compound (9.5 g, 67%).

$^1$H NMR (400 MHz, $CD_2Cl_2$) δ=7.27 (m, 5H), 4.38 (s, 2H), 2.36 (s, 3H), 2.21 (s, 3H).

HR MS (m/z, MH+) meas. 233.0839.

3-Chloro-6-(4-fluoro-benzyl)-4,5-dimethyl-pyridazine (compound 43)

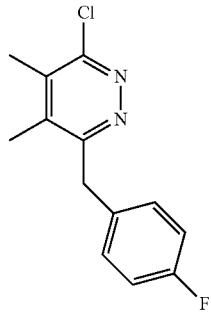 [SMILES: Cc1c(Cl)nnc(Cc2ccc(F)cc2)c1C]

Analogous to compound 42 above, 3-chloro-6-(4-fluoro-benzyl)-4,5-dimethyl-pyridazine is prepared from 4,5-dimethyl-1,4-dichloro-pyridazine and para-fluoro benzyl zinc bromide.

MS (m/z, MH+) meas. 251.1.

1-Benzyl-4-chloro-6,7-dihydro-5H-cyclopenta[d]pyridazine (compound 44)

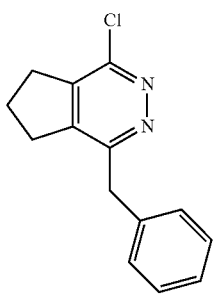 [SMILES: Clc1nnc(Cc2ccccc2)c2c1CCC2]

To a solution of 1,4-dichloro-6,7-dihydro-5H-cyclopenta[d]pyridazine (compound 39, 500 mg, 2.64 mmol) in THF (5 mL) is added Pd(PPh$_3$)$_4$ (383 mg, 0.33 mmol). The mixture is degassed and benzyl zinc bromide (11 mL, 0.5 M in THF, 5.6 mmol) is added. The mixture is heated at 60° C. for 5 h. The reaction mixture is cooled down to RT and saturated aq. NaHCO$_3$ solution is added and the mixture is extracted with EtOAc. The combined orgaqnic layers are washed with water, brine, dried over NaSO$_4$, filtered and concentrated. The crude product is purified by flash chromatography (EtOAc/heptane 10%-30%) to give compound 44 (490 mg, 76%).

$^1$H-NMR (400 MHz, $CD_2Cl_2$) δ=7.30-7.21 (m, 5H), 4.28 (s, 2H), 2.97 (m, 2H), 2.84 (m, 2H), 2.09 (m, 2H).

HR MS (m/z, MH+) meas. 245.0848.

1-Chloro-4-(4-fluoro-benzyl)-6,7-dihydro-5H-cyclopenta[d]pyridazine (compound 45)

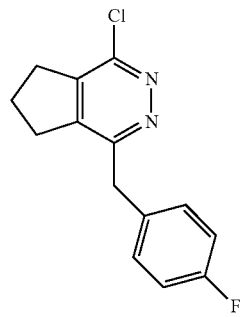 [SMILES: Fc1ccc(Cc2nnc(Cl)c3c2CCC3)cc1]

Compound 45 is prepared analogous to compound 44 starting from of 1,4-dichloro-6,7-dihydro-5H-cyclopenta[d]pyridazine (compound 39) and para-fluorobenzyl zinc bromide.

$^1$H-NMR (400 MHz, $CD_2Cl_2$) δ=7.23 (m, 2H), 6.99 (m, 2H), 4.27 (s, 2H), 2.98 (m, 2H), 2.84 (m, 2H), 2.11 (m, 2H).

HR MS (m/z, MH+) meas. 263.0752.

1-Chloro-4-(4-fluoro-benzyl)-5,6,7,8-tetrahydrophthalazine (compound 46)

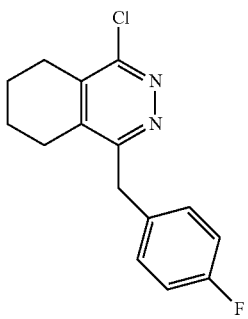 [SMILES: Fc1ccc(Cc2nnc(Cl)c3c2CCCC3)cc1]

To a solution of 1,4-dichloro-5,6,7,8-tetrahydro-phthalazine (compound 41, 0.50 g, 2.46 mmol) in THF (5 mL) are added 4-fluoro-benzyl zincchloride (0.5M in THF) (6.40 mL, 3.20 mmol) and palladium tetrakis triphenylphosphine (0.36 g, 0.31 mmol). The mixture is degassed and stirred at 50° C. overnight. Then the reaction mixture is cooled down to room temperature, sat. NaHCO$_3$ and water are added and the mixture is extracted with EtOAc. The combined organic layers are washed with brine, dried over Na$_2$SO$_4$, filtered and concentrated down. The crude product is purified by chromatography (EtOAc/heptane: 10%~40%) to give 1-chloro-4-(4-fluoro-benzyl)-5,6,7,8-tetrahydro-phthalazine (46) (0.51 g, 30%).

MS (m/z, MH+) meas. 277.11.

Synthesis of Intermediates XIII

General Protocol for the Amination of Chlorides XII with Piperazines to Yield Compounds 48-53 (Route A)

To a solution of XII (0.4 mmol) in NMP or DMF/dioxane (2 mL) is added the piperazine (0.6 mmol). The reaction mixture is heated at 190° C. for 4 h in a microwave reactor. It is cooled down to rt, diluted with DCM, washed with aq. NaHCO₃ solution and the organic layers are removed to afford the crude product. Flash chromatography of the crude product with EtOAc/heptane (20% to 50%) and then MeOH/DCM (5% to 20%) provides the product as a yellow solid after removal of the solvents (~50%-70%)

3-Benzyl-4,5-dimethyl-6-((R)-3-methyl-piperazin-1-yl)-pyridazine (compound 47)

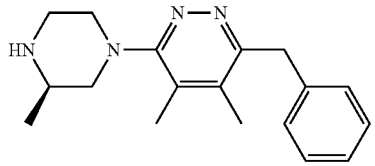 [SMILES: Cc1c(Cc2ccccc2)nnc(N2CCN[C@H](C)C2)c1C]

Preparation A:

3-Chloro-4,5-dimethyl-6-((R)-3-methyl-piperazin-1-yl)-pyridazine (400 mg, 1.66 mmol, 1 eq) is added to a solution of benzylzinc bromide (12.3 mL 0.5 M in THF, 6.64 mmol, 4 eq) and tetrakis(triphenylphosphine)palladium (100 mg, 0.08 mmol, 0.05 eq) in a microwave vial. The vial is sealed and irradiated in the microwave at 100° C. (high absorption setting) for 40 min. The reaction mixture is concentrated and purified by silica gel chromatography (5-20% EtOAc/heptane) to yield the desired compound (324 mg, 66%).

Preparation B:

To a solution of 3-benzyl-6-chloro-4,5-dimethyl-pyridazine (100 mg, 0.41 mmol) in NMP (2 mL) is added 2-(R)-methyl-piperazine (62 mg, 0.61 mmol). The reaction mixture is heated at 190° C. for 4 h in a microwave reactor. It is cooled down to rt, diluted with DCM, washed with aq. NaHCO₃ solution and the organic layers are removed to afford the crude product. Flash chromatography of the crude product with EtOAc/heptane (20% to 50%) and then MeOH/DCM (5% to 20%) provides the product as a yellow solid after removal of the solvents (74 mg, 61%).

¹H NMR (400 MHz, DMSO-d₆) δ=7.22-7.34 (m, 2H), 7.11-7.22 (m, 3H), 4.22 (s, 2H), 3.13-3.26 (m, 2H), 2.81-2.99 (m, 3H), 2.70-2.80 (m, 1H), 2.38-2.48 (m, 1H), 2.15 (s, 3H), 2.08 (s, 3H), 1.00 (d, J=6.5 Hz, 3H).

HR MS (m/z, MH+) meas. 297.2089.

Compound 46-53:

The following table (Table 4) lists compounds prepared by amination as described above:

TABLE 4

| Compound | Structure | HR MS [m/z, MH+] meas. |
|---|---|---|
| 48 | 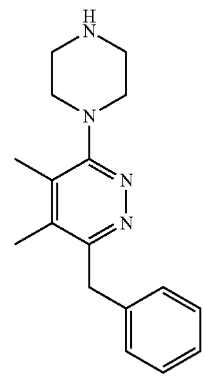 [SMILES: Cc1c(Cc2ccccc2)nnc(N2CCNCC2)c1C] | 283.1918 |
| 49 | 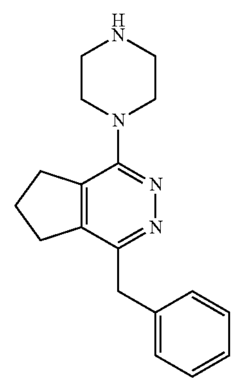 [SMILES: c1ccc(Cc2nnc(N3CCNCC3)c3c2CCC3)cc1] | 294.4028 |
| 50 | 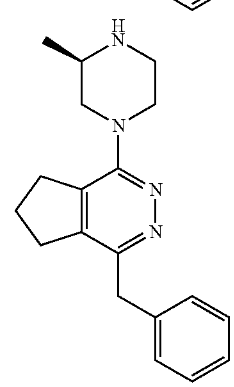 | 308 (MS) |
| 51 | 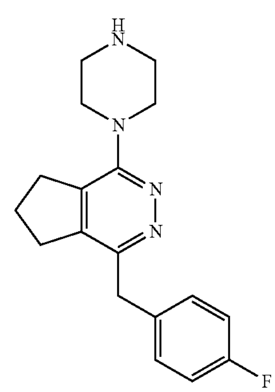 [SMILES: Fc1ccc(Cc2nnc(N3CCNCC3)c3c2CCC3)cc1] | 326 (MS) |

TABLE 4-continued

| Compound | Structure | HR MS [m/z, MH+] meas. |
|---|---|---|
| 52 | 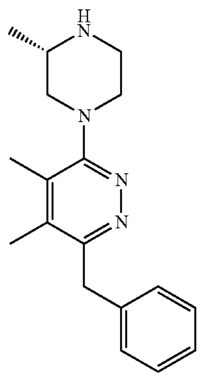 [SMILES: Cc1c(Cc2ccccc2)nnc(N2CCN[C@@H](C)C2)c1C] | 297.2088 |
| 53 | 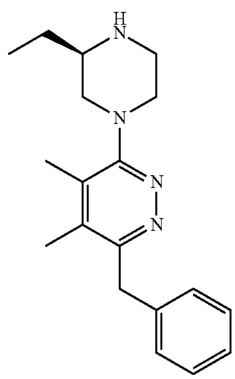 [SMILES: CC[C@@H]1CN(c2nnc(Cc3ccccc3)c(C)c2C)CCN1] | 311.5 (MS) |

Intermediates from Route B

3-Chloro-4,5-dimethyl-6-((R)-3-methyl-piperazin-1-yl)-pyridazine (compound 54)

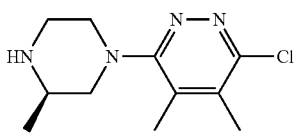 [SMILES: Cc1c(Cl)nnc(N2CCN[C@H](C)C2)c1C]

Solid K$_2$CO$_3$ (10 g, 72.4 mmol, 1.8 eq) is added to a solution of (R)-2-methyl-piperazine (4.00 g, 40 mmol, 1 eq) and 3,6-dichloro-4,5-dimethyl-pyridazine (8 g, 45.2 mml, 1.1 eq) in DMF (50 mL), and the resulting solution is stirred at 60° C. for 48 h. The reaction mixture is concentrated to ½ volume under reduced pressure and the minimum water (ca. 15 mL) required to dissolve the solid salts is added, followed by the addition of dichloromethane (100 mL). The organic layer is separated, dried over sodium sulfate and concentrated under reduced pressure, then purified by silica gel column chromatography (2%-20% MeOH/CH$_2$Cl$_2$) to yield the desired compound as a white solid (4.7 g, 49%).

$^1$H NMR (400 MHz, CDCl$_3$) δ=3.08-3.21 (m, 2H), 2.73-2.92 (m, 4H,) 2.47 (dd, J=12.4 Hz, 10.2 Hz, 1H), 2.13 (s, 3H), 2.07 (s, 3H), 0.93 (d, J=6.3 Hz, 3H).

HR MS (m/z, MH+): meas. 241.1218.

3-Chloro-4,5-dimethyl-6-(piperazin-1-yl)-pyridazine (compound 55)

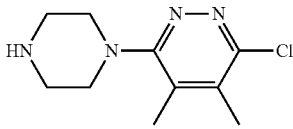

Compound 55 is prepared as described above from piperazine and 3,6-dichloro-4,5-dimethyl-pyridazine.

MS (m/z, MH+) meas. 227.

(R)-4-(6-Chloro-4,5-dimethyl-pyridazin-3-yl)-2-methyl-3,4,5,6-tetrahydro-2H-[1,2']bipyrazinyl-5'-carboxylic acid methyl ester (compound 56)

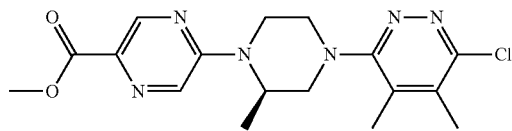 [SMILES: COC(=O)c1cnc(N2CCN(c3nnc(Cl)c(C)c3C)C[C@H]2C)cn1]

3-Chloro-4,5-dimethyl-6-((R)-3-methyl-piperazin-1-yl)-pyridazine (1.20 g, 4.88 mmol), 5-chloro-pyrazine-2-carboxylic acid methyl ester (946 mg, 5.37 mmol), triethylamine (3.40 mL, 24.4 mmol), and 1,4-dioxane (10 mL) are combined in a 100 mL round-bottom flask fitted with a reflux condenser and heated to 80° C. for 24 h. The reaction is then allowed to cool to room temperature and stirred for 48 h. A beige solid precipitates during this time which is isolated by filtration, rinsing with H$_2$O. The precipitate is dried in vacuo to afford the title compound (1.30 g, 71%).

MS (m/z, MH+) meas. 377.3.

2-[(R)-4-(6-Chloro-4,5-dimethyl-pyridazin-3-yl)-2-methyl-3,4,5,6-tetrahydro-2H-[1,2']bipyrazinyl-5'-yl]-propan-2-ol (compound 57)

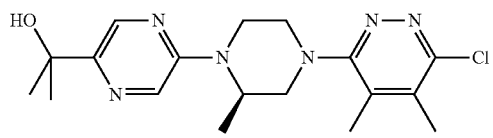

(R)-4-(6-Chloro-4,5-dimethyl-pyridazin-3-yl)-2-methyl-3,4,5,6-tetrahydro-2H-[1,2']bipyrazinyl-5'-carboxylic acid methyl ester (400 mg, 1.04 mmol) is suspended in THF (12 mL) and cooled to −78° C. Methylmagnesium iodide (2.8 mL, 3 M in diethyl ether, 8.4 mmol) is added dropwise. The reaction is stirred for 30 min, warmed to 0° C., and stirred an additional 30 min. Sat. aq. NH$_4$Cl (10 mL) is added to quench, followed by additional H$_2$O (40 mL). The organics are extracted with EtOAc (3×50 mL), dried and concentrated to give the desired product as a beige powder (415 mg, quant.).

MS (m/z, MH+) meas. 359.3.

2-[(R)-4-(6-Chloro-4,5-dimethyl-pyridazin-3-yl)-2-methyl-piperazin-1-yl]-4-trifluoromethyl-pyrimidine-5-carboxylic acid methyl ester (compound 58)

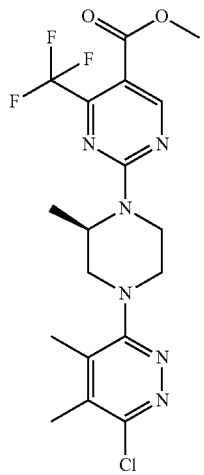 [SMILES: COC(=O)c1cnc(N2CCN(c3nnc(Cl)c(C)c3C)C[C@H]2C)nc1C(F)(F)F]

Triethylamine (2.0 mL, 14.4 mmol, 2.9 eq) is added to a solution of 2-chloro-4-trifluoromethyl-pyrimidine-5-carboxylic acid methyl ester (1.25 g, 5.0 mmol, 1 eq), 3-chloro-4,5-dimethyl-6-((R)-3-methyl-piperazin-1-yl)-pyridazine (1.20 g, 5.0 mmol, 1 eq) in dichloromethane (40 mL) and the resulting solution is stirred at rt for 2 h. The reaction mixture is diluted with dichloromethane (50 mL) and washed with water (25 mL), then brine (25 mL). The organic layer is separated, dried over sodium sulfate and concentrated under reduced pressure to a white residue. The desired compound is isolated by silica gel chromatography (10-75% EtOAc/heptane) as a white solid (1.83 g, 82%).

$^1$H NMR (400 MHz, DMSO-$d_6$) δ=9.00 (s, 1H), 4.92-5.15 (m, 1H), 4.54-4.76 (m, 1H), 3.84 (s, 3H), 3.59 (d, J=14.0 Hz, 1H), 3.50 (t, J=12.8 Hz, 2H), 3.08 (dd, J=12.8 Hz, 3.3 Hz, 1H), 2.89-2.99 (m, 1H), 2.36 (s, 3H), 2.33 (s, 3H), 1.39 (d, J=7.0 Hz, 3H).

HR MS (m/z, MH+): meas. 445.1373.

2-[(R)-4-(6-Chloro-4,5-dimethyl-pyridazin-3-yl)-2-methyl-piperazin-1-yl]-4-trifluoromethyl-pyrimidine-5-carboxylic acid ethyl ester (compound 59)

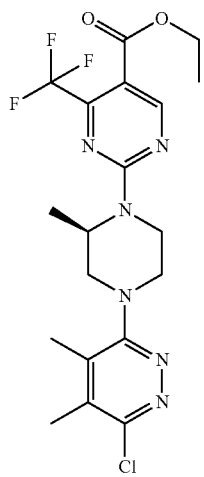 [SMILES: CCOC(=O)c1cnc(N2CCN(c3nnc(Cl)c(C)c3C)C[C@H]2C)nc1C(F)(F)F]

Following the protocol above with 2-chloro-4-trifluoromethyl-pyrimidine-5-carboxylic acid ethyl ester (400 mg, 1.57 mmol, 1 eq) and 3-chloro-4,5-dimethyl-6-((R)-3-methyl-piperazin-1-yl)-pyridazine (400 mg, 1.66 mmol, 1 eq) affords 700 mg of desired product as a white solid (97%).

$^1$H NMR (400 MHz, DMSO-$d_6$) δ=8.94 (s, 1H), 5.12-5.18 (m, 1H), 4.70-4.85 (m, 1H), 4.35 (q, J=7.0 Hz, 2H), 3.48-3.56 (m, 2H), 3.40 (d, J=12.5 Hz, 1H), 3.21 (d, J=10.5 Hz, 1H), 3.02-3.14 (m, 1H), 2.36 (s, 3H), 2.35 (s, 3H), 1.44 (d, J=7.0 Hz, 3H), 1.37 (t, J=7.0 Hz, 3H).

3-Chloro-4,5-dimethyl-6-[(R)-3-methyl-4-(5-trifluoromethyl-pyridin-2-yl)-piperazin-1-yl]-pyridazine (compound 60)

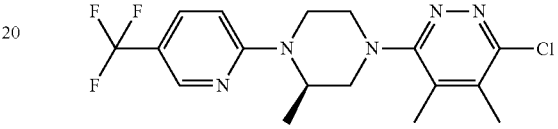

Combine 3,6-dichloro-4,5-dimethyl-pyridazine (100 mg, 0.554 mmol), (R)-2-methylpiperazine (85 mg, 0.831 mmol), potassium carbonate (383 mg, 2.77 mmol) and DMF (1 mL) in vial. Heat in the microwave at 120° C. for 3.25 h. Add 2-chloro-5-trifluoromethylpyridine (181 mg, 0.997 mmol) and heat at 180° C. for 30 min. The crude reaction is purified directly by flash chromatography on silica gel (0-40% EtOAc in heptanes) to afford the title compound as a light yellow solid (78 mg, 37%).

MS (m/z, MH+) meas. 386.4

Intermediates from Route C

3-Chloro-4,5-dimethyl-6-[4-(5-trifluoromethyl-pyridin-2-yl)-piperazin-1-yl]-pyridazine (compound

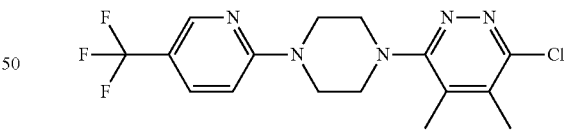

1-(5-Trifluoromethyl-pyridin-2-yl)-piperazine (10 g, 43.3 mmol) is combined with 3,6-dichloro-4,5-dimethyl-pyridazine (14.4 g, 84.3 mmol), triethylamine (8.25 mL), and NMP (40 mL). The reaction mixture is irradiated to a temperature of 180° C. for 25 min, and then concentrated in vacuo. The residue is purified by flash chromatography on silica gel (0-8% MeOH/CH$_2$Cl$_2$) to afford the title compound (13.2 g, 82%).

$^1$H NMR (400 MHz, DMSO-$d_6$) δ=8.48-8.41 (m, 1H), 7.84 (dd, J=9.1 Hz, 2.4 Hz, 1H), 7.03 (d, J=9.1 Hz, 1H), 3.88-3.76 (m, 4H), 3.28-3.20 (m, 4H), 2.31 (s, 6H).

1-Chloro-4-[4-(5-trifluoromethyl-pyridin-2-yl)-piperazin-1-yl]-6,7-dihydro-5H-cyclopenta[d]pyridazine (compound 62)

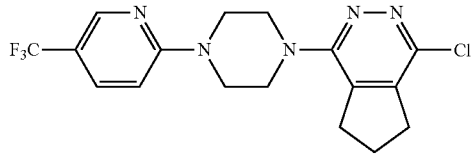 [SMILES: FC(F)(F)c1ccc(N2CCN(c3nnc(Cl)c4c3CCC4)CC2)nc1]

To a solution of 4-dichloro-6,7-dihydro-5H-cyclopenta[d]pyridazine (compound 39, 500 mg, 2.64 mmol) in NMP (5 mL) is added 1-[5-trifluoromethyl)-pyrid-2-yl)-piperazine (581 mg, 2.51 mmol) followed by triethyl amine (1.1 mL, 7.9 mmol). The mixture was heated in a microwave reactor for 170° C. for 60 min. Water was added to the reaction mixture and extracted with EtOAc. The combined organic extracts were washed with water, brine, dried over $Na_2SO_4$, filtered and concentrated. The crude product was tritirated with methanol to provide the title compound (483 mg, 48%).

$^1$H NMR ($CD_2Cl_2$) δ=8.41 (s, 1H), 7.68 (dd, J=8.9 Hz, 2.5 Hz, 1H), 6.73 (d, J=8.9 Hz, 1H), 3.80 (m, 4H), 3.60 (m, 4H), 3.04 (m, 2H), 2.95 (m, 2H), 2.16 (m, 2H).
HR MS (m/z, MH+): meas. 384.1190.

1-Chloro-4-[4-(5-trifluoromethyl-pyridin-2-yl)-piperazin-1-yl]-5,6,7,8-tetrahydro-phthalazine (compound 63)

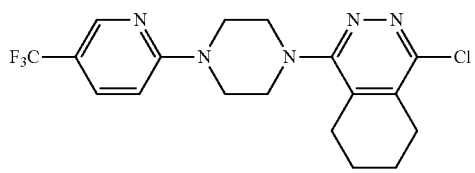 [SMILES: FC(F)(F)c1ccc(N2CCN(c3nnc(Cl)c4c3CCCC4)CC2)nc1]

To a solution of 1,4-dichloro-5,6,7,8-tetrahydro-phthalazine (compound 25, 100 mg, 0.492 mmol) in NMP (3 mL) is added 1-[5-trifluoromethyl)-pyrid-2-yl)-piperazine (114 mg, 0.492 mmol) followed by triethyl amine (218 µL, 1.57 mmol). The mixture was heated in a microwave reactor for 140° C. for 60 min. Water was added to the reaction mixture and extracted with EtOAc. The combined organic extracts were washed with water, brine, dried over $Na_2SO_4$, filtered and concentrated. The crude product was purified by flash chromatography on silica gel (EtOAc/heptane 10% to 70%) to yield 96 mg (49%) of the title compound.

$^1$H NMR (400 MHz, $CD_2Cl_2$) δ=8.41 (s, 1H), 7.73 (dd, J=9.0 Hz, 2.5 Hz, 1H), 6.79 (d, J=9.0 Hz, 1H), 3.85 (m, 4H), 3.40 (m, 4H), 2.76-2.68 (m, 4H), 1.93 (m, 2H), 1.80 (m, 2H).
HR MS (m/z, MH+) meas. 398.1359.

6-[4-(4-Chloro-5,6,7,8-tetrahydro-phthalazin-1-yl)-piperazin-1-yl]-nicotinic acid ethyl ester (compound 64)

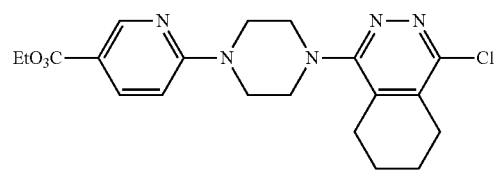

The compound is prepared in a similar fashion as described above.
MS (m/z, MH+) meas. 402.2

6-[(S)-4-(4-Chloro-6,7-dihydro-5H-cyclopenta[d]pyridazin-1-yl)-3-methyl-piperazin-1-yl]-nicotinic acid methyl ester (compound 65)

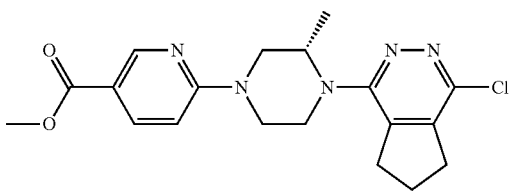 [SMILES: COC(=O)c1ccc(N2CCN(c3nnc(Cl)c4c3CCC4)[C@@H](C)C2)nc1]

To a solution of 1,4-dichloro-6,7-dihydro-5H-cyclopenta[d]pyridazine (150 mg, 0.79 mmol) in NMP (5 mL) is added (S)-3-methyl-3,4,5,6-tetrahydro-2H-[1,2']bipyrazinyl-5'-carboxylic acid ethyl ester (297 mg, 1.19 mmol) and triethyl amine (332 µL, 2.39 mmol). The reaction mixture is heated in a microwave reactor at 195° C. for 4 h. Water and EtOAc is added. The layers are separated and the aqueous layer is extracted with EtOAc. The combined organic layers are washed with water, brine, dried over $Na_2SO_4$, filtered and concentrated. The crude product is purified by flash chromatography (EtOAx/heptane 10% to 70%) to yield 50 mg (16%) of the title compound.

4-(6-Chloro-4,5-dimethyl-pyridazin-3-yl)-3,4,5,6-tetrahydro-2H-[1,2']bipyrazinyl-5'-carboxylic acid methyl ester (compound 66)

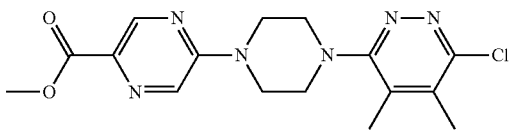

To the solution of 3,4,5,6-tetrahydro-2H-[1,2']bipyrazinyl-5'-carboxylic acid methyl ester (250 mg, 1.07 mmol) in NMP (5 mL) is added 3,6-dichloro-4,5-dimethyl-pyridazine (237 mg, 1.33 mmol) and TEA (446 µl, 3.21 mmol), the reaction mixture is stirred at 190° C. for 60 min. Water is added to the mixture and extracted with EtOAc. The combined organic layers are washed with water, brine, dried over $Na_2SO_4$, filtered and concentrated. The crude product is purified by HPLC, (acetonitrile/water: 10%~95% with 3% 1-propanol) to give white powder (165 mg, 43%).

$^1$H-NMR (400 MHz, DMSO-$d_6$) δ=8.69 (s, 1H), 8.44 (s, 1H), 3.92 (t, J=5.0 Hz, 4H), 3.83 (s, 3H), 3.27 (m, 4H), 2.41 (s, 3H), 2.32 (s, 3H).
MS (m/z, MH+) meas. 363.

Synthesis of Examples 65-72

General Protocol for the Negishi Coupling of Pyridazine Chlorides IIIA with Aryl Zinc Bromides to Yield Examples 65-69 (Route B/C)

To a solution of chloropyridazine IIIa (0.15 mmol, 1 eq.) in THF (5 ml) is added Pd(PPh$_3$)$_4$ (12.5 mol %). The mixture is degassed and aryl zincbromide (0.225, 1.5 eq., e.g. as a 0.5 M solution in THF) is added and the mixture is heated in a microwave reactor at 80° C. for 30 min. The reaction mixture is cooled to rt, water is added and the mixture is extracted with EtOAc. The combined organic extracts are washed with water, brine, dried over sodium sulfate, filtered and concentrated. The crude product is purified by flash chromatography on silica gel with EtOAc/heptane as eluent to yield examples Ip.

The following table (Table 5) lists compounds prepared by Negishi coupling as described above:

TABLE 5

| Example | Structure | HR MS [m/z, MH+] meas. |
|---|---|---|
| 65 | 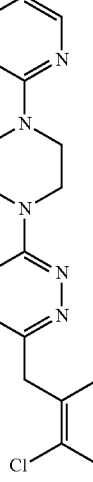 | 474.1670 |
| 66 | | 476.1865 |
| 67 | 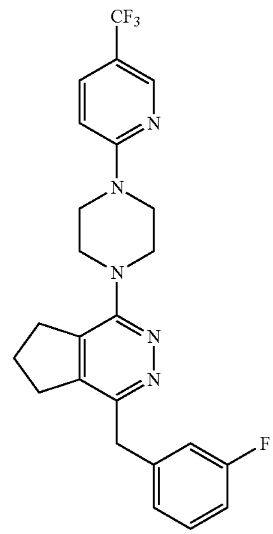 [SMILES: Fc1cccc(Cc2nnc(N3CCN(c4ccc(C(F)(F)F)cn4)CC3)c3c2CCC3)c1] | 458.1974 |
| 68 | 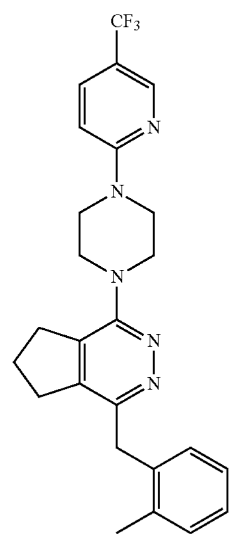 [SMILES: Cc1ccccc1Cc1nnc(N2CCN(c3ccc(C(F)(F)F)cn3)CC2)c2c1CCC2] | 454.2226 |
| 69 | 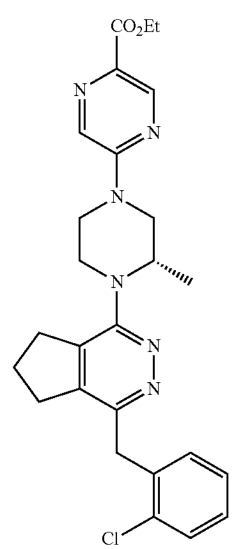 [SMILES: CCOC(=O)c1cnc(N2CCN(c3nnc(Cc4ccccc4Cl)c4c3CCC4)[C@@H](C)C2)cn1] | 492 (MS) |

Example 70

2-(6-{(S)-4-[4-(2-Chloro-benzyl)-6,7-dihydro-5H-cyclopenta[d]pyridazin-1-yl]-3-methyl-piperazin-1-yl}-pyridin-3-yl)-propan-2-ol

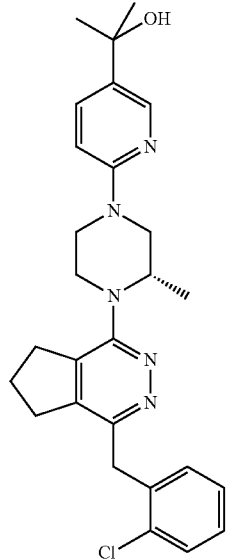 [SMILES: C[C@H]1CN(c2ccc(C(C)(C)O)cn2)CCN1c1nnc(Cc2ccccc2Cl)c2c1CCC2]

To a solution of (S)-4-[4-(2-chloro-benzyl)-6,7-dihydro-5H-cyclopenta[d]pyridazin-1-yl]-3-methyl-3,4,5,6-tetrahydro-2H-[1,2']bipyrazinyl-5'-carboxylic acid ethyl ester (35 mg, 0.071 mmol) in THF (5 mL) is added methyl magnesium iodide (3 M in ether, 0.19 mL, 0.57 mmol) at 0° C. and the mixture is stirred ar rt for 30 min. Sat. NaHCO$_3$ solution and EtOAc is added. The layers are separated and the aqueous layer is extracetd with EtOAc. The combined organic layers are washed with water, brine, dried over Na$_2$SO$_4$, filtered and concentrated. The crude product is purified by HPLC (acetonitrile/water with 0.1% TFA, 10% to 50%). The product is isolated as the free base after treatment of the salt with Na$_2$CO$_3$ solution (11 mg, 32%) HR MS (m/z, MH+) meas. 478.2367.

Example 71

2-{(R)-4-[6-(2,4-difluoro-benzyl)-4,5-dimethyl-pyridazin-3-yl]-2-methyl-piperazin-1-yl}-4-trifluoromethyl-pyrimidine-5-carboxylic acid ethyl ester

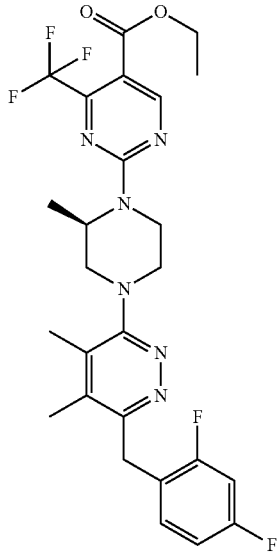 [SMILES: CCOC(=O)c1cnc(N2CCN(c3nnc(Cc4ccc(F)cc4F)c(C)c3C)C[C@H]2C)nc1C(F)(F)F]

To a solution of 2-[(R)-4-(6-chloro-4,5-dimethyl-pyridazin-3-yl)-2-methyl-piperazin-1-yl]-4-trifluoromethyl-pyrimidine-5-carboxylic acid ethyl ester (229 mg, 0.50 mmol, 1 eq) and THF (1.4 mL) in a microwave vial is added 2,4-difluorobenzylzinc bromide (2.0 mL 0.5 M solution in THF, 2.0 mmol, 4 eq) and tetrakis(triphenylphosphine)palladium (25 mg, 0.03 mmol, 0.05 eq). The vial is sealed and heated in the microwave at 60° C. (high absorption setting) for 25 min. An additional aliquot of 2,4-diflorobenzylzinc bromide (1.0 mL 0.5 M solution in THF, 1.0 mmol, 2 eq) is added and the reaction mixture is heated in the microwave at 100° C. (high absorption setting) for 5 min. The reaction mixture is quenched with water (10 mL) and then extracted with EtOAc (2×25 mL). The combined organic fractions are dried over magnesium sulfate, concentrated and purified by silica gel chromatography (25-75% EtOAc/Heptane) to yield the desired compound (225 mg, 81%).

$^1$H NMR (400 MHz, CDCl$_3$) δ=8.86 (s, 1H), 7.12 (t, J=7.3 Hz, 1H), 6.76-6.83 (m, 2H), 4.99-5.07 (m, 1H), 4.64-4.73 (m, 1H), 4.28 (q, J=7.0 Hz, 2H), 3.35-3.46 (m, 2H), 3.31 (d, J=12.5 Hz, 1H), 3.10 (d, J=10.5 Hz, 1H), 2.90-3.02 (m, 1H), 2.25 (s, 3H), 2.24 (s, 3H), 1.36 (d, J=7.0 Hz, 3H), 1.29 (t, J=7.0 Hz, 3H).

Example 72

2-(2-{(R)-4-[6-(2,4-Difluoro-benzyl)-4,5-dimethyl-pyridazin-3-yl]-2-methyl-piperazin-1-yl{-4-trifluoromethyl-pyrimidin-5-yl)-propan-2-ol

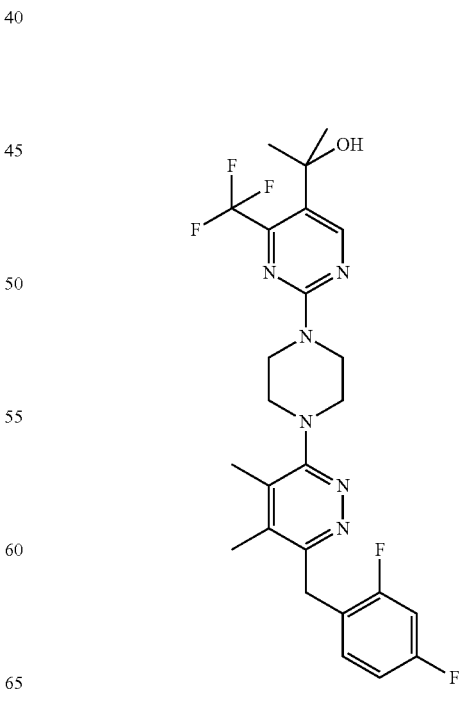

To a solution of 2-}(R)-4-[6-(2,4-difluoro-benzyl)-4,5-dimethyl-pyridazin-3-yl]-2-methyl-piperazin-1-yl}-4-trifluoromethyl-pyrimidine-5-carboxylic acid ethyl ester (220 mg, 0.40 mmol, 1 eq) in THF (1.0 mL), cooled in an ice bath, is added a solution of MeMgBr (2 mL, 3 M in ether, 6 mmol, 15 eq.). The solution is allowed to warm to rt for 30 min. The reaction is quenched with the careful addition of saturated NH₄Cl, then extracted with EtOAc. The organic layer is dried over sodium sulfate, then concentrated. The product is isolated by silica gel column chromatography (25-75% EtOAc/heptane) to yield the desired compound as a white solid (27 mg, 13%).

¹H NMR (400 MHz, CDCl₃) δ=8.74 (s, 1H), 7.21 (tt, J=8.3 Hz, 6.5 Hz, 1H), 6.85-6.94 (m, 1H), 4.95-5.05 (m, 1H), 4.64 (dd, J=12.5 Hz, 3.3 Hz, 1H), 4.26 (s, 2H), 3.49 (d, J=12.4 Hz, 1H), 3.36-3.44 (m, 2H), 3.19 (dd, J=12.5 Hz, 3.8 Hz, 1H), 3.05 (td, J=12.0 Hz, 3.3 Hz, 1H), 2.35 (s, 3H), 2.33 (s, 3H), 1.70 (s, 6H), 1.42 (d, J=6.7 Hz, 3H).

HR MS (m/z, MH+) meas. 537.2408.

Synthesis of Examples 73-87

General Protocol for the Amination of Aromatic Chlorides with Amines XIII to Yield Examples 74 to 86 (Route A)

To a solution of amine XIII (0.5 mmol, 1 eq.) and the aromatic halide (1 mmol, 2 eq.) in NMP (2.5 ml) is added triethylamine (1.5 mmol, 3 eq.). The mixture is heated in a microwave reactor to temperatures between 140° C. and 190° C. (depending on the reactivity of the aromatic halide) for 30 min. After LC MS shows completion of the reaction, water and EtOAc is added and the layers are separated and the aqueous layer is extracted with EtOAc. The combined organic layers were washed with water, brine, dried over sodium sulfate, filtered and concentrated. The product is purified by flash chromatography on silica gel with EtOAc/heptane as eluent to yield examples Ip.

Example 73

(R)-4-(6-Benzyl-4,5-dimethyl-pyridazin-3-yl)-2-methyl-3,4,5,6-tetrahydro-2H-[1,2']bipyrazinyl-5'-carboxylic acid methyl ester

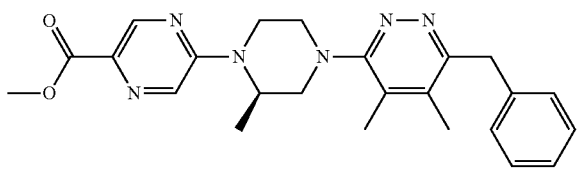 [SMILES: COC(=O)c1cnc(N2CCN(c3nnc(Cc4ccccc4)c(C)c3C)C[C@H]2C)cn1]

A mixture of compound 47 (6.0 g, 20.27 mmol), 5-chloro-pyrazine-2-carboxylic acid methyl ester (5.3 g, 30.30 mmol), Et₃N (6.2 g, 60.60 mmol) and dioxane (100 mL) is heated to reflux overnight. Solvent is removed. Saturated NH₄Cl solution is added and extracted with EtOAc. The organic layer is concentrated to afford the crude product that is purified by chromatography on silica gel (EtOAc/heptane: 50%~100%) to give the title compound (6.6 g, 76%) as a yellow solid.

¹H NMR (400 MHz, CD₂Cl₂) δ=8.81 (s, 1H), 8.21 (s, 1H), 7.29 (m, 5H), 4.83 (m, 1H), 4.43 (m, 1H), 4.33 (s, 2H), 3.94 (s, 3H), 3.52 (m, 3H), 3.27 (m, 1H), 3.14 (m, 1H),), 2.31 (s, 3H), 2.17 (s, 3H), 1.49 (d, J=6.5 Hz, 3H).

HR MS (m/z. MH+) meas. 433.2348.

Examples 74-86

The following table (Table 6) lists examples of compounds prepared by amination as described in the general procedure:

TABLE 6

| Example | Structure | HR MS [m/z, MH+] meas. |
|---|---|---|
| 74 | 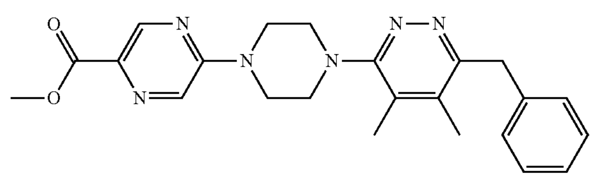 | 419 (MS) |
| 75 | 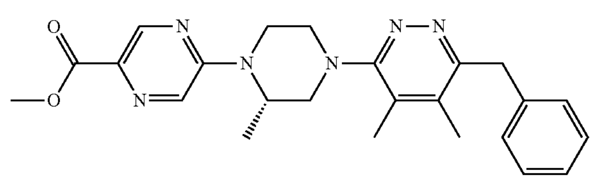 [SMILES: COC(=O)c1cnc(N2CCN(c3nnc(Cc4ccccc4)c(C)c3C)C[C@@H]2C)cn1] | 433.2341 |
| 76 | 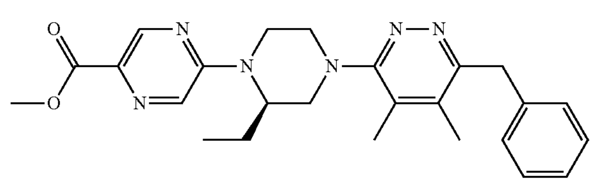 | 447.6 (MS) |

TABLE 6-continued

| Example | Structure | HR MS [m/z, MH+] meas. |
|---|---|---|
| 77 | 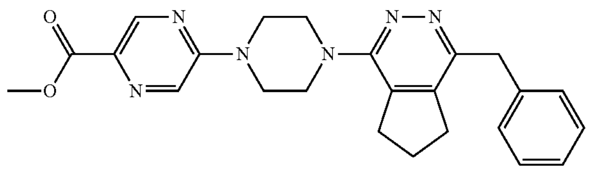 [SMILES: COC(=O)c1cnc(N2CCN(c3nnc(Cc4ccccc4)c4c3CCC4)CC2)cn1] | 431 (MS) |
| 78 | 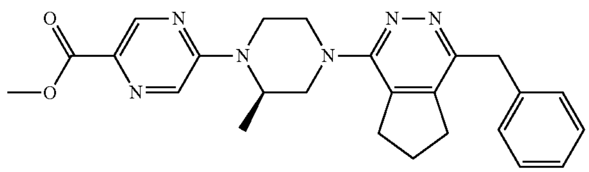 [SMILES: COC(=O)c1cnc(N2CCN(c3nnc(Cc4ccccc4)c4c3CCC4)C[C@H]2C)cn1] | 445.2353 |
| 79 | 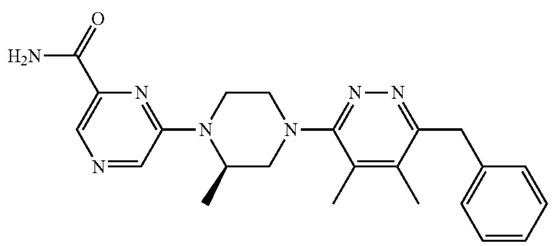 [SMILES: Cc1c(Cc2ccccc2)nnc(N2CCN(c3cncc(C(N)=O)n3)[C@H](C)C2)c1C] | 417.4825 |
| 80 | 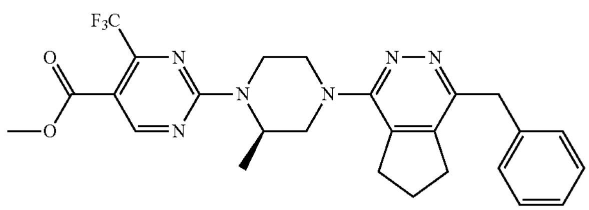 [SMILES: COC(=O)c1cnc(N2CCN(c3nnc(Cc4ccccc4)c4c3CCC4)C[C@H]2C)nc1C(F)(F)F] | 513.2225 |
| 81 | 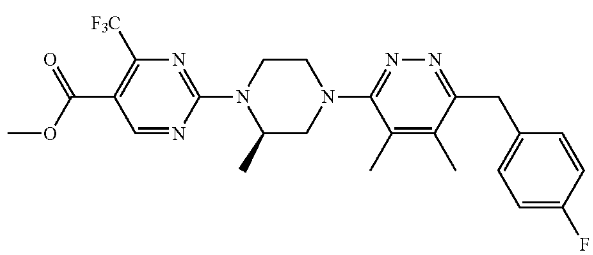 [SMILES: COC(=O)c1cnc(N2CCN(c3nnc(Cc4ccc(F)cc4)c(C)c3C)C[C@H]2C)nc1C(F)(F)F] | 519.2140 |
| 82 | 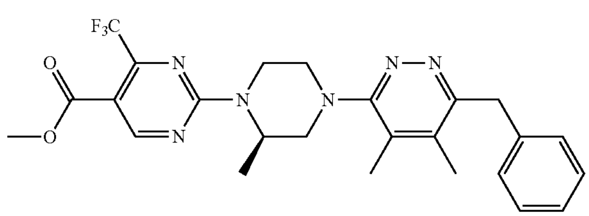 [SMILES: COC(=O)c1cnc(N2CCN(c3nnc(Cc4ccccc4)c(C)c3C)C[C@H]2C)nc1C(F)(F)F] | 501.2207 |
| 83 | 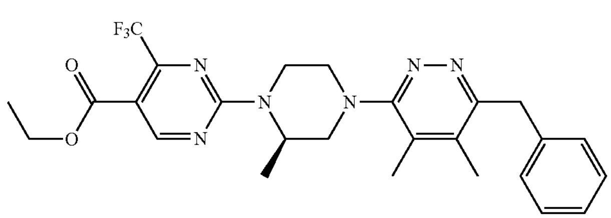 [SMILES: CCOC(=O)c1cnc(N2CCN(c3nnc(Cc4ccccc4)c(C)c3C)C[C@H]2C)nc1C(F)(F)F] | 515.2383 |

TABLE 6-continued

| Example | Structure | HR MS [m/z, MH+] meas. |
|---|---|---|
| 84 | 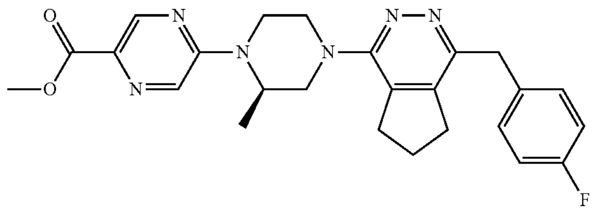 [SMILES: COC(=O)c1cnc(N2CCN(c3nnc(Cc4ccc(F)cc4)c4c3CCC4)C[C@H]2C)cn1] | 463 (MS) |
| 85 | 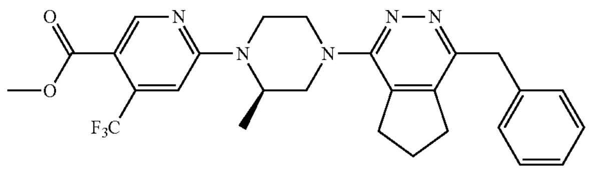 | 512 (MS) |
| 86 | 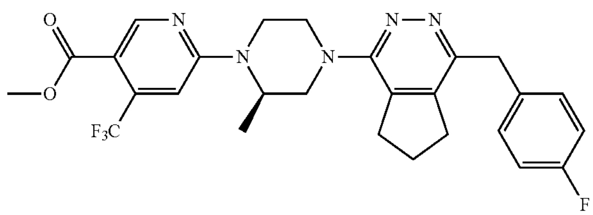 [SMILES: COC(=O)c1cnc(N2CCN(c3nnc(Cc4ccc(F)cc4)c4c3CCC4)C[C@H]2C)cc1C(F)(F)F] | 530 (MS) |

Example 87

3-Benzyl-4,5-dimethyl-6-[(R)-3-methyl-4-(4-trifluoro-methanesulfonylphenyl)-piperazin-1-yl]-pyridazine

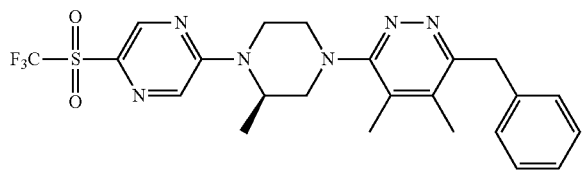 [SMILES: Cc1c(Cc2ccccc2)nnc(N2CCN(c3cnc(S(=O)(=O)C(F)(F)F)cn3)[C@H](C)C2)c1C]

To the solution of 3-benzyl-4,5-dimethyl-6-((R)-3-methyl-piperazin-1-yl)-pyridazine (80 mg, 0.257 mmol) in dioxane (5 mL) is added 1-chloro-4-trifluoromethanesulfonyl-benzene (95.2 mg, 0.385 mmol), potassium hydroxid pellets (101 mg, 1.55 mmol), naphthoquinone imidazolin-2-ylidene-Pd (0) (175 mg, 0.129 mmol). The mixture is heated in a microwave reactor at 100° C. for 120 min. Water is added to the mixture and extracted with EtOAc. The combined organic layers are washed with water, brine, dried over $Na_2SO_4$, filtered and concentrated down. The crude product is purified by HPLC (acetonitrile/water: 10%~95% with 3% 1-propanol), to give a light yellow colored powder (55 mg, 89%).

$^1$H-NMR (400 MHz, DMSO-$d_6$) δ=7.81 (d, J=9.1 Hz, 2H), 7.17-7.30 (m, 7H), 4.51 (m, 1H), 4.26 (s, 2H), 3.97 (d, J=12.6 Hz, 1H), 3.55 (d, J=12.2 Hz, 1H), 3.42 (m, 2H), 3.14 (m, 1H), 3.00 (m, 1H), 2.26 (s, 3H), 2.13 (s, 3H), 1.31 (d, J=6.5 Hz, 3H).

HR MS (m/z, MH+) meas. 505.1872 calc. 505.1885.

Synthesis of Examples 88-115

General Protocol for the Grignard Reaction with Esters

To a solution of the ester (0.5 mmol, 1 eq.) in THF (3 mL) is added alkyl magnesium bromide or iodide (4 mmol, 8 eq., solution in ether) at −78° C. The reaction mixture is stirred at 0° C. for 2 h then diluted with DCM and washed with $NH_4Cl$ and water. The combined organic layers are washed with water, brine, dried over $Na_2SO_4$, filtered and concentrated down. Purification by HPLC of the crude product with acetonitrile in water provides the tertiary alcohols (main product) next to smaller amounts of the corresponding methyl ketones. The solvents are removed with a lyophilizer to provide the products as white powders.

Example 88

2-[(R)-4-(6-Benzyl-4,5-dimethyl-pyridazin-3-yl)-2-methyl-3,4,5,6-tetrahydro-2H-[1,2']bipyrazinyl-5'-yl]-propan-2-ol

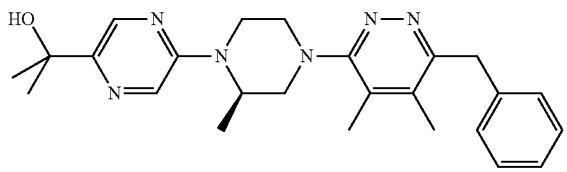 [SMILES: Cc1c(Cc2ccccc2)nnc(N2CCN(c3cnc(C(C)(C)O)cn3)[C@H](C)C2)c1C]

To a solution of (R)-4-(6-benzyl-4,5-dimethyl-pyridazin-3-yl)-2-methyl-3,4,5,6-tetrahydro-2H-[1,2']bipyrazinyl-5'-carboxylic acid methyl ester (840 mg, 1.85 mmol) in THF (12 mL) is added methyl magnesium bromide (5 mL, 15 mmol, 3M in ether) at −78° C. The reaction mixture is stirred at 0° C. for 2 h then diluted with DCM and washed with NH$_4$Cl and water. The combined organic layers are washed with water, brine, dried over Na$_2$SO$_4$, filtered and concentrated down. Purification by HPLC of the crude product with acetonitrile in water (from 10% to 95% with 3% 1-propanol) at 220 nm wavelength detection provides the desired alcohol (400 mg, 50%) next to small amounts of the corresponding methyl ketone (example 95). The solvents are removed with a lyophilizer to provide the products as white powders.

$^1$H NMR (400 MHz, CD$_2$Cl$_2$) δ=8.28 (s, 1H), 8.10 (s, 1H), 7.25 (m, 5H), 4.83 (m, 1H), 4.33 (s, 2H), 4.20 (m 1H), 3.78 (s, 1H), 3.57 (m, 1H), 3.44 (m, 2H), 3.29 (m, 1H), 3.14 (m, 1H), 2.31 (s, 3H), 2.16 (s, 3H), 1.56 (s, 6H), 1.40 (d, J=6.5 Hz, 3H). HR MS (m/z, MH+) meas. 433.2713, calc. 433.2716.

Examples 89-111

The following table (Table 7) lists examples of compounds prepared by Grignard addition as described above:

TABLE 7

| Example | Structure | HR MS [m/z; MH+] meas. |
|---|---|---|
| 89 | 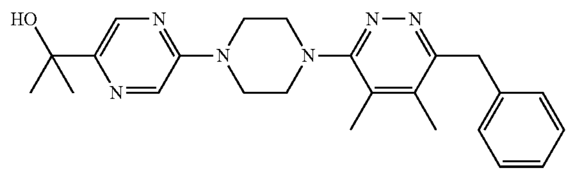 [SMILES: Cc1c(Cc2ccccc2)nnc(N2CCN(c3cnc(C(C)(C)O)cn3)CC2)c1C] | 419.2546 |
| 90 | 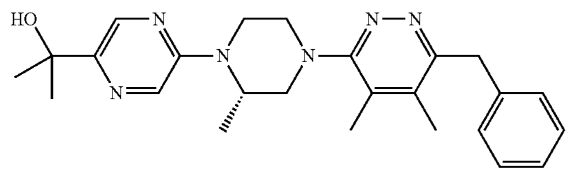 [SMILES: Cc1c(Cc2ccccc2)nnc(N2CCN(c3cnc(C(C)(C)O)cn3)[C@@H](C)C2)c1C] | 433.2716 |
| 91 | 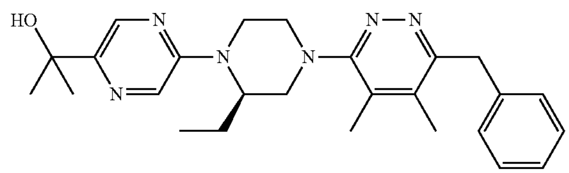 [SMILES: CC[C@@H]1CN(c2nnc(Cc3ccccc3)c(C)c2C)CCN1c1cnc(C(C)(C)O)cn1] | 447.2865 |
| 92 | 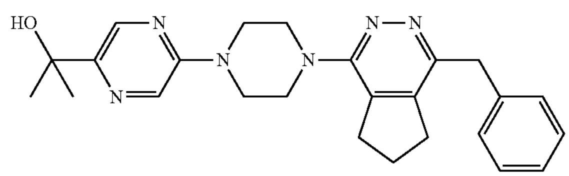 [SMILES: CC(C)(O)c1cnc(N2CCN(c3nnc(Cc4ccccc4)c4c3CCC4)CC2)cn1] | 421.2559 |
| 93 | 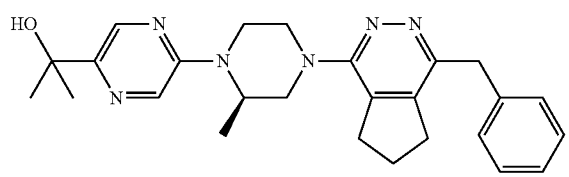 [SMILES: C[C@@H]1CN(c2nnc(Cc3ccccc3)c3c2CCC3)CCN1c1cnc(C(C)(C)O)cn1] | 445.2710 |
| 94 | 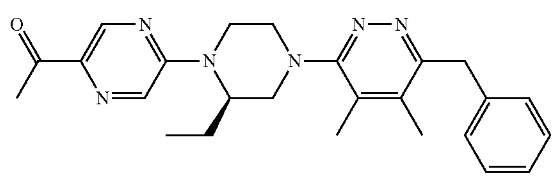 [SMILES: CC[C@@H]1CN(c2nnc(Cc3ccccc3)c(C)c2C)CCN1c1cnc(C(C)=O)cn1] | 431.5 (MS) |
| 95 | 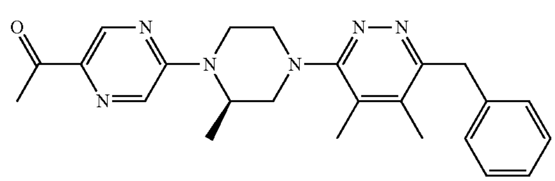 [SMILES: CC(=O)c1cnc(N2CCN(c3nnc(Cc4ccccc4)c(C)c3C)C[C@H]2C)cn1] | 417.2395. |

TABLE 7-continued

| Example | Structure | HR MS [m/z; MH+] meas. |
|---------|-----------|------------------------|
| 96 | 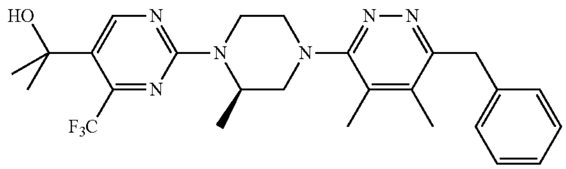 | 501.2599 |
| 97 | 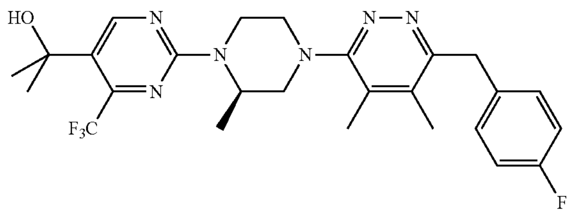 [SMILES: Cc1c(Cc2ccc(F)cc2)nnc(N2CCN(c3ncc(C(C)(C)O)c(C(F)(F)F)n3)[C@H](C)C2)c1C] | 519.2485 |
| 98 | 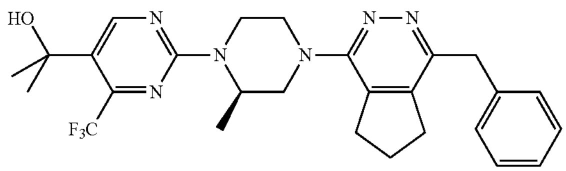 | 513.2584 |
| 99 | 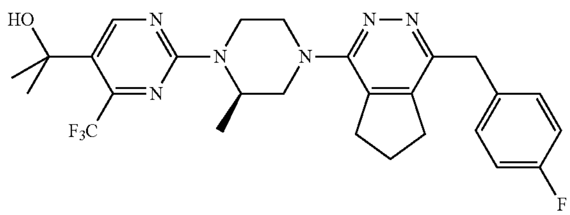 | 531.2509 |
| 100 | 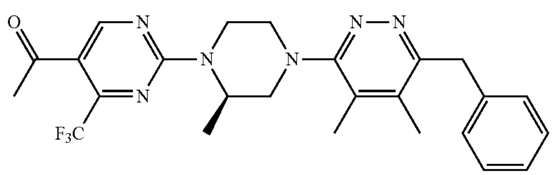 [SMILES: CC(=O)c1cnc(N2CCN(c3nnc(Cc4ccccc4)c(C)c3C)C[C@H]2C)nc1C(F)(F)F] | 485.2271 |
| 101 | 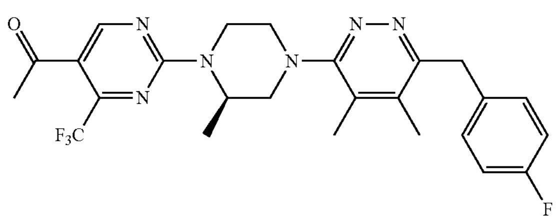 [SMILES: CC(=O)c1cnc(N2CCN(c3nnc(Cc4ccc(F)cc4)c(C)c3C)C[C@H]2C)nc1C(F)(F)F] | 503.2163 |
| 102 | 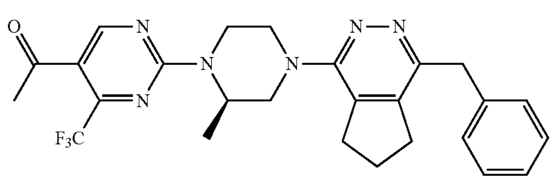 [SMILES: CC(=O)c1cnc(N2CCN(c3nnc(Cc4ccccc4)c4c3CCC4)C[C@H]2C)nc1C(F)(F)F] | 497.2258 |
| 103 | 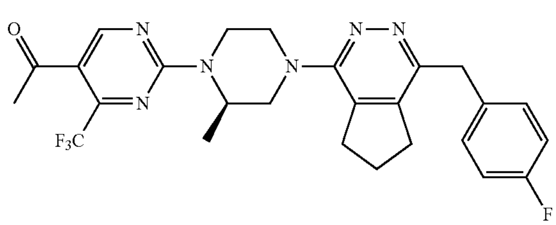 [SMILES: CC(=O)c1cnc(N2CCN(c3nnc(Cc4ccc(F)cc4)c4c3CCC4)C[C@H]2C)nc1C(F)(F)F] | 515 (MS) |

TABLE 7-continued

| Example | Structure | HR MS [m/z; MH+] meas. |
|---|---|---|
| 104 | 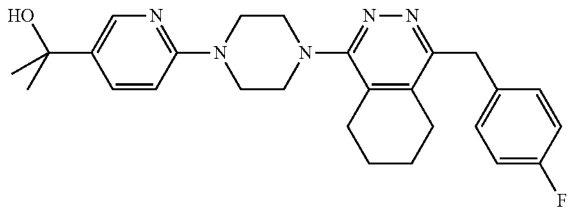 [SMILES: CC(C)(O)c1ccc(N2CCN(c3nnc(Cc4ccc(F)cc4)c4c3CCCC4)CC2)nc1] | 462.2679 |
| 105 | 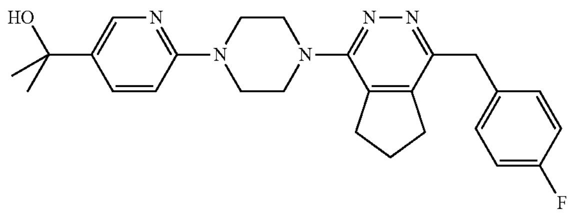 [SMILES: CC(C)(O)c1ccc(N2CCN(c3nnc(Cc4ccc(F)cc4)c4c3CCC4)CC2)nc1] | 448.2250 |
| 106 | 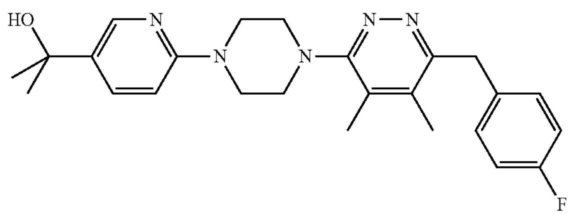 [SMILES: Cc1c(Cc2ccc(F)cc2)nnc(N2CCN(c3ccc(C(C)(C)O)cn3)CC2)c1C] | 436.2532 |
| 107 | 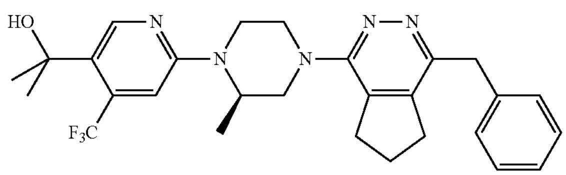 [SMILES: C[C@@H]1CN(c2nnc(Cc3ccccc3)c3c2CCC3)CCN1c1cc(C(F)(F)F)c(C(C)(C)O)cn1] | 512 (MS) |
| 108 | 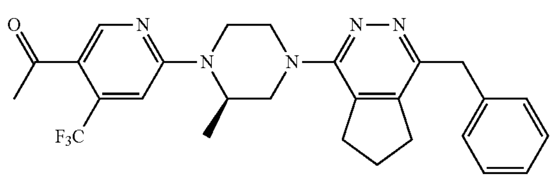 | 496 (MS) |
| 109 | 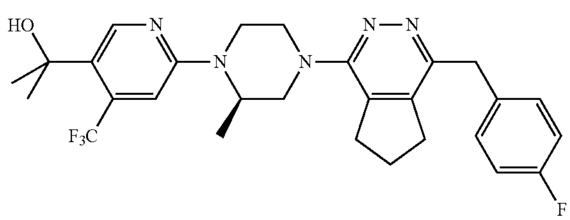 [SMILES: C[C@@H]1CN(c2nnc(Cc3ccc(F)cc3)c3c2CCC3)CCN1c1cc(C(F)(F)F)c(C(C)(C)O)cn1] | 530.2543 |
| 110 | 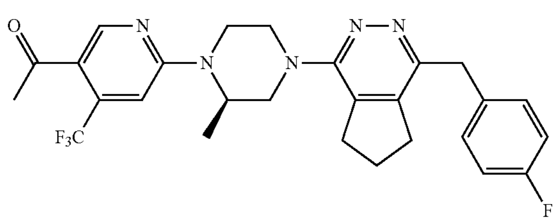 | 514.2247 |
| 111 | 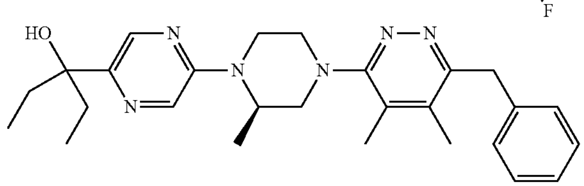 | 461.3036 |

Example 112

2-[(R)-4-(6-Benzyl-4,5-dimethyl-pyridazin-3-yl)-2-methyl-3,4,5,6-tetrahydro-2H-[1,2']bipyrazinyl-5'-yl]-2,2-dimethoxy-ethanol

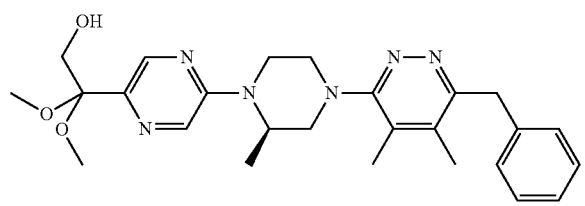 [SMILES: COC(CO)(OC)c1cnc(N2CCN(c3nnc(Cc4ccccc4)c(C)c3C)C[C@H]2C)cn1]

To a solution of KOH (33 mg, 0.38 mmol) and methanol (5 mL) is added example 95 (20 mg, 0.048 mmol) in methanol (1 mL) and then iodobenzene diacetate (23 mg, 0.072 mmol) in portions at 0° C. The mixture is stirred at rt overnight. Solvent is removed to give a crude product that is purified by HPLC (acetonitrile/water (1% NH$_4$OH), 30%~100%) to give the title compound (12 mg, 52%) as a yellow solid.

$^1$H NMR (400 MHz, CD$_2$Cl$_2$) δ=8.42 (s, 1H), 8.18 (s, 1H), 7.29 (m, 5H), 4.72 (m, 1H), 4.32 (s, 2H), 4.30 (m, 1H), 3.94 (d, J=6.0 Hz, 2H), 3.58 (m, 1H), 3.47 (m, 2H), 3.28 (m, 1H), 3.26 (s, 6H), 3.13 (m, 1H), 2.31 (s, 3H), 2.16 (s, 3H), 1.44 (d, J=6.5 Hz, 3H).

Example 113

1-[(R)-4-(6-Benzyl-4,5-dimethyl-pyridazin-3-yl)-2-methyl-3,4,5,6-tetrahydro-2H-[1,2']bipyrazinyl-5'-yl]-ethanol

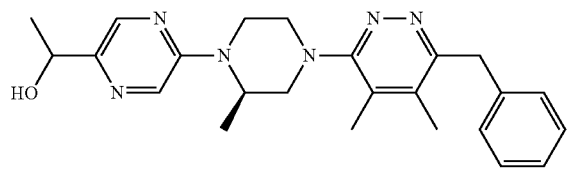 [SMILES: Cc1c(Cc2ccccc2)nnc(N2CCN(c3cnc(C(C)O)cn3)[C@H](C)C2)c1C]

To a solution of example 95 (50 mg, 0.12 mmol) and MeOH (3 mL) is added NaBH$_4$ (10 mg, 0.24 mmol) at 0° C., afterwards the reaction mixture is stirred at rt an additional 0.5 h. Solvent is removed and water is added, then extracted with DCM. The organic layer is concentrated to afford the title compound (38 mg, 76%) as a white solid.

$^1$H NMR (400 MHz, CD$_2$Cl$_2$) δ=8.04 (s, 1H), 8.01 (s, 1H), 7.15 (m, 5H), 4.73 (m, 1H), 4.57 (m, 1H), 4.21 (s, 2H), 4.07 (m, 1H), 3.46 (m, 1H), 3.33 (m, 2H), 3.15 (m, 1H), 3.01 (m, 2H), 2.19 (s, 3H), 2.05 (s, 3H), 1.39 (d, J=6.5 Hz, 3H), 1.30 (d, J=6.5 Hz, 3H).

HR MS (m/z, MH+) meas. 419.2543.

Example 114

1-[(R)-4-(6-Benzyl-4,5-dimethyl-pyridazin-3-yl)-2-methyl-3,4,5,6-tetrahydro-2H-[1,2']bipyrazinyl-5'-yl)-2-hydroxy-ethanone

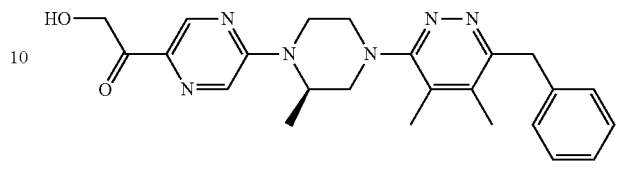

To a solution of KOH (224 mg, 4.0 mmol) and CH$_3$OH (10 mL) is added 1-[(R)-4-(6-benzyl-4,5-dimethyl-pyridazin-3-yl)-2-methyl-3,4,5,6-tetrahydro-2H-[1,2']bipyrazinyl-5'-yl)-ethanone (400 mg, 1.0 mmol) in CH$_3$OH (10 mL) and then iodobenzene diacetate (464 mg, 1.5 mmole) in portions at 0° C. The mixture is stirred at room temperature overnight. The solvent is removed and then extracted with DCM. The organic layer is washed with aqueous NH$_4$Cl and afterwards concentrated to yield crude example 112. This material is dissolved in water and then 6 N HCl (5 mL) is added. The mixture is stirred at room temperature for 3 h. Afterwards it is made basic with NaHCO$_3$ and extracted with DCM. The organic layer is concentrated to give a crude product that is purified by chromatography on silica gel (EtOAc/Heptane: 50%~100%) to give the title compound (240 mg, 58%) as a yellow solid.

$^1$H NMR (400 MHz, CD$_2$Cl$_2$) δ=8.82 (s, 1H), 8.15 (s, 1H), 7.27 (m, 5H), 4.91 (s, 2H), 4.86 (m, 1H), 4.48 (m, 1H), 4.33 (s, 2H), 3.57 (m, 2H), 3.46 (m, 1H), 3.30 (m, 2H), 3.14 (m, 1H), 2.31 (s, 3H), 2.17 (s, 3H), 1.50 (d, J=6.5 Hz, 3H).

HR MS (m/z, MH+) meas. 433.2340.

Example 115

1-[(R)-4-(6-Benzyl-4,5-dimethyl-pyridazin-3-yl)-2-methyl-3,4,5,6-tetrahydro-2H-[1,2']bipyrazinyl-5'-yl)-ethane-1,2-diol

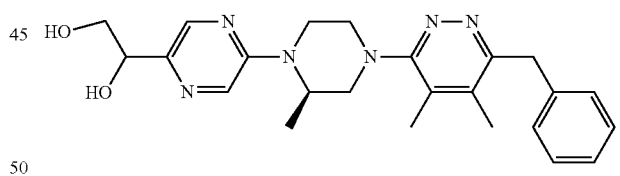

To a solution of 1-[(R)-4-(6-Benzyl-4,5-dimethyl-pyridazin-3-yl)-2-methyl-3,4,5,6-tetrahydro-2H-[1,2']bipyrazinyl-5'-yl)-2-hydroxy-ethanone (example 114, 110 mg, 0.25 mmol) and EtOH (20 ml) is added NaBH$_4$ (14 mg, 0.38 mmol) at 0° C. The mixture is warmed up to room temperature and stirred for 3 h. The reaction solution is acidified with 3N HCl to pH~7 and the organic solvent is removed. The residue is dissolved in saturated NaHCO$_3$ solution and extracted with DCM. The organic layer is concentrated to afford the title compound (96 mg, 91%) as a white solid.

$^1$H NMR (400 MHz, CD$_2$Cl$_2$) δ=8.09 (s, 1H), 8.00 (s, 1H), 7.18 (m, 5H), 4.64 (m, 1H), 4.57 (m, 1H), 4.26 (s, 2H), 4.10 (m, 1H), 3.60 (m, 2H), 3.48 (m, 1H), 3.34 (m, 2H), 3.18 (m, 1H), 3.02 (m, 1H), 2.21 (s, 3H), 2.06 (s, 3H), 1.30 (d, J=6.5 Hz, 3H).

HR MS (m/z, MH+) meas. 435.2511.

Synthesis of Examples 116 and 117

Example 116

(R)-4-(6-Benzyl-4,5-dimethyl-pyridazin-3-yl)-2-methyl-3,4,5,6-tetrahydro-2H-[1,2']bipyrazinyl-5'-carboxylic acid

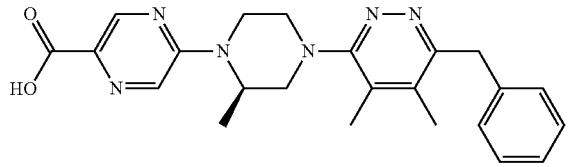 [SMILES: Cc1c(Cc2ccccc2)nnc(N2CCN(c3cnc(C(=O)O)cn3)[C@H](C)C2)c1C]

(R)-4-(6-Benzyl-4,5-dimethyl-pyridazin-3-yl)-2-methyl-3,4,5,6-tetrahydro-2H-[1,2']bipyrazinyl-5'-carboxylic acid methyl ester (1.8 g, 4.16 mmol) is combined with LiOH (998 mg, 42 mmol), H$_2$O (20 mL), THF (20 mL), and MeOH (10 mL). The combined mixture is allowed to stir at room temperature for 16 h. It is concentrated to remove organic solvents in vacuo. Additional water is added and the pH is adjusted to 4.0 with HCl or phosphate buffer. The solution is extracted with EtOAc and the combined organic extracts are washed with brine. The extract is dried over sodium sulfate and filtered to remove the drying agent. The filtrate is concentrated to afford the title compound (1.46 g, 84%).

$^1$H NMR (400 MHz, CD$_2$Cl$_2$) δ=8.89 (s, 1H), 8.10 (s, 1H), 7.27 (m, 5H), 4.84 (m, 1H), 4.44 (m, 1H), 4.34 (s, 2H), 3.58 (m, 3H), 3.31 (m, 1H), 3.16 (m, 1H), 2.32 (s, 3H), 2.18 (s, 3H), 1.50 (d, J=6.5 Hz, 3H).

HR MS (m/z, MH+) meas. 419.2200.

Example 117

2-[(R)-4-(6-Benzyl-4,5-dimethyl-pyridazin-3-yl)-2-methyl-piperazin-1-yl]-4-trifluoromethyl-pyrimidine-5-carboxylic acid

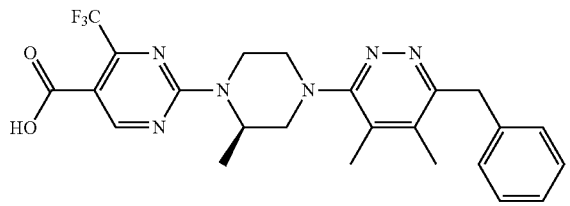 [SMILES: Cc1c(Cc2ccccc2)nnc(N2CCN(c3ncc(C(=O)O)c(C(F)(F)F)n3)[C@H](C)C2)c1C]

To a solution of methyl 2-[(R)-4-(6-benzyl-4,5-dimethyl-pyridazin-3-yl)-2-methyl-piperazin-1-yl]-4-trifluoromethyl-pyrimidine-5-carboxylate (500 mg, 1.0 mmol, 1.0 eq) in THF (5 mL) is added an aqueous solution of LiOH (1 M, 2.0 mL, 2.0 mmol, 2.0 eq) and the resulting solution is heated to 75° C. for 4 h. The reaction mixture is diluted with EtOAc (50 mL) and washed with water (3×15 mL). The combined aqueous washes were adjusted to pH 6 with aqueous HCl (1 M), then extracted with dichloromethane (3×50 mL). The combined organic layers are dried over sodium sulfate and concentrated under reduced pressure to yield the desired product as a white solid (470 mg, 96%).

$^1$H NMR (400 MHz, MeOH-d$_4$) δ=8.97 (s, 1H), 7.23-7.30 (m, 2H), 7.10-7.22 (m, 3H), 5.11-5.23 (m, 1H), 4.77-4.86 (m, 1H), 4.31 (s, 2H), 3.52-3.64 (m, 2H), 3.50 (d, J=12.5 Hz, 1H), 3.17 (dd, J=12.5 Hz, 3.5 Hz, 1H), 2.97-3.09 (m, 1H), 2.37 (s, 3H), 2.17 (s, 3H), 1.47 (d, J=6.5 Hz, 3H).

HR MS (m/z, MH+) meas. 487.2088.

Synthesis of Examples 118-144

General Protocol for the Amide Formation with Acid Example 116 to Yield Further Examples 118 to 140

Method A:

A mixture of example 116 (40 mg, 0.10 mmol) and SOCl$_2$ (10 mL) is heated to reflux for 1 h and then solvent is removed. The residue is dissolved in DCM (2 mL) and transferred to a solution of amine (0.14 mmole) and DCM (3 mL). The reaction mixture is stirred at rt for 2 h. Water (10 mL) is added and the mixture extracted with DCM (3×20 mL). The organic layer is concentrated to give a crude product that is purified by HPLC [acetonitrile/water (1% NH$_4$OH), 30%-100%] to afford the product (examples 118 to 132, 20%~84%).

Method B:

A mixture of example 116 (40 mg, 0.10 mmol), HATU (73 mg, 0.14 mmole), diisopropylethyl amine (37 mg, 0.29 mmol), dimethylacetamide (1.5 ml) and amine (0.14 mmole) is stirred at rt for 10 h. The crude product is purified by HPLC (acetonitrile/water (3% propanol), 30%~100%) to afford the product (examples 133 to 140, 37%~55%).

Examples 118-140

The following table (Table 8) lists examples of compounds prepared by amide formation as described above:

TABLE 8

| Example | Structure | HR MS [m/z, MH+] meas. |
|---|---|---|
| 118 | 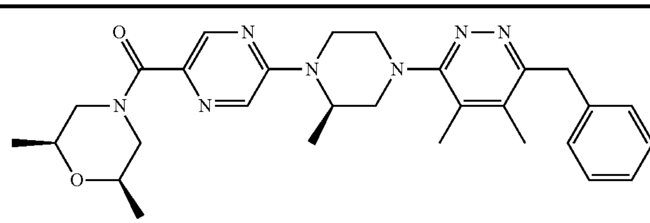 | 516.3076 |

TABLE 8-continued

| Example | Structure | HR MS [m/z, MH+] meas. |
|---|---|---|
| 119 | 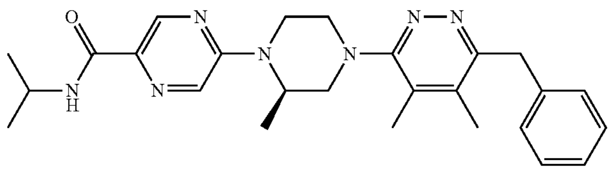 [SMILES: Cc1c(Cc2ccccc2)nnc(N2CCN(c3cnc(C(=O)NC(C)C)cn3)[C@H](C)C2)c1C] | 460.2810 |
| 120 | 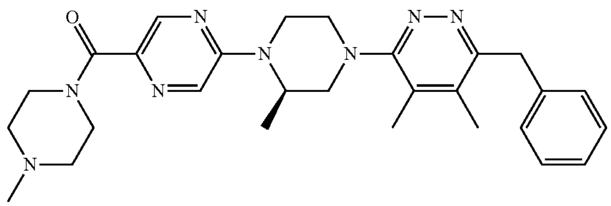 [SMILES: Cc1c(Cc2ccccc2)nnc(N2CCN(c3cnc(C(=O)N4CCN(C)CC4)cn3)[C@H](C)C2)c1C] | 501.3091 |
| 121 | 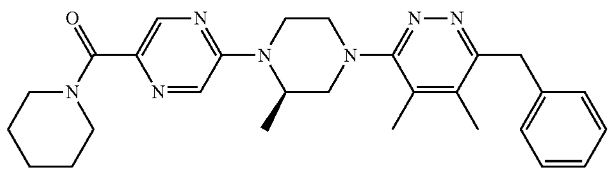 [SMILES: Cc1c(Cc2ccccc2)nnc(N2CCN(c3cnc(C(=O)N4CCCCC4)cn3)[C@H](C)C2)c1C] | 486.2969 |
| 122 | 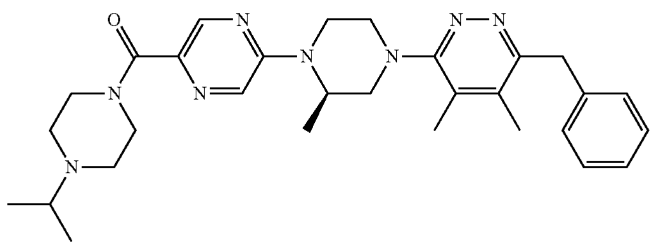 [SMILES: Cc1c(Cc2ccccc2)nnc(N2CCN(c3cnc(C(=O)N4CCN(C(C)C)CC4)cn3)[C@H](C)C2)c1C] | 529.3404 |
| 123 | 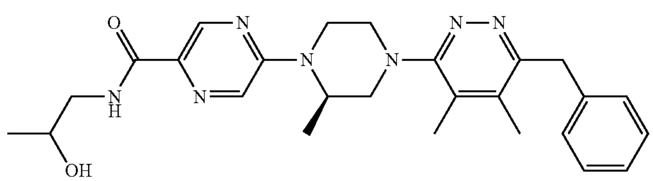 [SMILES: Cc1c(Cc2ccccc2)nnc(N2CCN(c3cnc(C(=O)NCC(C)O)cn3)[C@H](C)C2)c1C] | 476.2772 |
| 124 | 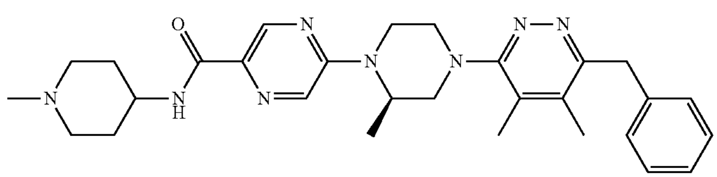 [SMILES: Cc1c(Cc2ccccc2)nnc(N2CCN(c3cnc(C(=O)NC4CCN(C)CC4)cn3)[C@H](C)C2)c1C] | 515.3204 |
| 125 | 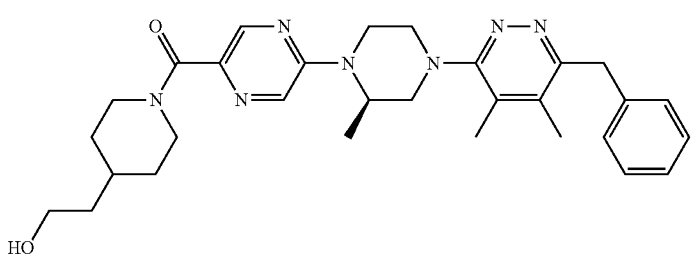 [SMILES: Cc1c(Cc2ccccc2)nnc(N2CCN(c3cnc(C(=O)N4CCC(CCO)CC4)cn3)[C@H](C)C2)c1C] | 530.3240 |
| 126 | 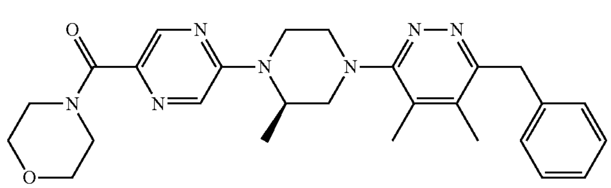 [SMILES: Cc1c(Cc2ccccc2)nnc(N2CCN(c3cnc(C(=O)N4CCOCC4)cn3)[C@H](C)C2)c1C] | 488.2773 |

TABLE 8-continued

| Example | Structure | HR MS [m/z, MH+] meas. |
|---|---|---|
| 127 | 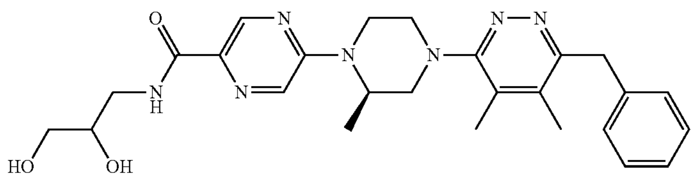 [SMILES: Cc1c(Cc2ccccc2)nnc(N2CCN(c3cnc(C(=O)NCC(O)CO)cn3)[C@H](C)C2)c1C] | 492.2732 |
| 128 | 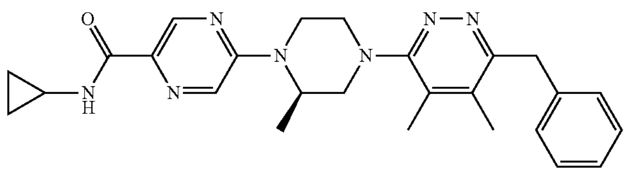 [SMILES: Cc1c(Cc2ccccc2)nnc(N2CCN(c3cnc(C(=O)NC4CC4)cn3)[C@H](C)C2)c1C] | 458.2668 |
| 129 | 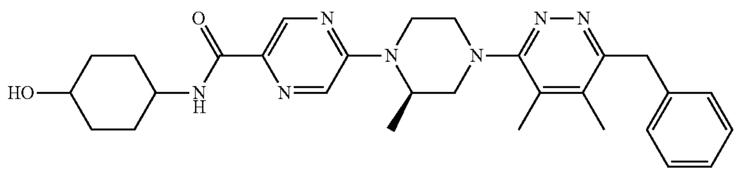 [SMILES: Cc1c(Cc2ccccc2)nnc(N2CCN(c3cnc(C(=O)NC4CCC(O)CC4)cn3)[C@H](C)C2)c1C] | 502.2933 |
| 130 | 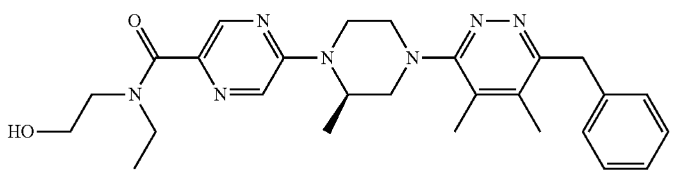 [SMILES: CCN(CCO)C(=O)c1cnc(N2CCN(c3nnc(Cc4ccccc4)c(C)c3C)C[C@H]2C)cn1] | 490.2907 |
| 131 | 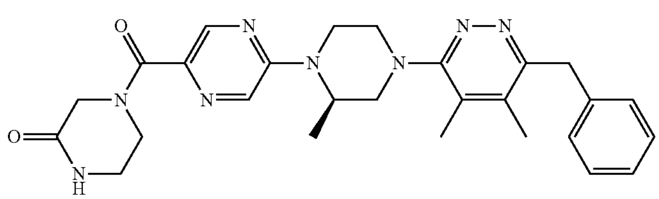 [SMILES: Cc1c(Cc2ccccc2)nnc(N2CCN(c3cnc(C(=O)N4CCNC(=O)C4)cn3)[C@H](C)C2)c1C] | 501.2723 |
| 132 | 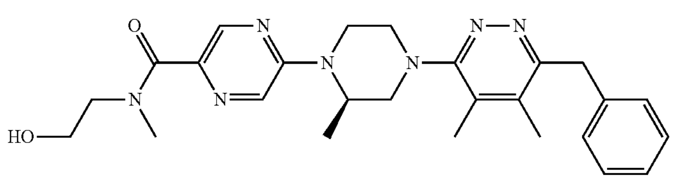 | 476.2763 |
| 133 | 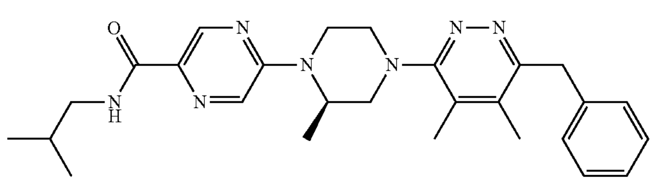 [SMILES: Cc1c(Cc2ccccc2)nnc(N2CCN(c3cnc(C(=O)NCC(C)C)cn3)[C@H](C)C2)c1C] | 474.2962 |
| 134 | 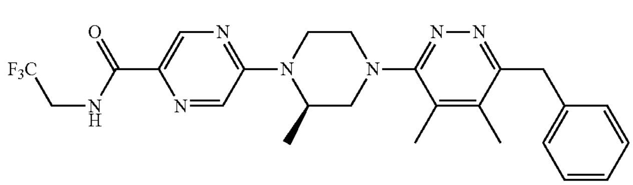 [SMILES: Cc1c(Cc2ccccc2)nnc(N2CCN(c3cnc(C(=O)NCC(F)(F)F)cn3)[C@H](C)C2)c1C] | 500.2369 |

TABLE 8-continued

| Example | Structure | HR MS [m/z, MH+] meas. |
|---|---|---|
| 135 | 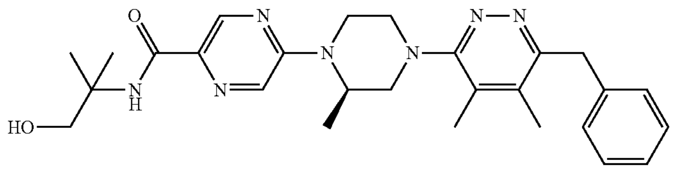 | 490.2918 |
| 136 | 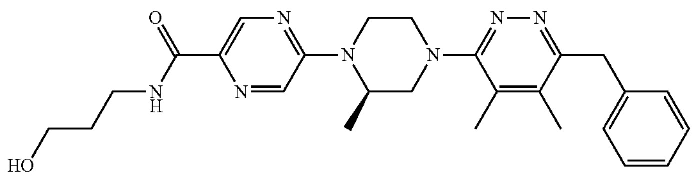 [SMILES: Cc1c(Cc2ccccc2)nnc(N2CCN(c3cnc(C(=O)NCCCO)cn3)[C@H](C)C2)c1C] | 476.2776 |
| 137 | 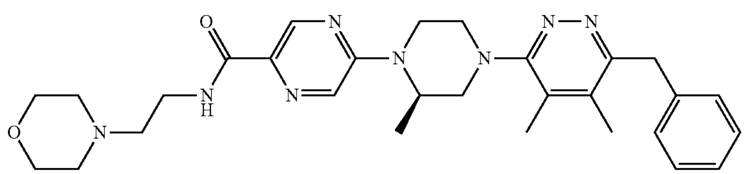 [SMILES: Cc1c(Cc2ccccc2)nnc(N2CCN(c3cnc(C(=O)NCCN4CCOCC4)cn3)[C@H](C)C2)c1C] | 531.3190 |
| 138 | 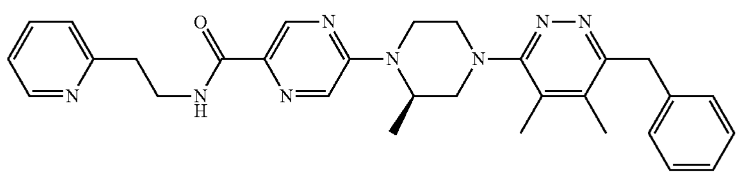 [SMILES: Cc1c(Cc2ccccc2)nnc(N2CCN(c3cnc(C(=O)NCCc4ccccn4)cn3)[C@H](C)C2)c1C] | 523.2917 |
| 139 | 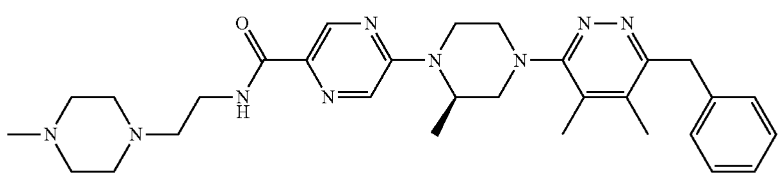 [SMILES: Cc1c(Cc2ccccc2)nnc(N2CCN(c3cnc(C(=O)NCCN4CCN(C)CC4)cn3)[C@H](C)C2)c1C] | 544.3489 |
| 140 | 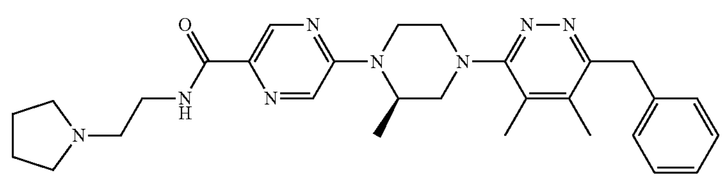 [SMILES: Cc1c(Cc2ccccc2)nnc(N2CCN(c3cnc(C(=O)NCCN4CCCC4)cn3)[C@H](C)C2)c1C] | 515.3224 |

Example 141

2-[(R)-4-(6-Benzyl-4,5-dimethyl-pyridazin-3-yl)-2-methyl-piperazin-1-yl]-4-trifluoromethyl-pyrimidine-5-carboxylic acid (2-hydroxy-ethyl)-methyl-amide

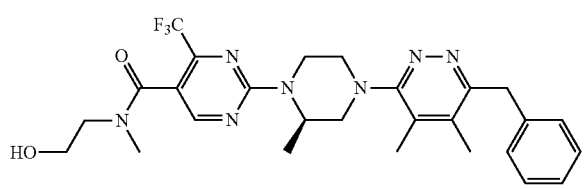 [SMILES: Cc1c(Cc2ccccc2)nnc(N2CCN(c3ncc(C(=O)N(C)CCO)c(C(F)(F)F)n3)[C@H](C)C2)c1C]

To a solution of 2-[(R)-4-(6-benzyl-4,5-dimethyl-pyridazin-3-yl)-2-methyl-piperazin-1-yl]-4-trifluoromethyl-pyrimidine-5-carboxylic acid (45 mg, 0.1 mmol, 1 eq) in THF (2 mL) is added an excess of oxalyl chloride (100 μL, 1.2 mmol, 12 eq,) and a catalytic amount of DMF, and the resulting solution is stirred at rt for 45 min, at which time N-2-hydroxyethyl, N-methyl amine (200 μL, 2.5 mmol, 25 eq) is added, and the reaction is stirred for an additional 1 h. The reaction mixture is diluted with EtOAc (50 mL) and washed with water (2×10 mL) followed by brine (2×10 mL). The organic layer is dried over sodium sulfate and concentrated under reduced pressure to a white residue. The desired compound is isolated by silica gel chromatography (CH$_2$Cl$_2$—20% MeOH/CH$_2$Cl$_2$) as a white solid (43 mg, 79%).

$^1$H NMR (400 MHz, MeOH-d$_4$) δ=8.55 (d, J=2.6 Hz, 1H), 7.22-7.29 (m, 2H), 7.11-7.20 (m, 3H), 5.05-5.15 (m, 1H), 4.69-4.79 (m, 1H), 4.30 (s, 2H), 3.80 (t, J=5.7 Hz, 2H), 3.66 (t, J=5.6 Hz, 2H), 3.50-3.60 (m, 2H), 3.43-3.50 (m, 2H), 3.15 (dt, J=12.6 Hz, 4.2 Hz, 1H), 2.97-3.07 (m, 1H), 2.35 (s, 3H), 2.16 (s, 3H), 1.45 (d, J=8.3 Hz, 3H).

HR MS (m/z, MH+) meas. 544.2647.

Example 142

(R)-4-(6-Benzyl-4,5-dimethyl-pyridazin-3-yl)-2-methyl-3,4,5,6-tetrahydro-2H-[1,2']bipyrazinyl-5'-carboxylic acid methoxy-methyl-amide

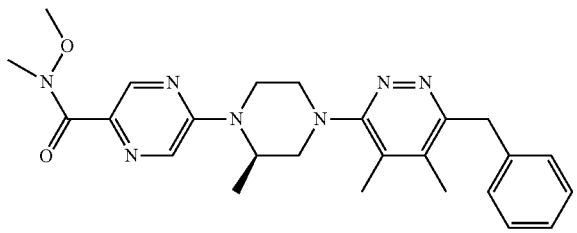 [SMILES: CON(C)C(=O)c1cnc(N2CCN(c3nnc(Cc4ccccc4)c(C)c3C)C[C@H]2C)cn1]

(R)-4-(6-Benzyl-4,5-dimethyl-pyridazin-3-yl)-2-methyl-3,4,5,6-tetrahydro-2H-[1,2']bipyrazinyl-5'-carboxylic acid (50 mg, 0.120 mmol) is dissolved in $CH_2Cl_2$ (300 µL). The mixture is cooled to 0° C. and oxalyl chloride (32 µL, 0.358 mmol) is added followed by DMF (3 drops). While stirring, the reaction is warmed to room temperature over 3 h. Diisopropylethylamine (209 µL, 1.2 mmol) is added dropwise followed by addition of N,O-dimethylhydroxylamine hydrochloride (14 mg, 0.144 mmol). Allow the reaction to stir for 16 h. Concentrate the crude mixture in vacuo. The residue is purified by flash chromatography on silica gel (MeOH/$CH_2Cl_2$) to afford the title compound (42 mg, 76%).

Alternative Route to Prepare Example 95

Example 95

1-[(R)-4-(6-Benzyl-4,5-dimethyl-pyridazin-3-yl)-2-methyl-3,4,5,6-tetrahydro-2H-[1,2']bipyrazinyl-5'-yl]-ethanone

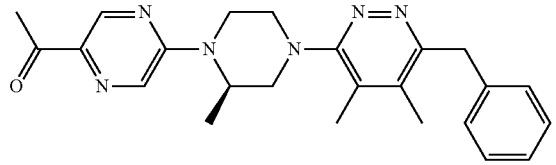 [SMILES: CC(=O)c1cnc(N2CCN(c3nnc(Cc4ccccc4)c(C)c3C)C[C@H]2C)cn1]

(R)-4-(6-Benzyl-4,5-dimethyl-pyridazin-3-yl)-2-methyl-3,4,5,6-tetrahydro-2H-[1,2']bipyrazinyl-5'-carboxylic acid methoxy-methyl-amide (example 142, 450 mg, 0.975 mmol) is dissolved in THF (1 mL) and cooled to 0° C. A dropwise addition of methyl magnesium iodide (325 µL, 0.975 mmol) is added dropwise. Reaction is warmed to room temperature and continues to stir for 16 h. Add $H_2O$ (1 drop) and concentrate reaction mixture in vacuo. The residue is purified by flash chromatography on silica gel (60-100% EtOAc/Heptane and 0-8% MeOH/EtOAc) to afford the title compound (350 mg, 86%).

Example 143

(R)-4-(6-Benzyl-4,5-dimethyl-pyridazin-3-yl)-5'-isopropenyl-2-methyl-3,4,5,6-tetrahydro-2H-[1,2']bipyrazinyl

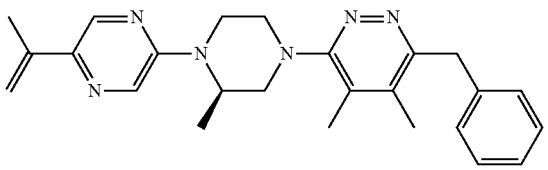 [SMILES: C=C(C)c1cnc(N2CCN(c3nnc(Cc4ccccc4)c(C)c3C)C[C@H]2C)cn1]

Methyltriphenylphosphonium iodide (410 mg, 1.010 mmol) is added to THF (5.5 mL) and cooled to 5° C. Potassium tert-butoxide (1.1 mL, 1M in THF, 1.1 mmol) is added dropwise and the reaction is stirred for 30 min. 1-[(R)-4-(6-Benzyl-4,5-dimethyl-pyridazin-3-yl)-2-methyl-3,4,5,6-tetrahydro-2H-[1,2']bipyrazinyl-5'-yl]-ethanone (350 mg, 0.841 mmol) in THF (1.5 mL) is added to the reaction. The reaction is allowed to stir 1 h at 5° C., and then the ice bath is removed and the reaction is allowed to stir an additional 16 h at room temperature. Remove THF in vacuo. The residue is purified by flash chromatography on silica gel (60-90% EtOAc/heptane) to afford the title compound (130 mg, 37%).

Example 144

2-[(R)-4-(6-Benzyl-4,5-dimethyl-pyridazin-3-yl)-2-methyl-3,4,5,6-tetrahydro-2H-[1,2']bipyrazinyl-5'-yl]-propane-1,2-diol

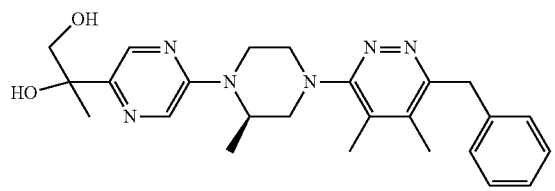 [SMILES: Cc1c(Cc2ccccc2)nnc(N2CCN(c3cnc(C(C)(O)CO)cn3)[C@H](C)C2)c1C]

(R)-4-(6-Benzyl-4,5-dimethyl-pyridazin-3-yl)-5'-isopropenyl-2-methyl-3,4,5,6-tetrahydro-2H-[1,2']bipyrazinyl (example 143, 120 mg, 0.290 mmol) is suspended in acetone (2 mL), tert-butanol (1 mL), and $H_2O$ (1 mL). To this suspension is added $K_2OsO_4$ (9.6 mg, 0.029 mmol) and NMO (37.4 mg, 0.319 mmol). The reaction is stirred at room temperature for 16 h. Concentrate in vacuo. Add $H_2O$ and extract with EtOAc. Wash the combined organics with brine and concentrate in vacuo. The residue is purified by flash chromatography on silica gel (MeOH/$CH_2Cl_2$) to afford the title compound (49.2 mg, 38%).

¹H NMR (400 MHz, DMSO-d₆) δ=8.32 (d, J=1.4 Hz, 1H), 8.27-8.16 (m, 1H), 7.33-7.23 (m, 2H), 7.22-7.13 (m, 3H), 4.98 (d, J=1.0 Hz, 1H), 4.74-4.62 (m, 1H), 4.58 (td, J=6.2 Hz, 1.0 Hz, 1H), 4.25 (s, 2H), 4.18 (dm, J=12.9 Hz, 1H), 3.55-3.46 (m, 1H), 3.49 (d, J=5.8 Hz, 2H), 3.40 (dm, J=12.4 Hz, 1H), 3.29 (td, J=12.5 Hz, 3.2 Hz, 1H), 3.07 (dd, J=12.3 Hz, 3.5 Hz, 1H), 2.95 (td, J=12.3, 3.2 Hz, 1H), 2.26 (s, 3H), 2.12 (s, 3H), 1.36 (s, 3H), 1.28 (d, J=6.4 Hz, 3H).

HR MS (m/z, MH+) meas. 449.2667, calc. 449.2665.

Synthesis of Examples 145-158

General Protocol for the Amination of Pyridazine Chlorides XII with Amines to Yield Examples 145 to 154 (Route A)

To a solution of pyridazine chlorides XII (0.34 mmol) in NMP or dioxane/DMF (3 mL) is added the substituted piperazine (0.49 mmol) and TEA (0.15 mL, 1.08 mmol). The mixture is heated in a microwave synthesizer at 210° C. for 60 min. Water is added and the resulting mixture is extracted with EtOAc. The combined organic layers are washed with water, brine, dried over Na₂SO₄, filtered and concentrated down. The crude product is purified by chromatography on silica gel (EtOAc/Hexane: 10%~70%) to give examples Ip Examples 145-154

The following table (Table 9) lists examples of compounds prepared by amination as described above:

TABLE 9

| Example | Structure | HR MS [m/z, MH+] meas. |
|---|---|---|
| 145 | | 433.2760 |
| 146 | 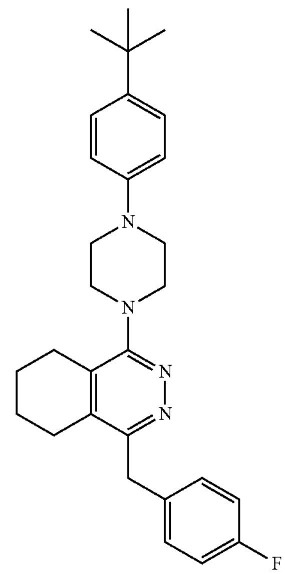 [SMILES: CC(C)(C)c1ccc(N2CCN(c3nnc(Cc4ccc(F)cc4)c4c3CCCC4)CC2)cc1] | 459.2924 |
| 147 | 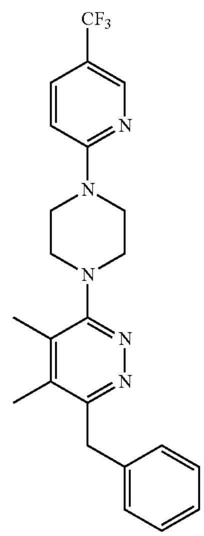 [SMILES: Cc1c(Cc2ccccc2)nnc(N2CCN(c3ccc(C(F)(F)F)cn3)CC2)c1C] | 428.2062 |
| 148 | 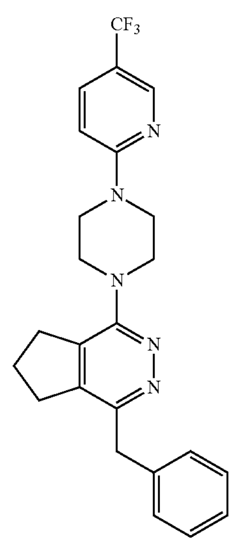 [SMILES: FC(F)(F)c1ccc(N2CCN(c3nnc(Cc4ccccc4)c4c3CCC4)CC2)nc1] | 440.2065 |

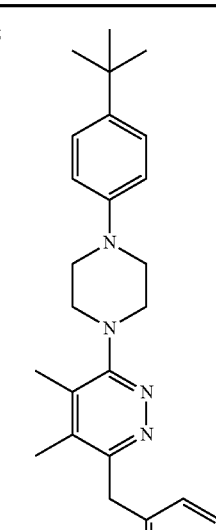

TABLE 9-continued

| Example | Structure | HR MS [m/z, MH+] meas. |
|---|---|---|
| 149 | (structure with CF3-pyridine, piperazine, dimethylpyridazine, 4-fluorobenzyl) | 446.1960 |
| 150 | (structure with CF3-pyridine, piperazine, cyclopentane-fused pyridazine, 4-fluorobenzyl) | 458.1984 |
| 151 | (structure with CF3-pyridine, piperazine, cyclohexane-fused pyridazine, 4-fluorobenzyl) | 472.2124 |
| 152 | (structure with CO2Et-pyridine, piperazine, cyclopentane-fused pyridazine, 4-fluorobenzyl) | 462 (MS) |
| 153 | (structure with CO2Et-pyridine, piperazine, dimethylpyridazine, 4-fluorobenzyl) | 450.2307 |
| 154 | (structure with CO2Et-pyridine, piperazine, cyclohexane-fused pyridazine, 4-fluorobenzyl) | 476.2472 |

Example 155

4-(6-Benzyl-4,5-dimethyl-pyridazin-3-yl)-piperazine-1-carboxylic acid phenyl ester

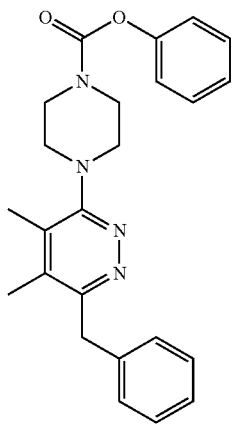 [SMILES: Cc1c(Cc2ccccc2)nnc(N2CCN(C(=O)Oc3ccccc3)CC2)c1C]

To a solution of 3-benzyl-4,5-dimethyl-6-piperazin-1-yl-pyridazine (60 mg, 0.21 mmol) and phenyl chloroformate (40 mg, 0.26 mmol) in CH$_2$Cl$_2$ (3 mL) at 25° C. is added N-methyl morpholine (0.07 mL, 0.60 mmol). After being stirred at 25° C. for 3 h, the mixture is diluted with CH$_2$Cl$_2$ (10 mL), and washed with saturated sodium bicarbonate (1 mL) and water (2×5 mL). The organic layer is concentrated and purified by HPLC (CH$_3$CN/H$_2$O: 22%~45% with 0.1% TFA) to give 4-(6-benzyl-4,5-dimethyl-pyridazin-3-yl)-piperazine-1-carboxylic acid phenyl ester (69 mg, 81%).

$^1$H-NMR (400 MHz, CDCl$_3$) δ=2.28 (3H, s), 2.41 (3H, s), 3.40 (4H, d), 3.81 (4H, d), 4.50 (2H, s), 7.13 (2H, d), 7.20 (2H, d), 7.27 (2H, m), 7.33 (2H, m), 7.38 (2H, m).

HR MS (m/z, MH+) meas. 403.2115.

Example 156

4-(6-Benzyl-4,5-dimethyl-pyridazin-3-yl)-piperazine-1-carboxylic acid phenylamide

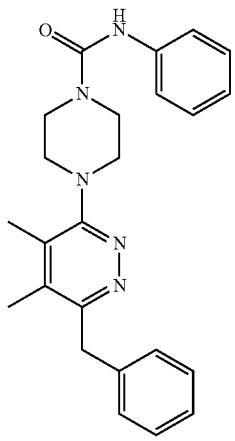 [SMILES: Cc1c(Cc2ccccc2)nnc(N2CCN(C(=O)Nc3ccccc3)CC2)c1C]

To a solution of 3-benzyl-4,5-dimethyl-6-piperazin-1-yl-pyridazine (60 mg, 0.21 mmol)) in CH$_2$Cl$_2$ (5 mL) at 25° C. is added phenyl isocyanate (33 mg, 0.28 mmol). After being stirred at 25° C. for 2 h, the reaction mixture is concentrated and purified by HPLC (CH$_3$CN/H$_2$O: 22%~45% with 0.1% TFA) to give 4-(6-benzyl-4,5-dimethyl-pyridazin-3-yl)-piperazine-1-carboxylic acid phenylamide (49 mg, 58%).

$^1$H-NMR (400 MHz, CDCl$_3$) δ=2.12 (3H, s), 2.21 (3H, s), 3.27 (4H, t), 3.67 (4H, t), 4.30 (2H, s), 7.01 (1H, t), 7.19 (3H, m), 7.25 (4H, m), 7.39 (2H, d).

HR MS (m/z, MH+) meas. 402.2279.

Example 157

4-(6-Benzyl-4,5-dimethyl-pyridazin-3-yl)-piperazine-1-carboxylic acid benzylamide

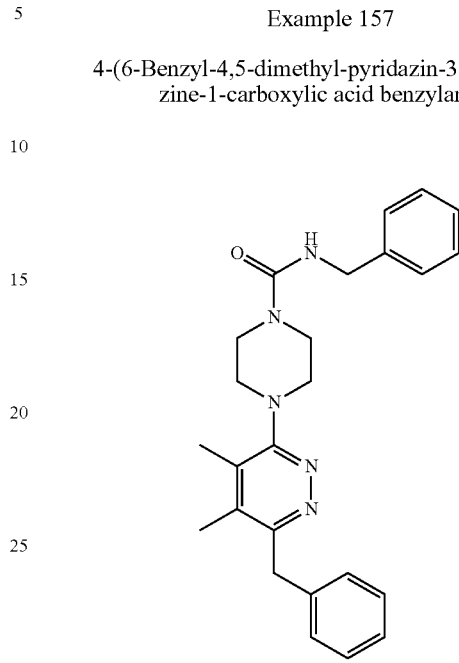

To a solution of 3-benzyl-4,5-dimethyl-6-piperazin-1-yl-pyridazine (60 mg, 0.21 mmol)) in CH$_2$Cl$_2$ (5 mL) at 25° C. is added benzyl isocyanate (37 mg, 0.28 mmol). After being stirred at 25° C. for 2 h, the reaction mixture is concentrated and purified by HPLC (CH$_3$CN/H$_2$O: 22%~45% with 0.1% TFA) to give 4-(6-benzyl-4,5-dimethyl-pyridazin-3-yl)-piperazine-1-carboxylic acid benzylamide (46 mg, 60%).

$^1$H-NMR (400 MHz, CDCl$_3$) δ=2.24 (3H, s), 2.34 (3H, s), 3.33 (4H, t), 3.58 (4H, t), 4.44 (2H, s), 4.49 (2H, s), 7.19 (2H, d), 7.26 (2H, m), 7.30 (2H, m), 7.32 (4H, m).

HR MS (m/z, MH+) meas. 416.2437.

Example 158

3-Benzyl-6-(4-benzyl-piperazin-1-yl)-4,5-dimethyl-pyridazine

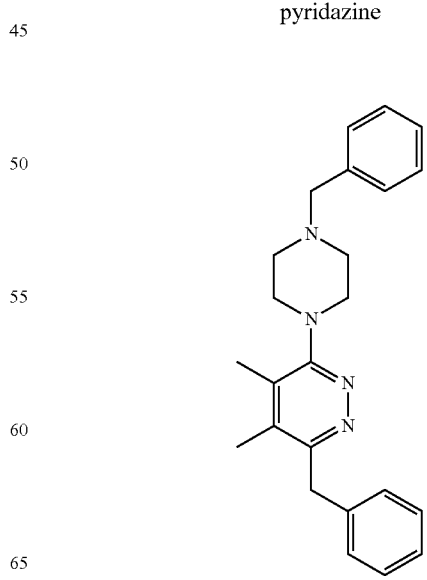

To a solution of 3-benzyl-4,5-dimethyl-6-piperazin-1-yl-pyridazine (40 mg, 0.14 mmol)) in CH$_2$Cl$_2$ (1.6 mL) and THF (1.6 mL) at 25° C. is added benzaldehyde (23 mg, 0.21 mmol), acetic acid (2 drops) and sodium triacetoxyborohydride (90 mg, 0.43 mmol). After being stirred at 25° C. for 2 h, the mixture is diluted with CH$_2$Cl$_2$ (10 mL) and washed with saturated sodium bicarbonate (2 mL) and water (5 mL). The organic layer is concentrated and purified by HPLC (CH$_3$CN/H$_2$O: 22% 45% with 0.1% TFA) to give 3-benzyl-6-(4-benzyl-piperazin-1-yl)-4,5-dimethyl-pyridazine (20 mg, 37%).

$^1$H-NMR (400 MHz, MeOH-d$_4$) δ=2.00 (3H, s), 2.11 (3H, s), 2.56 (4H, t), 3.12 (4H, t), 3.51 (2H, s), 4.16 (2H, s), 7.05 (3H, m), 7.15 (3H, m), 7.25 (4H, m).

HR MS (m/z, MH+) meas. 373.2378.

5-membered arylmethyl-pyridazines

Scheme 7 shows a general synthetic scheme for the preparation of compounds of Formula Iq to Is. Substituted chloro pyridazines Ma can be reacted with acetonitrile under treatment with a strong base (e.g LiHMDS) to form intermediates XIVa. Hydrolysis of the nitrile functionality provides acid intermediates XIVb and subsequent amid coupling with acid hydrazides yields intermediates XIVc. Intermediates XIVa can be reacted with hydroxylamine and N,N-dimethylformamide-dimethylacetal to examples Iq or can provide tetrazole examples Ir by reaction with sodium azide followed by alkylation (e.g. bromides or iodides). Intermediates XIVc can be condensed e.g. with triphenylphosphine to examples Is.

SCHEME 7

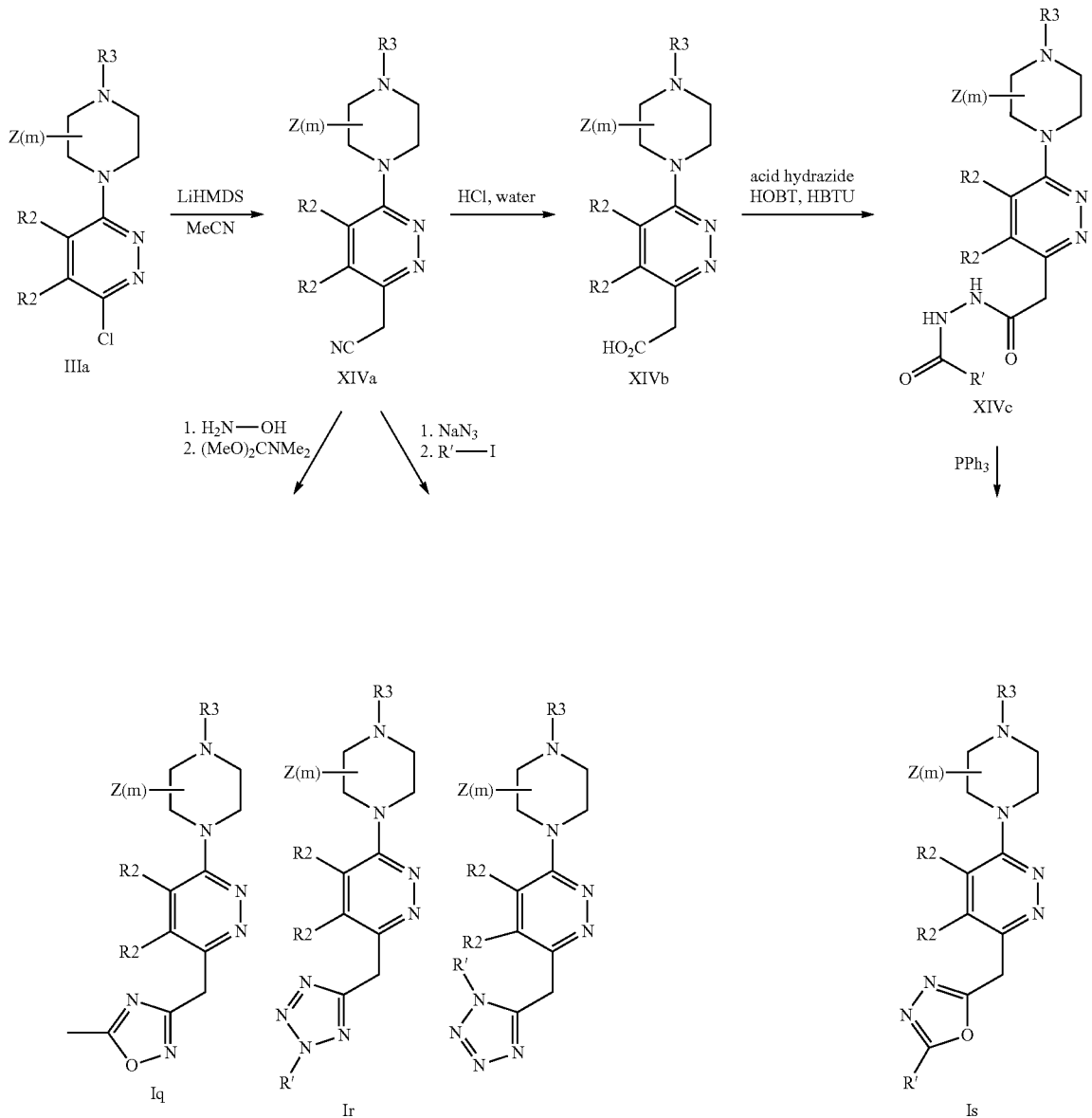

127

Synthesis of Intermediates XIV 4,5-Dimethyl-6-[4-(5-trifluoromethyl-pyridin-2-yl)-piperazin-1-yl]-pyridazin-3-yl-acetonitrile (compound 67)

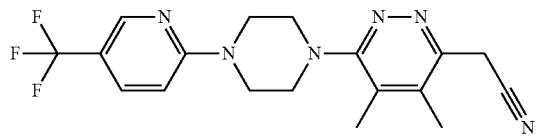 [SMILES: Cc1c(CC#N)nnc(N2CCN(c3ccc(C(F)(F)F)cn3)CC2)c1C]

3-Chloro-4,5-dimethyl-6-[4-(5-trifluoromethyl-pyridin-2-yl)-piperazin-1-yl]-pyridazine (1.0 g, 2.64 mmol), acetonitrile (0.225 mL, 4.22 mmol), and toluene (5 mL) are combined and cooled to 0° C. LiHMDS (8.4 mL, 1.0 M, 8.4 mmol) is added dropwise over 5 min. The reaction is stirred at 0° C. for 1 h, then warmed to room temperature and stirred an additional 16 h. The reaction is quenched by the addition of saturated aq. $NH_4Cl$, and the organics are extracted with EtOAc. The combined organic layers are dried over $MgSO_4$ and concentrated. The residue is purified by flash chromatography on silica gel (0-100% EtOAc in heptanes) to afford the title compound as an orange solid (500 mg, 50%).

$^1$H NMR (400 MHz, $CDCl_3$) δ=8.36 (s, 1H), 7.60 (dd, J=9.0 Hz, 2.5 Hz, 1H), 6.65 (d, J=9.0 Hz, 1H), 3.96 (s, 2H), 3.72-3.78 (m, 4H), 3.26-3.37 (m, 4H), 2.26 (d, J=13.1 Hz, 6H).

MS (m/z, MH+) meas. 377.2.

{4,5-Dimethyl-6-[4-(5-trifluoromethyl-pyridin-2-yl)-piperazin-1-yl]-pyridazin-3-yl}-acetic acid (compound 68)

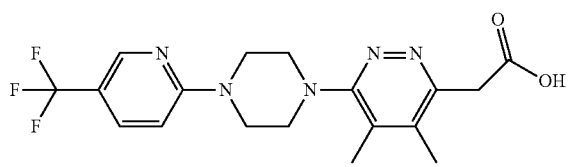 [SMILES: Cc1c(CC(=O)O)nnc(N2CCN(c3ccc(C(F)(F)F)cn3)CC2)c1C]

{4,5-Dimethyl-6-[4-(5-trifluoromethyl-pyridin-2-yl)-piperazin-1-yl]-pyridazin-3-yl}-acetonitrile (210 mg, 0.56 mmol) and 6 M HCl (1.0 mL) are added to a sealed tube and then heated to 100° C. for 16 h. The organics are extracted with $CH_2Cl_2$. The aqueous portion is neutralized to pH~7 with sodium bicarbonate solution and extracted with EtOAc. Target compound remains in the aqueous layer. This layer is concentrated under reduced pressure and the residue is triturated several times with MeOH, and then dried in vacuo to afford the title compound (280 mg, quant).

Acetic acid N'-(2-{4,5-dimethyl-6-[4-(5-trifluoromethyl-pyridin-2-yl)-piperazin-1-yl]-pyridazin-3-yl}-acetyl)-hydrazide (compound 69)

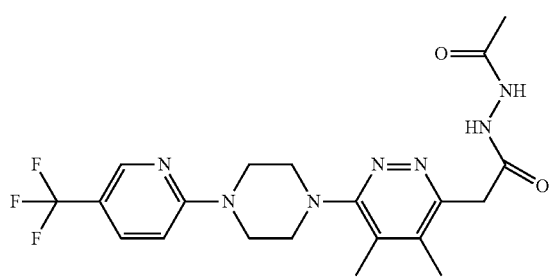 [SMILES: CC(=O)NNC(=O)Cc1nnc(N2CCN(c3ccc(C(F)(F)F)cn3)CC2)c(C)c1C]

128

Acetic acid hydrazide (20.6 mg, 0.28 mmol) is added to a round-bottom flask under $N_2$ followed by DMF (5 mL). Diisopropylethylamine (0.25 mL) is added and the reaction is stirred for 30 min. {4,5-Dimethyl-6-[4-(5-trifluoromethyl-pyridin-2-yl)-piperazin-1-yl]-pyridazin-3-yl}-acetic acid (110 mg, 0.28 mmol) is added and the reaction is stirred for 1 h. HOBT (42 mg, 0.311 mmol) and HBTU (116.8 mg, 0.31 mmol) are added and the reaction is allowed to stir for 16 h. The crude reaction mixture is purified via flash chromatography on silica gel (0-30% methanol in dichloromethane) to afford the title compound (114 mg, 90%).

Synthesis of Examples 159-162

Example 159

4,5-Dimethyl-3-(5-methyl-[1,2,4]oxadiazol-3-ylmethyl)-6-[4-(5-trifluoromethyl-pyridin-2-yl)-piperazin-1-yl]-pyridazine

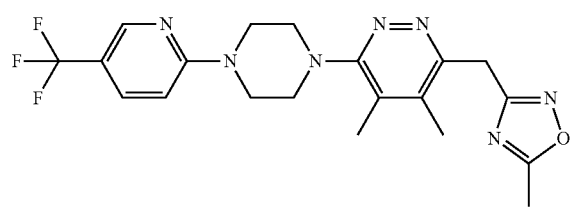 [SMILES: Cc1nc(Cc2nnc(N3CCN(c4ccc(C(F)(F)F)cn4)CC3)c(C)c2C)no1]

4,5-Dimethyl-6-[4-(5-trifluoromethyl-pyridin-2-yl)-piperazin-1-yl]-pyridazin-3-yl-acetonitrile (120 mg, 0.32 mmol) is combined with hydroxylamine (63 mg, 0.96 mmol) and THF (2 mL). The reaction mixture is heated to reflux for 3 h. Concentrate the reaction and redissolve the residue in dimethylacetamide dimethylacetal (500 µL). Heat this solution for 16 h at reflux. Concentrate the resulting mixture in vacuo. The residue is purified by flash chromatography on silica gel (MeOH/$CH_2Cl_2$) to afford the title compound (62.3 mg, 45%).

$^1$H NMR (400 MHz, DMSO-$d_6$) δ=8.44 (d, J=1.6 Hz, 1H), 7.83 (dd, J=9.1 Hz, 2.5 Hz, 1H), 7.03 (d, J=9.1 Hz, 1H), 4.34 (s, 2H), 3.86-3.76 (m, 4H), 3.26-3.18 (m, 4H), 2.54 (s, 3H), 2.27 (s, 3H), 2.22 (s, 3H).

HR MS (m/z, MH+): meas. 434.1913 calc. 434.1916.

Examples 160 and 161

4,5-Dimethyl-3-(1-methyl-1H-tetrazol-5-ylmethyl)-6-[4-(5-trifluoromethyl-pyridin-2-yl)-piperazin-1-yl]-pyridazine & 4,5-Dimethyl-3-(2-methyl-2H-tetrazol-5-ylmethyl)-6-[4-(5-trifluoromethyl-pyridin-2-yl)-piperazin-1-yl]-pyridazine

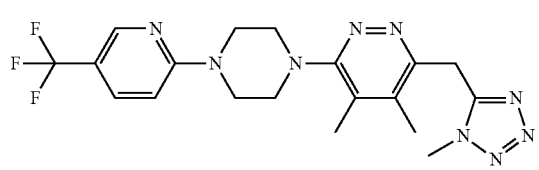

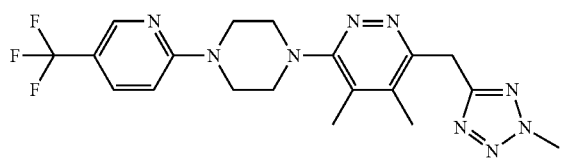

4,5-Dimethyl-6-[4-(5-trifluoromethyl-pyridin-2-yl)-piperazin-1-yl]-pyridazin-3-yl-acetonitrile (120 mg, 0.32 mmol) is combined with zinc (II) chloride (43.5 mg, 0.32 mmol) and sodium azide (25 mg, 0.38 mmol) in $H_2O$ (5 mL). The mixture is heated to reflux for 4 h, and then cooled to room temperature. The free tetrazole is isolated by filtration, dissolved in DMF (4.2 mL), and carried on without further purification. Cesium carbonate (128.5 mg, 0.395 mmol) is added and the reaction mixture is cooled to 0° C. Methyl iodide (16 μL, 0.263 mmol) is added dropwise, and the reaction is stirred and allowed to warm to room temperature over 16 h. Cool back to 0° C. and add additional methyl iodide (24 μL, 0.395 mmol). Allow reaction to warm to room temperature over 16 h. Concentrate reaction in vacuo and filter off solids. Wash with MeOH. Remaining solid is dissolved in $H_2O$ and TFA and is purified by HPLC ($CH_3CN/H_2O$) to afford the title compounds as a 57:43 mixture of regioisomers (22.2 mg, 20%).

$^1H$ NMR (mixture of compounds, 600 MHz, DMSO-$d_6$) δ=8.44 (s, 1H), 7.83 (d, J=9.1 Hz, 1H), 7.07-6.99 (m, 1H), 4.62 (s, 1.1H), 4.50 (s, 0.9H), 4.30 (s, 1.3H), 4.00 (s, 1.7H), 3.85-3.76 (m, 4H), 3.24-3.16 (m, 4H), 2.29 (s, 1.7H), 2.26 (s, 3H), 2.21 (s, 1.3H).

HR MS (m/z, MH+) meas. 434.2035, calc. 434.2029.

Example 162

4,5-Dimethyl-3-(5-methyl-[1,3,4]oxadiazol-2-ylmethyl)-6-[4-(5-trifluoromethyl-pyridin-2-yl)-piperazin-1-yl]-pyridazine

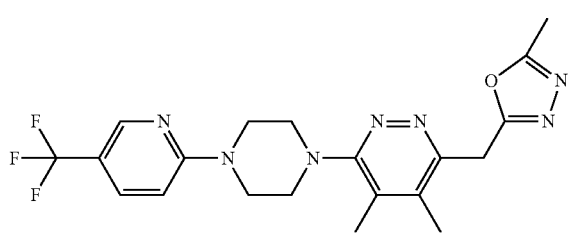 [SMILES: Cc1nnc(Cc2nnc(N3CCN(c4ccc(C(F)(F)F)cn4)CC3)c(C)c2C)o1]

Acetic acid N'-(2-{4,5-dimethyl-6-[4-(5-trifluoromethyl-pyridin-2-yl)-piperazin-1-yl]-pyridazin-3-yl}-acetyl)-hydrazide (114 mg, 0.248 mmol) is added to a round-bottom flask under $N_2$ followed by acetonitrile (3 mL), diisopropylethylamine (0.27 mL, 1.43 mmol) and triphenylphosphine (115.5 mg, 0.44 mmol) and the reaction is stirred for 30 min. Hexachloroethane (77.5 mg, 0.329 mmol) is then added and the reaction is stirred for 16 h. The crude mixture is purified via HPLC (ammonium hydroxide as a modifier) to afford the title compound (8 mg, 7%).

HR MS (m/z, MH+) meas. 434.1934, calc. 434.1916.

Synthesis of Examples 163 and 164

Examples 163 and 164 are prepared from incubation of 200 mg example 88 with recombinant human Cyp3A4 to yield after isolation and purification the compounds mentioned below as white solids.

Example 163

2-[(R)-4-(6-Benzyl-5-hydroxymethyl-4-methyl-pyridazin-3-yl)-2-methyl-3,4,5,6-tetrahydro-2H-[1,2']bipyrazinyl-5'-yl]-propan-2-ol

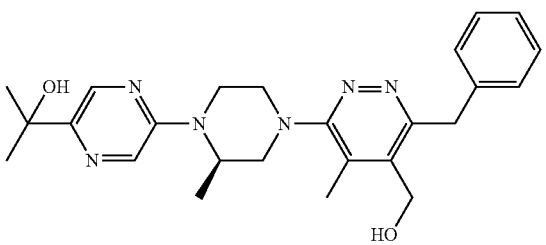 [SMILES: Cc1c(N2CCN(c3cnc(C(C)(C)O)cn3)[C@H](C)C2)nnc(Cc2ccccc2)c1CO]

Yield: 6.5 mg

Example 164

2-[(R)-4-(6-Benzyl-4-hydroxymethyl-5-methyl-pyridazin-3-yl)-2-methyl-3,4,5,6-tetrahydro-2H-[1,2']bipyrazinyl-5'-yl]-propan-2-ol

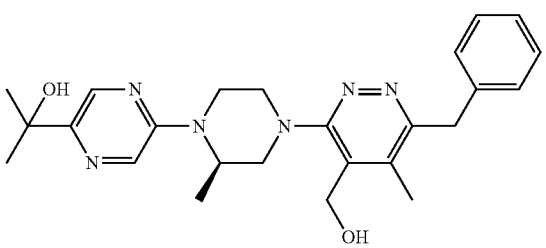 [SMILES: Cc1c(Cc2ccccc2)nnc(N2CCN(c3cnc(C(C)(C)O)cn3)[C@H](C)C2)c1CO]

Yield: 8.2 mg

The compounds of the present invention are a species of a genus of compounds shown in U.S. provisional application 60/89499. The following is comparative data showing improvements in potency and solubility by a comparison of the closest examples, e.g., compound nos. 92, 93, 93a, b, c from application 60/89499 with examples of the present invention:

| | application Ser. No. 60/89,499 | | | | |
|---|---|---|---|---|---|
| Example no. | RGA (1 nM Smo agonist) $IC_{50}$ [nM] | RGA (25 nM Smo agonist) $IC_{50}$ [nM] | Mouse Smo bdg., $IC_{50}$ [nM] | Human Smo bdg., $IC_{50}$ [nM] | equilibrium solubility at pH6.8 [μM] |
| 92 | 266 | 7558 | 197 | 247 | <5 |
| 93 | 367 | | 42 | | <5 |
| 93a | 211 | 356 | 61 | | <5 |

-continued application Ser. No. 60/89,499

| Example no. | RGA (1 nM Smo agonist) IC$_{50}$ [nM] | RGA (25 nM Smo agonist) IC$_{50}$ [nM] | Mouse Smo bdg., IC$_{50}$ [nM] | Human Smo bdg., IC$_{50}$ [nM] | equilibrium solubility at pH6.8 [µM] |
|---|---|---|---|---|---|
| 93b | 168 | 529 | 139 | 204 | <5 |
| 93c | 22 | 236 | 62 | 101 | <5 |

Examples of the Present Invention

| Example no. | RGA (1 nM Smo agonist) IC$_{50}$ [nM] | RGA (25 nM Smo agonist) IC$_{50}$ [nM] | Mouse Smo bdg., IC$_{50}$ [nM] | Human Smo bdg., IC$_{50}$ [nM] | equilibrium solubility at pH6.8 [µM] |
|---|---|---|---|---|---|
| 2 | 2 | 23 | 8 | 4 | |
| 48 | 2 | 25 | 8 | 5 | 425 |
| 50 | 6 | 114 | 32 | 29 | >1000 |
| 54 | 7 | 83 | 30 | 22 | 619 |
| 88 | 1 | 14 | 3 | 9 | 44 |
| 89 | 2 | 60 | 15 | 11 | 11 |
| 90 | 1 | 34 | 7 | 6 | 18 |
| 91 | 5 | 57 | 8 | 8 | |
| 92 | 4 | 58 | 10 | 10 | |
| 93 | 1 | 14 | 3 | 1 | 20 |
| 95 | 8 | 110 | 9 | 8 | |
| 96 | 6 | 62 | 4 | 3 | |
| 97 | 3 | 35 | 2 | 2 | |
| 98 | 11 | 69 | 6 | 6 | |
| 99 | 5 | 72 | 3 | 2 | |
| 104 | 5 | 70 | 9 | 14 | |
| 105 | 3 | 35 | 6 | 7 | |
| 106 | 5 | 76 | 5 | 7 | |
| 107 | 2 | 23 | 3 | 3 | |
| 108 | 4 | 33 | | | |
| 109 | 3 | 38 | 2 | 2 | |
| 111 | 1 | 18 | 2 | 1 | |
| 144 | 5 | 83 | 19 | 24 | 270 |

Biological Activity

Activity of the compounds was evaluated using a reporter gene assay (RGA) in TMHh12 cells. IC$_{50}$ for antagonism of Gli-luciferase activity was tested in the presence of increasing concentrations of a small molecule agonist which binds to Smo with 1 nM affinity and activates the Hh pathway (Frank-Kamenetsky et al 2002, Journal of Biology 1, 10.1-10.19). Antagonist compounds from screening which show increased IC$_{50}$s for Gli-luc as the agonist dose is increased may be directly interacting with Smo (either through competition for the same binding site on Smo, or via competition between an active conformational state of Smo that is induced by agonist and an inactive state that is induced by the test antagonist). In validation experiments, a variety of small molecule antagonists of Smo demonstrate "IC$_{50}$ shift" behavior.

Table 10 lists the IC$_{50}$ of antagonists determined in the presence of different (1 nM and 25 nM) concentrations of a small agonist of Smoothened (Frank-Kamenetsky et al 2002, Journal of Biology 1, 10.1-10.19).

A Smo binding assay was developed using radio-labeled smoothened agonist for compound competition. Table 10 lists the IC$_{50}$ for displacement of a small molecule agonist of Smoothened determined in a filter binding format for the mouse and human Smoothened receptor.

TABLE 10

| Example no. | RGA (1 nM Smo agonist) IC$_{50}$ [nM] | RGA (25 nM Smo agonist) IC$_{50}$ [nM] | Mouse Smo bdg., IC$_{50}$ [nM] | Human Smo bdg., IC$_{50}$ [nM] |
|---|---|---|---|---|
| 2 | <0.1 | <0.1 | <0.1 | <0.1 |
| 3 | 0.1-1 | 1-10 | 0.1-1 | 0.1-1 |
| 4 | 0.1-1 | 1-10 | 0.1-1 | 0.1-1 |
| 5 | <0.1 | 0.1-1 | <0.1 | <0.1 |
| 6 | 1-10 | 1-25 | <0.1 | <0.1 |
| 7 | 1-10 | 1-25 | <0.1 | <0.1 |
| 8 | 1-10 | 1-25 | 0.1-1 | 0.1-1 |
| 9 | 1-10 | 1-25 | 1-10 | 1-10 |
| 10 | <0.1 | <0.1 | | <0.1 |
| 11 | <0.1 | 1-10 | | <0.1 |
| 12 | <0.1 | 0.1-1 | <0.1 | <0.1 |
| 13 | <0.1 | <0.1 | <0.1 | <0.1 |
| 14 | 1-10 | 1-25 | 0.1-1 | 1-10 |
| 15 | <0.1 | 0.1-1 | <0.1 | <0.1 |
| 16 | <0.1 | 0.1-1 | 0.1-1 | 0.1-1 |
| 17 | 0.1-1 | 0.1-1 | 0.1-1 | 0.1-1 |
| 18 | 0.1-1 | 1-10 | <0.1 | <0.1 |
| 19 | 0.1-1 | 0.1-1 | <0.1 | <0.1 |
| 20 | <0.1 | 0.1-1 | <0.1 | <0.1 |
| 21 | 0.1-1 | 1-10 | <0.1 | <0.1 |
| 22 | 0.1-1 | 0.1-1 | 0.1-1 | 0.1-1 |
| 23 | 0.1-1 | 0.1-1 | <0.1 | 0.1-1 |
| 24 | 0.1-1 | 0.1-1 | | |
| 25 | 0.1-1 | 1-10 | <0.1 | <0.1 |
| 26 | 0.1-1 | 1-10 | 0.1-1 | 0.1-1 |
| 27 | 1-10 | 1-10 | 0.1-1 | 0.1-1 |
| 28 | 1-10 | 1-10 | <0.1 | <0.1 |
| 29 | 1-10 | 1-10 | <0.1 | <0.1 |
| 30 | 1-10 | 1-10 | 1-10 | 1-10 |
| 31 | <0.1 | <0.1 | <0.1 | <0.1 |
| 32 | <0.1 | <0.1 | <0.1 | <0.1 |
| 33 | <0.1 | <0.1 | <0.1 | <0.1 |
| 34 | <0.1 | 0.1-1 | <0.1 | <0.1 |
| 35 | <0.1 | <0.1 | <0.1 | <0.1 |
| 36 | <0.1 | <0.1 | <0.1 | <0.1 |
| 37 | <0.1 | 0.1-1 | 0.1-1 | <0.1 |
| 38 | <0.1 | 0.1-1 | <0.1 | <0.1 |
| 39 | <0.1 | 0.1-1 | 0.1-1 | 0.1-1 |
| 40 | <0.1 | 0.1-1 | 0.1-1 | 0.1-1 |
| 41 | 0.1-1 | 1-25 | <0.1 | 0.1-1 |
| 42 | <0.1 | 0.1-1 | <0.1 | <0.1 |
| 43 | <0.1 | <0.1 | <0.1 | <0.1 |
| 44 | <0.1 | 0.1-1 | 0.1-1 | 0.1-1 |
| 45 | 0.1-1 | 0.1-1 | <0.1 | <0.1 |
| 46 | <0.1 | <0.1 | <0.1 | 0.1-1 |
| 47 | | | <0.1 | <0.1 |
| 48 | <0.1 | <0.1 | <0.1 | <0.1 |
| 49 | <0.1 | 1-10 | 0.1-1 | 0.1-1 |
| 50 | <0.1 | <0.1 | <0.1 | <0.1 |
| 51 | | | | |
| 52 | <0.1 | <0.1 | <0.1 | <0.1 |
| 53 | <0.1 | 1-10 | 0.1-1 | 0.1-1 |
| 54 | <0.1 | 0.1-1 | <0.1 | <0.1 |
| 55 | | | | |
| 56 | 0.1-1 | 1-10 | 1-10 | 1-10 |
| 57 | 0.1-1 | 1-25 | 1-10 | 1-10 |
| 58 | 0.1-1 | 1-10 | 0.1-1 | 0.1-1 |
| 59 | 1-10 | 1-25 | 1-25 | 1-10 |
| 60 | 0.1-1 | 1-10 | 0.1-1 | 1-10 |
| 61 | 0.1-1 | 1-10 | 1-10 | 1-10 |
| 62 | 0.1-1 | 1-25 | 1-10 | 1-10 |
| 63 | 0.1-1 | 1-10 | 0.1-1 | 0.1-1 |
| 64 | <0.1 | 0.1-1 | | |
| 65 | 0.1-1 | 0.1-1 | <0.1 | 0.1-1 |
| 66 | <0.1 | 0.1-1 | <0.1 | <0.1 |
| 67 | 0.1-1 | 1-10 | <0.1 | 0.1-10 |
| 68 | 0.1-1 | 0.1-1 | 0.1-1 | 0.1-1 |
| 69 | | | | |
| 70 | <0.1 | <0.1 | <0.1 | <0.1 |
| 72 | <0.1 | 0.1-1 | <0.1 | <0.1 |
| 73 | <0.1 | 0.1-1 | <0.1 | <0.1 |
| 75 | 0.1-1 | 1-10 | <0.1 | <0.1 |
| 78 | <0.1 | 1-10 | <0.1 | <0.1 |
| 79 | 0.1-1 | 1-10 | 1-10 | 1-25 |

TABLE 10-continued

| Example no. | RGA (1 nM Smo agonist) IC$_{50}$ [nM] | RGA (25 nM Smo agonist) IC$_{50}$ [nM] | Mouse Smo bdg., IC$_{50}$ [nM] | Human Smo bdg., IC$_{50}$ [nM] |
|---|---|---|---|---|
| 80  | 0.1-1 | 0.1-1 | <0.1 | <0.1 |
| 81  | <0.1  | 0.1-1 | <0.1 | <0.1 |
| 83  | <0.1  | 0.1-1 | <0.1 | <0.1 |
| 87  | <0.1  | 0.1-1 | <0.1 | <0.1 |
| 88  | <0.1  | <0.1  | <0.1 | <0.1 |
| 89  | <0.1  | <0.1  | <0.1 | <0.1 |
| 90  | <0.1  | <0.1  | <0.1 | <0.1 |
| 91  | <0.1  | <0.1  | <0.1 | <0.1 |
| 92  | <0.1  | <0.1  | <0.1 | <0.1 |
| 93  | <0.1  | <0.1  | <0.1 | <0.1 |
| 94  | <0.1  | 0.1-1 | <0.1 | <0.1 |
| 95  | <0.1  | 0.1-1 | <0.1 | <0.1 |
| 96  | <0.1  | <0.1  | <0.1 | <0.1 |
| 97  | <0.1  | <0.1  | <0.1 | <0.1 |
| 98  | <0.1  | <0.1  | <0.1 | <0.1 |
| 99  | <0.1  | <0.1  | <0.1 | <0.1 |
| 100 | <0.1  | 0.1-1 | <0.1 | <0.1 |
| 101 | <0.1  | 0.1-1 | <0.1 | <0.1 |
| 102 | <0.1  | 0.1-1 | <0.1 | <0.1 |
| 104 | <0.1  | <0.1  | <0.1 | <0.1 |
| 105 | <0.1  | <0.1  | <0.1 | <0.1 |
| 106 | <0.1  | <0.1  | <0.1 | <0.1 |
| 107 | <0.1  | <0.1  | <0.1 | <0.1 |
| 108 | <0.1  | <0.1  |      |      |
| 109 | <0.1  | <0.1  | <0.1 | <0.1 |
| 110 | <0.1  | <0.1  | <0.1 | <0.1 |
| 111 | <0.1  | <0.1  | <0.1 | <0.1 |
| 112 | <0.1  | <0.1  | <0.1 | <0.1 |
| 113 | <0.1  | 0.1-1 | <0.1 | <0.1 |
| 114 | <0.1  | 0.1-1 | <0.1 | <0.1 |
| 115 | 0.1-1 | 1-10  | 0.1-1 | 0.1-1 |
| 116 | 1-10  | 1-25  | 1-25  | 0.1-1 |
| 117 | 1-10  | 1-25  | 1-10  | 1-10  |
| 118 | <0.1  | 0.1-1 | <0.1 | 0.1-1 |
| 119 | <0.1  | <0.1  | <0.1 | <0.1 |
| 120 | <0.1  | 0.1-1 | 0.1-1 | 0.1-1 |
| 121 | <0.1  | <0.1  | <0.1 | <0.1 |
| 122 | 0.1-1 | 1-10  | 0.1-1 | 0.1-1 |
| 123 | <0.1  | 0.1-1 | <0.1 | 0.1-1 |
| 125 | <0.1  | 0.1-1 | 0.1-1 | 0.1-1 |
| 126 | <0.1  | 0.1-1 | <0.1 | <0.1 |
| 127 | <0.1  | 0.1-1 | 0.1-1 | 0.1-1 |
| 128 | <0.1  | 0.1-1 | <0.1 | 0.1-1 |
| 129 | <0.1  | 0.1-1 | 0.1-1 | 0.1-1 |
| 130 | <0.1  | 0.1-1 | <0.1 | <0.1 |
| 131 | 0.1-1 | 1-10  | 0.1-1 | 0.1-1 |
| 132 | <0.1  | 0.1-1 | <0.1 | 0.1-1 |
| 133 | <0.1  | 0.1-1 | <0.1 | <0.1 |
| 134 | <0.1  | 0.1-1 | <0.1 | <0.1 |
| 135 | <0.1  | 0.1-1 | <0.1 | <0.1 |
| 136 | <0.1  | 0.1-1 | <0.1 | 0.1-1 |
| 137 | 0.1-1 | 0.1-1 | 0.1-1 | 0.1-1 |
| 138 | <0.1  | 0.1-1 | 0.1-1 | 0.1-1 |
| 139 | 0.1-1 | 1-10  | 1-10  | 1-10  |
| 140 | <0.1  | 1-10  | 0.1-1 | 0.1-1 |
| 141 | <0.1  | 0.1-1 | <0.1 | <0.1 |
| 143 | <0.1  | <0.1  | <0.1 | <0.1 |
| 144 | <0.1  | <0.1  | <0.1 | <0.1 |
| 145 | 0.1-1 | 0.1-1 | 0.1-1 | 0.1-1 |
| 146 | <0.1  | <0.1  | 0.1-1 | 0.1-1 |
| 147 | <0.1  | 0.1-1 | 0.1-1 | 0.1-1 |
| 148 | <0.1  | 0.1-1 | <0.1 | <0.1 |
| 149 | <0.1  | 0.1-1 | <0.1 | <0.1 |
| 150 | <0.1  | 0.1-1 | <0.1 | <0.1 |
| 151 | <0.1  | 0.1-1 | 0.1-1 | 0.1-1 |
| 153 | <0.1  | <0.1  | <0.1 | <0.1 |
| 154 | 0.1-1 | 1-10  | <0.1 | <0.1 |
| 155 | <0.1  | 0.1-1 | 0.1-1 | 0.1-1 |
| 156 | <0.1  | 0.1-1 | <0.1 | 0.1-1 |
| 157 | <0.1  | 0.1-1 | 0.1-1 | 0.1-1 |
| 158 | 1-10  | 1-25  | 1-10  | 1-10  |
| 159 | 0.1-1 | 1-10  | 1-10  | 1-10  |
| 160/161 | 1-10 | 1-25 | 1-10 | 1-10 |
| 162 | 0.1-1 | 1-25  | 1-25  | 1-25  |
| 163 | <0.1  | <0.1  | <0.1 | <0.1 |
| 164 | <0.1  | <0.1  | <0.1 | <0.1 |

Thus while there have been described what are presently believed to be preferred embodiments of the invention, those skilled in the art will realize that changes and modifications may be made thereto without departing from the spirit of the invention, and it is intended to claim all such changes and modifications as fall within the true scope of the invention.

We claim:

1. A compound, or a pharmaceutically acceptable salt thereof, selected from: (R)-4-(4,5-Dimethyl-6-phenoxy-pyridazin-3-yl)-2-methyl-3,4,5,6-tetrahydro-2H-[1,2']bipyrazinyl-5'-carboxylic methyl ester; (R)-4-(4,5-Dimethyl-6-phenylamino-pyridazin-3-yl)-2-methyl-3,4,5,6-tetrahydro-2H-[1,2']bipyrazinyl-5'-carboxylic acid methyl ester; (R)-4-(4,5-Dimethyl-6-phenylamino-pyridazin-3-yl)-2-methyl-3,4,5,6-tetra-hydro-2H-[1,2']bipyrazinyl-5'-carboxylic acid phenylamide; 2-[(R)-4-(4,5-Dimethyl-6-phenylamino-pyridazin-3-yl)-2-methyl-3,4,5,6-tetrahydro-2H-[1,2']bipyrazinyl-5'-yl]-propan-2-ol; (R)-4-[6-(4-fluoro-phenyl)-4,5-dimethyl-pyridazin-3-yl]-2-methyl-3,4,5,6-tetrahydro-2H-[1,2']bipyrazinyl-5'-carboxylic acid methyl ester; (R)-4-[6-(4-trifluoromethyl-phenyl)-4,5-dimethyl-pyridazin-3-yl]-2-methyl-3,4,5,6-tetrahydro-2H-[1,2']bipyrazinyl-5'-carboxylic acid methyl ester; (R)-4-[6-(4-trifluoromethyl-phenyl)-4,5-dimethyl-pyridazin-3-yl]-2-methyl-3,4,5,6-tetrahydro-2H-[1,2']bipyrazinyl-5'-carboxylic acid; (R)-4-[6-(4-fluoro-phenyl)-4,5-dimethyl-pyridazin-3-yl]-2-methyl-3,4,5,6-tetrahydro-2H-[1,2']bipyrazinyl-5'-carboxylic acid; Methyl 5-(4-(6-benzyl-4,5-dimethylpyridazin-3-yl)piperidin-1-yl)pyrazine-2-carboxylate; 2-{5-[4-(6-Benzyl-4,5-dimethyl-pyridazin-3-yl)-piperidin-1-yl]-pyrazin-2-yl}-propan-2-ol; 3-Benzyl-6-{1-[5-(1-methoxy-1-methyl-ethyl)-pyrazin-2-yl]-piperidin-4-yl}-4,5-dimethyl-pyridazine; 3-Benzyl-6-{1-[5-(trifluoromethyl)pyridin-2-yl]-piperidin-4-yl}-4,5-dimethyl-pyridazine; (R)-4-(6-Benzoyl-4,5-dimethyl-pyridazin-3-yl)-2-methyl-3,4,5,6-tetrahydro-2H-[1,2']bipyrazinyl-5'-carboxylic acid methyl ester; (6-{(R)-4-[4-(1-Hydroxy-1-methyl-ethyl)-phenyl]-3-methyl-piperazin-1-yl}-4,5-dimethyl-pyridazin-3-yl)-phenyl-methanone; (R)-4[6-(hydroxyl-phenyl-methyl)-4,5-dimethyl-pyridazin-3-yl]-2-methyl-3,4,5,6-tetrahydro-2H-[1,2]bipyrazinyl-5'-carboxylic acid methyl ester; (R)-4-(4,5-Dimethyl-6-pyridin-4-ylmethyl-pyridazin-3-yl)-2-methyl-3,4,5,6-tetrahydro-2H-[1,2']bipyrazinyl-5'-carboxylic acid methyl ester; (R)-4-(4,5-Dimethyl-6-pyridin-3-ylmethyl-pyridazin-3-yl)-2-methyl-3,4,5,6-tetrahydro-2H-[1,2']bipyrazinyl-5'-carboxylic acid methyl ester; 2-[(R)-4-(4,5-Dimethyl-6-pyridin-3-ylmethyl-pyridazin-3-yl)-2-methyl-3,4,5,6-tetrahydro-2H-[1,2']bipyrazinyl-5'-yl]-propan-2-ol; (R)-4-(4,5-Dimethyl-6-pyridin-2-ylmethyl-pyridazin-3-yl)-2-methyl-3,4,5,6-tetrahydro-2H-[1,2']bipyrazinyl-5'-carboxylic acid methyl ester; 2-{(R)-4-[6-(Difluoro-phenyl-methyl)-4,5-dimethyl-pyridazin-3-yl]-2-methyl-3,4,5,6-tetrahydro-2H-[1,2']bipyrazinyl-5'-yl}-propan-2-ol; 3-Benzyl-6-[4-(5-chloro-1H-imidazol-2-yl)-piperidin-1-yl]-4,5-dimethyl-pyridazine; 1'-(6-Benzyl-4,5-dimethyl-pyridazin-3-yl)-5-(1-hydroxy-1-methyl-ethyl)-2',3',5',6'-tetrahydro-1'H-[2,4']bipyridinyl-4'-carbonitrile; 3-Benzyl-4,5- dimethyl-6-[4-(4-trifluoromethyl-1H-imidazol-2-yl)-piperidin-1-yl]-pyridazine; 1'-(6-Benzyl-4,5-dimethyl-pyridazin-3-yl)-5-(1-hydroxy-1-methyl-ethyl)-2',3',5',6'-tetrahydro-1'H-[2,4']bipyridinyl-4'-ol; 2-[1'-(6-Benzyl-4,5-dimethyl-pyridazin-3-yl)-4'-fluoro-1',2',3',4',5',6'-hexahydro-[2,4']bipyridinyl-5-yl]-propan-2-ol; 2-(6-{(S)-4-[4-(2-Chloro-benzyl)-6,7-dihydro-5H-cyclopenta[d]pyridazin-1-yl]-3-methyl-piperazin-1-yl}-pyridin-3-yl)-propan-2-ol; (R)-4-(6-Benzyl-4,5-dimethyl-pyridazin-3-yl)-2-methyl-3,4,5,6-tetrahydro-2H-[1,2']bipyrazinyl-5'-carboxylic acid methyl ester; 3-Benzyl-4,5-dimethyl-6-[(R)-3-methyl-4-(4-trifluoro-methanesulfonylphenyl)-piperazin-1-yl]-pyridazine; 2-[(R)-4-(6-Benzyl-4,5-dimethyl-pyridazin-3-yl)-2-methyl-3,4,5,6-tetrahydro-2H-[1,2']bipyrazinyl-5'-yl]-2,2-dimethoxy-ethanol; 1-[(R)-4-(6-Benzyl-4,5-dimethyl-pyridazin-3-yl)-2-methyl-3,4,5,6-tetrahydro-2H-[1,2']bipyrazinyl-5'-yl]-ethanol; 1-[(R)-4-(6-Benzyl-4,5-dimethyl-pyridazin-3-yl)-2methyl-3,4,5,6-tetrahydro-2H-[1,2']bipyrazinyl-5'-yl]-2-hydroxy-ethanone; 1-[(R)-4-(6-Benzyl-4,5-dimethyl-pyridazin-3-yl)-2methyl-3,4,5,6-tetrahydro-2H-[1,2']bipyrazinyl-5'-yl]-ethane-1,2-diol; (R)-4-(6-Benzyl-4,5-dimethyl-pyridazin-3-yl)-2-methyl-3,4,5,6-tetrahydro-2H-[1,2']bipyrazinyl-5'-carboxylic acid; (R)-4-(6-Benzyl-4,5-dimethyl-pyridazin-3-yl)-2-methyl-3,4,5,6-tetrahydro-2H-[1,2']bipyrazinyl-5'-carboxylic acid methoxy-methyl-amide; (R)-4-(6-Benzyl-4,5-dimethyl-pyridazin-3-yl)-5'-isopropenyl-2-methyl-3,4,5,6-tetrahydro-2H-[1,2']bipyrazinyl; 4,5-Dimethyl-3-(5-methyl-[1,2,4]oxadiazol-3-yl-methyl)-6-[4-(5-trifluoro-methyl-pyridin-2-yl)-piperazin-1-yl]-pyridazine; 4,5-Dimethyl-3-(1-methyl-1H-tetrazol-5-ylmethyl)-6-[4-(5-trifluoromethyl-pyridin-2-yl)-piperazin-1-yl]-pyridazine; 4,5-Dimethyl-3-(2-methyl-2H-tetrazol-5-ylmethyl)-6-[4-(5-trifluoromethyl-pyridin-2-yl)-piperazin-1-yl]-pyridazine; 4,5-Dimethyl-3-(5-methyl-[1,3,4]oxadiazol-2-ylmethyl)-6-[4-(5-trifluoromethyl-pyridin-2-yl)-piperazin-1-yl]-pyridazine; 2-[(R)-4-(6-Benzyl-5-hydroxymethyl-4-methyl-pyridazin-3-yl)-2-methyl-3,4,5,6-tetrahydro-2H-[1,2']bipyrazinyl-5'-yl]-propan-2-ol; and 2-[(R)-4-(6-Benzyl-4-hydroxymethyl-5-methyl-pyridazin-3-yl)-2-methyl-3,4,5,6-tetrahydro-2H-[1,2']bipyrazinyl-5'-yl]-propan-2-ol.

2. A compound, or a pharmaceutically acceptable salt thereof, selected from:

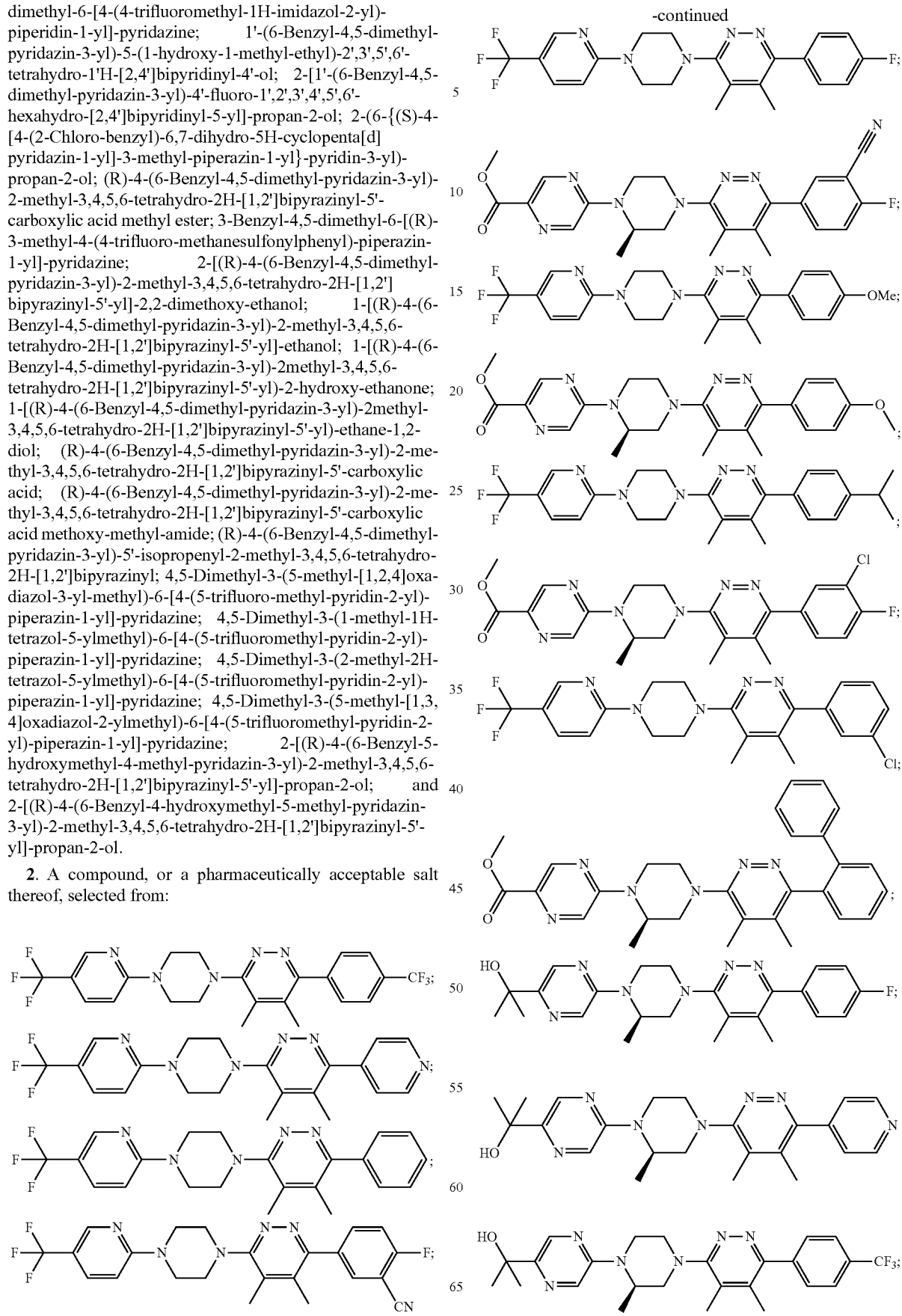

137
-continued
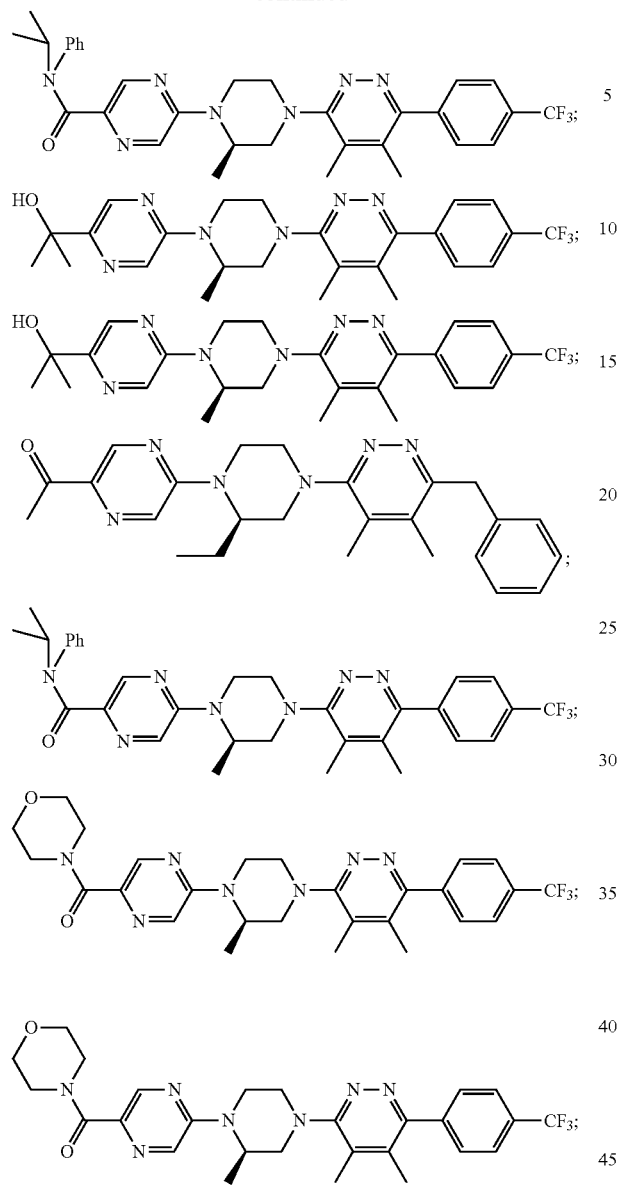
138
-continued
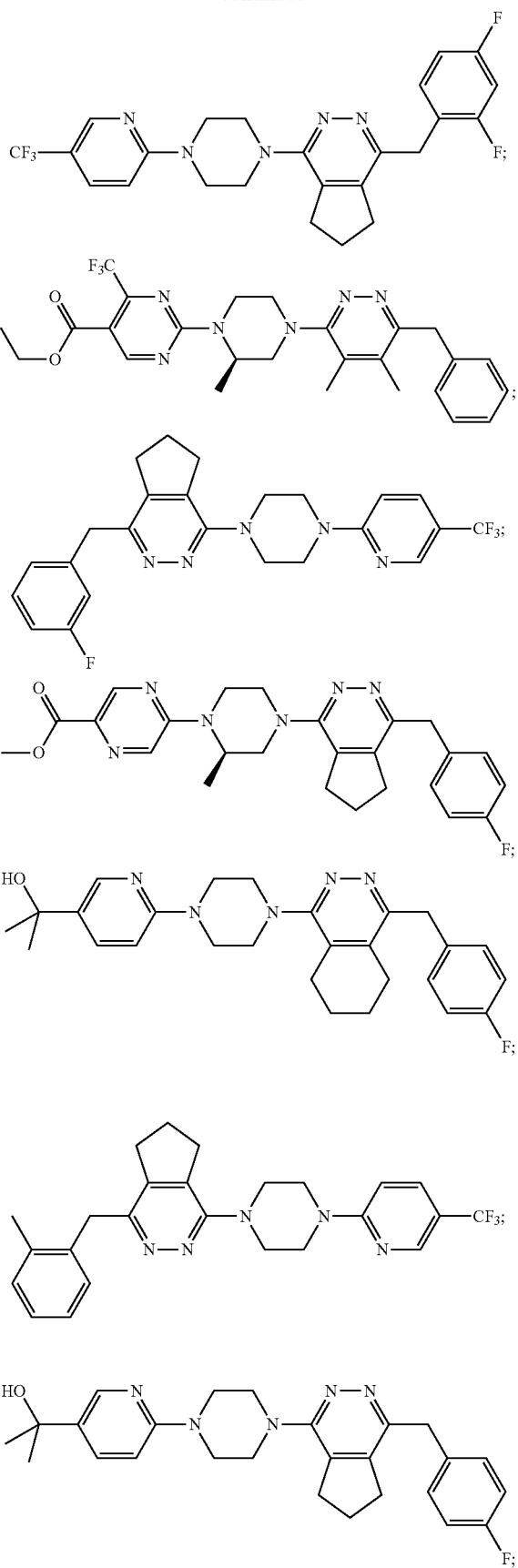

139
-continued
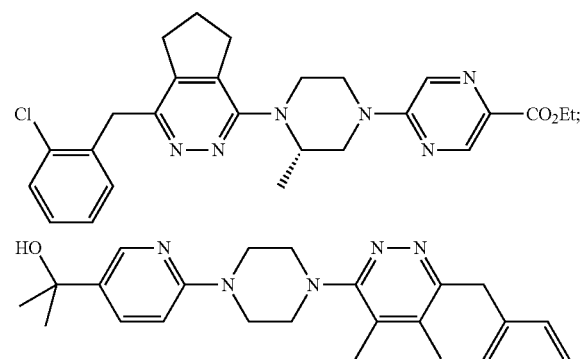
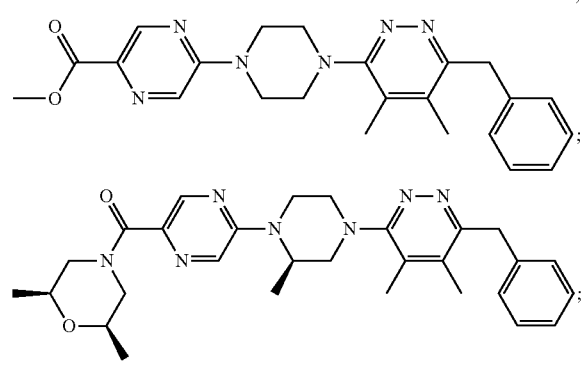
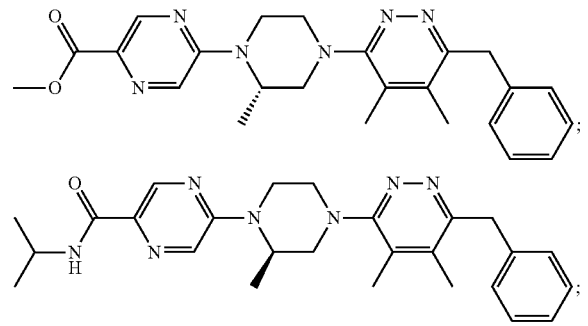
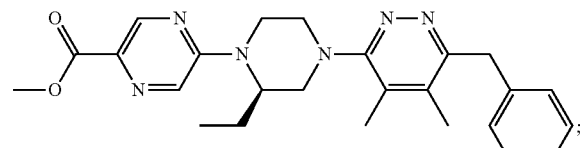
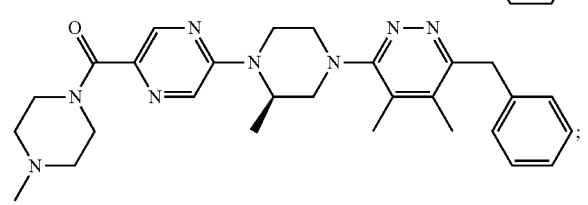
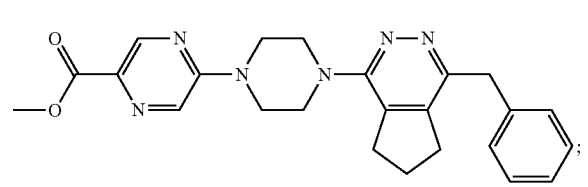
140
-continued
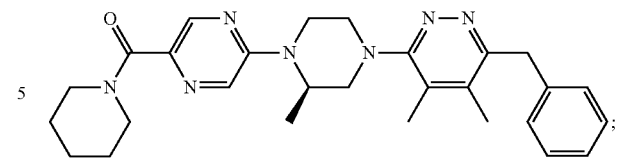
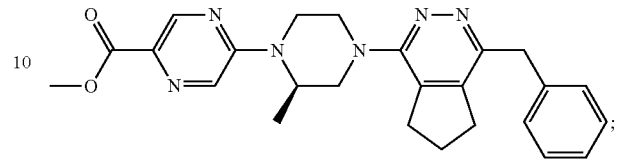
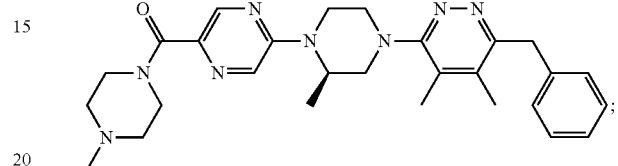
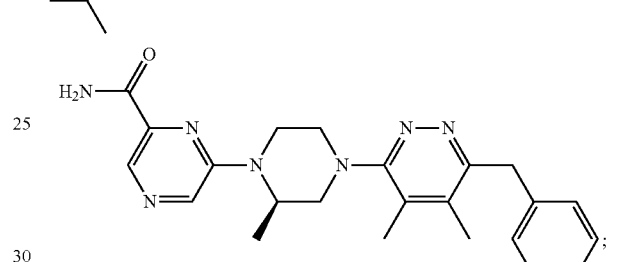
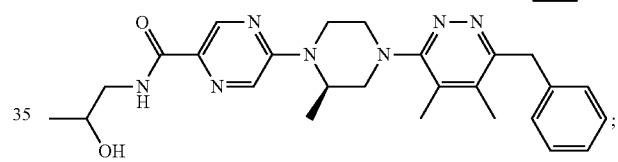
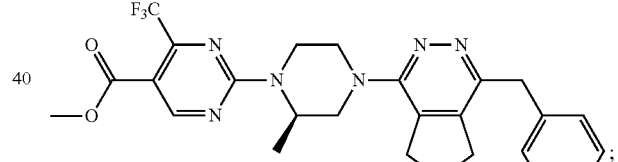
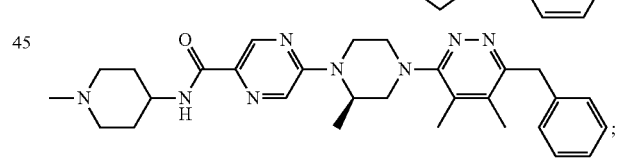
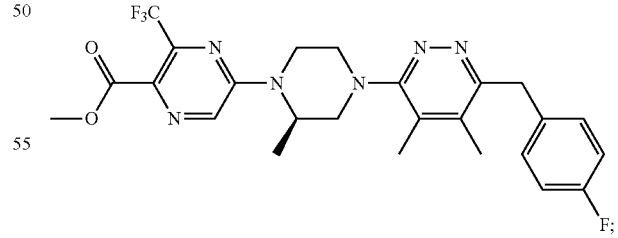
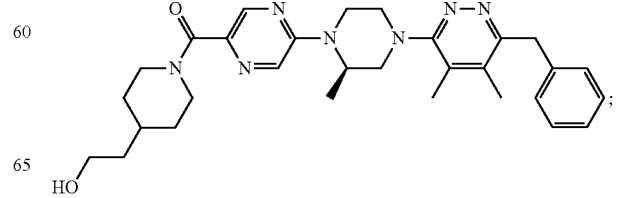

141
-continued
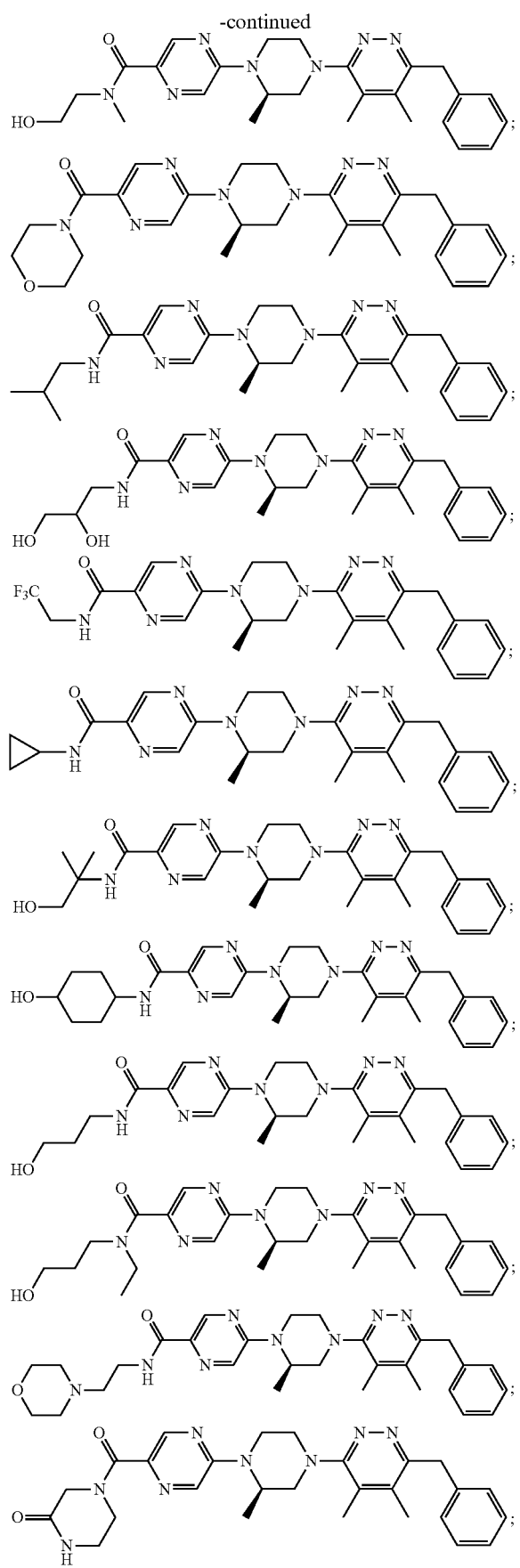
142
-continued
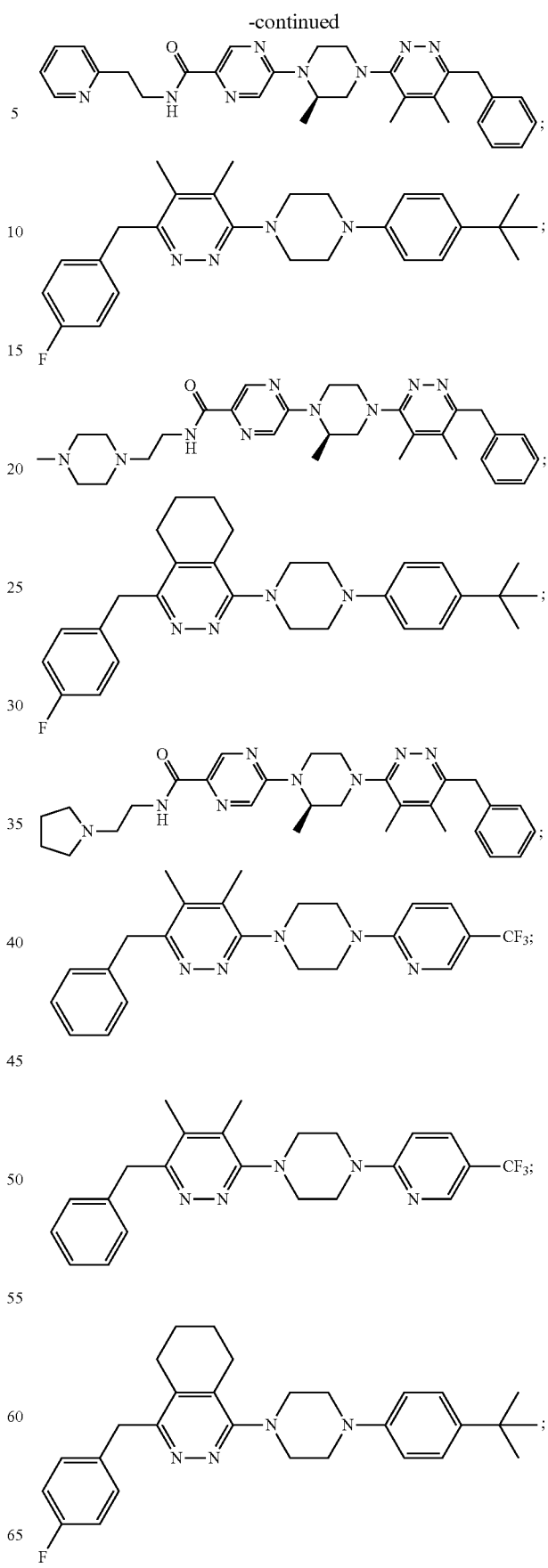

-continued
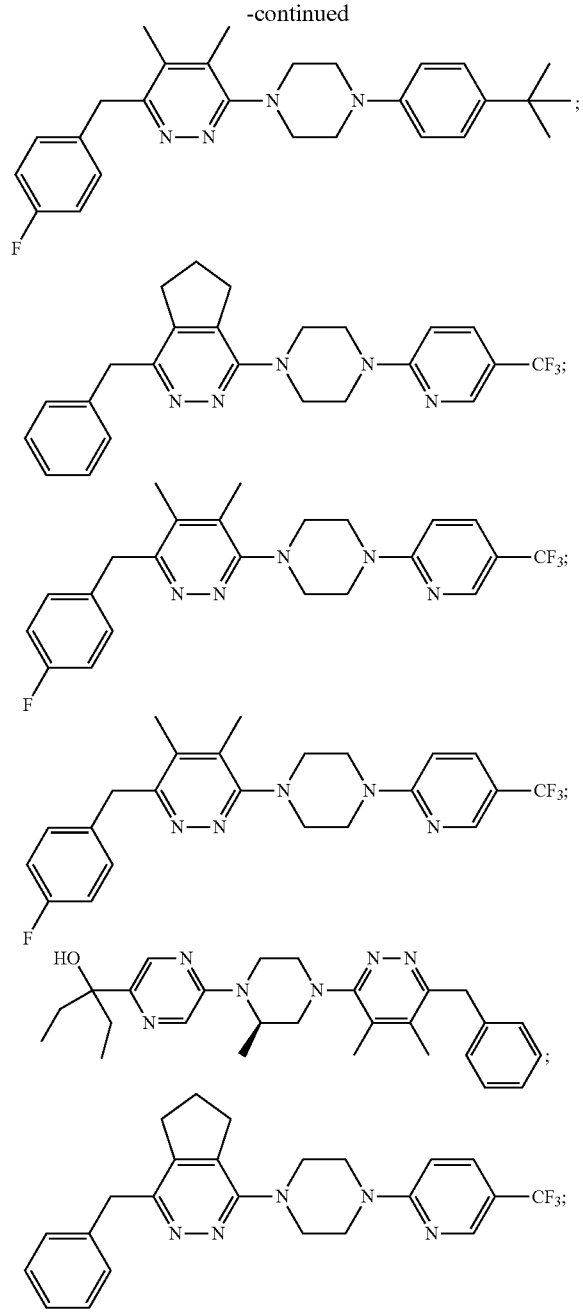
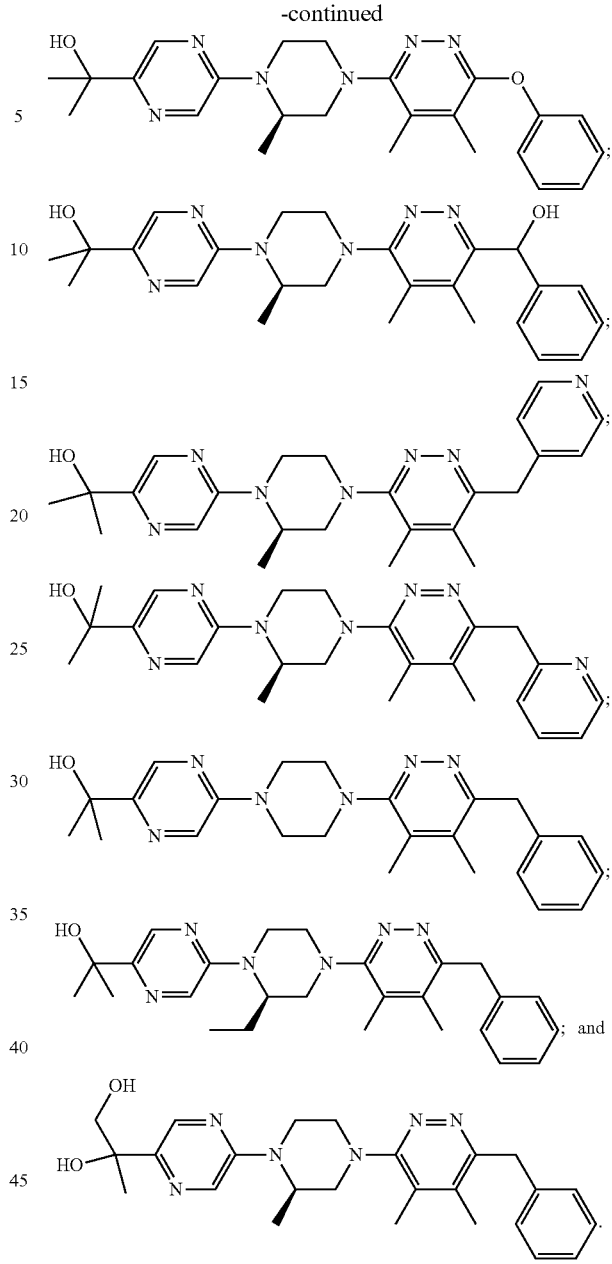
* * * * *